US012767719B2

(12) United States Patent
Lu et al.

(10) Patent No.: US 12,767,719 B2
(45) Date of Patent: Oct. 20, 2026

(54) CCR8 ANTIBODY AND APPLICATION THEREOF

(71) Applicant: HARBOUR BIOMED (SHANGHAI) CO., LTD., Shanghai (CN)

(72) Inventors: Shuang Lu, Shanghai (CN); Yongqiang Wang, Shanghai (CN); Xin Gan, Shanghai (CN); Fei Chen, Shanghai (CN); Jinqiu He, Shanghai (CN); Xiaohui Shao, Shanghai (CN); Shaoping Hu, Shanghai (CN); Chuchu Zhao, Shanghai (CN); Jiuqiao Zhao, Shanghai (CN); Yiping Rong, Shanghai (CN)

(73) Assignee: Harbour BioMed (Shanghai) Co., Ltd., Shanghai (CN)

( * ) Notice: Subject to any disclaimer, the term of this patent is extended or adjusted under 35 U.S.C. 154(b) by 852 days.

(21) Appl. No.: 18/043,327

(22) PCT Filed: Aug. 27, 2021

(86) PCT No.: PCT/CN2021/115061

§ 371 (c)(1),
(2) Date: Dec. 21, 2023

(87) PCT Pub. No.: WO2022/042690

PCT Pub. Date: Mar. 3, 2022

(65) Prior Publication Data

US 2024/0132603 A1 Apr. 25, 2024
US 2024/0228635 A9 Jul. 11, 2024

(30) Foreign Application Priority Data

Aug. 28, 2020 (CN) ......................... 202010888581.2

(51) Int. Cl.

| | |
|---|---|
| ***C07K 16/28*** | (2006.01) |
| ***A61K 47/68*** | (2017.01) |
| ***A61P 35/00*** | (2006.01) |
| ***C07K 14/705*** | (2006.01) |

(52) U.S. Cl.
CPC ...... *C07K 16/2866* (2013.01); *A61K 47/6849* (2017.08); *A61P 35/00* (2018.01); *C07K 14/7051* (2013.01); *C07K 2317/21* (2013.01); *C07K 2317/24* (2013.01); *C07K 2317/31* (2013.01); *C07K 2317/569* (2013.01)

(58) Field of Classification Search
None
See application file for complete search history.

(56) References Cited

FOREIGN PATENT DOCUMENTS

| | | | |
|---|---|---|---|
| CN | 109475627 | A | 3/2019 |
| CN | 110835371 | A | 2/2020 |
| CN | 110835374 | A | 2/2020 |
| WO | WO 01/58484 | A2 | 8/2001 |
| WO | WO 03/096020 | A2 | 11/2003 |
| WO | WO 2007/044756 | A2 | 4/2007 |
| WO | WO 2018/112032 | A1 | 6/2018 |
| WO | 2020138489 | A1 | 7/2020 |

OTHER PUBLICATIONS

Al-Lazikani et al., Standard conformations for the canonical structures of immunoglobulins. J Mol Biol. Nov. 7, 1997;273(4):927-48.
Altschul et al., Basic local alignment search tool. J Mol Biol. Oct. 5, 1990;215(3):403-10.
Lipman et al., Rapid and sensitive protein similarity searches. Science. Mar. 22, 1985;227(4693):1435-41.
Pearson et al., Improved tools for biological sequence comparison. Proc Natl Acad Sci U S A. Apr. 1988;85(8):2444-8.

*Primary Examiner* — Maher M Haddad
(74) *Attorney, Agent, or Firm* — Mintz Levin Cohn Ferris Glovsky and Popeo, P.C.

(57) ABSTRACT

Involved is an isolated antigen binding protein, being capable of binding CCR8 derived from a primate animal. Further involved are a pharmaceutical composition comprising the antigen binding protein, and an application of the antigen binding protein and/or the pharmaceutical composition in the prevention and/or treatment of a tumor or a cancer.

20 Claims, 27 Drawing Sheets

Specification includes a Sequence Listing.

SEQUENCE LISTING

```
<160> NUMBER OF SEQ ID NOS: 368

<210> SEQ ID NO 1
<211> LENGTH: 25
<212> TYPE: PRT
<213> ORGANISM: Artificial Sequence
<220> FEATURE:
<223> OTHER INFORMATION: H-FR1

<400> SEQUENCE: 1

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25


<210> SEQ ID NO 2
<211> LENGTH: 25
<212> TYPE: PRT
<213> ORGANISM: Artificial Sequence
<220> FEATURE:
<223> OTHER INFORMATION: PR004122|pHBM005089-VH|H-FR1;
      PR004127|pHBM005094-VH|H-FR1; PR004249|pHBM005373-VH|H-FR1

<400> SEQUENCE: 2

Glu Val Gln Leu Val Glu Thr Gly Gly Gly Leu Val Gln Pro Lys Gly
1               5                   10                  15

Ser Leu Lys Leu Ser Cys Ala Ala Ser
            20                  25


<210> SEQ ID NO 3
<211> LENGTH: 25
<212> TYPE: PRT
<213> ORGANISM: Artificial Sequence
<220> FEATURE:
<223> OTHER INFORMATION: PR004124|pHBM005091-VH|H-FR1

<400> SEQUENCE: 3

Glu Val Lys Val Glu Glu Ser Gly Gly Gly Leu Val Gln Pro Gly Gly
1               5                   10                  15

Ser Met Lys Leu Ser Cys Ala Ala Ser
            20                  25


<210> SEQ ID NO 4
<211> LENGTH: 25
<212> TYPE: PRT
<213> ORGANISM: Artificial Sequence
<220> FEATURE:
<223> OTHER INFORMATION: PR004130|pHBM005096-VH|H-FR1

<400> SEQUENCE: 4

Glu Val Gln Leu Val Glu Ser Gly Gly Gly Leu Val Gln Phe Lys Gly
1               5                   10                  15

Ser Leu Lys Leu Ser Cys Gly Thr Ser
            20                  25
```

<210> SEQ ID NO 5
<211> LENGTH: 25
<212> TYPE: PRT
<213> ORGANISM: Artificial Sequence
<220> FEATURE:
<223> OTHER INFORMATION: H-FR1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: PR004265|pHBM005403-VH|H-FR1

<400> SEQUENCE: 6

Glu Val Gln Leu Val Glu Ser Gly Gly Gly Leu Val Gln Pro Gly Gly
1               5                   10                  15

Ser Arg Lys Leu Ser Cys Ala Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: H-FR1

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: H-FR1

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: PR004974|pHBM006117-VH|H-FR1;
      PR005293|pHBM006504-VH|H-FR1

<400> SEQUENCE: 9

Gln Ile Thr Leu Lys Glu Ser Gly Pro Thr Leu Val Lys Pro Thr Gln
1               5                   10                  15

Thr Leu Thr Leu Thr Cys Thr Phe Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: PR005124|pHBM006274-VH|H-FR1;
PR005127|pHBM006280-VH|H-FR1

<400> SEQUENCE: 10

```
Gln Val Gln Leu Val Glu Ser Gly Gly Gly Val Val Gln Pro Gly Arg
1               5                   10                  15

Ser Leu Arg Leu Ser Cys Val Ala Ser
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: PR005125|pHBM006276-VH|H-FR1;
PR005128|pHBM006281-VH|H-FR1

<400> SEQUENCE: 11

```
Gln Val Gln Leu Val Glu Ser Gly Gly Gly Val Val Gln Pro Gly Arg
1               5                   10                  15

Ser Leu Arg Leu Ser Cys Ala Ala Ser
            20                  25
```

<210> SEQ ID NO 12
<211> LENGTH: 25
<212> TYPE: PRT
<213> ORGANISM: Artificial Sequence
<220> FEATURE:
<223> OTHER INFORMATION: PR005329|pHBM006537-VH|H-FR1;
PR005332|pHBM006540-VH|H-FR1

<400> SEQUENCE: 12

```
Glu Val Lys Leu Leu Glu Ser Gly Gly Gly Leu Val Gln Pro Lys Gly
1               5                   10                  15

Ser Leu Lys Leu Ser Cys Ala Ala Ser
            20                  25
```

<210> SEQ ID NO 13
<211> LENGTH: 25
<212> TYPE: PRT
<213> ORGANISM: Artificial Sequence
<220> FEATURE:
<223> OTHER INFORMATION: PR005330|pHBM006538-VH|H-FR1;
PR005333|pHBM006541-VH|H-FR1

<400> SEQUENCE: 13

```
Glu Val Lys Leu Val Glu Ser Gly Gly Gly Leu Val Gln Pro Gly Gly
1               5                   10                  15

Ser Arg Lys Leu Ser Cys Ala Ala Ser
            20                  25
```

<210> SEQ ID NO 14
<211> LENGTH: 25
<212> TYPE: PRT
<213> ORGANISM: Artificial Sequence
<220> FEATURE:
<223> OTHER INFORMATION: PR005335|pHBM006543-VH|H-FR1

<400> SEQUENCE: 14

Gln Val Gln Leu Val Gln Ser Gly Gly Gly Leu Val Gln Pro Gly Gly
1 5 10 15

Ser Leu Arg Leu Ser Cys Thr Ala Ser
20 25

<210> SEQ ID NO 15
<211> LENGTH: 7
<212> TYPE: PRT
<213> ORGANISM: Artificial Sequence
<220> FEATURE:
<223> OTHER INFORMATION: HCDR1

<400> SEQUENCE: 15

Gly Phe Thr Phe Asn Thr Asn
1 5

<210> SEQ ID NO 16
<211> LENGTH: 7
<212> TYPE: PRT
<213> ORGANISM: Artificial Sequence
<220> FEATURE:
<223> OTHER INFORMATION: HCDR1

<400> SEQUENCE: 16

Gly Phe Thr Phe Asn Thr Tyr
1 5

<210> SEQ ID NO 17
<211> LENGTH: 7
<212> TYPE: PRT
<213> ORGANISM: Artificial Sequence
<220> FEATURE:
<223> OTHER INFORMATION: PR004123|pHBM005090-VH|HCDR1

<400> SEQUENCE: 17

Glu Phe Thr Phe Asn Thr Tyr
1 5

<210> SEQ ID NO 18
<211> LENGTH: 7
<212> TYPE: PRT
<213> ORGANISM: Artificial Sequence
<220> FEATURE:
<223> OTHER INFORMATION: PR004126|pHBM005093-VH|HCDR1

<400> SEQUENCE: 18

Gly Phe Thr Phe Ser Thr Asn
1 5

<210> SEQ ID NO 19
<211> LENGTH: 7
<212> TYPE: PRT
<213> ORGANISM: Artificial Sequence
<220> FEATURE:
<223> OTHER INFORMATION: HCDR1

<400> SEQUENCE: 19

Gly Phe Thr Phe Ser Ser Tyr
1 5

<210> SEQ ID NO 20
<211> LENGTH: 7
<212> TYPE: PRT
<213> ORGANISM: Artificial Sequence
<220> FEATURE:
<223> OTHER INFORMATION: PR004265|pHBM005403-VH|HCDR1

<400> SEQUENCE: 20

Gly Phe Thr Phe Ser Ser Phe
1 5

<210> SEQ ID NO 21
<211> LENGTH: 7
<212> TYPE: PRT
<213> ORGANISM: Artificial Sequence
<220> FEATURE:
<223> OTHER INFORMATION: PR004327|pHBM005431-VH|HCDR1

<400> SEQUENCE: 21

Gly Phe Thr Phe Gln Thr Tyr
1 5

<210> SEQ ID NO 22
<211> LENGTH: 7
<212> TYPE: PRT
<213> ORGANISM: Artificial Sequence
<220> FEATURE:
<223> OTHER INFORMATION: HCDR1

<400> SEQUENCE: 22

Gly Phe Thr Phe Ser Thr Tyr
1 5

<210> SEQ ID NO 23
<211> LENGTH: 9
<212> TYPE: PRT
<213> ORGANISM: Artificial Sequence
<220> FEATURE:
<223> OTHER INFORMATION: PR004974|pHBM006117-VH|HCDR1;
PR005293|pHBM006504-VH|HCDR1

<400> SEQUENCE: 23

Gly Phe Ser Leu Ser Thr Ser Gly Val
1 5

<210> SEQ ID NO 24
<211> LENGTH: 7
<212> TYPE: PRT
<213> ORGANISM: Artificial Sequence
<220> FEATURE:
<223> OTHER INFORMATION: PR005331|pHBM006539-VH|HCDR1;
PR005336|pHBM006544-VH|HCDR1

<400> SEQUENCE: 24

Gly Phe Thr Phe Ser Asn Tyr
1 5

<210> SEQ ID NO 25
<211> LENGTH: 7
<212> TYPE: PRT
<213> ORGANISM: Artificial Sequence
<220> FEATURE:
<223> OTHER INFORMATION: PR005335|pHBM006543-VH|HCDR1

<400> SEQUENCE: 25

Gly Phe Thr Phe Ser Tyr Tyr
1 5

<210> SEQ ID NO 26
<211> LENGTH: 19
<212> TYPE: PRT
<213> ORGANISM: Artificial Sequence
<220> FEATURE:
<223> OTHER INFORMATION: H-FR2

<400> SEQUENCE: 26

Ala Met Asn Trp Val Arg Gln Ala Pro Gly Lys Gly Leu Glu Trp Val
1 5 10 15

Ala Arg Ile

<210> SEQ ID NO 27
<211> LENGTH: 19
<212> TYPE: PRT
<213> ORGANISM: Artificial Sequence
<220> FEATURE:
<223> OTHER INFORMATION: H-FR2

<400> SEQUENCE: 27

Ala Met Asn Trp Val Arg Gln Ala Pro Gly Lys Gly Leu Glu Trp Val
1 5 10 15

Gly Arg Ile

<210> SEQ ID NO 28
<211> LENGTH: 19
<212> TYPE: PRT
<213> ORGANISM: Artificial Sequence
<220> FEATURE:
<223> OTHER INFORMATION: PR004264|pHBM005401-VH|H-FR2;
PR004275|pHBM005295-VH|H-FR2

<400> SEQUENCE: 28

Ala Met Ser Trp Val Arg Gln Ala Pro Gly Lys Gly Leu Glu Trp Val
1 5 10 15

Ser Ala Ile

<210> SEQ ID NO 29
<211> LENGTH: 19
<212> TYPE: PRT
<213> ORGANISM: Artificial Sequence
<220> FEATURE:
<223> OTHER INFORMATION: PR004265|pHBM005403-VH|H-FR2

<400> SEQUENCE: 29

Gly Met His Trp Val Arg Gln Val Pro Glu Lys Gly Leu Glu Trp Val
1 5 10 15

Ala Tyr Ile

<210> SEQ ID NO 30
<211> LENGTH: 19
<212> TYPE: PRT
<213> ORGANISM: Artificial Sequence
<220> FEATURE:
<223> OTHER INFORMATION: H-FR2

<400> SEQUENCE: 30

Ala Met Asn Trp Val Arg Gln Ala Pro Gly Lys Gly Leu Glu Trp Val
1 5 10 15

Ser Arg Ile

<210> SEQ ID NO 31
<211> LENGTH: 19
<212> TYPE: PRT
<213> ORGANISM: Artificial Sequence
<220> FEATURE:
<223> OTHER INFORMATION: H-FR2

<400> SEQUENCE: 31

Ala Met Asn Trp Val Arg Gln Ala Ser Gly Lys Gly Leu Glu Trp Val
1               5                   10                  15

Gly Arg Ile

<210> SEQ ID NO 32
<211> LENGTH: 19
<212> TYPE: PRT
<213> ORGANISM: Artificial Sequence
<220> FEATURE:
<223> OTHER INFORMATION: PR004970|pHBM006115-VH|H-FR2

<400> SEQUENCE: 32

Trp Met Ser Trp Val Pro Gln Ala Pro Gly Lys Gly Leu Glu Trp Val
1               5                   10                  15

Ala Asn Ile

<210> SEQ ID NO 33
<211> LENGTH: 19
<212> TYPE: PRT
<213> ORGANISM: Artificial Sequence
<220> FEATURE:
<223> OTHER INFORMATION: PR004974|pHBM006117-VH|H-FR2;
PR005293|pHBM006504-VH|H-FR2

<400> SEQUENCE: 33

Gly Val Gly Trp Ile Arg Gln Pro Pro Gly Lys Ala Leu Glu Trp Leu
1               5                   10                  15

Ala Leu Ile

<210> SEQ ID NO 34
<211> LENGTH: 19
<212> TYPE: PRT
<213> ORGANISM: Artificial Sequence
<220> FEATURE:
<223> OTHER INFORMATION: PR005124|pHBM006274-VH|H-FR2;
PR005127|pHBM006280-VH|H-FR2

<400> SEQUENCE: 34

Gly Met His Trp Val Arg Gln Ala Pro Gly Lys Gly Leu Glu Trp Val
1               5                   10                  15

Ala Val Ile

<210> SEQ ID NO 35
<211> LENGTH: 19
<212> TYPE: PRT
<213> ORGANISM: Artificial Sequence
<220> FEATURE:
<223> OTHER INFORMATION: PR005125|pHBM006276-VH|H-FR2;
PR005128|pHBM006281-VH|H-FR2

<400> SEQUENCE: 35

Gly Met His Trp Val Arg Gln Val Pro Gly Lys Gly Leu Glu Trp Val
1               5                   10                  15

Ala Val Ile

<210> SEQ ID NO 36
<211> LENGTH: 19
<212> TYPE: PRT
<213> ORGANISM: Artificial Sequence
<220> FEATURE:
<223> OTHER INFORMATION: PR005331|pHBM006539-VH|H-FR2;
PR005335|pHBM006543-VH|H-FR2; PR005336|pHBM006544-VH|H-FR2

<400> SEQUENCE: 36

Trp Leu Ser Trp Val Arg Gln Ala Pro Gly Lys Gly Leu Glu Trp Val
1 5 10 15

Ala Asn Ile

<210> SEQ ID NO 37
<211> LENGTH: 8
<212> TYPE: PRT
<213> ORGANISM: Artificial Sequence
<220> FEATURE:
<223> OTHER INFORMATION: PR004120|pHBM005087-VH|HCDR2

<400> SEQUENCE: 37

Arg Ser Lys Met Asn Asn Tyr Ala
1 5

<210> SEQ ID NO 38
<211> LENGTH: 8
<212> TYPE: PRT
<213> ORGANISM: Artificial Sequence
<220> FEATURE:
<223> OTHER INFORMATION: HCDR2

<400> SEQUENCE: 38

Arg Ser Lys Ser Asn Asn Tyr Ala
1 5

<210> SEQ ID NO 39
<211> LENGTH: 8
<212> TYPE: PRT
<213> ORGANISM: Artificial Sequence
<220> FEATURE:
<223> OTHER INFORMATION: PR004123|pHBM005090-VH|HCDR2

<400> SEQUENCE: 39

Arg Thr Lys Ser Asn Asn Phe Ala
1 5

<210> SEQ ID NO 40
<211> LENGTH: 6
<212> TYPE: PRT
<213> ORGANISM: Artificial Sequence
<220> FEATURE:
<223> OTHER INFORMATION: PR004264|pHBM005401-VH|HCDR2;
PR004275|pHBM005295-VH|HCDR2

<400> SEQUENCE: 40

Ser Gly Ser Gly Gly Ser
1 5

<210> SEQ ID NO 41
<211> LENGTH: 6
<212> TYPE: PRT
<213> ORGANISM: Artificial Sequence
<220> FEATURE:
<223> OTHER INFORMATION: PR004265|pHBM005403-VH|HCDR2

<400> SEQUENCE: 41

Ser Ser Gly Ser Arg Thr
1 5

<210> SEQ ID NO 42
<211> LENGTH: 6
<212> TYPE: PRT
<213> ORGANISM: Artificial Sequence
<220> FEATURE:
<223> OTHER INFORMATION: PR004970|pHBM006115-VH|HCDR2;
PR005331|pHBM006539-VH|HCDR2; PR005336|pHBM006544-VH|HCDR2

<400> SEQUENCE: 42

Lys Gln Asp Gly Ser Ala
1 5

<210> SEQ ID NO 43
<211> LENGTH: 5
<212> TYPE: PRT
<213> ORGANISM: Artificial Sequence
<220> FEATURE:
<223> OTHER INFORMATION: PR004974|pHBM006117-VH|HCDR2;
PR005293|pHBM006504-VH|HCDR2

<400> SEQUENCE: 43

Tyr Trp Asn Asp Asp
1 5

<210> SEQ ID NO 44
<211> LENGTH: 6
<212> TYPE: PRT
<213> ORGANISM: Artificial Sequence
<220> FEATURE:
<223> OTHER INFORMATION: PR005124|pHBM006274-VH|HCDR2;
PR005127|pHBM006280-VH|HCDR2

<400> SEQUENCE: 44

Trp His Asp Gly Ser Asn
1 5

<210> SEQ ID NO 45
<211> LENGTH: 6
<212> TYPE: PRT
<213> ORGANISM: Artificial Sequence
<220> FEATURE:
<223> OTHER INFORMATION: PR005125|pHBM006276-VH|HCDR2;
PR005128|pHBM006281-VH|HCDR2

<400> SEQUENCE: 45

Trp Tyr Asp Gly Ser Lys
1 5

<210> SEQ ID NO 46
<211> LENGTH: 8
<212> TYPE: PRT
<213> ORGANISM: Artificial Sequence
<220> FEATURE:
<223> OTHER INFORMATION: PR005329|pHBM006537-VH|HCDR2;
PR005332|pHBM006540-VH|HCDR2

<400> SEQUENCE: 46

Arg Thr Lys Ser Asn Asn Tyr Ala
1 5

<210> SEQ ID NO 47
<211> LENGTH: 6
<212> TYPE: PRT
<213> ORGANISM: Artificial Sequence
<220> FEATURE:
<223> OTHER INFORMATION: PR005335|pHBM006543-VH|HCDR2

<400> SEQUENCE: 47

Lys Gln Asp Gly Ser Thr
1 5

<210> SEQ ID NO 48
<211> LENGTH: 8
<212> TYPE: PRT

<213> ORGANISM: Artificial Sequence
<220> FEATURE:
<223> OTHER INFORMATION: HCDR2

<400> SEQUENCE: 48

Arg Ser Lys Ser Asn Tyr Tyr Ala
1               5

<210> SEQ ID NO 49
<211> LENGTH: 41
<212> TYPE: PRT
<213> ORGANISM: Artificial Sequence
<220> FEATURE:
<223> OTHER INFORMATION: PR004120|pHBM005087-VH|H-FR3;
PR004121|pHBM005088-VH|H-FR3; PR004127|pHBM005094-VH|H-FR3

<400> SEQUENCE: 49

Thr Tyr Tyr Ala Asp Ser Val Lys Asp Arg Phe Thr Ile Ser Arg Asp
1               5                   10                  15

Asp Ser Gln Asn Met Leu Tyr Leu Gln Met Asn Asn Leu Lys Thr Glu
            20                  25                  30

Asp Thr Ala Met Tyr Tyr Cys Val Arg
        35                  40

<210> SEQ ID NO 50
<211> LENGTH: 41
<212> TYPE: PRT
<213> ORGANISM: Artificial Sequence
<220> FEATURE:
<223> OTHER INFORMATION: H-FR3

<400> SEQUENCE: 50

Thr Tyr Tyr Ala Asp Ser Val Lys Asp Arg Phe Thr Ile Ser Arg Asp
1               5                   10                  15

Asp Ser Gln Ser Met Leu Tyr Leu Gln Met Asn Asn Leu Lys Thr Glu
            20                  25                  30

Asp Thr Ala Met Tyr Tyr Cys Val Arg
        35                  40

<210> SEQ ID NO 51
<211> LENGTH: 41
<212> TYPE: PRT
<213> ORGANISM: Artificial Sequence
<220> FEATURE:
<223> OTHER INFORMATION: PR004123|pHBM005090-VH|H-FR3

<400> SEQUENCE: 51

Thr Tyr Tyr Ala Asp Ser Val Lys Asp Arg Phe Thr Ile Ser Arg Asp
1               5                   10                  15

Asp Ser Gln Ser Met Leu Phe Leu Gln Met Asn Asn Leu Lys Thr Glu
            20                  25                  30

Asp Thr Ala Met Tyr Tyr Cys Val Arg
        35                  40

<210> SEQ ID NO 52
<211> LENGTH: 41
<212> TYPE: PRT
<213> ORGANISM: Artificial Sequence
<220> FEATURE:
<223> OTHER INFORMATION: PR004130|pHBM005096-VH|H-FR3

<400> SEQUENCE: 52

Thr Phe Tyr Ala Asp Ser Val Lys Asp Arg Phe Thr Ile Ser Arg Asp
1               5                   10                  15

Asp Ser Gln Asn Met Leu Tyr Leu Gln Met Asn Asn Leu Lys Thr Glu
20 25 30

Asp Thr Ala Met Tyr Tyr Cys Val Arg
35 40

<210> SEQ ID NO 53
<211> LENGTH: 41
<212> TYPE: PRT
<213> ORGANISM: Artificial Sequence
<220> FEATURE:
<223> OTHER INFORMATION: PR004264|pHBM005401-VH|H-FR3

<400> SEQUENCE: 53

Thr Tyr Tyr Ala Asp Ser Val Lys Gly Arg Phe Thr Ile Ser Arg Asp
1 5 10 15

Asn Ser Lys Asn Thr Leu Tyr Leu Gln Met Asn Ser Leu Arg Ala Glu
20 25 30

Asp Thr Ala Val Tyr Tyr Cys Ala Thr
35 40

<210> SEQ ID NO 54
<211> LENGTH: 41
<212> TYPE: PRT
<213> ORGANISM: Artificial Sequence
<220> FEATURE:
<223> OTHER INFORMATION: PR004265|pHBM005403-VH|H-FR3

<400> SEQUENCE: 54

Ile Tyr Tyr Thr Asp Thr Val Lys Gly Arg Phe Thr Ile Ser Arg Asp
1 5 10 15

Asn Pro Lys Asn Thr Leu Phe Leu Gln Met Thr Ser Leu Arg Ser Glu
20 25 30

Asp Thr Ala Ile Tyr Tyr Cys Val Arg
35 40

<210> SEQ ID NO 55
<211> LENGTH: 41
<212> TYPE: PRT
<213> ORGANISM: Artificial Sequence
<220> FEATURE:
<223> OTHER INFORMATION: PR004275|pHBM005295-VH|H-FR3

<400> SEQUENCE: 55

Thr Tyr Tyr Ala Asp Ser Val Lys Gly Arg Phe Thr Ile Ser Arg Asp
1 5 10 15

Asn Ser Lys Asn Thr Leu Tyr Leu Gln Met Asn Ser Leu Arg Ala Glu
20 25 30

Asp Thr Ala Val Tyr Tyr Cys Ala Arg
35 40

<210> SEQ ID NO 56
<211> LENGTH: 41
<212> TYPE: PRT
<213> ORGANISM: Artificial Sequence
<220> FEATURE:
<223> OTHER INFORMATION: H-FR3

<400> SEQUENCE: 56

Thr Tyr Tyr Ala Asp Ser Val Lys Asp Arg Phe Thr Ile Ser Arg Asp
1 5 10 15

Asp Ser Lys Ser Thr Leu Tyr Leu Gln Met Asn Ser Leu Lys Thr Glu
20 25 30

Asp Thr Ala Val Tyr Tyr Cys Val Arg
        35                  40

<210> SEQ ID NO 57
<211> LENGTH: 41
<212> TYPE: PRT
<213> ORGANISM: Artificial Sequence
<220> FEATURE:
<223> OTHER INFORMATION: H-FR3

<400> SEQUENCE: 57

Thr Tyr Tyr Ala Asp Ser Val Lys Asp Arg Phe Thr Ile Ser Arg Asp
1               5                   10                  15

Asp Ser Lys Ser Thr Leu Tyr Leu Gln Met Asn Ser Leu Arg Ala Glu
            20                  25                  30

Asp Thr Ala Val Tyr Tyr Cys Val Arg
        35                  40

<210> SEQ ID NO 58
<211> LENGTH: 41
<212> TYPE: PRT
<213> ORGANISM: Artificial Sequence
<220> FEATURE:
<223> OTHER INFORMATION: PR004970|pHBM006115-VH|H-FR3

<400> SEQUENCE: 58

Lys Phe Tyr Val Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Asp Thr Ala Val Tyr Tyr Cys Ala Arg
        35                  40

<210> SEQ ID NO 59
<211> LENGTH: 41
<212> TYPE: PRT
<213> ORGANISM: Artificial Sequence
<220> FEATURE:
<223> OTHER INFORMATION: PR004974|pHBM006117-VH|H-FR3;
      PR005293|pHBM006504-VH|H-FR3

<400> SEQUENCE: 59

Lys Arg Tyr Ser Pro Ser Leu Lys Ser Arg Leu Thr Ile Thr Lys Asp
1               5                   10                  15

Thr Ser Lys Asn Gln Val Val Leu Thr Met Thr Asn Met Asp Pro Val
            20                  25                  30

Asp Thr Ala Thr Tyr Tyr Cys Ala His
        35                  40

<210> SEQ ID NO 60
<211> LENGTH: 41
<212> TYPE: PRT
<213> ORGANISM: Artificial Sequence
<220> FEATURE:
<223> OTHER INFORMATION: PR005124|pHBM006274-VH|H-FR3;
      PR005127|pHBM006280-VH|H-FR3

<400> SEQUENCE: 60

Ile Phe Tyr Ala Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

```
Asp Thr Ala Val Tyr Trp Cys Ala Arg
        35                  40


<210> SEQ ID NO 61
<211> LENGTH: 41
<212> TYPE: PRT
<213> ORGANISM: Artificial Sequence
<220> FEATURE:
<223> OTHER INFORMATION: PR005125|pHBM006276-VH|H-FR3;
      PR005128|pHBM006281-VH|H-FR3

<400> SEQUENCE: 61

Lys Tyr Tyr Ala Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Arg
        35                  40


<210> SEQ ID NO 62
<211> LENGTH: 41
<212> TYPE: PRT
<213> ORGANISM: Artificial Sequence
<220> FEATURE:
<223> OTHER INFORMATION: PR005329|pHBM006537-VH|H-FR3;
      PR005332|pHBM006540-VH|H-FR3

<400> SEQUENCE: 62

Thr Tyr Tyr Ala Asp Ser Val Lys Asp Arg Phe Thr Ile Ser Arg Asp
1               5                   10                  15

Asp Ser His Ser Met Leu Tyr Leu Gln Met Asn Asn Leu Lys Thr Glu
            20                  25                  30

Asp Thr Ala Met Tyr Tyr Cys Val Arg
        35                  40


<210> SEQ ID NO 63
<211> LENGTH: 41
<212> TYPE: PRT
<213> ORGANISM: Artificial Sequence
<220> FEATURE:
<223> OTHER INFORMATION: PR005331|pHBM006539-VH|H-FR3;
      PR005336|pHBM006544-VH|H-FR3

<400> SEQUENCE: 63

Lys Tyr Tyr Val Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Asp Thr Ala Val Tyr Tyr Cys Val Arg
        35                  40


<210> SEQ ID NO 64
<211> LENGTH: 41
<212> TYPE: PRT
<213> ORGANISM: Artificial Sequence
<220> FEATURE:
<223> OTHER INFORMATION: PR005335|pHBM006543-VH|H-FR3

<400> SEQUENCE: 64

Thr Tyr Tyr Val Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30
```

Asp Thr Ala Val Tyr Tyr Cys Ala Arg
        35                  40

<210> SEQ ID NO 65
<211> LENGTH: 12
<212> TYPE: PRT
<213> ORGANISM: Artificial Sequence
<220> FEATURE:
<223> OTHER INFORMATION: HCDR3

<400> SEQUENCE: 65

Gly Lys Glu Asn Gly Asn Tyr Tyr Ala Met Asp Phe
1               5                   10

<210> SEQ ID NO 66
<211> LENGTH: 12
<212> TYPE: PRT
<213> ORGANISM: Artificial Sequence
<220> FEATURE:
<223> OTHER INFORMATION: PR004124|pHBM005091-VH|HCDR3;
      PR005330|pHBM006538-VH|HCDR3; PR005333|pHBM006541-VH|HCDR3

<400> SEQUENCE: 66

Gly Lys Asp Tyr Gly Asn Tyr Tyr Ala Met Asp Phe
1               5                   10

<210> SEQ ID NO 67
<211> LENGTH: 12
<212> TYPE: PRT
<213> ORGANISM: Artificial Sequence
<220> FEATURE:
<223> OTHER INFORMATION: PR004129|pHBM005095-VH|HCDR3

<400> SEQUENCE: 67

Gly Lys Asp Tyr Gly Asn Tyr Tyr Ala Met Asp Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: HCDR3

<400> SEQUENCE: 68

Gly Lys Glu Asn Gly Asn Tyr Tyr Ala Met Asp Tyr
1               5                   10

<210> SEQ ID NO 69
<211> LENGTH: 5
<212> TYPE: PRT
<213> ORGANISM: Artificial Sequence
<220> FEATURE:
<223> OTHER INFORMATION: PR004264|pHBM005401-VH|HCDR3

<400> SEQUENCE: 69

Gln Gly Phe Asp Tyr
1               5

<210> SEQ ID NO 70
<211> LENGTH: 11
<212> TYPE: PRT
<213> ORGANISM: Artificial Sequence
<220> FEATURE:
<223> OTHER INFORMATION: PR004265|pHBM005403-VH|HCDR3

<400> SEQUENCE: 70

Gly Gly Leu Arg Pro Tyr Trp Tyr Phe Asp Val
1 5 10

<210> SEQ ID NO 71
<211> LENGTH: 10
<212> TYPE: PRT
<213> ORGANISM: Artificial Sequence
<220> FEATURE:
<223> OTHER INFORMATION: PR004275|pHBM005295-VH|HCDR3

<400> SEQUENCE: 71

Arg Trp Gly Lys Gly Gly Leu Phe Asp Tyr
1 5 10

<210> SEQ ID NO 72
<211> LENGTH: 12
<212> TYPE: PRT
<213> ORGANISM: Artificial Sequence
<220> FEATURE:
<223> OTHER INFORMATION: HCDR3

<400> SEQUENCE: 72

Gly Lys Glu Asn Ala Asn Tyr Tyr Ala Met Asp Phe
1 5 10

<210> SEQ ID NO 73
<211> LENGTH: 12
<212> TYPE: PRT
<213> ORGANISM: Artificial Sequence
<220> FEATURE:
<223> OTHER INFORMATION: HCDR3

<400> SEQUENCE: 73

Gly Lys Glu Gln Gly Asn Tyr Tyr Ala Met Asp Phe
1 5 10

<210> SEQ ID NO 74
<211> LENGTH: 6
<212> TYPE: PRT
<213> ORGANISM: Artificial Sequence
<220> FEATURE:
<223> OTHER INFORMATION: PR004970|pHBM006115-VH|HCDR3

<400> SEQUENCE: 74

Ser Trp Gly Phe Ala Tyr
1 5

<210> SEQ ID NO 75
<211> LENGTH: 17
<212> TYPE: PRT
<213> ORGANISM: Artificial Sequence
<220> FEATURE:
<223> OTHER INFORMATION: PR004974|pHBM006117-VH|HCDR3;
PR005293|pHBM006504-VH|HCDR3

<400> SEQUENCE: 75

Arg Arg Leu Arg Tyr Ser Gly Arg Tyr Tyr Tyr Tyr Tyr Gly Thr Asp
1 5 10 15

Val

<210> SEQ ID NO 76
<211> LENGTH: 13
<212> TYPE: PRT
<213> ORGANISM: Artificial Sequence
<220> FEATURE:
<223> OTHER INFORMATION: PR005124|pHBM006274-VH|HCDR3;
PR005127|pHBM006280-VH|HCDR3

<400> SEQUENCE: 76

His Arg Arg Ser Asp Tyr Trp Tyr Tyr Gly Met Asp Val
1 5 10

<210> SEQ ID NO 77
<211> LENGTH: 15
<212> TYPE: PRT
<213> ORGANISM: Artificial Sequence
<220> FEATURE:
<223> OTHER INFORMATION: PR005125|pHBM006276-VH|HCDR3;
PR005128|pHBM006281-VH|HCDR3

<400> SEQUENCE: 77

Gly Gly Phe Tyr Tyr Gly Ser Gly Asn Tyr Ser Leu Phe Asp Tyr
1 5 10 15

<210> SEQ ID NO 78
<211> LENGTH: 12
<212> TYPE: PRT
<213> ORGANISM: Artificial Sequence
<220> FEATURE:
<223> OTHER INFORMATION: PR005329|pHBM006537-VH|HCDR3;
PR005332|pHBM006540-VH|HCDR3

<400> SEQUENCE: 78

Gly Lys Asp Asn Gly Asn Tyr Tyr Ala Met Asp Phe
1 5 10

<210> SEQ ID NO 79
<211> LENGTH: 6
<212> TYPE: PRT
<213> ORGANISM: Artificial Sequence
<220> FEATURE:
<223> OTHER INFORMATION: PR005331|pHBM006539-VH|HCDR3;
PR005335|pHBM006543-VH|HCDR3; PR005336|pHBM006544-VH|HCDR3

<400> SEQUENCE: 79

Asn Trp Gly Phe Asp Tyr
1 5

<210> SEQ ID NO 80
<211> LENGTH: 12
<212> TYPE: PRT
<213> ORGANISM: Artificial Sequence
<220> FEATURE:
<223> OTHER INFORMATION: HCDR3

<400> SEQUENCE: 80

Gly Lys Glu His Gly Asn Tyr Tyr Ala Met Asp Phe
1 5 10

<210> SEQ ID NO 81
<211> LENGTH: 12
<212> TYPE: PRT
<213> ORGANISM: Artificial Sequence
<220> FEATURE:
<223> OTHER INFORMATION: HCDR3

<400> SEQUENCE: 81

Gly Lys Glu Ile Gly Asn Tyr Tyr Ala Met Asp Phe
1 5 10

<210> SEQ ID NO 82
<211> LENGTH: 12
<212> TYPE: PRT
<213> ORGANISM: Artificial Sequence
<220> FEATURE:
<223> OTHER INFORMATION: PR005763|pHBM007005-VH|HCDR3;
PR006161|pHBM006987-VH|HCDR3; PR006274|pHBM007523-VH|HCDR3

<400> SEQUENCE: 82

Gly Lys Glu His Gly Lys Tyr Tyr Ala Met Asp Phe
1 5 10

<210> SEQ ID NO 83
<211> LENGTH: 12
<212> TYPE: PRT
<213> ORGANISM: Artificial Sequence
<220> FEATURE:
<223> OTHER INFORMATION: PR005787|pHBM007006-VH|HCDR3;
PR006166|pHBM006988-VH|HCDR3; PR006275|pHBM007524-VH|HCDR3

<400> SEQUENCE: 83

Gly Lys Glu Ile Gly Lys Tyr Tyr Ala Met Asp Phe
1 5 10

<210> SEQ ID NO 84
<211> LENGTH: 11
<212> TYPE: PRT
<213> ORGANISM: Artificial Sequence
<220> FEATURE:
<223> OTHER INFORMATION: PR004120|pHBM005087-VH|H-FR4;
PR004123|pHBM005090-VH|H-FR4; PR004125|pHBM005092-VH|H-FR4;
PR004126|pHBM005093-VH|H-FR4; PR004128|pHBM005092-VH|H-FR4;
PR004250|pHBM005374-VH|H-FR4; PR004251|pHBM005374-VH|H-FR4;
PR004324|pHBM005374-VH|H-FR4; PR004325|pHBM005374-VH|H-FR4;
PR004326|pHBM005430-VH|H-FR4; PR004327|pHBM005431-VH|H-FR4;
PR004328|pHBM005432-VH|H-FR4; PR004329|pHBM005433-VH|H-FR4;
PR004339|pHBM005374-VH|H-FR4; PR004340|pHBM005374-VH|H-FR4;
PR004342|pHBM005374-VH|H-FR4; PR004343|pHBM005374-VH|H-FR4;
PR004344|pHBM005374-VH|H-FR4; PR004345|pHBM005374-VH|H-FR4;
PR004346|pHBM005374-VH|H-FR4; PR005170|pHBM005092-VH|H-FR4;
PR005171|pHBM005092-VH|H-FR4; PR005172|pHBM005092-VH|H-FR4;
PR005329|pHBM006537-VH|H-FR4; PR005332|pHBM006540-VH|H-FR4

<400> SEQUENCE: 84

Trp Gly Gln Gly Thr Ser Val Thr Val Ser Ala
1 5 10

<210> SEQ ID NO 85
<211> LENGTH: 11
<212> TYPE: PRT
<213> ORGANISM: Artificial Sequence
<220> FEATURE:
<223> OTHER INFORMATION: |H-FR4

<400> SEQUENCE: 85

Trp Gly Gln Gly Thr Ser Val Thr Val Ser Ser
1 5 10

<210> SEQ ID NO 86
<211> LENGTH: 11
<212> TYPE: PRT
<213> ORGANISM: Artificial Sequence
<220> FEATURE:
<223> OTHER INFORMATION: PR004124|pHBM005091-VH|H-FR4

<400> SEQUENCE: 86

Trp Gly Gln Gly Thr Ser Leu Thr Val Ser Ser
1 5 10

<210> SEQ ID NO 87
<211> LENGTH: 11
<212> TYPE: PRT
<213> ORGANISM: Artificial Sequence

<220> FEATURE:
<223> OTHER INFORMATION: H-FR4

<400> SEQUENCE: 87

Trp Gly Gln Gly Thr Leu Val Thr Val Ser Ser
1 5 10

<210> SEQ ID NO 88
<211> LENGTH: 11
<212> TYPE: PRT
<213> ORGANISM: Artificial Sequence
<220> FEATURE:
<223> OTHER INFORMATION: PR004265|pHBM005403-VH|H-FR4

<400> SEQUENCE: 88

Trp Gly Ala Gly Thr Thr Val Thr Val Ser Ala
1 5 10

<210> SEQ ID NO 89
<211> LENGTH: 11
<212> TYPE: PRT
<213> ORGANISM: Artificial Sequence
<220> FEATURE:
<223> OTHER INFORMATION: H-FR4

<400> SEQUENCE: 89

Trp Gly Gln Gly Thr Thr Val Thr Val Ser Ser
1 5 10

<210> SEQ ID NO 90
<211> LENGTH: 23
<212> TYPE: PRT
<213> ORGANISM: Artificial Sequence
<220> FEATURE:
<223> OTHER INFORMATION: L-FR1

<400> SEQUENCE: 90

Asp Ile Val Met Thr Gln Ala Ala Thr Ser Val Leu Val Thr Pro Gly
1 5 10 15

Glu Ser Val Ser Ile Ser Cys
20

<210> SEQ ID NO 91
<211> LENGTH: 23
<212> TYPE: PRT
<213> ORGANISM: Artificial Sequence
<220> FEATURE:
<223> OTHER INFORMATION: PR004121|pHBM005099-VL|L-FR1;
PR004126|pHBM005104-VL|L-FR1

<400> SEQUENCE: 91

Asp Ile Val Ile Thr Gln Ala Ala Pro Ser Val Pro Val Thr Pro Gly
1 5 10 15

Glu Ser Val Ser Ile Ser Cys
20

<210> SEQ ID NO 92
<211> LENGTH: 23
<212> TYPE: PRT
<213> ORGANISM: Artificial Sequence
<220> FEATURE:
<223> OTHER INFORMATION: |L-FR1

<400> SEQUENCE: 92

Asp Ile Val Met Thr Gln Ala Ala Pro Ser Val Pro Val Thr Pro Gly
1 5 10 15

Glu Ser Val Ser Ile Ser Cys
20

<210> SEQ ID NO 93
<211> LENGTH: 23
<212> TYPE: PRT
<213> ORGANISM: Artificial Sequence
<220> FEATURE:
<223> OTHER INFORMATION: PR004124|pHBM005102-VL|L-FR1

<400> SEQUENCE: 93

Asp Ile Val Met Thr Gln Asp Glu Leu Ser Asn Pro Val Thr Ser Gly
1 5 10 15

Glu Ser Val Ser Ile Ser Cys
20

<210> SEQ ID NO 94
<211> LENGTH: 23
<212> TYPE: PRT
<213> ORGANISM: Artificial Sequence
<220> FEATURE:
<223> OTHER INFORMATION: PR004129|pHBM005107-VL|L-FR1

<400> SEQUENCE: 94

Asp Ile Leu Leu Thr Gln Ser Pro Ala Ile Leu Ser Val Ser Pro Gly
1 5 10 15

Glu Arg Val Ser Phe Ser Cys
20

<210> SEQ ID NO 95
<211> LENGTH: 23
<212> TYPE: PRT
<213> ORGANISM: Artificial Sequence
<220> FEATURE:
<223> OTHER INFORMATION: PR004264|pHBM005402-VL|L-FR1;
PR005335|pHBM006548-VL|L-FR1

<400> SEQUENCE: 95

Asp Val Val Met Thr Gln Ser Pro Leu Ser Leu Pro Val Thr Leu Gly
1 5 10 15

Gln Pro Ala Ser Ile Ser Cys
20

<210> SEQ ID NO 96
<211> LENGTH: 23
<212> TYPE: PRT
<213> ORGANISM: Artificial Sequence
<220> FEATURE:
<223> OTHER INFORMATION: PR004265|pHBM005404-VL|L-FR1

<400> SEQUENCE: 96

Asp Ile Val Leu Ile Gln Ser Pro Ala Ile Met Ser Ala Ser Pro Gly
1 5 10 15

Glu Lys Val Thr Ile Ser Cys
20

<210> SEQ ID NO 97
<211> LENGTH: 23
<212> TYPE: PRT
<213> ORGANISM: Artificial Sequence
<220> FEATURE:
<223> OTHER INFORMATION: PR004275|pHBM005296-VL|L-FR1

<400> SEQUENCE: 97

Asp Ile Gln Leu Thr Gln Ser Pro Ser Thr Leu Ser Ala Ser Val Gly
1 5 10 15

Asp Arg Val Thr Ile Thr Cys
20

<210> SEQ ID NO 98
<211> LENGTH: 23
<212> TYPE: PRT
<213> ORGANISM: Artificial Sequence
<220> FEATURE:
<223> OTHER INFORMATION: L-FR1

<400> SEQUENCE: 98

Asp Ile Val Met Thr Gln Ser Pro Leu Ser Leu Pro Val Thr Pro Gly
1 5 10 15

Glu Pro Ala Ser Ile Ser Cys
20

<210> SEQ ID NO 99
<211> LENGTH: 23
<212> TYPE: PRT
<213> ORGANISM: Artificial Sequence
<220> FEATURE:
<223> OTHER INFORMATION: L-FR1

<400> SEQUENCE: 99

Asp Ile Val Met Thr Gln Ser Pro Leu Ser Leu Pro Val Thr Leu Gly
1 5 10 15

Gln Pro Ala Ser Ile Ser Cys
20

<210> SEQ ID NO 100
<211> LENGTH: 23
<212> TYPE: PRT
<213> ORGANISM: Artificial Sequence
<220> FEATURE:
<223> OTHER INFORMATION: PR004970|pHBM006122-VL|L-FR1

<400> SEQUENCE: 100

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 101
<211> LENGTH: 23
<212> TYPE: PRT
<213> ORGANISM: Artificial Sequence
<220> FEATURE:
<223> OTHER INFORMATION: PR004974|pHBM006126-VL|L-FR1;
PR005293|pHBM006126-VL|L-FR1

<400> SEQUENCE: 101

Glu Ile Val Met Thr Gln Ser Pro Ala Thr Leu Ser Val Ser Pro Gly
1 5 10 15

Glu Arg Ala Thr Leu Ser Cys
20

<210> SEQ ID NO 102
<211> LENGTH: 23
<212> TYPE: PRT
<213> ORGANISM: Artificial Sequence
<220> FEATURE:
<223> OTHER INFORMATION: PR005124|pHBM006275-VL|L-FR1;
PR005127|pHBM006275-VL|L-FR1

<400> SEQUENCE: 102

Asp Val Val Met Thr Gln Ser Pro Leu Ser Leu Pro Val Thr Pro Gly
1 5 10 15

Glu Pro Ala Ser Ile Ser Cys
20

<210> SEQ ID NO 103
<211> LENGTH: 23
<212> TYPE: PRT
<213> ORGANISM: Artificial Sequence
<220> FEATURE:
<223> OTHER INFORMATION: PR005125|pHBM006277-VL|L-FR1;
PR005128|pHBM006277-VL|L-FR1

<400> SEQUENCE: 103

Asp Ile Val Met Thr Gln Ser Pro Leu Ser Leu Ser Val Thr Leu Gly
1 5 10 15

Gln Pro Ala Ser Ile Ser Cys
20

<210> SEQ ID NO 104
<211> LENGTH: 16
<212> TYPE: PRT
<213> ORGANISM: Artificial Sequence
<220> FEATURE:
<223> OTHER INFORMATION: PR004120|pHBM005098-VL|LCDR1;
PR004127|pHBM005105-VL|LCDR1; PR005330|pHBM006546-VL|LCDR1;
PR005333|pHBM006546-VL|LCDR1

<400> SEQUENCE: 104

Arg Ser Ser Lys Ser Leu Leu Tyr Ser Asn Gly Asn Thr Tyr Leu Tyr
1 5 10 15

<210> SEQ ID NO 105
<211> LENGTH: 16
<212> TYPE: PRT
<213> ORGANISM: Artificial Sequence
<220> FEATURE:
<223> OTHER INFORMATION: PR004121|pHBM005099-VL|LCDR1;
PR004122|pHBM005100-VL|LCDR1; PR004123|pHBM005101-VL|LCDR1;
PR004124|pHBM005102-VL|LCDR1

<400> SEQUENCE: 105

Arg Ser Ser Lys Ser Leu Leu His Ser Asn Gly Asn Thr Tyr Leu Tyr
1 5 10 15

<210> SEQ ID NO 106
<211> LENGTH: 16
<212> TYPE: PRT
<213> ORGANISM: Artificial Sequence
<220> FEATURE:
<223> OTHER INFORMATION: LCDR1

<400> SEQUENCE: 106

Arg Ser Ser Lys Ser Leu Leu His Ser Asn Gly Lys Ile Tyr Leu Tyr
1 5 10 15

<210> SEQ ID NO 107
<211> LENGTH: 16
<212> TYPE: PRT
<213> ORGANISM: Artificial Sequence
<220> FEATURE:
<223> OTHER INFORMATION: PR004131|pHBM005109-VL|LCDR1;
PR004252|pHBM005109-VL|LCDR1; PR004345|pHBM005454-VL|LCDR1

<400> SEQUENCE: 107

Arg Ser Asn Lys Ser Leu Leu His Ser Asn Gly Asn Thr Tyr Leu Tyr
1 5 10 15

<210> SEQ ID NO 108
<211> LENGTH: 16
<212> TYPE: PRT
<213> ORGANISM: Artificial Sequence
<220> FEATURE:
<223> OTHER INFORMATION: PR004264|pHBM005402-VL|LCDR1

<400> SEQUENCE: 108

Arg Ser Ser Gln Ser Leu Val Tyr Ser Asp Gly Asn Thr Tyr Leu Asn
1 5 10 15

<210> SEQ ID NO 109
<211> LENGTH: 10
<212> TYPE: PRT
<213> ORGANISM: Artificial Sequence
<220> FEATURE:
<223> OTHER INFORMATION: PR004265|pHBM005404-VL|LCDR1

<400> SEQUENCE: 109

Ser Ala Ser Ser Ser Val Ser Tyr Met Tyr
1 5 10

<210> SEQ ID NO 110
<211> LENGTH: 11
<212> TYPE: PRT
<213> ORGANISM: Artificial Sequence
<220> FEATURE:
<223> OTHER INFORMATION: PR004275|pHBM005296-VL|LCDR1

<400> SEQUENCE: 110

Arg Ala Ser Gln Ser Ile Ser Ser Trp Leu Ala
1 5 10

<210> SEQ ID NO 111
<211> LENGTH: 16
<212> TYPE: PRT
<213> ORGANISM: Artificial Sequence
<220> FEATURE:
<223> OTHER INFORMATION: PR004324|pHBM005456-VL|LCDR1;
PR004662|pHBM005790-VL|LCDR1

<400> SEQUENCE: 111

Arg Ser Ser Lys Ser Leu Leu His Ser Asn Ala Lys Ile Tyr Leu Tyr
1 5 10 15

<210> SEQ ID NO 112
<211> LENGTH: 16
<212> TYPE: PRT
<213> ORGANISM: Artificial Sequence
<220> FEATURE:
<223> OTHER INFORMATION: PR004325|pHBM005457-VL|LCDR1

<400> SEQUENCE: 112

Arg Ser Ser Lys Ser Leu Leu His Ser Gln Gly Lys Ile Tyr Leu Tyr
1 5 10 15

<210> SEQ ID NO 113
<211> LENGTH: 11
<212> TYPE: PRT
<213> ORGANISM: Artificial Sequence
<220> FEATURE:
<223> OTHER INFORMATION: PR004970|pHBM006122-VL|LCDR1

<400> SEQUENCE: 113

Arg Ala Ser Gln Gly Ile Ser Asn Tyr Leu Ala
1 5 10

<210> SEQ ID NO 114
<211> LENGTH: 11
<212> TYPE: PRT
<213> ORGANISM: Artificial Sequence
<220> FEATURE:
<223> OTHER INFORMATION: PR004974|pHBM006126-VL|LCDR1; PR005293|pHBM006126-VL|LCDR1

<400> SEQUENCE: 114

Arg Ala Ser Gln Ser Val Ser Ser Asn Leu Val
1 5 10

<210> SEQ ID NO 115
<211> LENGTH: 16
<212> TYPE: PRT
<213> ORGANISM: Artificial Sequence
<220> FEATURE:
<223> OTHER INFORMATION: PR005124|pHBM006275-VL|LCDR1; PR005127|pHBM006275-VL|LCDR1

<400> SEQUENCE: 115

Arg Ser Ser Gln Ser Leu Leu His Ser Asn Gly Tyr Asn Tyr Leu Asp
1 5 10 15

<210> SEQ ID NO 116
<211> LENGTH: 16
<212> TYPE: PRT
<213> ORGANISM: Artificial Sequence
<220> FEATURE:
<223> OTHER INFORMATION: PR005125|pHBM006277-VL|LCDR1; PR005128|pHBM006277-VL|LCDR1

<400> SEQUENCE: 116

Arg Ser Ser Gln Ser Leu Val Phe Ser Asn Gly Asn Thr Tyr Leu Asn
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: PR005331|pHBM006549-VL|LCDR1; PR005335|pHBM006548-VL|LCDR1; PR005336|pHBM006549-VL|LCDR1

<400> SEQUENCE: 117

Arg Ser Ser Gln Ser Leu Val Tyr Ser Asn Gly Asn Thr Tyr Leu Asn
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: L-FR2

<400> SEQUENCE: 118

Trp Phe Leu Gln Arg Pro Gly Gln Ser Pro Gln Leu Leu Ile Tyr
1 5 10 15

<210> SEQ ID NO 119
<211> LENGTH: 15
<212> TYPE: PRT
<213> ORGANISM: Artificial Sequence
<220> FEATURE:

<223> OTHER INFORMATION: PR004264|pHBM005402-VL|L-FR2;
PR005125|pHBM006277-VL|L-FR2; PR005128|pHBM006277-VL|L-FR2;
PR005331|pHBM006549-VL|L-FR2; PR005335|pHBM006548-VL|L-FR2;
PR005336|pHBM006549-VL|L-FR2

<400> SEQUENCE: 119

Trp Phe Gln Gln Arg Pro Gly Gln Ser Pro Arg Arg Leu Ile Tyr
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: PR004265|pHBM005404-VL|L-FR2

<400> SEQUENCE: 120

Trp Tyr Gln Gln Lys Pro Gly Ser Ser Pro Lys Pro Trp Ile Tyr
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: PR004275|pHBM005296-VL|L-FR2

<400> SEQUENCE: 121

Trp Tyr Gln Gln Lys Pro Gly Lys Ala Pro Lys Leu Leu Ile Tyr
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: PR004339|pHBM005447-VL|L-FR2;
PR004340|pHBM005448-VL|L-FR2; PR004342|pHBM005450-VL|L-FR2;
PR004519|pHBM005447-VL|L-FR2

<400> SEQUENCE: 122

Trp Phe Leu Gln Lys Pro Gly Gln Ser Pro Gln Leu Leu Ile Tyr
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: PR004343|pHBM005452-VL|L-FR2;
PR004344|pHBM005453-VL|L-FR2; PR004345|pHBM005454-VL|L-FR2

<400> SEQUENCE: 123

Trp Phe Gln Gln Arg Pro Gly Gln Ser Pro Arg Leu Leu Ile Tyr
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: PR004970|pHBM006122-VL|L-FR2

<400> SEQUENCE: 124

Trp Tyr Gln Gln Lys Pro Gly Lys Val Pro Lys Leu Leu Ile Tyr
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: PR004974|pHBM006126-VL|L-FR2;
PR005293|pHBM006126-VL|L-FR2

<400> SEQUENCE: 125

Trp Tyr Gln Gln Lys Pro Gly Gln Ala Pro Arg Leu Leu Ile Tyr
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: PR005124|pHBM006275-VL|L-FR2;
PR005127|pHBM006275-VL|L-FR2

<400> SEQUENCE: 126

Trp Tyr Leu Gln Lys Pro Gly Gln Ser Pro Gln Leu Leu Ile Tyr
1 5 10 15

<210> SEQ ID NO 127
<211> LENGTH: 7
<212> TYPE: PRT
<213> ORGANISM: Artificial Sequence
<220> FEATURE:
<223> OTHER INFORMATION: LCDR2

<400> SEQUENCE: 127

Arg Met Ser Asn Leu Ala Ser
1 5

<210> SEQ ID NO 128
<211> LENGTH: 7
<212> TYPE: PRT
<213> ORGANISM: Artificial Sequence
<220> FEATURE:
<223> OTHER INFORMATION: PR004264|pHBM005402-VL|LCDR2;
PR005331|pHBM006549-VL|LCDR2; PR005335|pHBM006548-VL|LCDR2;
PR005336|pHBM006549-VL|LCDR2

<400> SEQUENCE: 128

Lys Val Ser Asn Arg Asp Ser
1 5

<210> SEQ ID NO 129
<211> LENGTH: 7
<212> TYPE: PRT
<213> ORGANISM: Artificial Sequence
<220> FEATURE:
<223> OTHER INFORMATION: PR004265|pHBM005404-VL|LCDR2

<400> SEQUENCE: 129

Arg Thr Ser Asn Leu Ala Ser
1 5

<210> SEQ ID NO 130
<211> LENGTH: 7
<212> TYPE: PRT
<213> ORGANISM: Artificial Sequence
<220> FEATURE:
<223> OTHER INFORMATION: PR004275|pHBM005296-VL|LCDR2

<400> SEQUENCE: 130

Lys Ala Ser Ser Leu Glu Ser 1 5

<210> SEQ ID NO 131
<211> LENGTH: 7
<212> TYPE: PRT
<213> ORGANISM: Artificial Sequence
<220> FEATURE:
<223> OTHER INFORMATION: PR004970|pHBM006122-VL|LCDR2

<400> SEQUENCE: 131

Ala Ala Ser Thr Leu Gln Ser
1 5

<210> SEQ ID NO 132
<211> LENGTH: 7
<212> TYPE: PRT
<213> ORGANISM: Artificial Sequence
<220> FEATURE:
<223> OTHER INFORMATION: PR004974|pHBM006126-VL|LCDR2; PR005293|pHBM006126-VL|LCDR2

<400> SEQUENCE: 132

Gly Ala Ser Ile Arg Ala Thr
1 5

<210> SEQ ID NO 133
<211> LENGTH: 7
<212> TYPE: PRT
<213> ORGANISM: Artificial Sequence
<220> FEATURE:
<223> OTHER INFORMATION: PR005124|pHBM006275-VL|LCDR2; PR005127|pHBM006275-VL|LCDR2

<400> SEQUENCE: 133

Leu Gly Ser Asn Arg Ala Ser
1 5

<210> SEQ ID NO 134
<211> LENGTH: 7
<212> TYPE: PRT
<213> ORGANISM: Artificial Sequence
<220> FEATURE:
<223> OTHER INFORMATION: PR005125|pHBM006277-VL|LCDR2; PR005128|pHBM006277-VL|LCDR2

<400> SEQUENCE: 134

Lys Val Ser Lys Arg Asp Ser
1 5

<210> SEQ ID NO 135
<211> LENGTH: 32
<212> TYPE: PRT
<213> ORGANISM: Artificial Sequence
<220> FEATURE:
<223> OTHER INFORMATION: L-FR3

<400> SEQUENCE: 135

Gly Val Pro Asp Arg Phe Ser Gly Ser Gly Ser Gly Thr Ala Phe Thr
1 5 10 15

Leu Arg Ile Ser Arg Val Glu Ala Glu Asp Val Gly Val Tyr Tyr Cys
20 25 30

<210> SEQ ID NO 136
<211> LENGTH: 32
<212> TYPE: PRT
<213> ORGANISM: Artificial Sequence
<220> FEATURE:

<223> OTHER INFORMATION: L-FR3

<400> SEQUENCE: 136

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: PR004265|pHBM005404-VL|L-FR3

<400> SEQUENCE: 137

Gly Val Pro Ala Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: PR004275|pHBM005296-VL|L-FR3;
      PR004970|pHBM006122-VL|L-FR3

<400> SEQUENCE: 138

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: PR004974|pHBM006126-VL|L-FR3;
      PR005293|pHBM006126-VL|L-FR3

<400> SEQUENCE: 139

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: PR005329|pHBM006545-VL|L-FR3;
      PR005332|pHBM006545-VL|L-FR3

<400> SEQUENCE: 140

Gly Val Pro Asp Arg Phe Ser Ser Ser Gly Ser Gly Thr Asp Phe Thr
1               5                   10                  15

Leu Arg Ile Ser Arg Val Glu Ala Glu Asp Val Gly Val Tyr Tyr Cys
            20                  25                  30

<210> SEQ ID NO 141

<211> LENGTH: 9
<212> TYPE: PRT
<213> ORGANISM: Artificial Sequence
<220> FEATURE:
<223> OTHER INFORMATION: PR004120|pHBM005098-VL|LCDR3;
PR004121|pHBM005099-VL|LCDR3; PR004123|pHBM005101-VL|LCDR3;
PR004124|pHBM005102-VL|LCDR3; PR004126|pHBM005104-VL|LCDR3;
PR004127|pHBM005105-VL|LCDR3; PR004129|pHBM005107-VL|LCDR3;
PR004130|pHBM005108-VL|LCDR3; PR004342|pHBM005450-VL|LCDR3;
PR004346|pHBM005455-VL|LCDR3; PR005329|pHBM006545-VL|LCDR3;
PR005330|pHBM006546-VL|LCDR3; PR005332|pHBM006545-VL|LCDR3;
PR005333|pHBM006546-VL|LCDR3

<400> SEQUENCE: 141

Met Gln His Leu Glu Tyr Pro Phe Thr
1               5

<210> SEQ ID NO 142
<211> LENGTH: 9
<212> TYPE: PRT
<213> ORGANISM: Artificial Sequence
<220> FEATURE:
<223> OTHER INFORMATION: LCDR3

<400> SEQUENCE: 142

Met Gln His Leu Glu Tyr Pro Leu Thr
1               5

<210> SEQ ID NO 143
<211> LENGTH: 10
<212> TYPE: PRT
<213> ORGANISM: Artificial Sequence
<220> FEATURE:
<223> OTHER INFORMATION: PR004264|pHBM005402-VL|LCDR3

<400> SEQUENCE: 143

Met Gln Gly Thr His Trp Pro Pro Ile Thr
1               5                   10

<210> SEQ ID NO 144
<211> LENGTH: 9
<212> TYPE: PRT
<213> ORGANISM: Artificial Sequence
<220> FEATURE:
<223> OTHER INFORMATION: PR004265|pHBM005404-VL|LCDR3

<400> SEQUENCE: 144

Gln Gln Arg Ser Ser Tyr Pro Pro Thr
1               5

<210> SEQ ID NO 145
<211> LENGTH: 9
<212> TYPE: PRT
<213> ORGANISM: Artificial Sequence
<220> FEATURE:
<223> OTHER INFORMATION: PR004275|pHBM005296-VL|LCDR3

<400> SEQUENCE: 145

Gln Lys Tyr Asn Ser Ala Pro Pro Thr
1               5

<210> SEQ ID NO 146
<211> LENGTH: 9
<212> TYPE: PRT
<213> ORGANISM: Artificial Sequence
<220> FEATURE:
<223> OTHER INFORMATION: PR004970|pHBM006122-VL|LCDR3

<400> SEQUENCE: 146

Gln Lys Tyr Asn Ser Ala Pro Trp Thr
1               5

<210> SEQ ID NO 147
<211> LENGTH: 9
<212> TYPE: PRT
<213> ORGANISM: Artificial Sequence
<220> FEATURE:
<223> OTHER INFORMATION: PR004974|pHBM006126-VL|LCDR3;
PR005293|pHBM006126-VL|LCDR3

<400> SEQUENCE: 147

Gln Gln Tyr Asn Asn Trp Pro Tyr Thr
1               5

<210> SEQ ID NO 148
<211> LENGTH: 9
<212> TYPE: PRT
<213> ORGANISM: Artificial Sequence
<220> FEATURE:
<223> OTHER INFORMATION: PR005124|pHBM006275-VL|LCDR3;
PR005127|pHBM006275-VL|LCDR3

<400> SEQUENCE: 148

Met Gln Ala Leu Gln Thr Pro Tyr Thr
1               5

<210> SEQ ID NO 149
<211> LENGTH: 8
<212> TYPE: PRT
<213> ORGANISM: Artificial Sequence
<220> FEATURE:
<223> OTHER INFORMATION: PR005125|pHBM006277-VL|LCDR3;
PR005128|pHBM006277-VL|LCDR3

<400> SEQUENCE: 149

Met Gln Gly Thr His Trp Ile Thr
1               5

<210> SEQ ID NO 150
<211> LENGTH: 9
<212> TYPE: PRT
<213> ORGANISM: Artificial Sequence
<220> FEATURE:
<223> OTHER INFORMATION: PR005170|pHBM006323-VL|LCDR3

<400> SEQUENCE: 150

Met Gln His Leu Glu Tyr Pro Ile Thr
1               5

<210> SEQ ID NO 151
<211> LENGTH: 9
<212> TYPE: PRT
<213> ORGANISM: Artificial Sequence
<220> FEATURE:
<223> OTHER INFORMATION: PR005171|pHBM006324-VL|LCDR3

<400> SEQUENCE: 151

Met Gln His Leu Glu Tyr Pro Met Thr
1               5

<210> SEQ ID NO 152
<211> LENGTH: 9
<212> TYPE: PRT
<213> ORGANISM: Artificial Sequence
<220> FEATURE:
<223> OTHER INFORMATION: PR005172|pHBM006325-VL|LCDR3

<400> SEQUENCE: 152

Met Gln His Leu Glu Tyr Pro Val Thr
1               5

<210> SEQ ID NO 153
<211> LENGTH: 9
<212> TYPE: PRT
<213> ORGANISM: Artificial Sequence
<220> FEATURE:
<223> OTHER INFORMATION: PR005331|pHBM006549-VL|LCDR3;
      PR005335|pHBM006548-VL|LCDR3; PR005336|pHBM006549-VL|LCDR3

<400> SEQUENCE: 153

Met Gln Gly Thr His Trp Pro Ile Thr
1               5

<210> SEQ ID NO 154
<211> LENGTH: 10
<212> TYPE: PRT
<213> ORGANISM: Artificial Sequence
<220> FEATURE:
<223> OTHER INFORMATION: PR004120|pHBM005098-VL|L-FR4

<400> SEQUENCE: 154

Phe Gly Gly Gly Thr Lys Leu Glu Ile Lys
1               5                   10

<210> SEQ ID NO 155
<211> LENGTH: 10
<212> TYPE: PRT
<213> ORGANISM: Artificial Sequence
<220> FEATURE:
<223> OTHER INFORMATION: PR004121|pHBM005099-VL|L-FR4;
      PR004127|pHBM005105-VL|L-FR4

<400> SEQUENCE: 155

Phe Gly Gly Gly Thr Lys Leu Glu Met Lys
1               5                   10

<210> SEQ ID NO 156
<211> LENGTH: 10
<212> TYPE: PRT
<213> ORGANISM: Artificial Sequence
<220> FEATURE:
<223> OTHER INFORMATION: PR004122|pHBM005100-VL|L-FR4;
      PR004126|pHBM005104-VL|L-FR4; PR004249|pHBM005100-VL|L-FR4;
      PR004265|pHBM005404-VL|L-FR4

<400> SEQUENCE: 156

Phe Gly Ala Gly Thr Lys Leu Glu Leu Lys
1               5                   10

<210> SEQ ID NO 157
<211> LENGTH: 10
<212> TYPE: PRT
<213> ORGANISM: Artificial Sequence
<220> FEATURE:
<223> OTHER INFORMATION: PR004123|pHBM005101-VL|L-FR4;
      PR004124|pHBM005102-VL|L-FR4; PR005330|pHBM006546-VL|L-FR4;
      PR005333|pHBM006546-VL|L-FR4

<400> SEQUENCE: 157

Phe Gly Gly Gly Thr Lys Leu Glu Leu Lys
1               5                   10

<210> SEQ ID NO 158

<211> LENGTH: 10
<212> TYPE: PRT
<213> ORGANISM: Artificial Sequence
<220> FEATURE:
<223> OTHER INFORMATION: PR004125|pHBM005103-VL|L-FR4;
PR004250|pHBM005103-VL|L-FR4

<400> SEQUENCE: 158

Phe Gly Ala Gly Thr Lys Leu Glu Met Lys
1 5 10

<210> SEQ ID NO 159
<211> LENGTH: 10
<212> TYPE: PRT
<213> ORGANISM: Artificial Sequence
<220> FEATURE:
<223> OTHER INFORMATION: PR004128|pHBM005106-VL|L-FR4;
PR004131|pHBM005109-VL|L-FR4; PR004251|pHBM005106-VL|L-FR4;
PR004252|pHBM005109-VL|L-FR4; PR004324|pHBM005456-VL|L-FR4;
PR004325|pHBM005457-VL|L-FR4; PR004326|pHBM005106-VL|L-FR4;
PR004327|pHBM005106-VL|L-FR4; PR004328|pHBM005106-VL|L-FR4;
PR004329|pHBM005106-VL|L-FR4; PR004330|pHBM005106-VL|L-FR4;
PR004331|pHBM005106-VL|L-FR4; PR004332|pHBM005106-VL|L-FR4;
PR004333|pHBM005106-VL|L-FR4; PR004334|pHBM005106-VL|L-FR4;
PR004335|pHBM005106-VL|L-FR4; PR004336|pHBM005106-VL|L-FR4;
PR004337|pHBM005106-VL|L-FR4; PR004338|pHBM005106-VL|L-FR4;
PR005170|pHBM006323-VL|L-FR4; PR005171|pHBM006324-VL|L-FR4;
PR005172|pHBM006325-VL|L-FR4; PR005329|pHBM006545-VL|L-FR4;
PR005332|pHBM006545-VL|L-FR4

<400> SEQUENCE: 159

Phe Gly Ala Gly Thr Lys Leu Glu Ile Lys
1 5 10

<210> SEQ ID NO 160
<211> LENGTH: 10
<212> TYPE: PRT
<213> ORGANISM: Artificial Sequence
<220> FEATURE:
<223> OTHER INFORMATION: PR004129|pHBM005107-VL|L-FR4

<400> SEQUENCE: 160

Phe Gly Ser Gly Thr Lys Leu Glu Ile Asn
1 5 10

<210> SEQ ID NO 161
<211> LENGTH: 10
<212> TYPE: PRT
<213> ORGANISM: Artificial Sequence
<220> FEATURE:
<223> OTHER INFORMATION: PR004130|pHBM005108-VL|L-FR4

<400> SEQUENCE: 161

Phe Gly Ser Gly Thr Lys Leu Glu Ile Lys
1 5 10

<210> SEQ ID NO 162
<211> LENGTH: 10
<212> TYPE: PRT
<213> ORGANISM: Artificial Sequence
<220> FEATURE:
<223> OTHER INFORMATION: PR004264|pHBM005402-VL|L-FR4;
PR005125|pHBM006277-VL|L-FR4; PR005128|pHBM006277-VL|L-FR4;
PR005331|pHBM006549-VL|L-FR4; PR005335|pHBM006548-VL|L-FR4;
PR005336|pHBM006549-VL|L-FR4

<400> SEQUENCE: 162

Phe Gly Gln Gly Thr Arg Leu Glu Ile Lys
1 5 10

<210> SEQ ID NO 163
<211> LENGTH: 10
<212> TYPE: PRT
<213> ORGANISM: Artificial Sequence
<220> FEATURE:
<223> OTHER INFORMATION: PR004275|pHBM005296-VL|L-FR4

<400> SEQUENCE: 163

```
Phe Gly Pro Gly Thr Lys Val Asp Ile Lys
1               5                   10
```

<210> SEQ ID NO 164
<211> LENGTH: 10
<212> TYPE: PRT
<213> ORGANISM: Artificial Sequence
<220> FEATURE:
<223> OTHER INFORMATION: L-FR4

<400> SEQUENCE: 164

```
Phe Gly Gln Gly Thr Lys Leu Glu Ile Lys
1               5                   10
```

<210> SEQ ID NO 165
<211> LENGTH: 10
<212> TYPE: PRT
<213> ORGANISM: Artificial Sequence
<220> FEATURE:
<223> OTHER INFORMATION: PR004970|pHBM006122-VL|L-FR4

<400> SEQUENCE: 165

```
Phe Gly Gln Gly Thr Lys Val Glu Ile Lys
1               5                   10
```

<210> SEQ ID NO 166
<211> LENGTH: 10
<212> TYPE: PRT
<213> ORGANISM: Artificial Sequence
<220> FEATURE:
<223> OTHER INFORMATION: PR005124|pHBM006275-VL|L-FR4;
PR005127|pHBM006275-VL|L-FR4

<400> SEQUENCE: 166

```
Phe Gly Gln Gly Thr Lys Val Asp Ile Lys
1               5                   10
```

<210> SEQ ID NO 167
<211> LENGTH: 123
<212> TYPE: PRT
<213> ORGANISM: Artificial Sequence
<220> FEATURE:
<223> OTHER INFORMATION: PR004120|pHBM005087-VH|VH

<400> SEQUENCE: 167

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Met Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
```

```
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala
        115                 120


<210> SEQ ID NO 168
<211> LENGTH: 123
<212> TYPE: PRT
<213> ORGANISM: Artificial Sequence
<220> FEATURE:
<223> OTHER INFORMATION: PR004121|pHBM005088-VH|VH

<400> SEQUENCE: 168

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser
        115                 120


<210> SEQ ID NO 169
<211> LENGTH: 123
<212> TYPE: PRT
<213> ORGANISM: Artificial Sequence
<220> FEATURE:
<223> OTHER INFORMATION: PR004122|pHBM005089-VH|VH;
      PR004249|pHBM005373-VH|VH

<400> SEQUENCE: 169

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser
        115                 120


<210> SEQ ID NO 170
```

<211> LENGTH: 123
<212> TYPE: PRT
<213> ORGANISM: Artificial Sequence
<220> FEATURE:
<223> OTHER INFORMATION: PR004123|pHBM005090-VH|VH

<400> SEQUENCE: 170

Glu Val Gln Leu Val Glu Ser Gly Gly Gly Leu Val Gln Pro Lys Gly
1 5 10 15

Ser Leu Lys Leu Ser Cys Ala Ala Ser Glu Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Thr Lys Ser Asn Asn Phe Ala Thr Tyr Tyr Ala Asp
50 55 60

Ser Val Lys Asp Arg Phe Thr Ile Ser Arg Asp Asp Ser Gln Ser Met
65 70 75 80

Leu Phe Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ala
115 120

<210> SEQ ID NO 171
<211> LENGTH: 123
<212> TYPE: PRT
<213> ORGANISM: Artificial Sequence
<220> FEATURE:
<223> OTHER INFORMATION: PR004124|pHBM005091-VH|VH

<400> SEQUENCE: 171

Glu Val Lys Val Glu Glu Ser Gly Gly Gly Leu Val Gln Pro Gly Gly
1 5 10 15

Ser Met Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Tyr Gly Asn Tyr Tyr Ala Met Asp Phe
100 105 110

Trp Gly Gln Gly Thr Ser Leu Thr Val Ser Ser
115 120

<210> SEQ ID NO 172
<211> LENGTH: 123
<212> TYPE: PRT
<213> ORGANISM: Artificial Sequence
<220> FEATURE:
<223> OTHER INFORMATION: PR004125|pHBM005092-VH|VH;
PR004128|pHBM005092-VH|VH; PR004250|pHBM005374-VH|VH;
PR004251|pHBM005374-VH|VH; PR004324|pHBM005374-VH|VH;
PR004325|pHBM005374-VH|VH; PR004339|pHBM005374-VH|VH;
PR004340|pHBM005374-VH|VH; PR004342|pHBM005374-VH|VH;
PR004343|pHBM005374-VH|VH; PR004344|pHBM005374-VH|VH;
PR004345|pHBM005374-VH|VH; PR004346|pHBM005374-VH|VH;

PR005170|pHBM005092-VH|VH; PR005171|pHBM005092-VH|VH;
PR005172|pHBM005092-VH|VH

<400> SEQUENCE: 172

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala
        115                 120
```

<210> SEQ ID NO 173
<211> LENGTH: 123
<212> TYPE: PRT
<213> ORGANISM: Artificial Sequence
<220> FEATURE:
<223> OTHER INFORMATION: PR004126|pHBM005093-VH|VH

<400> SEQUENCE: 173

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Ser Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala
        115                 120
```

<210> SEQ ID NO 174
<211> LENGTH: 123
<212> TYPE: PRT
<213> ORGANISM: Artificial Sequence
<220> FEATURE:
<223> OTHER INFORMATION: PR004127|pHBM005094-VH|VH

<400> SEQUENCE: 174

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30
```

```
Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser
        115                 120


<210> SEQ ID NO 175
<211> LENGTH: 123
<212> TYPE: PRT
<213> ORGANISM: Artificial Sequence
<220> FEATURE:
<223> OTHER INFORMATION: PR004129|pHBM005095-VH|VH

<400> SEQUENCE: 175

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Asp Tyr Gly Asn Tyr Tyr Ala Met Asp Tyr
            100                 105                 110

Trp Gly Gln Gly Thr Ser Val Thr Val Ser Ser
        115                 120


<210> SEQ ID NO 176
<211> LENGTH: 123
<212> TYPE: PRT
<213> ORGANISM: Artificial Sequence
<220> FEATURE:
<223> OTHER INFORMATION: PR004130|pHBM005096-VH|VH

<400> SEQUENCE: 176

Glu Val Gln Leu Val Glu Ser Gly Gly Gly Leu Val Gln Phe Lys Gly
1               5                   10                  15

Ser Leu Lys Leu Ser Cys Gly Thr Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Phe Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95
```

Tyr Cys Val Arg Gly Lys Glu Asn Gly Asn Tyr Tyr Ala Met Asp Phe
100 105 110

Trp Gly Gln Gly Thr Ser Val Thr Val Ser Ser
115 120

<210> SEQ ID NO 177
<211> LENGTH: 123
<212> TYPE: PRT
<213> ORGANISM: Artificial Sequence
<220> FEATURE:
<223> OTHER INFORMATION: PR004131|pHBM005097-VH|VH;
PR004252|pHBM005375-VH|VH

<400> SEQUENCE: 177

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Tyr
100 105 110

Trp Gly Gln Gly Thr Ser Val Thr Val Ser Ser
115 120

<210> SEQ ID NO 178
<211> LENGTH: 114
<212> TYPE: PRT
<213> ORGANISM: Artificial Sequence
<220> FEATURE:
<223> OTHER INFORMATION: PR004264|pHBM005401-VH|VH

<400> SEQUENCE: 178

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Gln Gly Phe Asp Tyr Trp Gly Gln Gly Thr Leu Val Thr Val
100 105 110

Ser Ser

<210> SEQ ID NO 179
<211> LENGTH: 120
<212> TYPE: PRT

<213> ORGANISM: Artificial Sequence
<220> FEATURE:
<223> OTHER INFORMATION: PR004265|pHBM005403-VH|VH

<400> SEQUENCE: 179

Glu Val Gln Leu Val Glu Ser Gly Gly Gly Leu Val Gln Pro Gly Gly
1 5 10 15

Ser Arg Lys Leu Ser Cys Ala Ala Ser Gly Phe Thr Phe Ser Ser Phe
20 25 30

Gly Met His Trp Val Arg Gln Val Pro Glu Lys Gly Leu Glu Trp Val
35 40 45

Ala Tyr Ile Ser Ser Gly Ser Arg Thr Ile Tyr Tyr Thr Asp Thr Val
50 55 60

Lys Gly Arg Phe Thr Ile Ser Arg Asp Asn Pro Lys Asn Thr Leu Phe
65 70 75 80

Leu Gln Met Thr Ser Leu Arg Ser Glu Asp Thr Ala Ile Tyr Tyr Cys
85 90 95

Val Arg Gly Gly Leu Arg Pro Tyr Trp Tyr Phe Asp Val Trp Gly Ala
100 105 110

Gly Thr Thr Val Thr Val Ser Ala
115 120

<210> SEQ ID NO 180
<211> LENGTH: 119
<212> TYPE: PRT
<213> ORGANISM: Artificial Sequence
<220> FEATURE:
<223> OTHER INFORMATION: PR004275|pHBM005295-VH|VH

<400> SEQUENCE: 180

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Trp Gly Lys Gly Gly Leu Phe Asp Tyr Trp Gly Gln Gly
100 105 110

Thr Leu Val Thr Val Ser Ser
115

<210> SEQ ID NO 181
<211> LENGTH: 123
<212> TYPE: PRT
<213> ORGANISM: Artificial Sequence
<220> FEATURE:
<223> OTHER INFORMATION: PR004326|pHBM005430-VH|VH

<400> SEQUENCE: 181

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Ala Asn Tyr Tyr Ala Met Asp Phe
100 105 110

Trp Gly Gln Gly Thr Ser Val Thr Val Ser Ala
115 120

<210> SEQ ID NO 182
<211> LENGTH: 123
<212> TYPE: PRT
<213> ORGANISM: Artificial Sequence
<220> FEATURE:
<223> OTHER INFORMATION: PR004327|pHBM005431-VH|VH

<400> SEQUENCE: 182

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Gln Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ala
115 120

<210> SEQ ID NO 183
<211> LENGTH: 123
<212> TYPE: PRT
<213> ORGANISM: Artificial Sequence
<220> FEATURE:
<223> OTHER INFORMATION: PR004328|pHBM005432-VH|VH

<400> SEQUENCE: 183

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr

```
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala
        115                 120


<210> SEQ ID NO 184
<211> LENGTH: 123
<212> TYPE: PRT
<213> ORGANISM: Artificial Sequence
<220> FEATURE:
<223> OTHER INFORMATION: PR004329|pHBM005433-VH|VH

<400> SEQUENCE: 184

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Gln Gly Asn Tyr Tyr Ala Met Asp Phe
            100                 105                 110

Trp Gly Gln Gly Thr Ser Val Thr Val Ser Ala
        115                 120


<210> SEQ ID NO 185
<211> LENGTH: 123
<212> TYPE: PRT
<213> ORGANISM: Artificial Sequence
<220> FEATURE:
<223> OTHER INFORMATION: PR004330|pHBM005435-VH|VH;
      PR004519|pHBM005435-VH|VH; PR004522|pHBM005435-VH|VH;
      PR004525|pHBM005435-VH|VH; PR004669|pHBM005793-VH|VH

<400> SEQUENCE: 185

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser
        115                 120
```

```
<210> SEQ ID NO 186
<211> LENGTH: 123
<212> TYPE: PRT
<213> ORGANISM: Artificial Sequence
<220> FEATURE:
<223> OTHER INFORMATION: PR004331|pHBM005436-VH|VH

<400> SEQUENCE: 186

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser
        115                 120


<210> SEQ ID NO 187
<211> LENGTH: 123
<212> TYPE: PRT
<213> ORGANISM: Artificial Sequence
<220> FEATURE:
<223> OTHER INFORMATION: PR004332|pHBM005437-VH|VH

<400> SEQUENCE: 187

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Thr Val Thr Val Ser Ser
        115                 120


<210> SEQ ID NO 188
<211> LENGTH: 123
<212> TYPE: PRT
<213> ORGANISM: Artificial Sequence
<220> FEATURE:
<223> OTHER INFORMATION: PR004333|pHBM005439-VH|VH;
      PR004520|pHBM005439-VH|VH; PR004523|pHBM005439-VH|VH;
      PR004526|pHBM005439-VH|VH; PR004668|pHBM005792-VH|VH

<400> SEQUENCE: 188
```

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Asn Gly Asn Tyr Tyr Ala Met Asp Phe
100 105 110

Trp Gly Gln Gly Thr Thr Val Thr Val Ser Ser
115 120

<210> SEQ ID NO 189
<211> LENGTH: 123
<212> TYPE: PRT
<213> ORGANISM: Artificial Sequence
<220> FEATURE:
<223> OTHER INFORMATION: PR004334|pHBM005440-VH|VH

<400> SEQUENCE: 189

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Asn
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Asn Gly Asn Tyr Tyr Ala Met Asp Phe
100 105 110

Trp Gly Gln Gly Thr Thr Val Thr Val Ser Ser
115 120

<210> SEQ ID NO 190
<211> LENGTH: 123
<212> TYPE: PRT
<213> ORGANISM: Artificial Sequence
<220> FEATURE:
<223> OTHER INFORMATION: PR004335|pHBM005441-VH|VH

<400> SEQUENCE: 190

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Asn Gly Asn Tyr Tyr Ala Met Asp Tyr
100 105 110

Trp Gly Gln Gly Thr Thr Val Thr Val Ser Ser
115 120

<210> SEQ ID NO 191
<211> LENGTH: 123
<212> TYPE: PRT
<213> ORGANISM: Artificial Sequence
<220> FEATURE:
<223> OTHER INFORMATION: PR004336|pHBM005443-VH|VH;
PR004521|pHBM005443-VH|VH; PR004524|pHBM005443-VH|VH;
PR004527|pHBM005443-VH|VH

<400> SEQUENCE: 191

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Ser Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Asn Gly Asn Tyr Tyr Ala Met Asp Phe
100 105 110

Trp Gly Gln Gly Thr Thr Val Thr Val Ser Ser
115 120

<210> SEQ ID NO 192
<211> LENGTH: 123
<212> TYPE: PRT
<213> ORGANISM: Artificial Sequence
<220> FEATURE:
<223> OTHER INFORMATION: PR004337|pHBM005444-VH|VH

<400> SEQUENCE: 192

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Thr Asn
20 25 30

Ala Met Asn Trp Val Arg Gln Ala Ser Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Asn Gly Asn Tyr Tyr Ala Met Asp Phe
100 105 110

```
Trp Gly Gln Gly Thr Thr Val Thr Val Ser Ser
        115                 120


<210> SEQ ID NO 193
<211> LENGTH: 123
<212> TYPE: PRT
<213> ORGANISM: Artificial Sequence
<220> FEATURE:
<223> OTHER INFORMATION: PR004338|pHBM005445-VH|VH

<400> SEQUENCE: 193

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Thr Val Thr Val Ser Ser
        115                 120


<210> SEQ ID NO 194
<211> LENGTH: 123
<212> TYPE: PRT
<213> ORGANISM: Artificial Sequence
<220> FEATURE:
<223> OTHER INFORMATION: PR004660|pHBM005788-VH|VH;
      PR004662|pHBM005788-VH|VH

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg Gly Lys Glu Asn Ala Asn Tyr Tyr Ala Met Asp Phe
            100                 105                 110

Trp Gly Gln Gly Thr Thr Val Thr Val Ser Ser
        115                 120


<210> SEQ ID NO 195
<211> LENGTH: 123
<212> TYPE: PRT
<213> ORGANISM: Artificial Sequence
<220> FEATURE:
```

<223> OTHER INFORMATION: PR004661|pHBM005789-VH|VH;
PR004663|pHBM005789-VH|VH

<400> SEQUENCE: 195

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Gln Gly Asn Tyr Tyr Ala Met Asp Phe
100 105 110

Trp Gly Gln Gly Thr Thr Val Thr Val Ser Ser
115 120

<210> SEQ ID NO 196
<211> LENGTH: 123
<212> TYPE: PRT
<213> ORGANISM: Artificial Sequence
<220> FEATURE:
<223> OTHER INFORMATION: PR004664|pHBM005786-VH|VH;
PR004666|pHBM005786-VH|VH; PR005565|pHBM006805-VH|VH;
PR005750|pHBM007021-VH|VH

<400> SEQUENCE: 196

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Asn Ala Asn Tyr Tyr Ala Met Asp Phe
100 105 110

Trp Gly Gln Gly Thr Thr Val Thr Val Ser Ser
115 120

<210> SEQ ID NO 197
<211> LENGTH: 123
<212> TYPE: PRT
<213> ORGANISM: Artificial Sequence
<220> FEATURE:
<223> OTHER INFORMATION: PR004665|pHBM005787-VH|VH;
PR004667|pHBM005787-VH|VH

<400> SEQUENCE: 197

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Gln Gly Asn Tyr Tyr Ala Met Asp Phe
100 105 110

Trp Gly Gln Gly Thr Thr Val Thr Val Ser Ser
115 120

<210> SEQ ID NO 198
<211> LENGTH: 115
<212> TYPE: PRT
<213> ORGANISM: Artificial Sequence
<220> FEATURE:
<223> OTHER INFORMATION: PR004970|pHBM006115-VH|VH

<400> SEQUENCE: 198

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Pro Gln Ala Pro Gly Lys Gly Leu Glu Trp Val
35 40 45

Ala Asn Ile Lys Gln Asp Gly Ser Ala Lys Phe Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ser Trp Gly Phe Ala Tyr Trp Gly Gln Gly Thr Leu Val Thr
100 105 110

Val Ser Ser
115

<210> SEQ ID NO 199
<211> LENGTH: 127
<212> TYPE: PRT
<213> ORGANISM: Artificial Sequence
<220> FEATURE:
<223> OTHER INFORMATION: PR004974|pHBM006117-VH|VH;
PR005293|pHBM006504-VH|VH

<400> SEQUENCE: 199

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Asp Asp Lys Arg Tyr Ser Pro Ser
50 55 60

Leu Lys Ser Arg Leu Thr Ile Thr Lys Asp Thr Ser Lys Asn Gln Val

```
65                  70                  75                  80

Val Leu Thr Met Thr Asn Met Asp Pro Val Asp Thr Ala Thr Tyr Tyr
                85                  90                  95

Cys Ala His Arg Arg Leu Arg Tyr Ser Gly Arg Tyr Tyr Tyr Tyr Tyr
            100                 105                 110

Gly Thr Asp Val Trp Gly Gln Gly Thr Thr Val Thr Val Ser Ser
        115                 120                 125


<210> SEQ ID NO 200
<211> LENGTH: 122
<212> TYPE: PRT
<213> ORGANISM: Artificial Sequence
<220> FEATURE:
<223> OTHER INFORMATION: PR005124|pHBM006274-VH|VH;
      PR005127|pHBM006280-VH|VH

<400> SEQUENCE: 200

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Trp Cys
                85                  90                  95

Ala Arg His Arg Arg Ser Asp Tyr Trp Tyr Tyr Gly Met Asp Val Trp
            100                 105                 110

Gly Gln Gly Thr Thr Val Thr Val Ser Ser
        115                 120


<210> SEQ ID NO 201
<211> LENGTH: 124
<212> TYPE: PRT
<213> ORGANISM: Artificial Sequence
<220> FEATURE:
<223> OTHER INFORMATION: PR005125|pHBM006276-VH|VH;
      PR005128|pHBM006281-VH|VH

<400> SEQUENCE: 201

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Val Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Tyr Tyr Gly Ser Gly Asn Tyr Ser Leu Phe Asp
            100                 105                 110

Tyr Trp Gly Gln Gly Thr Leu Val Thr Val Ser Ser
```

115 120

<210> SEQ ID NO 202
<211> LENGTH: 123
<212> TYPE: PRT
<213> ORGANISM: Artificial Sequence
<220> FEATURE:
<223> OTHER INFORMATION: PR005329|pHBM006537-VH|VH;
PR005332|pHBM006540-VH|VH

<400> SEQUENCE: 202

Glu Val Lys Leu Leu Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Thr Lys Ser Asn Asn Tyr Ala Thr Tyr Tyr Ala Asp
50 55 60

Ser Val Lys Asp Arg Phe Thr Ile Ser Arg Asp Asp Ser His Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Asn Gly Asn Tyr Tyr Ala Met Asp Phe
100 105 110

Trp Gly Gln Gly Thr Ser Val Thr Val Ser Ala
115 120

<210> SEQ ID NO 203
<211> LENGTH: 123
<212> TYPE: PRT
<213> ORGANISM: Artificial Sequence
<220> FEATURE:
<223> OTHER INFORMATION: PR005330|pHBM006538-VH|VH;
PR005333|pHBM006541-VH|VH

<400> SEQUENCE: 203

Glu Val Lys Leu Val Glu Ser Gly Gly Gly Leu Val Gln Pro Gly Gly
1 5 10 15

Ser Arg Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Tyr Gly Asn Tyr Tyr Ala Met Asp Phe
100 105 110

Trp Gly Gln Gly Thr Ser Val Thr Val Ser Ser
115 120

<210> SEQ ID NO 204
<211> LENGTH: 115
<212> TYPE: PRT
<213> ORGANISM: Artificial Sequence
<220> FEATURE:
<223> OTHER INFORMATION: PR005331|pHBM006539-VH|VH;

PR005336|pHBM006544-VH|VH

<400> SEQUENCE: 204

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Trp Leu Ser Trp Val Arg Gln Ala Pro Gly Lys Gly Leu Glu Trp Val
35 40 45

Ala Asn Ile Lys Gln Asp Gly Ser Ala Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Val Arg Asn Trp Gly Phe Asp Tyr Trp Gly Gln Gly Thr Leu Val Thr
100 105 110

Val Ser Ser
115

<210> SEQ ID NO 205
<211> LENGTH: 115
<212> TYPE: PRT
<213> ORGANISM: Artificial Sequence
<220> FEATURE:
<223> OTHER INFORMATION: PR005335|pHBM006543-VH|VH

<400> SEQUENCE: 205

Gln Val Gln Leu Val Gln Ser Gly Gly Gly Leu Val Gln Pro Gly Gly
1 5 10 15

Ser Leu Arg Leu Ser Cys Thr Ala Ser Gly Phe Thr Phe Ser Tyr Tyr
20 25 30

Trp Leu Ser Trp Val Arg Gln Ala Pro Gly Lys Gly Leu Glu Trp Val
35 40 45

Ala Asn Ile Lys Gln Asp Gly Ser Thr Thr Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asn Trp Gly Phe Asp Tyr Trp Gly Gln Gly Thr Leu Val Thr
100 105 110

Val Ser Ser
115

<210> SEQ ID NO 206
<211> LENGTH: 123
<212> TYPE: PRT
<213> ORGANISM: Artificial Sequence
<220> FEATURE:
<223> OTHER INFORMATION: PR005751|pHBM007019-VH|VH;
PR006154|pHBM007001-VH|VH; PR006272|pHBM007521-VH|VH

<400> SEQUENCE: 206

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

```
Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser
        115                 120


<210> SEQ ID NO 207
<211> LENGTH: 123
<212> TYPE: PRT
<213> ORGANISM: Artificial Sequence
<220> FEATURE:
<223> OTHER INFORMATION: PR005752|pHBM007009-VH|VH;
      PR006155|pHBM006991-VH|VH; PR006276|pHBM007525-VH|VH

<400> SEQUENCE: 207

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser
        115                 120


<210> SEQ ID NO 208
<211> LENGTH: 123
<212> TYPE: PRT
<213> ORGANISM: Artificial Sequence
<220> FEATURE:
<223> OTHER INFORMATION: PR005753|pHBM007020-VH|VH;
      PR006156|pHBM007002-VH|VH; PR006273|pHBM007522-VH|VH

<400> SEQUENCE: 208

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80
```

Leu Tyr Leu Gln Met Asn Ser Leu Lys Thr Glu Asp Thr Ala Val Tyr
85 90 95

Tyr Cys Val Arg Gly Lys Glu Ile Gly Asn Tyr Tyr Ala Met Asp Phe
100 105 110

Trp Gly Gln Gly Thr Thr Val Thr Val Ser Ser
115 120

<210> SEQ ID NO 209
<211> LENGTH: 123
<212> TYPE: PRT
<213> ORGANISM: Artificial Sequence
<220> FEATURE:
<223> OTHER INFORMATION: PR005754|pHBM007010-VH|VH;
PR006157|pHBM006992-VH|VH; PR006277|pHBM007526-VH|VH

<400> SEQUENCE: 209

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Ile Gly Asn Tyr Tyr Ala Met Asp Phe
100 105 110

Trp Gly Gln Gly Thr Thr Val Thr Val Ser Ser
115 120

<210> SEQ ID NO 210
<211> LENGTH: 123
<212> TYPE: PRT
<213> ORGANISM: Artificial Sequence
<220> FEATURE:
<223> OTHER INFORMATION: PR005763|pHBM007005-VH|VH;
PR006161|pHBM006987-VH|VH; PR006274|pHBM007523-VH|VH

<400> SEQUENCE: 210

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu His Gly Lys Tyr Tyr Ala Met Asp Phe
100 105 110

Trp Gly Gln Gly Thr Thr Val Thr Val Ser Ser
115 120

<210> SEQ ID NO 211
<211> LENGTH: 123
<212> TYPE: PRT
<213> ORGANISM: Artificial Sequence
<220> FEATURE:
<223> OTHER INFORMATION: PR005787|pHBM007006-VH|VH;
PR006166|pHBM006988-VH|VH; PR006275|pHBM007524-VH|VH

<400> SEQUENCE: 211

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Lys Tyr Tyr Ala Met Asp Phe
            100                 105                 110

Trp Gly Gln Gly Thr Thr Val Thr Val Ser Ser
        115                 120
```

<210> SEQ ID NO 212
<211> LENGTH: 112
<212> TYPE: PRT
<213> ORGANISM: Artificial Sequence
<220> FEATURE:
<223> OTHER INFORMATION: PR004120|pHBM005098-VL|VL

<400> SEQUENCE: 212

```
Asp Ile Val Met Thr Gln Ala Ala Thr Ser Val Leu Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110
```

<210> SEQ ID NO 213
<211> LENGTH: 112
<212> TYPE: PRT
<213> ORGANISM: Artificial Sequence
<220> FEATURE:
<223> OTHER INFORMATION: PR004121|pHBM005099-VL|VL

<400> SEQUENCE: 213

```
Asp Ile Val Ile Thr Gln Ala Ala Pro Ser Val Pro Val Thr Pro Gly
1               5                   10                  15
```

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gly Gly Thr Lys Leu Glu Met Lys
100 105 110

<210> SEQ ID NO 214
<211> LENGTH: 112
<212> TYPE: PRT
<213> ORGANISM: Artificial Sequence
<220> FEATURE:
<223> OTHER INFORMATION: PR004122|pHBM005100-VL|VL;
PR004249|pHBM005100-VL|VL

<400> SEQUENCE: 214

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Leu Lys
100 105 110

<210> SEQ ID NO 215
<211> LENGTH: 112
<212> TYPE: PRT
<213> ORGANISM: Artificial Sequence
<220> FEATURE:
<223> OTHER INFORMATION: PR004123|pHBM005101-VL|VL

<400> SEQUENCE: 215

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gly Gly Thr Lys Leu Glu Leu Lys

```
        100                 105                 110


<210> SEQ ID NO 216
<211> LENGTH: 112
<212> TYPE: PRT
<213> ORGANISM: Artificial Sequence
<220> FEATURE:
<223> OTHER INFORMATION: PR004124|pHBM005102-VL|VL

<400> SEQUENCE: 216

Asp Ile Val Met Thr Gln Asp Glu Leu Ser Asn Pro Val Thr Ser Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Leu Lys
            100                 105                 110


<210> SEQ ID NO 217
<211> LENGTH: 112
<212> TYPE: PRT
<213> ORGANISM: Artificial Sequence
<220> FEATURE:
<223> OTHER INFORMATION: PR004125|pHBM005103-VL|VL;
      PR004250|pHBM005103-VL|VL

<400> SEQUENCE: 217

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Met Lys
            100                 105                 110


<210> SEQ ID NO 218
<211> LENGTH: 112
<212> TYPE: PRT
<213> ORGANISM: Artificial Sequence
<220> FEATURE:
<223> OTHER INFORMATION: PR004126|pHBM005104-VL|VL

<400> SEQUENCE: 218

Asp Ile Val Ile Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
```

```
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110


<210> SEQ ID NO 219
<211> LENGTH: 112
<212> TYPE: PRT
<213> ORGANISM: Artificial Sequence
<220> FEATURE:
<223> OTHER INFORMATION: PR004127|pHBM005105-VL|VL

<400> SEQUENCE: 219

Asp Ile Val Met Thr Gln Ala Ala Thr Ser Val Leu Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Met Lys
            100                 105                 110


<210> SEQ ID NO 220
<211> LENGTH: 112
<212> TYPE: PRT
<213> ORGANISM: Artificial Sequence
<220> FEATURE:
<223> OTHER INFORMATION: PR004128|pHBM005106-VL|VL;
      PR004251|pHBM005106-VL|VL; PR004326|pHBM005106-VL|VL;
      PR004327|pHBM005106-VL|VL; PR004328|pHBM005106-VL|VL;
      PR004329|pHBM005106-VL|VL; PR004330|pHBM005106-VL|VL;
      PR004331|pHBM005106-VL|VL; PR004332|pHBM005106-VL|VL;
      PR004333|pHBM005106-VL|VL; PR004334|pHBM005106-VL|VL;
      PR004335|pHBM005106-VL|VL; PR004336|pHBM005106-VL|VL;
      PR004337|pHBM005106-VL|VL; PR004338|pHBM005106-VL|VL

<400> SEQUENCE: 220

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80
```

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Ile Lys
100 105 110

<210> SEQ ID NO 221
<211> LENGTH: 112
<212> TYPE: PRT
<213> ORGANISM: Artificial Sequence
<220> FEATURE:
<223> OTHER INFORMATION: PR004129|pHBM005107-VL|VL

<400> SEQUENCE: 221

Asp Ile Leu Leu Thr Gln Ser Pro Ala Ile Leu Ser Val Ser Pro Gly
1 5 10 15

Glu Arg Val Ser Phe Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Ser Gly Thr Lys Leu Glu Ile Asn
100 105 110

<210> SEQ ID NO 222
<211> LENGTH: 112
<212> TYPE: PRT
<213> ORGANISM: Artificial Sequence
<220> FEATURE:
<223> OTHER INFORMATION: PR004130|pHBM005108-VL|VL

<400> SEQUENCE: 222

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Ser Gly Thr Lys Leu Glu Ile Lys
100 105 110

<210> SEQ ID NO 223
<211> LENGTH: 112
<212> TYPE: PRT
<213> ORGANISM: Artificial Sequence
<220> FEATURE:
<223> OTHER INFORMATION: PR004131|pHBM005109-VL|VL;
PR004252|pHBM005109-VL|VL

<400> SEQUENCE: 223

Asp Ile Val Met Thr Gln Ala Ala Pro Ser Val Pro Val Thr Pro Gly
1 5 10 15

Glu Ser Val Ser Ile Ser Cys Arg Ser Asn Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Ile Lys
100 105 110

<210> SEQ ID NO 224
<211> LENGTH: 113
<212> TYPE: PRT
<213> ORGANISM: Artificial Sequence
<220> FEATURE:
<223> OTHER INFORMATION: PR004264|pHBM005402-VL|VL

<400> SEQUENCE: 224

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Pro Ile Thr Phe Gly Gln Gly Thr Arg Leu Glu Ile
100 105 110

Lys

<210> SEQ ID NO 225
<211> LENGTH: 106
<212> TYPE: PRT
<213> ORGANISM: Artificial Sequence
<220> FEATURE:
<223> OTHER INFORMATION: PR004265|pHBM005404-VL|VL

<400> SEQUENCE: 225

Asp Ile Val Leu Ile Gln Ser Pro Ala Ile Met Ser Ala Ser Pro Gly
1 5 10 15

Glu Lys Val Thr Ile Ser Cys Ser Ala Ser Ser Ser Val Ser Tyr Met
20 25 30

Tyr Trp Tyr Gln Gln Lys Pro Gly Ser Ser Pro Lys Pro Trp Ile Tyr
35 40 45

Arg Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

```
Asp Ala Ala Thr Tyr Tyr Cys Gln Gln Arg Ser Ser Tyr Pro Pro Thr
                85                  90                  95

Phe Gly Ala Gly Thr Lys Leu Glu Leu Lys
            100                 105


<210> SEQ ID NO 226
<211> LENGTH: 107
<212> TYPE: PRT
<213> ORGANISM: Artificial Sequence
<220> FEATURE:
<223> OTHER INFORMATION: PR004275|pHBM005296-VL|VL

<400> SEQUENCE: 226

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Pro
                85                  90                  95

Thr Phe Gly Pro Gly Thr Lys Val Asp Ile Lys
            100                 105


<210> SEQ ID NO 227
<211> LENGTH: 112
<212> TYPE: PRT
<213> ORGANISM: Artificial Sequence
<220> FEATURE:
<223> OTHER INFORMATION: PR004324|pHBM005456-VL|VL

<400> SEQUENCE: 227

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Ala Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110


<210> SEQ ID NO 228
<211> LENGTH: 112
<212> TYPE: PRT
<213> ORGANISM: Artificial Sequence
<220> FEATURE:
<223> OTHER INFORMATION: PR004325|pHBM005457-VL|VL

<400> SEQUENCE: 228
```

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Gln Gly Lys Ile Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Ile Lys
100 105 110

<210> SEQ ID NO 229
<211> LENGTH: 112
<212> TYPE: PRT
<213> ORGANISM: Artificial Sequence
<220> FEATURE:
<223> OTHER INFORMATION: PR004339|pHBM005447-VL|VL;
PR004519|pHBM005447-VL|VL; PR004520|pHBM005447-VL|VL;
PR004521|pHBM005447-VL|VL; PR004660|pHBM005447-VL|VL;
PR004661|pHBM005447-VL|VL; PR004668|pHBM005447-VL|VL

<400> SEQUENCE: 229

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Lys Ile Tyr Leu Tyr Trp Phe Leu Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 230
<211> LENGTH: 112
<212> TYPE: PRT
<213> ORGANISM: Artificial Sequence
<220> FEATURE:
<223> OTHER INFORMATION: PR004340|pHBM005448-VL|VL;
PR004522|pHBM005448-VL|VL; PR004523|pHBM005448-VL|VL;
PR004524|pHBM005448-VL|VL

<400> SEQUENCE: 230

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Asn Thr Tyr Leu Tyr Trp Phe Leu Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 231
<211> LENGTH: 112
<212> TYPE: PRT
<213> ORGANISM: Artificial Sequence
<220> FEATURE:
<223> OTHER INFORMATION: PR004342|pHBM005450-VL|VL

<400> SEQUENCE: 231

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Asn Thr Tyr Leu Tyr Trp Phe Leu Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gln Gly Thr Lys Leu Glu Ile Lys
100 105 110

<210> SEQ ID NO 232
<211> LENGTH: 112
<212> TYPE: PRT
<213> ORGANISM: Artificial Sequence
<220> FEATURE:
<223> OTHER INFORMATION: VL

<400> SEQUENCE: 232

Asp Ile Val Met Thr Gln Ser Pro Leu Ser Leu Pro Val Thr Leu Gly
1 5 10 15

Gln Pro Ala Ser Ile Ser Cys Arg Ser Ser Lys Ser Leu Leu His Ser
20 25 30

Asn Gly Lys Ile Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 233
<211> LENGTH: 112
<212> TYPE: PRT
<213> ORGANISM: Artificial Sequence
<220> FEATURE:
<223> OTHER INFORMATION: PR004344|pHBM005453-VL|VL

<400> SEQUENCE: 233

Asp Ile Val Met Thr Gln Ser Pro Leu Ser Leu Pro Val Thr Leu Gly
1 5 10 15

Gln Pro Ala Ser Ile Ser Cys Arg Ser Ser Lys Ser Leu Leu His Ser
20 25 30

Asn Gly Asn Thr Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 234
<211> LENGTH: 112
<212> TYPE: PRT
<213> ORGANISM: Artificial Sequence
<220> FEATURE:
<223> OTHER INFORMATION: PR004345|pHBM005454-VL|VL

<400> SEQUENCE: 234

Asp Ile Val Met Thr Gln Ser Pro Leu Ser Leu Pro Val Thr Leu Gly
1 5 10 15

Gln Pro Ala Ser Ile Ser Cys Arg Ser Asn Lys Ser Leu Leu His Ser
20 25 30

Asn Gly Asn Thr Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 235
<211> LENGTH: 112
<212> TYPE: PRT
<213> ORGANISM: Artificial Sequence
<220> FEATURE:
<223> OTHER INFORMATION: PR004346|pHBM005455-VL|VL

<400> SEQUENCE: 235

Asp Ile Val Met Thr Gln Ser Pro Leu Ser Leu Pro Val Thr Leu Gly
1 5 10 15

Gln Pro Ala Ser Ile Ser Cys Arg Ser Ser Lys Ser Leu Leu His Ser
20 25 30

Asn Gly Asn Thr Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110


<210> SEQ ID NO 236
<211> LENGTH: 112
<212> TYPE: PRT
<213> ORGANISM: Artificial Sequence
<220> FEATURE:
<223> OTHER INFORMATION: PR004662|pHBM005790-VL|VL;
      PR004663|pHBM005790-VL|VL

<400> SEQUENCE: 236

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Lys Ile Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110


<210> SEQ ID NO 237
<211> LENGTH: 112
<212> TYPE: PRT
<213> ORGANISM: Artificial Sequence
<220> FEATURE:
<223> OTHER INFORMATION: PR004666|pHBM005791-VL|VL;
      PR004667|pHBM005791-VL|VL; PR005565|pHBM005791-VL|VL;
      PR005750|pHBM005791-VL|VL; PR005751|pHBM005791-VL|VL;
      PR005752|pHBM005791-VL|VL; PR005753|pHBM005791-VL|VL;
      PR005754|pHBM005791-VL|VL; PR005763|pHBM005791-VL|VL;
      PR005787|pHBM005791-VL|VL; PR006154|pHBM005791-VL|VL;
      PR006155|pHBM005791-VL|VL; PR006156|pHBM005791-VL|VL;
      PR006157|pHBM005791-VL|VL; PR006161|pHBM005791-VL|VL;
      PR006166|pHBM005791-VL|VL; PR006272|pHBM005791-VL|VL;
      PR006273|pHBM005791-VL|VL; PR006274|pHBM005791-VL|VL;
      PR006275|pHBM005791-VL|VL; PR006276|pHBM005791-VL|VL;
      PR006277|pHBM005791-VL|VL

<400> SEQUENCE: 237

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu His Ser
            20                  25                  30

Asn Ala Lys Ile Tyr Leu Tyr Trp Phe Gln Gln Arg Pro Gly Gln Ser
        35                  40                  45

Pro Arg Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110
```

<210> SEQ ID NO 238
<211> LENGTH: 107
<212> TYPE: PRT
<213> ORGANISM: Artificial Sequence
<220> FEATURE:
<223> OTHER INFORMATION: PR004970|pHBM006122-VL|VL

<400> SEQUENCE: 238

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys
            100                 105
```

<210> SEQ ID NO 239
<211> LENGTH: 107
<212> TYPE: PRT
<213> ORGANISM: Artificial Sequence
<220> FEATURE:
<223> OTHER INFORMATION: PR004974|pHBM006126-VL|VL;
PR005293|pHBM006126-VL|VL

<400> SEQUENCE: 239

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Val Trp Tyr Gln Gln Lys Pro Gly Gln Ala Pro Arg Leu Leu Ile
        35                  40                  45

Tyr Gly Ala Ser Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105
```

<210> SEQ ID NO 240
<211> LENGTH: 112
<212> TYPE: PRT
<213> ORGANISM: Artificial Sequence
<220> FEATURE:
<223> OTHER INFORMATION: PR005124|pHBM006275-VL|VL;
PR005127|pHBM006275-VL|VL

<400> SEQUENCE: 240

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Val Asp Ile Lys
            100                 105                 110


<210> SEQ ID NO 241
<211> LENGTH: 111
<212> TYPE: PRT
<213> ORGANISM: Artificial Sequence
<220> FEATURE:
<223> OTHER INFORMATION: PR005125|pHBM006277-VL|VL;
      PR005128|pHBM006277-VL|VL

<400> SEQUENCE: 241

Asp Ile Val Met Thr Gln Ser Pro Leu Ser Leu Ser Val Thr Leu Gly
1               5                   10                  15

Gln Pro Ala Ser Ile Ser Cys Arg Ser Ser Gln Ser Leu Val Phe Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Ile Thr Phe Gly Gln Gly Thr Arg Leu Glu Ile Lys
            100                 105                 110


<210> SEQ ID NO 242
<211> LENGTH: 112
<212> TYPE: PRT
<213> ORGANISM: Artificial Sequence
<220> FEATURE:
<223> OTHER INFORMATION: PR005170|pHBM006323-VL|VL

<400> SEQUENCE: 242

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 243
<211> LENGTH: 112
<212> TYPE: PRT
<213> ORGANISM: Artificial Sequence
<220> FEATURE:
<223> OTHER INFORMATION: PR005171|pHBM006324-VL|VL

<400> SEQUENCE: 243

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Met Thr Phe Gly Ala Gly Thr Lys Leu Glu Ile Lys
            100                 105                 110
```

<210> SEQ ID NO 244
<211> LENGTH: 112
<212> TYPE: PRT
<213> ORGANISM: Artificial Sequence
<220> FEATURE:
<223> OTHER INFORMATION: PR005172|pHBM006325-VL|VL

<400> SEQUENCE: 244

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Val Thr Phe Gly Ala Gly Thr Lys Leu Glu Ile Lys
            100                 105                 110
```

<210> SEQ ID NO 245
<211> LENGTH: 112
<212> TYPE: PRT
<213> ORGANISM: Artificial Sequence
<220> FEATURE:
<223> OTHER INFORMATION: PR005329|pHBM006545-VL|VL;
      PR005332|pHBM006545-VL|VL

<400> SEQUENCE: 245

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30
```

```
Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Ile Lys
            100                 105                 110


<210> SEQ ID NO 246
<211> LENGTH: 112
<212> TYPE: PRT
<213> ORGANISM: Artificial Sequence
<220> FEATURE:
<223> OTHER INFORMATION: PR005330|pHBM006546-VL|VL;
      PR005333|pHBM006546-VL|VL

<400> SEQUENCE: 246

Asp Ile Val Met Thr Gln Ala Ala Thr Ser Val Leu Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Leu Lys
            100                 105                 110


<210> SEQ ID NO 247
<211> LENGTH: 112
<212> TYPE: PRT
<213> ORGANISM: Artificial Sequence
<220> FEATURE:
<223> OTHER INFORMATION: PR005331|pHBM006549-VL|VL;
      PR005336|pHBM006549-VL|VL

<400> SEQUENCE: 247

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110
```

```
<210> SEQ ID NO 248
<211> LENGTH: 112
<212> TYPE: PRT
<213> ORGANISM: Artificial Sequence
<220> FEATURE:
<223> OTHER INFORMATION: PR005335|pHBM006548-VL|VL

<400> SEQUENCE: 248

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110


<210> SEQ ID NO 249
<211> LENGTH: 453
<212> TYPE: PRT
<213> ORGANISM: Artificial Sequence
<220> FEATURE:
<223> OTHER INFORMATION: PR004120|pHBM005087|HC

<400> SEQUENCE: 249

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Met Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

```
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 250
<211> LENGTH: 453
<212> TYPE: PRT
<213> ORGANISM: Artificial Sequence
<220> FEATURE:
<223> OTHER INFORMATION: PR004121|pHBM005088|HC

<400> SEQUENCE: 250

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
```

```
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 251
<211> LENGTH: 453
<212> TYPE: PRT
<213> ORGANISM: Artificial Sequence
<220> FEATURE:
<223> OTHER INFORMATION: PR004122|pHBM005089|HC

<400> SEQUENCE: 251

Glu Val Gln Leu Val Glu Thr Gly Gly Gly Leu Val Gln Pro Lys Gly
```

-continued

```
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
435 440 445

Leu Ser Pro Gly Lys
450

<210> SEQ ID NO 252
<211> LENGTH: 453
<212> TYPE: PRT
<213> ORGANISM: Artificial Sequence
<220> FEATURE:
<223> OTHER INFORMATION: PR004123|pHBM005090|HC

<400> SEQUENCE: 252

Glu Val Gln Leu Val Glu Ser Gly Gly Gly Leu Val Gln Pro Lys Gly
1 5 10 15

Ser Leu Lys Leu Ser Cys Ala Ala Ser Glu Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Thr Lys Ser Asn Asn Phe Ala Thr Tyr Tyr Ala Asp
50 55 60

Ser Val Lys Asp Arg Phe Thr Ile Ser Arg Asp Asp Ser Gln Ser Met
65 70 75 80

Leu Phe Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ala Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 253
<211> LENGTH: 453
<212> TYPE: PRT
<213> ORGANISM: Artificial Sequence
<220> FEATURE:
<223> OTHER INFORMATION: PR004124|pHBM005091|HC

<400> SEQUENCE: 253

Glu Val Lys Val Glu Glu Ser Gly Gly Gly Leu Val Gln Pro Gly Gly
1 5 10 15

Ser Met Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Tyr Gly Asn Tyr Tyr Ala Met Asp Phe
100 105 110

Trp Gly Gln Gly Thr Ser Leu Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 254
<211> LENGTH: 453
<212> TYPE: PRT
<213> ORGANISM: Artificial Sequence
<220> FEATURE:
<223> OTHER INFORMATION: HC

<400> SEQUENCE: 254

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ala Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 255
<211> LENGTH: 453
<212> TYPE: PRT
<213> ORGANISM: Artificial Sequence
<220> FEATURE:
<223> OTHER INFORMATION: PR004126|pHBM005093|HC

<400> SEQUENCE: 255

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Ser Thr Asn
20 25 30

Ala Met Asn Trp Val Arg Gln Ala Pro Gly Lys Gly Leu Glu Trp Val
35 40 45

```
Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 256
<211> LENGTH: 453
<212> TYPE: PRT
<213> ORGANISM: Artificial Sequence
<220> FEATURE:
<223> OTHER INFORMATION: PR004127|pHBM005094|HC

<400> SEQUENCE: 256

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 257
<211> LENGTH: 453
<212> TYPE: PRT
<213> ORGANISM: Artificial Sequence
<220> FEATURE:
<223> OTHER INFORMATION: PR004129|pHBM005095|HC

<400> SEQUENCE: 257

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Asp Tyr Gly Asn Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 258
<211> LENGTH: 453
<212> TYPE: PRT
<213> ORGANISM: Artificial Sequence
<220> FEATURE:
<223> OTHER INFORMATION: PR004130|pHBM005096|HC

<400> SEQUENCE: 258

Glu Val Gln Leu Val Glu Ser Gly Gly Gly Leu Val Gln Phe Lys Gly
1 5 10 15

Ser Leu Lys Leu Ser Cys Gly Thr Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Phe Tyr Ala Asp
50 55 60

Ser Val Lys Asp Arg Phe Thr Ile Ser Arg Asp Asp Ser Gln Asn Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 259
<211> LENGTH: 453
<212> TYPE: PRT
<213> ORGANISM: Artificial Sequence
<220> FEATURE:
<223> OTHER INFORMATION: PR004131|pHBM005097|HC

<400> SEQUENCE: 259

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80
```

```
Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 260
<211> LENGTH: 453
<212> TYPE: PRT
<213> ORGANISM: Artificial Sequence
<220> FEATURE:
<223> OTHER INFORMATION: PR004249|pHBM005373|HC

<400> SEQUENCE: 260

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu 405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 261
<211> LENGTH: 453
<212> TYPE: PRT
<213> ORGANISM: Artificial Sequence
<220> FEATURE:
<223> OTHER INFORMATION: HC

<400> SEQUENCE: 261

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Glu Asn Gly Asn Tyr Tyr Ala Met Asp Phe
100 105 110

Trp Gly Gln Gly Thr Ser Val Thr Val Ser Ala Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu

```
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 262
<211> LENGTH: 453
<212> TYPE: PRT
<213> ORGANISM: Artificial Sequence
<220> FEATURE:
<223> OTHER INFORMATION: PR004252|pHBM005375|HC

<400> SEQUENCE: 262

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 263
<211> LENGTH: 444
<212> TYPE: PRT
<213> ORGANISM: Artificial Sequence
<220> FEATURE:
<223> OTHER INFORMATION: PR004264|pHBM005401|HC

<400> SEQUENCE: 263

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Gln Gly Phe Asp Tyr Trp Gly Gln Gly Thr Leu Val Thr Val
100 105 110

Ser Ser Ala Ser Thr Lys Gly Pro Ser Val Phe Pro Leu Ala Pro Ser

```
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Asp Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Glu Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 264
<211> LENGTH: 450
<212> TYPE: PRT
<213> ORGANISM: Artificial Sequence
<220> FEATURE:
<223> OTHER INFORMATION: PR004265|pHBM005403|HC

<400> SEQUENCE: 264

Glu Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Val Pro Glu Lys Gly Leu Glu Trp Val
```

```
        35                  40                  45

Ala Tyr Ile Ser Ser Gly Ser Arg Thr Ile Tyr Tyr Thr Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Val Arg Gly Gly Leu Arg Pro Tyr Trp Tyr Phe Asp Val Trp Gly Ala
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 265
<211> LENGTH: 449
<212> TYPE: PRT
<213> ORGANISM: Artificial Sequence
<220> FEATURE:
<223> OTHER INFORMATION: PR004275|pHBM005295|HC

<400> SEQUENCE: 265

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Trp Gly Lys Gly Gly Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 266
<211> LENGTH: 453
<212> TYPE: PRT
<213> ORGANISM: Artificial Sequence
<220> FEATURE:
<223> OTHER INFORMATION: PR004326|pHBM005430|HC

<400> SEQUENCE: 266

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Ala Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 267
<211> LENGTH: 453
<212> TYPE: PRT
<213> ORGANISM: Artificial Sequence
<220> FEATURE:
<223> OTHER INFORMATION: PR004327|pHBM005431|HC

<400> SEQUENCE: 267

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Gln Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 268
<211> LENGTH: 453
<212> TYPE: PRT
<213> ORGANISM: Artificial Sequence
<220> FEATURE:
<223> OTHER INFORMATION: PR004328|pHBM005432|HC

<400> SEQUENCE: 268

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80
```

```
Leu Tyr Leu Gln Met Asn Asn Leu Lys Thr Glu Asp Thr Ala Met Tyr
                85                  90                  95

Tyr Cys Val Arg Gly Lys Glu Asn Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 269
<211> LENGTH: 453
<212> TYPE: PRT
<213> ORGANISM: Artificial Sequence
<220> FEATURE:
<223> OTHER INFORMATION: PR004329|pHBM005433|HC

<400> SEQUENCE: 269

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Glu Gln Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 270
<211> LENGTH: 453
<212> TYPE: PRT
<213> ORGANISM: Artificial Sequence
<220> FEATURE:
<223> OTHER INFORMATION: PR004330|pHBM005435|HC; PR004519|pHBM005435|HC;
      PR004522|pHBM005435|HC; PR004525|pHBM005435|HC

<400> SEQUENCE: 270

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 271
<211> LENGTH: 453
<212> TYPE: PRT
<213> ORGANISM: Artificial Sequence
<220> FEATURE:
<223> OTHER INFORMATION: PR004331|pHBM005436|HC

<400> SEQUENCE: 271

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Asn Thr Asn
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Asn Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 272
<211> LENGTH: 453
<212> TYPE: PRT
<213> ORGANISM: Artificial Sequence
<220> FEATURE:
<223> OTHER INFORMATION: PR004332|pHBM005437|HC

<400> SEQUENCE: 272

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Tyr
            100                 105                 110
```

```
Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 273
<211> LENGTH: 453
<212> TYPE: PRT
<213> ORGANISM: Artificial Sequence
<220> FEATURE:
<223> OTHER INFORMATION: PR004333|pHBM005439|HC; PR004520|pHBM005439|HC; PR004523|pHBM005439|HC; PR004526|pHBM005439|HC

<400> SEQUENCE: 273

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Pro Gly Lys
    450


<210> SEQ ID NO 274
<211> LENGTH: 453
<212> TYPE: PRT
<213> ORGANISM: Artificial Sequence
<220> FEATURE:
<223> OTHER INFORMATION: PR004334|pHBM005440|HC

<400> SEQUENCE: 274

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 275
<211> LENGTH: 453
<212> TYPE: PRT
<213> ORGANISM: Artificial Sequence
<220> FEATURE:
<223> OTHER INFORMATION: PR004335|pHBM005441|HC

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 276
<211> LENGTH: 453
<212> TYPE: PRT
<213> ORGANISM: Artificial Sequence
<220> FEATURE:
<223> OTHER INFORMATION: PR004336|pHBM005443|HC; PR004521|pHBM005443|HC; PR004524|pHBM005443|HC; PR004527|pHBM005443|HC

<400> SEQUENCE: 276

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Ser Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Asn Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 277
<211> LENGTH: 453
<212> TYPE: PRT
<213> ORGANISM: Artificial Sequence
<220> FEATURE:
<223> OTHER INFORMATION: PR004337|pHBM005444|HC

<400> SEQUENCE: 277

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Ser Gly Lys Gly Leu Glu Trp Val
        35                  40                  45
```

```
Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 278
<211> LENGTH: 453
<212> TYPE: PRT
<213> ORGANISM: Artificial Sequence
<220> FEATURE:
<223> OTHER INFORMATION: PR004338|pHBM005445|HC

<400> SEQUENCE: 278

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 279
<211> LENGTH: 453
<212> TYPE: PRT
<213> ORGANISM: Artificial Sequence
<220> FEATURE:
<223> OTHER INFORMATION: PR004660|pHBM005788|HC; PR004662|pHBM005788|HC

<400> SEQUENCE: 279

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Asn Ala Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 280
<211> LENGTH: 453
<212> TYPE: PRT
<213> ORGANISM: Artificial Sequence
<220> FEATURE:
<223> OTHER INFORMATION: PR004661|pHBM005789|HC; PR004663|pHBM005789|HC

<400> SEQUENCE: 280

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Ser Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Arg Ala Glu Asp Thr Ala Val Tyr
85 90 95

Tyr Cys Val Arg Gly Lys Glu Gln Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 281
<211> LENGTH: 453
<212> TYPE: PRT
<213> ORGANISM: Artificial Sequence
<220> FEATURE:
<223> OTHER INFORMATION: PR004664|pHBM005786|HC; PR004666|pHBM005786|HC

<400> SEQUENCE: 281

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

```
Leu Tyr Leu Gln Met Asn Ser Leu Lys Thr Glu Asp Thr Ala Val Tyr
                85                  90                  95

Tyr Cys Val Arg Gly Lys Glu Asn Ala Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 282
<211> LENGTH: 453
<212> TYPE: PRT
<213> ORGANISM: Artificial Sequence
<220> FEATURE:
<223> OTHER INFORMATION: PR004665|pHBM005787|HC; PR004667|pHBM005787|HC

<400> SEQUENCE: 282

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Gln Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

```
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 283
<211> LENGTH: 453
<212> TYPE: PRT
<213> ORGANISM: Artificial Sequence
<220> FEATURE:
<223> OTHER INFORMATION: PR004668|pHBM005792|HC

<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
```

```
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 284
<211> LENGTH: 453
<212> TYPE: PRT
<213> ORGANISM: Artificial Sequence
<220> FEATURE:
<223> OTHER INFORMATION: PR004669|pHBM005793|HC

<400> SEQUENCE: 284

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 285
<211> LENGTH: 445
<212> TYPE: PRT
<213> ORGANISM: Artificial Sequence
<220> FEATURE:
<223> OTHER INFORMATION: PR004970|pHBM006115|HC

<400> SEQUENCE: 285

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Pro Gln Ala Pro Gly Lys Gly Leu Glu Trp Val
35 40 45

Ala Asn Ile Lys Gln Asp Gly Ser Ala Lys Phe Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ser Trp Gly Phe Ala Tyr Trp Gly Gln Gly Thr Leu Val Thr
100 105 110

Val Ser Ser Ala Ser Thr Lys Gly Pro Ser Val Phe Pro Leu Ala Pro

```
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 286
<211> LENGTH: 457
<212> TYPE: PRT
<213> ORGANISM: Artificial Sequence
<220> FEATURE:
<223> OTHER INFORMATION: PR004974|pHBM006117|HC

<400> SEQUENCE: 286

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
```

```
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Leu Arg Tyr Ser Gly Arg Tyr Tyr Tyr Tyr Tyr
            100                 105                 110

Gly Thr Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 287
<211> LENGTH: 452
<212> TYPE: PRT
<213> ORGANISM: Artificial Sequence
<220> FEATURE:
<223> OTHER INFORMATION: PR005124|pHBM006274|HC

<400> SEQUENCE: 287

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Trp Cys
                85                  90                  95

Ala Arg His Arg Arg Ser Asp Tyr Trp Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 288
<211> LENGTH: 454
<212> TYPE: PRT
<213> ORGANISM: Artificial Sequence
<220> FEATURE:
<223> OTHER INFORMATION: PR005125|pHBM006276|HC

<400> SEQUENCE: 288

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Val Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Tyr Tyr Gly Ser Gly Asn Tyr Ser Leu Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Glu Glu Met Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly Lys
450

<210> SEQ ID NO 289
<211> LENGTH: 452
<212> TYPE: PRT
<213> ORGANISM: Artificial Sequence
<220> FEATURE:
<223> OTHER INFORMATION: PR005127|pHBM006280|HC

<400> SEQUENCE: 289

Gln Val Gln Leu Val Glu Ser Gly Gly Gly Val Val Gln Pro Gly Arg
1 5 10 15

Ser Leu Arg Leu Ser Cys Val Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp His Asp Gly Ser Asn Ile Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Trp Cys
85 90 95

Ala Arg His Arg Arg Ser Asp Tyr Trp Tyr Tyr Gly Met Asp Val Trp
100 105 110

Gly Gln Gly Thr Thr Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

Gly Gly Pro Asp Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Glu Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 290
<211> LENGTH: 454
<212> TYPE: PRT
<213> ORGANISM: Artificial Sequence
<220> FEATURE:
<223> OTHER INFORMATION: PR005128|pHBM006281|HC

<400> SEQUENCE: 290

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Val Pro Gly Lys Gly Leu Glu Trp Val
35 40 45

Ala Val Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Arg Gly Gly Phe Tyr Tyr Gly Ser Gly Asn Tyr Ser Leu Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Asp Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Glu Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 291
<211> LENGTH: 457
<212> TYPE: PRT
<213> ORGANISM: Artificial Sequence
<220> FEATURE:

<223> OTHER INFORMATION: PR005293|pHBM006504|HC

<400> SEQUENCE: 291

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Leu Arg Tyr Ser Gly Arg Tyr Tyr Tyr Tyr Tyr
            100                 105                 110

Gly Thr Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Asp Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Glu Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn His Tyr Thr Gln
435 440 445

Lys Ser Leu Ser Leu Ser Pro Gly Lys
450 455

<210> SEQ ID NO 292
<211> LENGTH: 453
<212> TYPE: PRT
<213> ORGANISM: Artificial Sequence
<220> FEATURE:
<223> OTHER INFORMATION: PR005329|pHBM006537|HC

<400> SEQUENCE: 292

Glu Val Lys Leu Leu Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Thr Lys Ser Asn Asn Tyr Ala Thr Tyr Tyr Ala Asp
50 55 60

Ser Val Lys Asp Arg Phe Thr Ile Ser Arg Asp Asp Ser His Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Asn Gly Asn Tyr Tyr Ala Met Asp Phe
100 105 110

Trp Gly Gln Gly Thr Ser Val Thr Val Ser Ala Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 293
<211> LENGTH: 453
<212> TYPE: PRT
<213> ORGANISM: Artificial Sequence
<220> FEATURE:
<223> OTHER INFORMATION: PR005330|pHBM006538|HC

<400> SEQUENCE: 293

Glu Val Lys Leu Val Glu Ser Gly Gly Gly Leu Val Gln Pro Gly Gly
1 5 10 15

Ser Arg Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly Lys Asp Tyr Gly Asn Tyr Tyr Ala Met Asp Phe
100 105 110

Trp Gly Gln Gly Thr Ser Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 294
<211> LENGTH: 445
<212> TYPE: PRT
<213> ORGANISM: Artificial Sequence
<220> FEATURE:
<223> OTHER INFORMATION: PR005331|pHBM006539|HC

<400> SEQUENCE: 294

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Leu Ser Trp Val Arg Gln Ala Pro Gly Lys Gly Leu Glu Trp Val
        35                  40                  45

Ala Asn Ile Lys Gln Asp Gly Ser Ala Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asn Trp Gly Phe Asp Tyr Trp Gly Gln Gly Thr Leu Val Thr
            100                 105                 110
```

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 295
<211> LENGTH: 453
<212> TYPE: PRT
<213> ORGANISM: Artificial Sequence
<220> FEATURE:
<223> OTHER INFORMATION: PR005332|pHBM006540|HC

<400> SEQUENCE: 295

Glu Val Lys Leu Leu Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

```
Ala Met Asn Trp Val Arg Gln Ala Pro Gly Lys Gly Leu Glu Trp Val
        35                  40                  45

Ala Arg Ile Arg Thr Lys Ser Asn Asn Tyr Ala Thr Tyr Tyr Ala Asp
    50                  55                  60

Ser Val Lys Asp Arg Phe Thr Ile Ser Arg Asp Asp Ser His Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Asp Asn Gly Asn Tyr Tyr Ala Met Asp Phe
            100                 105                 110

Trp Gly Gln Gly Thr Ser Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
```

450

<210> SEQ ID NO 296
<211> LENGTH: 453
<212> TYPE: PRT
<213> ORGANISM: Artificial Sequence
<220> FEATURE:
<223> OTHER INFORMATION: PR005333|pHBM006541|HC

<400> SEQUENCE: 296

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Lys Asp Tyr Gly Asn Tyr Tyr Ala Met Asp Phe
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln

```
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 297
<211> LENGTH: 445
<212> TYPE: PRT
<213> ORGANISM: Artificial Sequence
<220> FEATURE:
<223> OTHER INFORMATION: PR005335|pHBM006543|HC

<400> SEQUENCE: 297

Gln Val Gln Leu Val Gln Ser Gly Gly Gly Leu Val Gln Pro Gly Gly
1               5                   10                  15

Ser Leu Arg Leu Ser Cys Thr Ala Ser Gly Phe Thr Phe Ser Tyr Tyr
            20                  25                  30

Trp Leu Ser Trp Val Arg Gln Ala Pro Gly Lys Gly Leu Glu Trp Val
        35                  40                  45

Ala Asn Ile Lys Gln Asp Gly Ser Thr Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
```

```
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 298
<211> LENGTH: 445
<212> TYPE: PRT
<213> ORGANISM: Artificial Sequence
<220> FEATURE:
<223> OTHER INFORMATION: PR005336|pHBM006544|HC

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Leu Ser Trp Val Arg Gln Ala Pro Gly Lys Gly Leu Glu Trp Val
        35                  40                  45

Ala Asn Ile Lys Gln Asp Gly Ser Ala Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asn Trp Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

```
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 299
<211> LENGTH: 453
<212> TYPE: PRT
<213> ORGANISM: Artificial Sequence
<220> FEATURE:
<223> OTHER INFORMATION: PR005565|pHBM006805|HC

<400> SEQUENCE: 299

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Ala Asn Tyr Tyr Ala Met Asp Phe
```

```
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 300
<211> LENGTH: 226
<212> TYPE: PRT
<213> ORGANISM: Artificial Sequence
<220> FEATURE:
<223> OTHER INFORMATION: PR005750|pHBM007021|HC

<400> SEQUENCE: 300

Glu Val Gln Leu Val Glu Ser Gly Gly Gly Leu Val Lys Pro Gly Gly
```

```
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Asn Ala Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

<210> SEQ ID NO 301
<211> LENGTH: 226
<212> TYPE: PRT
<213> ORGANISM: Artificial Sequence
<220> FEATURE:
<223> OTHER INFORMATION: PR005751|pHBM007019|HC

<400> SEQUENCE: 301

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 302
<211> LENGTH: 226
<212> TYPE: PRT
<213> ORGANISM: Artificial Sequence
<220> FEATURE:
<223> OTHER INFORMATION: PR005752|pHBM007009|HC

<400> SEQUENCE: 302

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 303
<211> LENGTH: 226
<212> TYPE: PRT
```

<213> ORGANISM: Artificial Sequence
<220> FEATURE:
<223> OTHER INFORMATION: PR005753|pHBM007020|HC

<400> SEQUENCE: 303

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

<210> SEQ ID NO 304
<211> LENGTH: 226
<212> TYPE: PRT
<213> ORGANISM: Artificial Sequence
<220> FEATURE:
<223> OTHER INFORMATION: PR005754|pHBM007010|HC

<400> SEQUENCE: 304

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95
```

Tyr Cys Val Arg Gly Lys Glu Ile Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys
225

<210> SEQ ID NO 305
<211> LENGTH: 226
<212> TYPE: PRT
<213> ORGANISM: Artificial Sequence
<220> FEATURE:
<223> OTHER INFORMATION: PR005763|pHBM007005|HC

<400> SEQUENCE: 305

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu His Gly Lys Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys
225

<210> SEQ ID NO 306
<211> LENGTH: 226
<212> TYPE: PRT
<213> ORGANISM: Artificial Sequence
<220> FEATURE:
<223> OTHER INFORMATION: PR005787|pHBM007006|HC

<400> SEQUENCE: 306

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Ile Gly Lys Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys
225

<210> SEQ ID NO 307
<211> LENGTH: 453
<212> TYPE: PRT
<213> ORGANISM: Artificial Sequence
<220> FEATURE:
<223> OTHER INFORMATION: PR006154|pHBM007001|HC

<400> SEQUENCE: 307

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

```
Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 308
<211> LENGTH: 453

<212> TYPE: PRT
<213> ORGANISM: Artificial Sequence
<220> FEATURE:
<223> OTHER INFORMATION: PR006155|pHBM006991|HC

<400> SEQUENCE: 308

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu His Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 309
<211> LENGTH: 453
<212> TYPE: PRT
<213> ORGANISM: Artificial Sequence
<220> FEATURE:
<223> OTHER INFORMATION: PR006156|pHBM007002|HC

<400> SEQUENCE: 309

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Ile Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Asp Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Glu Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 310
<211> LENGTH: 453
<212> TYPE: PRT
<213> ORGANISM: Artificial Sequence
<220> FEATURE:
<223> OTHER INFORMATION: PR006157|pHBM006992|HC

<400> SEQUENCE: 310

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu Ile Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

```
Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 311
<211> LENGTH: 453
<212> TYPE: PRT
<213> ORGANISM: Artificial Sequence
<220> FEATURE:
<223> OTHER INFORMATION: PR006161|pHBM006987|HC

<400> SEQUENCE: 311

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95
```

```
Tyr Cys Val Arg Gly Lys Glu His Gly Lys Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 312
<211> LENGTH: 453
<212> TYPE: PRT
<213> ORGANISM: Artificial Sequence
<220> FEATURE:
<223> OTHER INFORMATION: PR006166|pHBM006988|HC

<400> SEQUENCE: 312

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Lys Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
```

420 425 430

Val Met His Glu Ala Leu His Asn His Tyr Thr Gln Lys Ser Leu Ser
435 440 445

Leu Ser Pro Gly Lys
450

<210> SEQ ID NO 313
<211> LENGTH: 453
<212> TYPE: PRT
<213> ORGANISM: Artificial Sequence
<220> FEATURE:
<223> OTHER INFORMATION: PR006272|pHBM007521|HC

<400> SEQUENCE: 313

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu His Gly Asn Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala

```
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 314
<211> LENGTH: 453
<212> TYPE: PRT
<213> ORGANISM: Artificial Sequence
<220> FEATURE:
<223> OTHER INFORMATION: PR006273|pHBM007522|HC

<400> SEQUENCE: 314

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
```

225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 315
<211> LENGTH: 453
<212> TYPE: PRT
<213> ORGANISM: Artificial Sequence
<220> FEATURE:
<223> OTHER INFORMATION: PR006274|pHBM007523|HC

<400> SEQUENCE: 315

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ser Asn Tyr Tyr Ala Thr Tyr Tyr Ala Asp
50 55 60

Ser Val Lys Asp Arg Phe Thr Ile Ser Arg Asp Asp Ser Lys Ser Thr
65 70 75 80

Leu Tyr Leu Gln Met Asn Ser Leu Lys Thr Glu Asp Thr Ala Val Tyr
85 90 95

Tyr Cys Val Arg Gly Lys Glu His Gly Lys Tyr Tyr Ala Met Asp Phe
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly

```
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 316
<211> LENGTH: 453
<212> TYPE: PRT
<213> ORGANISM: Artificial Sequence
<220> FEATURE:
<223> OTHER INFORMATION: PR006275|pHBM007524|HC

<400> SEQUENCE: 316

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
```

```
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Lys Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 317
<211> LENGTH: 453
<212> TYPE: PRT
<213> ORGANISM: Artificial Sequence
<220> FEATURE:
<223> OTHER INFORMATION: PR006276|pHBM007525|HC

<400> SEQUENCE: 317

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu His Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 318
<211> LENGTH: 453
<212> TYPE: PRT
<213> ORGANISM: Artificial Sequence
<220> FEATURE:
<223> OTHER INFORMATION: PR006277|pHBM007526|HC

<400> SEQUENCE: 318

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Tyr Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg Gly Lys Glu Ile Gly Asn Tyr Tyr Ala Met Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 319
<211> LENGTH: 219
<212> TYPE: PRT
<213> ORGANISM: Artificial Sequence
<220> FEATURE:
<223> OTHER INFORMATION: PR004120|pHBM005098|LC

<400> SEQUENCE: 319

Asp Ile Val Met Thr Gln Ala Ala Thr Ser Val Leu Val Thr Pro Gly
1 5 10 15

Glu Ser Val Ser Ile Ser Cys Arg Ser Ser Lys Ser Leu Leu Tyr Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 320
<211> LENGTH: 219
<212> TYPE: PRT
<213> ORGANISM: Artificial Sequence
<220> FEATURE:
<223> OTHER INFORMATION: PR004121|pHBM005099|LC

<400> SEQUENCE: 320

Asp Ile Val Ile Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gly Gly Thr Lys Leu Glu Met Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 321
<211> LENGTH: 219
<212> TYPE: PRT
<213> ORGANISM: Artificial Sequence
<220> FEATURE:
<223> OTHER INFORMATION: PR004122|pHBM005100|LC; PR004249|pHBM005100|LC

<400> SEQUENCE: 321

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser 35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Leu Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 322
<211> LENGTH: 219
<212> TYPE: PRT
<213> ORGANISM: Artificial Sequence
<220> FEATURE:
<223> OTHER INFORMATION: PR004123|pHBM005101|LC

<400> SEQUENCE: 322

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gly Gly Thr Lys Leu Glu Leu Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu 180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 323
<211> LENGTH: 219
<212> TYPE: PRT
<213> ORGANISM: Artificial Sequence
<220> FEATURE:
<223> OTHER INFORMATION: PR004124|pHBM005102|LC

<400> SEQUENCE: 323

Asp Ile Val Met Thr Gln Asp Glu Leu Ser Asn Pro Val Thr Ser Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 324
<211> LENGTH: 219
<212> TYPE: PRT
<213> ORGANISM: Artificial Sequence
<220> FEATURE:
<223> OTHER INFORMATION: PR004125|pHBM005103|LC; PR004250|pHBM005103|LC

<400> SEQUENCE: 324

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

```
Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Met Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 325
<211> LENGTH: 219
<212> TYPE: PRT
<213> ORGANISM: Artificial Sequence
<220> FEATURE:
<223> OTHER INFORMATION: PR004126|pHBM005104|LC

<400> SEQUENCE: 325

Asp Ile Val Ile Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 326
<211> LENGTH: 219
<212> TYPE: PRT
<213> ORGANISM: Artificial Sequence
<220> FEATURE:
<223> OTHER INFORMATION: PR004127|pHBM005105|LC

<400> SEQUENCE: 326

Asp Ile Val Met Thr Gln Ala Ala Thr Ser Val Leu Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Met Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 327
<211> LENGTH: 219
<212> TYPE: PRT
<213> ORGANISM: Artificial Sequence
<220> FEATURE:
<223> OTHER INFORMATION: PR004128|pHBM005106|LC; PR004251|pHBM005106|LC;
      PR004326|pHBM005106|LC; PR004327|pHBM005106|LC;
      PR004328|pHBM005106|LC; PR004329|pHBM005106|LC;
      PR004330|pHBM005106|LC; PR004331|pHBM005106|LC;
      PR004332|pHBM005106|LC; PR004333|pHBM005106|LC;
      PR004334|pHBM005106|LC; PR004335|pHBM005106|LC;
      PR004336|pHBM005106|LC; PR004337|pHBM005106|LC;
      PR004338|pHBM005106|LC

<400> SEQUENCE: 327

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser

```
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 328
<211> LENGTH: 219
<212> TYPE: PRT
<213> ORGANISM: Artificial Sequence
<220> FEATURE:
<223> OTHER INFORMATION: PR004129|pHBM005107|LC

<400> SEQUENCE: 328

Asp Ile Leu Leu Thr Gln Ser Pro Ala Ile Leu Ser Val Ser Pro Gly
1               5                   10                  15

Glu Arg Val Ser Phe Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Asn
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 329
<211> LENGTH: 219
<212> TYPE: PRT
<213> ORGANISM: Artificial Sequence
<220> FEATURE:
<223> OTHER INFORMATION: PR004130|pHBM005108|LC

<400> SEQUENCE: 329

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 330
<211> LENGTH: 219
<212> TYPE: PRT
<213> ORGANISM: Artificial Sequence
<220> FEATURE:
<223> OTHER INFORMATION: PR004131|pHBM005109|LC; PR004252|pHBM005109|LC

<400> SEQUENCE: 330

Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
            20                  25                  30
```

```
Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 331
<211> LENGTH: 220
<212> TYPE: PRT
<213> ORGANISM: Artificial Sequence
<220> FEATURE:
<223> OTHER INFORMATION: PR004264|pHBM005402|LC

<400> SEQUENCE: 331

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Ile Thr Phe Gly Gln Gly Thr Arg Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 332
<211> LENGTH: 213
<212> TYPE: PRT
<213> ORGANISM: Artificial Sequence
<220> FEATURE:
<223> OTHER INFORMATION: PR004265|pHBM005404|LC

<400> SEQUENCE: 332

Asp Ile Val Leu Ile Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 333
<211> LENGTH: 214
<212> TYPE: PRT
<213> ORGANISM: Artificial Sequence
<220> FEATURE:
<223> OTHER INFORMATION: PR004275|pHBM005296|LC

<400> SEQUENCE: 333

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Pro
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 334
<211> LENGTH: 219
<212> TYPE: PRT
<213> ORGANISM: Artificial Sequence
<220> FEATURE:
<223> OTHER INFORMATION: PR004324|pHBM005456|LC

<400> SEQUENCE: 334

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Ala Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 335
<211> LENGTH: 219
<212> TYPE: PRT
<213> ORGANISM: Artificial Sequence
<220> FEATURE:
<223> OTHER INFORMATION: PR004325|pHBM005457|LC

<400> SEQUENCE: 335

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Gln Gly Lys Ile Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Leu Thr Phe Gly Ala Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 336
<211> LENGTH: 219
<212> TYPE: PRT
<213> ORGANISM: Artificial Sequence
<220> FEATURE:
<223> OTHER INFORMATION: LC

<400> SEQUENCE: 336

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Lys Ile Tyr Leu Tyr Trp Phe Leu Gln Lys Pro Gly Gln Ser
35 40 45

Pro Gln Leu Leu Ile Tyr Arg Met Ser Asn Leu Ala Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 337
<211> LENGTH: 219
<212> TYPE: PRT
<213> ORGANISM: Artificial Sequence
<220> FEATURE:
<223> OTHER INFORMATION: PR004340|pHBM005448|LC; PR004522|pHBM005448|LC;
      PR004523|pHBM005448|LC; PR004524|pHBM005448|LC

<400> SEQUENCE: 337

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 338
<211> LENGTH: 219
<212> TYPE: PRT
<213> ORGANISM: Artificial Sequence
<220> FEATURE:
<223> OTHER INFORMATION: PR004342|pHBM005450|LC

<400> SEQUENCE: 338

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 339
<211> LENGTH: 219
<212> TYPE: PRT
<213> ORGANISM: Artificial Sequence
<220> FEATURE:
<223> OTHER INFORMATION: PR004343|pHBM005452|LC; PR004525|pHBM005452|LC;
      PR004526|pHBM005452|LC; PR004527|pHBM005452|LC;
      PR004664|pHBM005452|LC; PR004665|pHBM005452|LC;
      PR004669|pHBM005452|LC

<400> SEQUENCE: 339

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu His Ser
            20                  25                  30

Asn Gly Lys Ile Tyr Leu Tyr Trp Phe Gln Gln Arg Pro Gly Gln Ser
        35                  40                  45
```

Pro Arg Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 340
<211> LENGTH: 219
<212> TYPE: PRT
<213> ORGANISM: Artificial Sequence
<220> FEATURE:
<223> OTHER INFORMATION: PR004344|pHBM005453|LC

<400> SEQUENCE: 340

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu His Ser
            20                  25                  30

Asn Gly Asn Thr Tyr Leu Tyr Trp Phe Gln Gln Arg Pro Gly Gln Ser
        35                  40                  45

Pro Arg Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 341
<211> LENGTH: 219
<212> TYPE: PRT
<213> ORGANISM: Artificial Sequence
<220> FEATURE:
<223> OTHER INFORMATION: PR004345|pHBM005454|LC

<400> SEQUENCE: 341

Asp Ile Val Met Thr Gln Ser Pro Leu Ser Leu Pro Val Thr Leu Gly
1 5 10 15

Gln Pro Ala Ser Ile Ser Cys Arg Ser Asn Lys Ser Leu Leu His Ser
20 25 30

Asn Gly Asn Thr Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 342
<211> LENGTH: 219
<212> TYPE: PRT
<213> ORGANISM: Artificial Sequence
<220> FEATURE:
<223> OTHER INFORMATION: PR004346|pHBM005455|LC

<400> SEQUENCE: 342

Asp Ile Val Met Thr Gln Ser Pro Leu Ser Leu Pro Val Thr Leu Gly
1 5 10 15

Gln Pro Ala Ser Ile Ser Cys Arg Ser Ser Lys Ser Leu Leu His Ser
20 25 30

Asn Gly Asn Thr Tyr Leu Tyr Trp Phe Gln Gln Arg Pro Gly Gln Ser
35 40 45

Pro Arg Leu Leu Ile Tyr Arg Met Ser Asn Leu Ala Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 343
<211> LENGTH: 219
<212> TYPE: PRT
<213> ORGANISM: Artificial Sequence
<220> FEATURE:
<223> OTHER INFORMATION: PR004662|pHBM005790|LC; PR004663|pHBM005790|LC

<400> SEQUENCE: 343

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Lys Ile Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

195                 200                 205

Pro Val Thr Lys Ser Phe Asn Arg Gly Glu Cys
    210                 215

<210> SEQ ID NO 344
<211> LENGTH: 219
<212> TYPE: PRT
<213> ORGANISM: Artificial Sequence
<220> FEATURE:
<223> OTHER INFORMATION: LC

<400> SEQUENCE: 344

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu His Ser
            20                  25                  30

Asn Ala Lys Ile Tyr Leu Tyr Trp Phe Gln Gln Arg Pro Gly Gln Ser
        35                  40                  45

Pro Arg Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 345
<211> LENGTH: 214
<212> TYPE: PRT
<213> ORGANISM: Artificial Sequence
<220> FEATURE:
<223> OTHER INFORMATION: PR004970|pHBM006122|LC

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65 70 75 80

Glu Asp Val Ala Thr Tyr Tyr Cys Gln Lys Tyr Asn Ser Ala Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 346
<211> LENGTH: 214
<212> TYPE: PRT
<213> ORGANISM: Artificial Sequence
<220> FEATURE:
<223> OTHER INFORMATION: PR004974|pHBM006126|LC; PR005293|pHBM006126|LC

<400> SEQUENCE: 346

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Val Trp Tyr Gln Gln Lys Pro Gly Gln Ala Pro Arg Leu Leu Ile
35 40 45

Tyr Gly Ala Ser Ile Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 347
<211> LENGTH: 219
<212> TYPE: PRT
<213> ORGANISM: Artificial Sequence
<220> FEATURE:
<223> OTHER INFORMATION: PR005124|pHBM006275|LC; PR005127|pHBM006275|LC

<400> SEQUENCE: 347

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Tyr Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 348
<211> LENGTH: 218
<212> TYPE: PRT
<213> ORGANISM: Artificial Sequence
<220> FEATURE:
<223> OTHER INFORMATION: PR005125|pHBM006277|LC; PR005128|pHBM006277|LC

<400> SEQUENCE: 348

Asp Ile Val Met Thr Gln Ser Pro Leu Ser Leu Ser Val Thr Leu Gly
1 5 10 15

Gln Pro Ala Ser Ile Ser Cys Arg Ser Ser Gln Ser Leu Val Phe Ser
20 25 30

Asn Gly Asn Thr Tyr Leu Asn Trp Phe Gln Gln Arg Pro Gly Gln Ser
35 40 45

Pro Arg Arg Leu Ile Tyr Lys Val Ser Lys Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Ile Thr Phe Gly Gln Gly Thr Arg Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 349
<211> LENGTH: 219
<212> TYPE: PRT
<213> ORGANISM: Artificial Sequence
<220> FEATURE:
<223> OTHER INFORMATION: PR005170|pHBM006323|LC

<400> SEQUENCE: 349

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Ser
20 25 30

Asn Gly Lys Ile Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Ile Thr Phe Gly Ala Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 350
<211> LENGTH: 219
<212> TYPE: PRT
<213> ORGANISM: Artificial Sequence
<220> FEATURE:
<223> OTHER INFORMATION: PR005171|pHBM006324|LC

<400> SEQUENCE: 350

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Met Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 351
<211> LENGTH: 219
<212> TYPE: PRT
<213> ORGANISM: Artificial Sequence
<220> FEATURE:
<223> OTHER INFORMATION: PR005172|pHBM006325|LC

<400> SEQUENCE: 351

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
```

```
                85                  90                  95

Leu Glu Tyr Pro Val Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 352
<211> LENGTH: 219
<212> TYPE: PRT
<213> ORGANISM: Artificial Sequence
<220> FEATURE:
<223> OTHER INFORMATION: PR005329|pHBM006545|LC; PR005332|pHBM006545|LC

<400> SEQUENCE: 352

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 353
<211> LENGTH: 219
<212> TYPE: PRT
<213> ORGANISM: Artificial Sequence
<220> FEATURE:
<223> OTHER INFORMATION: PR005330|pHBM006546|LC; PR005333|pHBM006546|LC

<400> SEQUENCE: 353

```
Asp Ile Val Met Thr Gln Ala Ala Thr Ser Val Leu Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 354
<211> LENGTH: 219
<212> TYPE: PRT
<213> ORGANISM: Artificial Sequence
<220> FEATURE:
<223> OTHER INFORMATION: PR005331|pHBM006549|LC; PR005336|pHBM006549|LC

<400> SEQUENCE: 354

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95
```

```
Thr His Trp Pro Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 355
<211> LENGTH: 219
<212> TYPE: PRT
<213> ORGANISM: Artificial Sequence
<220> FEATURE:
<223> OTHER INFORMATION: PR005335|pHBM006548|LC

<400> SEQUENCE: 355

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 356
<211> LENGTH: 330
```

<212> TYPE: PRT
<213> ORGANISM: Artificial Sequence
<220> FEATURE:
<223> OTHER INFORMATION: human IgG1 constant region

<400> SEQUENCE: 356

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 357
<211> LENGTH: 330
<212> TYPE: PRT
<213> ORGANISM: Artificial Sequence
<220> FEATURE:
<223> OTHER INFORMATION: human IgG1 constant region(S239D,I332E)

<400> SEQUENCE: 357

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Asp Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Glu Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 358
<211> LENGTH: 107
<212> TYPE: PRT
<213> ORGANISM: Artificial Sequence
<220> FEATURE:
<223> OTHER INFORMATION: IgK constant region

<400> SEQUENCE: 358

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 359
<211> LENGTH: 7
<212> TYPE: PRT
<213> ORGANISM: Artificial Sequence
<220> FEATURE:
<223> OTHER INFORMATION: general formula of HCDR1 of monkey cross-binding activity antibody
<220> FEATURE:
<221> NAME/KEY: misc_feature
<222> LOCATION: (5)..(5)
<223> OTHER INFORMATION: Xaa = Asn, Gln or Ser
<220> FEATURE:
<221> NAME/KEY: misc_feature
<222> LOCATION: (7)..(7)
<223> OTHER INFORMATION: Xaa = Asn or Tyr

<400> SEQUENCE: 359

Gly Phe Thr Phe Xaa Thr Xaa
1 5

<210> SEQ ID NO 360
<211> LENGTH: 12
<212> TYPE: PRT
<213> ORGANISM: Artificial Sequence
<220> FEATURE:
<223> OTHER INFORMATION: general formula of HCDR3 of monkey cross-binding activity antibody
<220> FEATURE:
<221> NAME/KEY: misc_feature
<222> LOCATION: (4)..(4)
<223> OTHER INFORMATION: Xaa = Asn or Gln
<220> FEATURE:
<221> NAME/KEY: misc_feature
<222> LOCATION: (5)..(5)
<223> OTHER INFORMATION: Xaa = Ala or Gly
<220> FEATURE:
<221> NAME/KEY: misc_feature
<222> LOCATION: (12)..(12)
<223> OTHER INFORMATION: Xaa = Phe or Tyr

<400> SEQUENCE: 360

Gly Lys Glu Xaa Xaa Asn Tyr Tyr Ala Met Asp Xaa
1 5 10

<210> SEQ ID NO 361
<211> LENGTH: 16
<212> TYPE: PRT
<213> ORGANISM: Artificial Sequence
<220> FEATURE:
<223> OTHER INFORMATION: general formula of LCDR1 of monkey cross-binding activity antibody
<220> FEATURE:
<221> NAME/KEY: misc_feature
<222> LOCATION: (3)..(3)
<223> OTHER INFORMATION: Xaa = Asn or Ser
<220> FEATURE:
<221> NAME/KEY: misc_feature
<222> LOCATION: (10)..(10)

<223> OTHER INFORMATION: Xaa = Asn or Gln
<220> FEATURE:
<221> NAME/KEY: misc_feature
<222> LOCATION: (11)..(11)
<223> OTHER INFORMATION: Xaa = Ala or Gly
<220> FEATURE:
<221> NAME/KEY: misc_feature
<222> LOCATION: (12)..(12)
<223> OTHER INFORMATION: Xaa = Lys or Asn
<220> FEATURE:
<221> NAME/KEY: misc_feature
<222> LOCATION: (13)..(13)
<223> OTHER INFORMATION: Xaa = Ile or Thr

<400> SEQUENCE: 361

```
Arg Ser Xaa Lys Ser Leu Leu His Ser Xaa Xaa Xaa Xaa Tyr Leu Tyr
1               5                   10                  15
```

<210> SEQ ID NO 362
<211> LENGTH: 9
<212> TYPE: PRT
<213> ORGANISM: Artificial Sequence
<220> FEATURE:
<223> OTHER INFORMATION: general formula of LCDR3 of monkey
cross-binding activity antibody
<220> FEATURE:
<221> NAME/KEY: misc_feature
<222> LOCATION: (8)..(8)
<223> OTHER INFORMATION: Xaa = Ile, Leu, Met or Val

<400> SEQUENCE: 362

```
Met Gln His Leu Glu Tyr Pro Xaa Thr
1               5
```

<210> SEQ ID NO 363
<211> LENGTH: 7
<212> TYPE: PRT
<213> ORGANISM: Artificial Sequence
<220> FEATURE:
<223> OTHER INFORMATION: general formula of HCDR1 of non-monkey
cross-binding activity antibody
<220> FEATURE:
<221> NAME/KEY: misc_feature
<222> LOCATION: (1)..(1)
<223> OTHER INFORMATION: Xaa = Glu or Gly
<220> FEATURE:
<221> NAME/KEY: misc_feature
<222> LOCATION: (5)..(5)
<223> OTHER INFORMATION: Xaa = Asn or Ser
<220> FEATURE:
<221> NAME/KEY: misc_feature
<222> LOCATION: (7)..(7)
<223> OTHER INFORMATION: Xaa = Asn or Tyr

<400> SEQUENCE: 363

```
Xaa Phe Thr Phe Xaa Thr Xaa
1               5
```

<210> SEQ ID NO 364
<211> LENGTH: 8
<212> TYPE: PRT
<213> ORGANISM: Artificial Sequence
<220> FEATURE:
<223> OTHER INFORMATION: general formula of HCDR2 of non-monkey
cross-binding activity antibody
<220> FEATURE:
<221> NAME/KEY: misc_feature
<222> LOCATION: (2)..(2)
<223> OTHER INFORMATION: Xaa = Ser or Thr
<220> FEATURE:
<221> NAME/KEY: misc_feature
<222> LOCATION: (4)..(4)
<223> OTHER INFORMATION: Xaa = Met or Ser
<220> FEATURE:
<221> NAME/KEY: misc_feature
<222> LOCATION: (7)..(7)
<223> OTHER INFORMATION: Xaa = Phe or Tyr

<400> SEQUENCE: 364

Arg Xaa Lys Xaa Asn Asn Xaa Ala
1 5

<210> SEQ ID NO 365
<211> LENGTH: 12
<212> TYPE: PRT
<213> ORGANISM: Artificial Sequence
<220> FEATURE:
<223> OTHER INFORMATION: general formula of HCDR3 of non-monkey cross-binding activity antibody
<220> FEATURE:
<221> NAME/KEY: misc_feature
<222> LOCATION: (3)..(3)
<223> OTHER INFORMATION: Xaa = Asp or Glu
<220> FEATURE:
<221> NAME/KEY: misc_feature
<222> LOCATION: (4)..(4)
<223> OTHER INFORMATION: Xaa = Asn or Tyr
<220> FEATURE:
<221> NAME/KEY: misc_feature
<222> LOCATION: (12)..(12)
<223> OTHER INFORMATION: Xaa = Phe or Tyr

<400> SEQUENCE: 365

Gly Lys Xaa Xaa Gly Asn Tyr Tyr Ala Met Asp Xaa
1 5 10

<210> SEQ ID NO 366
<211> LENGTH: 16
<212> TYPE: PRT
<213> ORGANISM: Artificial Sequence
<220> FEATURE:
<223> OTHER INFORMATION: general formula of LCDR1 of non-monkey cross-binding activity antibody
<220> FEATURE:
<221> NAME/KEY: misc_feature
<222> LOCATION: (8)..(8)
<223> OTHER INFORMATION: Xaa = His or Tyr

<400> SEQUENCE: 366

Arg Ser Ser Lys Ser Leu Leu Xaa Ser Asn Gly Asn Thr Tyr Leu Tyr
1 5 10 15

<210> SEQ ID NO 367
<211> LENGTH: 8
<212> TYPE: PRT
<213> ORGANISM: Artificial Sequence
<220> FEATURE:
<223> OTHER INFORMATION: general formula of HCDR2 of PR4666 mutant
<220> FEATURE:
<221> NAME/KEY: misc_feature
<222> LOCATION: (6)..(6)
<223> OTHER INFORMATION: Xaa = Asn or Tyr

<400> SEQUENCE: 367

Arg Ser Lys Ser Asn Xaa Tyr Ala
1 5

<210> SEQ ID NO 368
<211> LENGTH: 12
<212> TYPE: PRT
<213> ORGANISM: Artificial Sequence
<220> FEATURE:
<223> OTHER INFORMATION: general formula of HCDR3 of PR4666 mutant
<220> FEATURE:

```
<221> NAME/KEY: misc_feature
<222> LOCATION: (4)..(4)
<223> OTHER INFORMATION: Xaa = His, Ile or Asn
<220> FEATURE:
<221> NAME/KEY: misc_feature
<222> LOCATION: (5)..(5)
<223> OTHER INFORMATION: Xaa = Ala or Gly
<220> FEATURE:
<221> NAME/KEY: misc_feature
<222> LOCATION: (6)..(6)
<223> OTHER INFORMATION: Xaa = Lys or Asn

<400> SEQUENCE: 368

Gly Lys Glu Xaa Xaa Xaa Tyr Tyr Ala Met Asp Phe
1               5                   10
```

CCR8 ANTIBODY AND APPLICATION THEREOF

CROSS REFERENCE TO RELATED APPLICATIONS

The present application is a United States National Phase under 35 U.S.C. § 371 of International Application No. PCT/CN2021/115061, filed Aug. 27, 2021, which claims priority to Chinese Patent Application No. 202010888581.2, filed on Aug. 28, 2020.

REFERENCE TO SEQUENCE LISTING

The application contains a Sequence Listing that has been filed electronically in the form of a text file, created Feb. 27, 2023, and named "C22W3295-sequence listing in En.TXT" (494,077 bytes), the contents of which are incorporated by reference herein in their entirety.

TECHNICAL FIELD

The present invention relates to the technical field of biomedicine or biopharmaceutical, and particularly relates to an anti-CCR8 monoclonal antibody molecule and use thereof.

BACKGROUND

Tumor-infiltrating $CD4^{+}FoxP3^{+}$ regulatory cells (Tregs) are one of the major cell populations that play an immunosuppressive role in the tumor microenvironment (TME). It has been well demonstrated that systemic removal of cells including tumor-infiltrating $CD4^{+}FoxP3^{+}$ Tregs can enhance the anti-tumor effect on a large number of mouse tumor models.

Chemokine receptor CCR8, also known as CY6, CKR-L1 or TER1, is a G-protein coupled seven-transmembrane protein. In humans and mice, it is found to be predominantly expressed on Tregs, to a lesser extent on Th2, and not on Th1. In breast cancer, the expression of human CCR8 is high on Tregs residing at the tumor site as compared to that in normal tissue and peripheral blood, and this fraction of $CCR8^{+}$ Treg cells has been shown to be a population of cells that play a major role in immunosuppression. Upon analysis, the high expression of CCR8 is positively correlated with survival rates of various tumors, including breast cancer, kidney cancer, pancreatic cancer, bladder cancer, gastric cancer, cervical cancer, colon cancer and the like.

CCL1 is one of the major ligands for endogenous expression of CCR8. CCL1 is overexpressed in various tumor tissues and recruits Treg cells expressing CCR8 to infiltrate tumor tissues. By blocking the action of CCL1-CCR8, the immunosuppression caused by Tregs can be blocked, so that the anti-tumor effect is increased.

Targeting CCR8 to remove $CCR8^{+}$ Tregs from the tumor environment or blocking CCL1-mediated migration of $CCR8^{+}$ Tregs to tumor tissue may be a potential new avenue for tumor immunotherapy.

SUMMARY

The present application provides an isolated antigen-binding protein, which is capable of binding to CCR8 derived from a primate (human and/or monkey), blocking the binding of CCR8 to its ligand CCL1, blocking intracellular calcium flux signals caused by CCL1, and preventing cell migration caused by CCL1, and has ADCC reporter gene biological activity and NK cell-mediated ADCC biological activity. The isolated antigen-binding protein of the present application can also specifically targets tumor issue-infiltrating Treg cells with immunosuppressive activity, and shows significant anti-tumor activity in animal experiments.

In one aspect, the present application provides an isolated antigen-binding protein, which comprises an antibody heavy chain or a fragment thereof, wherein the antibody heavy chain or the fragment thereof comprises an HCDR1, an HCDR2 and an HCDR3, wherein the HCDR1 comprises an amino acid sequence set forth in SEQ ID NO: 359, the HCDR2 comprises an amino acid sequence set forth in SEQ ID NO: 38, and the HCDR3 comprises an amino acid sequence set forth in SEQ ID NO: 360. In certain embodiments, the HCDR1 comprises an amino acid sequence set forth in any one of SEQ ID NOs: 15, 16, 21 and 22, the HCDR2 comprises an amino acid sequence set forth in SEQ ID NO: 38, and the HCDR3 comprises an amino acid sequence set forth in any one of SEQ ID NOs: 65, 68, 72 and 73.

In certain embodiments, the HCDR1, HCDR2 and HCDR3 comprise amino acid sequences selected from any one of the following groups:

(1) HCDR1: SEQ ID NO: 15, HCDR2: SEQ ID NO: 38, and HCDR3: SEQ ID NO: 65;

(2) HCDR1: SEQ ID NO: 16, HCDR2: SEQ ID NO: 38, and HCDR3: SEQ ID NO: 65;

(3) HCDR1: SEQ ID NO: 16, HCDR2: SEQ ID NO: 38, and HCDR3: SEQ ID NO: 68;

(4) HCDR1: SEQ ID NO: 16, HCDR2: SEQ ID NO: 38, and HCDR3: SEQ ID NO: 72;

(5) HCDR1: SEQ ID NO: 16, HCDR2: SEQ ID NO: 38, and HCDR3: SEQ ID NO: 73;

(6) HCDR1: SEQ ID NO: 21, HCDR2: SEQ ID NO: 38, and HCDR3: SEQ ID NO: 65;

(7) HCDR1: SEQ ID NO: 22, HCDR2: SEQ ID NO: 38, and HCDR3: SEQ ID NO: 65;

(8) HCDR1: SEQ ID NO: 22, HCDR2: SEQ ID NO: 38, and HCDR3: SEQ ID NO: 72; and (9) HCDR1: SEQ ID NO: 22, HCDR2: SEQ ID NO: 38, and HCDR3: SEQ ID NO: 73.

In certain embodiments, the antigen-binding protein comprises an antibody heavy chain variable region VH, wherein the VH comprises an amino acid sequence set forth in any one of SEQ ID NOs: 169, 172, 177 and 181-197.

In certain embodiments, the antigen-binding protein further comprises an antibody heavy chain constant region.

In certain embodiments, the heavy chain constant region is derived from a human IgG constant region.

In certain embodiments, the heavy chain constant region is derived from a human IgG1 constant region.

In certain embodiments, the heavy chain constant region comprises an amino acid sequence set forth in any one of SEQ ID NOs: 356-357.

In certain embodiments, the antigen-binding protein comprises an antibody heavy chain, wherein the antibody heavy chain comprises an amino acid sequence set forth in any one of SEQ ID NOs: 251, 254, 259-262 and 266-284.

In certain embodiments, the antigen-binding protein comprises an antibody light chain or a fragment thereof, wherein the antibody light chain or the fragment thereof comprises an LCDR1, an LCDR2 and an LCDR3, wherein the LCDR1 comprises an amino acid sequence set forth in SEQ ID NO: 361, the LCDR2 comprises an amino acid sequence set forth in SEQ ID NO: 127, and the LCDR3 comprises an amino acid sequence set forth in SEQ ID NO: 362.

In certain embodiments, the LCDR1 comprises an amino acid sequence set forth in any one of SEQ ID NOs: 105, 106, 107, 111 and 112, the LCDR2 comprises an amino acid sequence set forth in SEQ ID NO: 127, and the LCDR3 comprises an amino acid sequence set forth in any one of SEQ ID NOs: 142, 150, 151 and 152.

In certain embodiments, the LCDR1, LCDR2 and LCDR3 comprise amino acid sequences selected from any one of the following groups:

(1) LCDR1: SEQ ID NO: 105, LCDR2: SEQ ID NO: 127, and LCDR3: SEQ ID NO: 142;

(2) LCDR1: SEQ ID NO: 106, LCDR2: SEQ ID NO: 127, and LCDR3: SEQ ID NO: 142;

(3) LCDR1: SEQ ID NO: 106, LCDR2: SEQ ID NO: 127, and LCDR3: SEQ ID NO: 150;

(4) LCDR1: SEQ ID NO: 106, LCDR2: SEQ ID NO: 127, and LCDR3: SEQ ID NO: 151;

(5) LCDR1: SEQ ID NO: 106, LCDR2: SEQ ID NO: 127, and LCDR3: SEQ ID NO: 152;

(6) LCDR1: SEQ ID NO: 107, LCDR2: SEQ ID NO: 127, and LCDR3: SEQ ID NO: 142;

(7) LCDR1: SEQ ID NO: 111, LCDR2: SEQ ID NO: 127, and LCDR3: SEQ ID NO: 142; and (8) LCDR1: SEQ ID NO: 112, LCDR2: SEQ ID NO: 127, and LCDR3: SEQ ID NO: 142.

In certain embodiments, the antigen-binding protein comprises an antibody light chain variable region VL, wherein the VL comprises an amino acid sequence set forth in any one of SEQ ID NOs: 214, 217, 220, 223, 227-230, 232-234, 236, 237, 242, 243 and 244.

In certain embodiments, the antigen-binding protein further comprises an antibody light chain constant region.

In certain embodiments, the light chain constant region comprises an amino acid sequence set forth in SEQ ID NO: 358.

In certain embodiments, the antigen-binding protein comprises an antibody light chain, wherein the antibody light chain comprises an amino acid sequence set forth in any one of SEQ ID NOs: 321, 324, 327, 330, 334-337, 339-341, 343, 344, 349, 350 and 351.

In certain embodiments, the antigen-binding protein comprises an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 105, LCDR2: SEQ ID NO: 127, LCDR3: SEQ ID NO: 142; HCDR1: SEQ ID NO: 15, HCDR2: SEQ ID NO: 38, and HCDR3: SEQ ID NO: 65;

(2) LCDR1: SEQ ID NO: 105, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(3) LCDR1: SEQ ID NO: 106, LCDR2: SEQ ID NO: 127, LCDR3: SEQ ID NO: 142; HCDR1: SEQ ID NO: 15, HCDR2: SEQ ID NO: 38, and HCDR3: SEQ ID NO: 65;

(4) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(5) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 68;

(6) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 72;

(7) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 73;

(8) LCDR1: SEQ ID NO: 106, LCDR2: SEQ ID NO: 127, LCDR3: SEQ ID NO: 142; HCDR1: SEQ ID NO: 21, HCDR2: SEQ ID NO: 38, and HCDR3: SEQ ID NO: 65;

(9) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 65;

(10) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72;

(11) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 73;

(12) LCDR1: SEQ ID NO: 106, LCDR2: SEQ ID NO: 127, LCDR3: SEQ ID NO: 150; HCDR1: SEQ ID NO: 16, HCDR2: SEQ ID NO: 38, and HCDR3: SEQ ID NO: 65;

(13) LCDR1: SEQ ID NO: 106, LCDR2: SEQ ID NO: 127, LCDR3: SEQ ID NO: 151; HCDR1: SEQ ID NO: 16, HCDR2: SEQ ID NO: 38, and HCDR3: SEQ ID NO: 65;

(14) LCDR1: SEQ ID NO: 106, LCDR2: SEQ ID NO: 127, LCDR3: SEQ ID NO: 152; HCDR1: SEQ ID NO: 16, HCDR2: SEQ ID NO: 38, and HCDR3: SEQ ID NO: 65;

(15) LCDR1: SEQ ID NO: 107, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(16) LCDR1: SEQ ID NO: 107, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 68;

(17) LCDR1: SEQ ID NO: 111, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(18) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72;

(19) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 73; and

(20) LCDR1: SEQ ID NO: 112, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65.

In certain embodiments, the antigen-binding protein comprises an antibody heavy chain variable region VH and an antibody light chain variable region VL, wherein the VH and VL comprise amino acid sequences selected from any one of the following groups:

(1) VL: SEQ ID NO: 214, and VH: SEQ ID NO: 169;
(2) VL: SEQ ID NO: 217, and VH: SEQ ID NO: 172;
(3) VL: SEQ ID NO: 220, and VH: SEQ ID NO: 172;
(4) VL: SEQ ID NO: 223, and VH: SEQ ID NO: 177;
(5) VL: SEQ ID NO: 227, and VH: SEQ ID NO: 172;
(6) VL: SEQ ID NO: 228, and VH: SEQ ID NO: 172;
(7) VL: SEQ ID NO: 220, and VH: SEQ ID NO: 181;
(8) VL: SEQ ID NO: 220, and VH: SEQ ID NO: 182;
(9) VL: SEQ ID NO: 220, and VH: SEQ ID NO: 183;
(10) VL: SEQ ID NO: 220, and VH: SEQ ID NO: 184;
(11) VL: SEQ ID NO: 220, and VH: SEQ ID NO: 185;
(12) VL: SEQ ID NO: 220, and VH: SEQ ID NO: 186;
(13) VL: SEQ ID NO: 220, and VH: SEQ ID NO: 187;
(14) VL: SEQ ID NO: 220, and VH: SEQ ID NO: 188;
(15) VL: SEQ ID NO: 220, and VH: SEQ ID NO: 189;
(16) VL: SEQ ID NO: 220, and VH: SEQ ID NO: 190;
(17) VL: SEQ ID NO: 220, and VH: SEQ ID NO: 191;
(18) VL: SEQ ID NO: 220, and VH: SEQ ID NO: 192;
(19) VL: SEQ ID NO: 220, and VH: SEQ ID NO: 193;
(20) VL: SEQ ID NO: 229, and VH: SEQ ID NO: 172;
(21) VL: SEQ ID NO: 230, and VH: SEQ ID NO: 172;
(22) VL: SEQ ID NO: 232, and VH: SEQ ID NO: 172;
(23) VL: SEQ ID NO: 233, and VH: SEQ ID NO: 172;
(24) VL: SEQ ID NO: 234, and VH: SEQ ID NO: 172;
(25) VL: SEQ ID NO: 229, and VH: SEQ ID NO: 185;
(26) VL: SEQ ID NO: 229, and VH: SEQ ID NO: 191;
(27) VL: SEQ ID NO: 230, and VH: SEQ ID NO: 185;
(28) VL: SEQ ID NO: 230, and VH: SEQ ID NO: 188;
(29) VL: SEQ ID NO: 230, and VH: SEQ ID NO: 191;
(30) VL: SEQ ID NO: 232, and VH: SEQ ID NO: 188;
(31) VL: SEQ ID NO: 232, and VH: SEQ ID NO: 191;
(32) VL: SEQ ID NO: 229, and VH: SEQ ID NO: 194;
(33) VL: SEQ ID NO: 229, and VH: SEQ ID NO: 195;
(34) VL: SEQ ID NO: 236, and VH: SEQ ID NO: 194;
(35) VL: SEQ ID NO: 236, and VH: SEQ ID NO: 195;
(36) VL: SEQ ID NO: 232, and VH: SEQ ID NO: 196;
(37) VL: SEQ ID NO: 232, and VH: SEQ ID NO: 197;
(38) VL: SEQ ID NO: 237, and VH: SEQ ID NO: 196;
(39) VL: SEQ ID NO: 237, and VH: SEQ ID NO: 197;
(40) VL: SEQ ID NO: 229, and VH: SEQ ID NO: 188;
(41) VL: SEQ ID NO: 232, and VH: SEQ ID NO: 185;
(42) VL: SEQ ID NO: 242, and VH: SEQ ID NO: 172;
(43) VL: SEQ ID NO: 243, and VH: SEQ ID NO: 172; and
(44) VL: SEQ ID NO: 244, and VH: SEQ ID NO: 172.

In another aspect, the present application provides an isolated antigen-binding protein, which comprises an antibody heavy chain or a fragment thereof, wherein the antibody heavy chain or the fragment thereof comprises an HCDR1, an HCDR2 and an HCDR3, wherein the HCDR1 comprises an amino acid sequence set forth in SEQ ID NO: 363, the HCDR2 comprises an amino acid sequence set forth in SEQ ID NO: 364, and the HCDR3 comprises an amino acid sequence set forth in SEQ ID NO: 365.

In certain embodiments, the HCDR1 comprises an amino acid sequence set forth in any one of SEQ ID NOs: 15-18, the HCDR2 comprises an amino acid sequence set forth in any one of SEQ ID NOs: 37-39, and the HCDR3 comprises an amino acid sequence set forth in any one of SEQ ID NOs: 65-67.

In certain embodiments, the HCDR1, HCDR2 and HCDR3 comprise amino acid sequences selected from any one of the following groups:

(1) HCDR1: SEQ ID NO: 15, HCDR2: SEQ ID NO: 37, and HCDR3: SEQ ID NO: 65;
(2) HCDR1: SEQ ID NO: 15, HCDR2: SEQ ID NO: 38, and HCDR3: SEQ ID NO: 65;
(3) HCDR1: SEQ ID NO: 16, HCDR2: SEQ ID NO: 38, and HCDR3: SEQ ID NO: 65;
(4) HCDR1: SEQ ID NO: 16, HCDR2: SEQ ID NO: 38, and HCDR3: SEQ ID NO: 66;
(5) HCDR1: SEQ ID NO: 16, HCDR2: SEQ ID NO: 38, and HCDR3: SEQ ID NO: 67;
(6) HCDR1: SEQ ID NO: 17, HCDR2: SEQ ID NO: 39, and HCDR3: SEQ ID NO: 65; and
(7) HCDR1: SEQ ID NO: 18, HCDR2: SEQ ID NO: 38, and HCDR3: SEQ ID NO: 65.

In certain embodiments, the antigen-binding protein comprises an antibody heavy chain variable region VH, wherein the VH comprises an amino acid sequence set forth in any one of SEQ ID NOs: 167, 168 and 170-176.

In certain embodiments, the antigen-binding protein further comprises an antibody heavy chain constant region.

In certain embodiments, the heavy chain constant region is derived from a human IgG constant region.

In certain embodiments, the heavy chain constant region is derived from a human IgG1 constant region.

In certain embodiments, the heavy chain constant region comprises an amino acid sequence set forth in any one of SEQ ID NOs: 356-357.

In certain embodiments, the antigen-binding protein comprises an antibody heavy chain, wherein the antibody heavy comprises an amino acid sequence set forth in any one of SEQ ID NOs: 249, 250, 252, 253, 255, 256, 257, 258 and 261.

In certain embodiments, the antigen-binding protein comprises an antibody light chain or a fragment thereof, wherein the antibody light chain or the fragment thereof comprises an LCDR1, an LCDR2 and an LCDR3, wherein the LCDR1 comprises an amino acid sequence set forth in SEQ ID NO: 366, the LCDR2 comprises an amino acid sequence set forth in SEQ ID NO: 127, and the LCDR3 comprises an amino acid sequence set forth in SEQ ID NO: 141.

In certain embodiments, the LCDR1, LCDR2 and LCDR3 comprise amino acid sequences selected from any one of the following groups:

(1) LCDR1: SEQ ID NO: 104, LCDR2: SEQ ID NO: 127, and LCDR3: SEQ ID NO: 141; and
(2) LCDR1: SEQ ID NO: 105, LCDR2: SEQ ID NO: 127, and LCDR3: SEQ ID NO: 141.

In certain embodiments, the antigen-binding protein comprises an antibody light chain variable region VL, wherein the VL comprises an amino acid sequence set forth in any one of SEQ ID NOs: 212, 213, 215, 216, 218, 219, 221, 222, 231 and 235.

In certain embodiments, the antigen-binding protein further comprises an antibody light chain constant region.

In certain embodiments, the light chain constant region comprises an amino acid sequence set forth in SEQ ID NO: 358.

In certain embodiments, the antigen-binding protein comprises an antibody light chain, wherein the antibody light chain comprises an amino acid sequence set forth in any one of SEQ ID NOs: 319, 320, 322, 323, 325, 326, 328, 329, 338 and 342.

In certain embodiments, the antigen-binding protein comprises an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 104, LCDR2: SEQ ID NO: 127, LCDR3: SEQ ID NO: 141; HCDR1: SEQ ID NO: 15, HCDR2: SEQ ID NO: 37, and HCDR3: SEQ ID NO: 65;
(2) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 65;
(3) LCDR1: SEQ ID NO: 105, LCDR2: SEQ ID NO: 127, LCDR3: SEQ ID NO: 141; HCDR1: SEQ ID NO: 17, HCDR2: SEQ ID NO: 39, and HCDR3: SEQ ID NO: 65;
(4) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 66;
(5) LCDR1: SEQ ID NO: 105, LCDR2: SEQ ID NO: 127, LCDR3: SEQ ID NO: 141; HCDR1: SEQ ID NO: 18, HCDR2: SEQ ID NO: 38, and HCDR3: SEQ ID NO: 65;
(6) LCDR1: SEQ ID NO: 104, LCDR2: SEQ ID NO: 127, LCDR3: SEQ ID NO: 141; HCDR1: SEQ ID NO: 15, HCDR2: SEQ ID NO: 38, and HCDR3: SEQ ID NO: 65; and
(7) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 67.

In certain embodiments, the antigen-binding protein comprises an antibody heavy chain variable region VH and an antibody light chain variable region VL, wherein the VH and VL comprise amino acid sequences selected from any one of the following groups:

(1) VL: SEQ ID NO: 212, and VH: SEQ ID NO: 167;
(2) VL: SEQ ID NO: 213, and VH: SEQ ID NO: 168;
(3) VL: SEQ ID NO: 215, and VH: SEQ ID NO: 170;
(4) VL: SEQ ID NO: 216, and VH: SEQ ID NO: 171;
(5) VL: SEQ ID NO: 218, and VH: SEQ ID NO: 173;
(6) VL: SEQ ID NO: 219, and VH: SEQ ID NO: 174;
(7) VL: SEQ ID NO: 221, and VH: SEQ ID NO: 175;
(8) VL: SEQ ID NO: 222, and VH: SEQ ID NO: 176;
(9) VL: SEQ ID NO: 231, and VH: SEQ ID NO: 172; and
(10) VL: SEQ ID NO: 235, and VH: SEQ ID NO: 172.

In another aspect, the present application provides an isolated antigen-binding protein, which comprises an antibody heavy chain or a fragment thereof, wherein the antibody heavy chain or the fragment thereof comprises an HCDR1, an HCDR2 and an HCDR3, wherein the HCDR1 comprises an amino acid sequence set forth in any one of SEQ ID NOs: 16, 19, 20, 23, 24 and 25, the HCDR2 comprises an amino acid sequence set forth in any one of SEQ ID NOs: 38 and 40-47, and the HCDR3 comprises an amino acid sequence set forth in any one of SEQ ID NOs: 66, 69, 70, 71 and 74-79. In certain embodiments, the HCDR1, HCDR2 and HCDR3 comprise amino acid sequences selected from any one of the following groups:

(1) HCDR1: SEQ ID NO: 19, HCDR2: SEQ ID NO: 40, and HCDR3: SEQ ID NO: 69;
(2) HCDR1: SEQ ID NO: 20, HCDR2: SEQ ID NO: 41, and HCDR3: SEQ ID NO: 70;
(3) HCDR1: SEQ ID NO: 19, HCDR2: SEQ ID NO: 40, and HCDR3: SEQ ID NO: 71;
(4) HCDR1: SEQ ID NO: 19, HCDR2: SEQ ID NO: 42, and HCDR3: SEQ ID NO: 74;
(5) HCDR1: SEQ ID NO: 19, HCDR2: SEQ ID NO: 44, and HCDR3: SEQ ID NO: 76;
(6) HCDR1: SEQ ID NO: 19, HCDR2: SEQ ID NO: 45, and HCDR3: SEQ ID NO: 77;
(7) HCDR1: SEQ ID NO: 23, HCDR2: SEQ ID NO: 43, and HCDR3: SEQ ID NO: 75;
(8) HCDR1: SEQ ID NO: 16, HCDR2: SEQ ID NO: 46, and HCDR3: SEQ ID NO: 78;
(9) HCDR1: SEQ ID NO: 16, HCDR2: SEQ ID NO: 38, and HCDR3: SEQ ID NO: 66;
(10) HCDR1: SEQ ID NO: 25, HCDR2: SEQ ID NO: 47, and HCDR3: SEQ ID NO: 79; and
(11) HCDR1: SEQ ID NO: 24, HCDR2: SEQ ID NO: 42, and HCDR3: SEQ ID NO: 79.

In certain embodiments, the antigen-binding protein comprises an antibody heavy chain variable region VH, wherein the VH comprises an amino acid sequence set forth in any one of SEQ ID NOs: 178, 179, 180 and 198-205.

In certain embodiments, the antigen-binding protein further comprises an antibody heavy chain constant region.

In certain embodiments, the heavy chain constant region is derived from a human IgG constant region.

In certain embodiments, the heavy chain constant region is derived from a human IgG1 constant region.

In certain embodiments, the heavy chain constant region comprises an amino acid sequence set forth in any one of SEQ ID NOs: 356-357.

In certain embodiments, the antigen-binding protein comprises an antibody heavy chain, wherein the antibody heavy chain comprises an amino acid sequence set forth in any one of SEQ ID NOs: 263, 264, 265 and 285-298.

In certain embodiments, the antigen-binding protein comprises an antibody light chain or a fragment thereof, wherein the antibody light chain or a fragment thereof comprises an LCDR1, an LCDR2 and an LCDR3, wherein the LCDR1 comprises an amino acid sequence set forth in any one of SEQ ID NOs: 104, 105, 108-110 and 113-117, the LCDR2 comprises an amino acid sequence set forth in any one of SEQ ID NOs: 127-134, and the LCDR3 comprises an amino acid sequence set forth in any one of SEQ ID NOs: 141, 143-149 and 153.

In certain embodiments, the LCDR1, LCDR2 and LCDR3 comprise amino acid sequences selected from any one of the following groups:

(1) LCDR1: SEQ ID NO: 108, LCDR2: SEQ ID NO: 128, and LCDR3: SEQ ID NO: 143;
(2) LCDR1: SEQ ID NO: 109, LCDR2: SEQ ID NO: 129, and LCDR3: SEQ ID NO: 144;
(3) LCDR1: SEQ ID NO: 110, LCDR2: SEQ ID NO: 130, and LCDR3: SEQ ID NO: 145;
(4) LCDR1: SEQ ID NO: 113, LCDR2: SEQ ID NO: 131, and LCDR3: SEQ ID NO: 146;
(5) LCDR1: SEQ ID NO: 115, LCDR2: SEQ ID NO: 133, and LCDR3: SEQ ID NO: 148;
(6) LCDR1: SEQ ID NO: 116, LCDR2: SEQ ID NO: 134, and LCDR3: SEQ ID NO: 149;
(7) LCDR1: SEQ ID NO: 114, LCDR2: SEQ ID NO: 132, and LCDR3: SEQ ID NO: 147;
(8) LCDR1: SEQ ID NO: 105, LCDR2: SEQ ID NO: 127, and LCDR3: SEQ ID NO: 141;
(9) LCDR1: SEQ ID NO: 104, LCDR2: SEQ ID NO: 127, and LCDR3: SEQ ID NO: 141; and
(10) LCDR1: SEQ ID NO: 117, LCDR2: SEQ ID NO: 128, and LCDR3: SEQ ID NO: 153.

In certain embodiments, the antigen-binding protein comprises an antibody light chain variable region VL, wherein the VL comprises an amino acid sequence set forth in any one of SEQ ID NOs: 224-226, 238-241 and 245-248.

In certain embodiments, the antigen-binding protein further comprises an antibody light chain constant region.

In certain embodiments, the light chain constant region comprises an amino acid sequence set forth in SEQ ID NO: 358.

In certain embodiments, the antigen-binding protein comprises an antibody light chain, wherein the antibody light chain comprises amino acid sequences set forth in SEQ ID NOs: 331-333, 345-348 and 352-355.

In certain embodiments, the antigen-binding protein comprises an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 108, LCDR2: SEQ ID NO: 128, LCDR3: SEQ ID NO: 143; HCDR1: SEQ ID NO: 19, HCDR2: SEQ ID NO: 40, and HCDR3: SEQ ID NO: 69;

(2) LCDR1: SEQ ID NO: 109, LCDR2: SEQ ID NO: 129, LCDR3: SEQ ID NO: 144; HCDR1: SEQ ID NO: 20, HCDR2: SEQ ID NO: 41, and HCDR3: SEQ ID NO: 70;

(3) LCDR1: SEQ ID NO: 110, LCDR2: SEQ ID NO: 130, LCDR3: SEQ ID NO: 145; HCDR1: SEQ ID NO: 19, HCDR2: SEQ ID NO: 40, and HCDR3: SEQ ID NO: 71;

(4) LCDR1: SEQ ID NO: 113, LCDR2: SEQ ID NO: 131, LCDR3: SEQ ID NO: 146; HCDR1: SEQ ID NO: 19, HCDR2: SEQ ID NO: 42, and HCDR3: SEQ ID NO: 74;

(5) LCDR1: SEQ ID NO: 115, LCDR2: SEQ ID NO: 133, LCDR3: SEQ ID NO: 148; HCDR1: SEQ ID NO: 19, HCDR2: SEQ ID NO: 44, and HCDR3: SEQ ID NO: 76;

(6) LCDR1: SEQ ID NO: 116, LCDR2: SEQ ID NO: 134, LCDR3: SEQ ID NO: 149; HCDR1: SEQ ID NO: 19, HCDR2: SEQ ID NO: 45, and HCDR3: SEQ ID NO: 77;

(7) LCDR1: SEQ ID NO: 114, LCDR2: SEQ ID NO: 132, LCDR3: SEQ ID NO: 147; HCDR1: SEQ ID NO: 23, HCDR2: SEQ ID NO: 43, and HCDR3: SEQ ID NO: 75;

(8) LCDR1: SEQ ID NO: 105, LCDR2: SEQ ID NO: 127, LCDR3: SEQ ID NO: 141; HCDR1: SEQ ID NO: 16, HCDR2: SEQ ID NO: 46, and HCDR3: SEQ ID NO: 78;

(9) LCDR1: SEQ ID NO: 104, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 66;

(10) LCDR1: SEQ ID NO: 117, LCDR2: SEQ ID NO: 128, LCDR3: SEQ ID NO: 153; HCDR1: SEQ ID NO: 25, HCDR2: SEQ ID NO: 47, and HCDR3: SEQ ID NO: 79; and

(11) LCDR1: SEQ ID NO: 117, LCDR2: SEQ ID NO: 128, LCDR3: SEQ ID NO: 153; HCDR1: SEQ ID NO: 24, HCDR2: SEQ ID NO: 42, and HCDR3: SEQ ID NO: 79.

In certain embodiments, the antigen-binding protein comprises an antibody heavy chain variable region VH and an antibody light chain variable region VL, wherein the VH and VL comprise amino acid sequences selected from any one of the following groups:

(1) VL: SEQ ID NO: 224, and VH: SEQ ID NO: 178;

(2) VL: SEQ ID NO: 225, and VH: SEQ ID NO: 179;

(3) VL: SEQ ID NO: 226, and VH: SEQ ID NO: 180;

(4) VL: SEQ ID NO: 238, and VH: SEQ ID NO: 198;

(5) VL: SEQ ID NO: 240, and VH: SEQ ID NO: 200;

(6) VL: SEQ ID NO: 241, and VH: SEQ ID NO: 201;

(7) VL: SEQ ID NO: 239, and VH: SEQ ID NO: 199;

(8) VL: SEQ ID NO: 245, and VH: SEQ ID NO: 202;

(9) VL: SEQ ID NO: 246, and VH: SEQ ID NO: 203;

(10) VL: SEQ ID NO: 248, and VH: SEQ ID NO: 205; and

(11) VL: SEQ ID NO: 247, and VH: SEQ ID NO: 204.

In another aspect, the present application provides an isolated antigen-binding protein, which comprises an antibody heavy chain or a fragment thereof, wherein the antibody heavy chain or the fragment thereof comprises an HCDR1, an HCDR2 and an HCDR3, wherein the HCDR1 comprises an amino acid sequence set forth in SEQ ID NO: 22, the HCDR2 comprises an amino acid sequence set forth in SEQ ID NO: 367, and the HCDR3 comprises an amino acid sequence set forth in SEQ ID NO: 368.

In certain embodiments, the HCDR1 comprises an amino acid sequence set forth in SEQ ID NO: 22, the HCDR2 comprises an amino acid sequence set forth in any one of SEQ ID NOs: 38 and 48, and the HCDR3 comprises an amino acid sequence set forth in any one of SEQ ID NOs: 72, 80, 81, 82 and 83.

In certain embodiments, the HCDR1, HCDR2 and HCDR3 comprise amino acid sequences selected from any one of the following groups:

(1) HCDR1: SEQ ID NO: 22, HCDR2: SEQ ID NO: 38, and HCDR3: SEQ ID NO: 72;

(2) HCDR1: SEQ ID NO: 22, HCDR2: SEQ ID NO: 38, and HCDR3: SEQ ID NO: 80;

(3) HCDR1: SEQ ID NO: 22, HCDR2: SEQ ID NO: 38, and HCDR3: SEQ ID NO: 81;

(4) HCDR1: SEQ ID NO: 22, HCDR2: SEQ ID NO: 48, and HCDR3: SEQ ID NO: 80;

(5) HCDR1: SEQ ID NO: 22, HCDR2: SEQ ID NO: 48, and HCDR3: SEQ ID NO: 81;

(6) HCDR1: SEQ ID NO: 22, HCDR2: SEQ ID NO: 48, and HCDR3: SEQ ID NO: 82; and (7) HCDR1: SEQ ID NO: 22, HCDR2: SEQ ID NO: 48, and HCDR3: SEQ ID NO: 83.

In certain embodiments, the antigen-binding protein comprises an antibody heavy chain variable region VH, wherein the VH comprises an amino acid sequence set forth in any one of SEQ ID NOs: 196 and 206-211.

In certain embodiments, the antigen-binding protein further comprises an antibody heavy chain constant region.

In certain embodiments, the heavy chain constant region is derived from a human IgG constant region.

In certain embodiments, the heavy chain constant region is derived from a human IgG1 constant region.

In certain embodiments, the heavy chain constant region comprises an amino acid sequence set forth in any one of SEQ ID NOs: 356-357.

In certain embodiments, the antigen-binding protein comprises an antibody heavy chain, wherein the antibody heavy chain comprises an amino acid sequence set forth in any one of SEQ ID NOs: 299-318.

In certain embodiments, the antigen-binding protein comprises an antibody light chain or a fragment thereof, wherein the antibody light chain or the fragment thereof comprises an LCDR1, an LCDR2 and an LCDR3, wherein the LCDR1 comprises an amino acid sequence set forth in SEQ ID NO: 111, the LCDR2 comprises an amino acid sequence set forth in SEQ ID NO: 127, and the LCDR3 comprises an amino acid sequence set forth in SEQ ID NO: 142.

In certain embodiments, the antigen-binding protein comprises an antibody light chain variable region VL, wherein the VL comprises an amino acid sequence set forth in SEQ ID NO: 237.

In certain embodiments, the antigen-binding protein further comprises an antibody light chain constant region.

In certain embodiments, the light chain constant region comprises an amino acid sequence set forth in SEQ ID NO: 358.

In certain embodiments, the antigen-binding protein comprises an antibody light chain, wherein the antibody light chain comprises an amino acid sequence set forth in SEQ ID NO: 344.

In certain embodiments, the antigen-binding protein comprises an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72;

(2) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 80;

(3) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 81;

(4) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 80;

(5) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 81;

(6) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 82; and (7) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 83.

In certain embodiments, the antigen-binding protein comprises an antibody heavy chain variable region VH and an antibody light chain variable region VL, wherein the VH and VL comprise amino acid sequences selected from any one of the following groups:

(1) VL: SEQ ID NO: 237, and VH: SEQ ID NO: 196;

(2) VL: SEQ ID NO: 237, and VH: SEQ ID NO: 206;

(3) VL: SEQ ID NO: 237, and VH: SEQ ID NO: 207;

(4) VL: SEQ ID NO: 237, and VH: SEQ ID NO: 208;

(5) VL: SEQ ID NO: 237, and VH: SEQ ID NO: 209;

(6) VL: SEQ ID NO: 237, and VH: SEQ ID NO: 210; and (7) VL: SEQ ID NO: 237, and VH: SEQ ID NO: 211.

In certain embodiments, the antigen-binding protein has one or more of the following properties:

a) being capable of binding to CCR8 derived from a primate with an $EC_{50}$ value of $2\times10^{-8}$ M or less;

b) being capable of blocking the binding of CCR8 to a ligand CCL1;

c) being capable of inhibiting calcium influx caused by CCL1; and d) being capable of inhibiting cell migration induced by CCL1.

In certain embodiments, the primate includes human and/or monkey.

In certain embodiments, the antigen-binding protein includes an antibody or an antigen-binding fragment thereof.

In certain embodiments, the antigen-binding protein includes a full-length antibody; a Fab; a Fab'; an $F(ab')_2$; an Fv, preferably an scFv; a di-scFv; a bispecific antibody; a multispecific antibody; a heavy-chain antibody; and/or a single-domain antibody; or a monoclonal antibody and/or a polyclonal antibody prepared from the above antibodies.

In certain embodiments, the antibody is selected from the following group: a monoclonal antibody, a chimeric antibody, a humanized antibody and a fully human antibody.

In another aspect, the present application provides one or more isolated nucleic acid molecules encoding the isolated antigen-binding protein.

In another aspect, the present application provides one or more vectors comprising the nucleic acid molecule.

In another aspect, the present application provides one or more cells comprising the nucleic acid molecule or the vector.

In another aspect, the present application provides a method for preparing the isolated antigen-binding protein, which comprises culturing the cells under conditions that enable the expression of the isolated antigen-binding protein.

In another aspect, the present application provides a chimeric antigen receptor comprising the antigen-binding protein.

In another aspect, the present application provides a genetically modified cell comprising the chimeric antigen receptor. In certain embodiments, the genetically modified cell includes a eukaryotic cell. In certain embodiments, the genetically modified cell includes an isolated human cell. In certain embodiments, the genetically modified cell includes an immune cell, such as a T cell or an NK cell.

In another aspect, the present application provides an antibody-drug conjugate comprising a cytotoxic agent and the antigen-binding protein.

In another aspect, the present application provides a pharmaceutical composition comprising the isolated antigen-binding protein, the nucleic acid molecule, the vector, the cell, the chimeric antigen receptor, the genetically modified cell, and/or the antibody-drug conjugate, and optionally a pharmaceutically acceptable carrier.

In another aspect, the present application provides a kit or an administration device comprising the antigen-binding protein, the nucleic acid molecule, the vector, the cell, the chimeric antigen receptor, the genetically modified cell, the antibody-drug conjugate, and/or the pharmaceutical composition; preferably, the kit further comprises (i) a device for administering the antigen-binding protein, the nucleic acid molecule, the vector, the cell, the chimeric antigen receptor, the genetically modified cell, the antibody-drug conjugate, and/or the pharmaceutical composition; and/or (ii) instructions.

In another aspect, the present application provides an use of the antigen-binding protein, the nucleic acid molecule, the vector, the cell, the chimeric antigen receptor, the genetically modified cell, the antibody-drug conjugate, and/or the pharmaceutical composition in the preparation of a medicament for preventing, alleviating and/or treating a CCR8-mediated disease or disorder.

In certain embodiments, the CCR8-mediated disease or disorder includes a tumor. In certain embodiments, the CCR8-mediated disease or disorder includes a solid tumor. In certain embodiments, the CCR8-mediated disease or disorder includes a non-solid tumor.

In certain embodiments, the CCR8-mediated disease or disorder includes breast cancer, kidney cancer, pancreatic cancer, bladder cancer, gastric cancer, cervical cancer and/or colon cancer.

In another aspect, the present application provides a method for inhibiting calcium influx caused by CCL1, which comprises administering the isolated antigen-binding protein and/or the pharmaceutical composition.

In certain embodiments, the method is an in vitro method or a method for non-diagnostic purposes.

In another aspect, the present application provides a method for inhibiting cell migration induced by CCL1, which comprises administering the isolated antigen-binding protein and/or the pharmaceutical composition.

In certain embodiments, the method is an in vitro method or a method for non-diagnostic purposes.

In another aspect, the present application provides a method for preventing, alleviating or treating a CCR8-mediated disease or disorder, which comprises administering to a subject in need thereof the antigen-binding protein, the nucleic acid molecule, the vector, the cell, the chimeric antigen receptor, the genetically modified cell, the antibody-drug conjugate, and/or the pharmaceutical composition.

In certain embodiments, the CCR8-mediated disease or disorder includes a tumor. In certain embodiments, the CCR8-mediated disease or disorder includes a solid tumor. In certain embodiments, the CCR8-mediated disease or disorder includes a non-solid tumor.

In certain embodiments, the CCR8-mediated disease or disorder includes breast cancer, kidney cancer, pancreatic cancer, bladder cancer, gastric cancer, cervical cancer and/or colon cancer.

In another aspect, the present application provides the antigen-binding protein, the nucleic acid molecule, the vector, the cell, the chimeric antigen receptor, the genetically modified cell, the antibody-drug conjugate, and/or the pharmaceutical composition, for use in preventing, alleviating or treating a CCR8-mediated disease or disorder.

In certain embodiments, the CCR8-mediated disease or disorder includes a tumor. In certain embodiments, the CCR8-mediated disease or disorder includes a solid tumor. In certain embodiments, the CCR8-mediated disease or disorder includes a non-solid tumor.

In certain embodiments, the CCR8-mediated disease or disorder includes breast cancer, kidney cancer, pancreatic cancer, bladder cancer, gastric cancer, cervical cancer and/or colon cancer.

Other aspects and advantages of the present application will be readily apparent to those skilled in the art from the following detailed description. Only exemplary embodiments of the present application have been shown and described in the following detailed description. As will be recognized by those skilled in the art, the content of the present application enables those skilled in the art to make changes to the specific embodiments disclosed without departing from the spirit and scope of the invention to which the present application pertains. Accordingly, descriptions in the drawings and specification are only illustrative rather than restrictive.

BRIEF DESCRIPTION OF THE DRAWINGS

Specific features of the invention to which the present application pertains are set forth in appended claims. Features and advantages of the invention to which the present application pertains will be better understood by reference to the exemplary embodiments and drawings described in detail below.

The drawings are briefly described as follows:

FIGS. 1A, 1B, 1C and 1D show the results of the binding of CCR8 chimeric antibodies to human CCR8 on the cell surface, wherein FIG. 1A: CHO-K1, FIG. 1B: HEK293, FIG. 1C: Baf3, and FIG. 1D: CHO-K1.

DETAILED DESCRIPTION

Figure 1A:
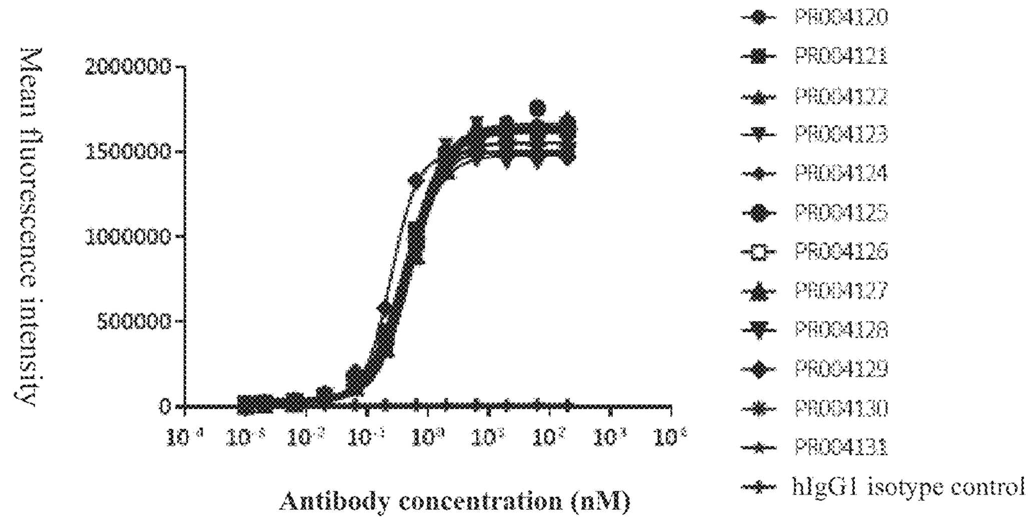
Figure 1B:
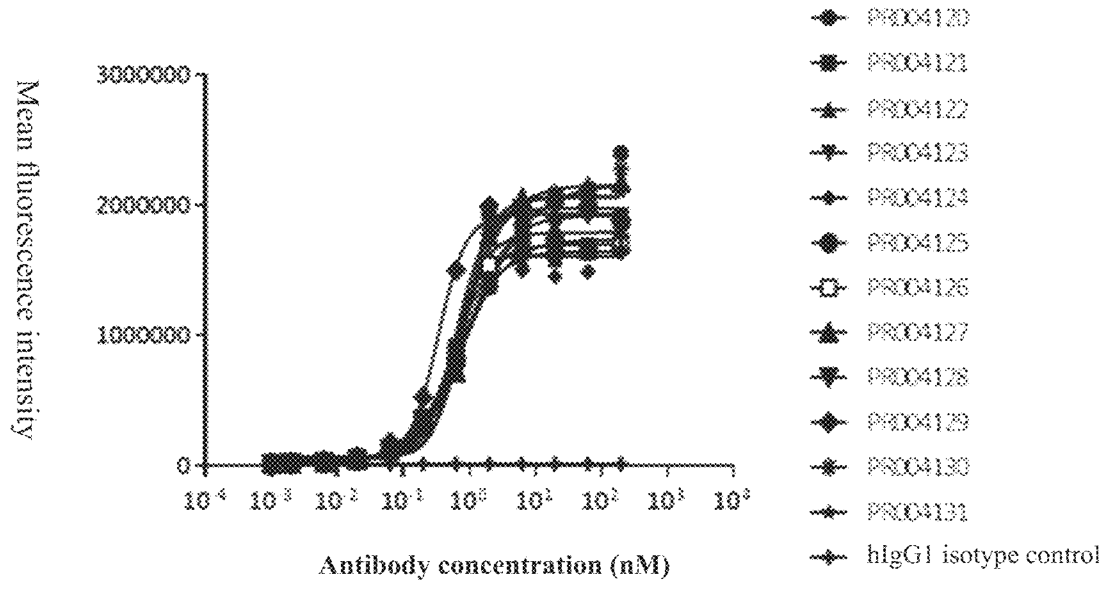
Figure 1C:
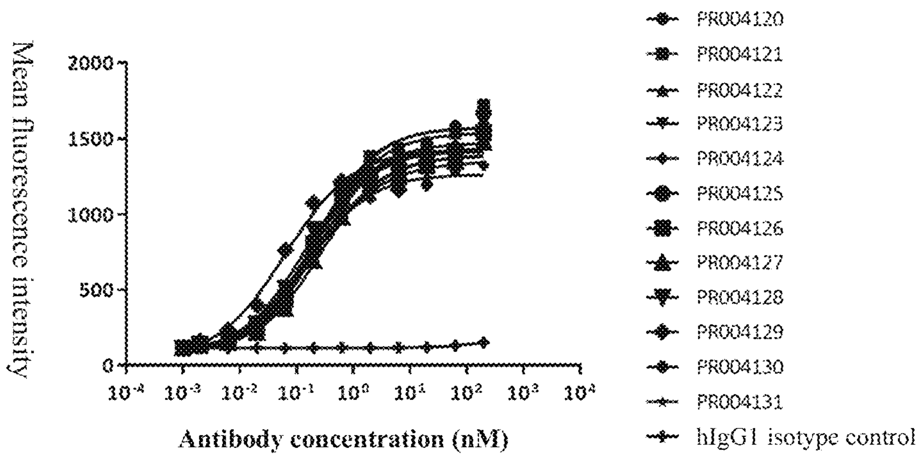
Figure 1D:
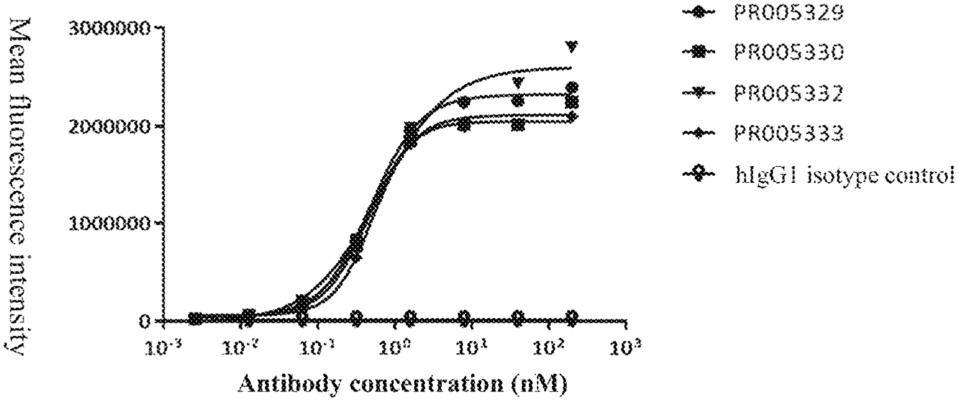

The embodiments of the present invention are described below with reference to specific examples, and other advantages and effects of the present invention will be readily apparent to those skilled in the art from the disclosure of the present specification.

Definitions of Terms

In the present application, the term "antigen-binding protein" generally refers to a protein comprising a moiety that binds to an antigen, and optionally a scaffold or framework moiety that allows the antigen-binding moiety to adopt a conformation that facilitates binding of the antigen-binding protein to the antigen. An antibody may typically comprise an antibody light chain variable region (VL) or an antibody heavy chain variable region (VH), or both. The VH and VL regions can be further divided into hypervariable regions termed complementarity determining regions (CDRs), which are scattered over more conserved regions termed framework regions (FRs or FWRs). Each VH and VL can consist of three CDRs and four FRs arranged from amino-terminus to carboxyl-terminus in the following order: FR1, CDR1, FR2, CDR2, FR3, CDR3 and FR4. The variable regions of the heavy and light chains comprise binding domains that interact with antigens. Examples of the antigen-binding proteins include, but are not limited to, antibodies, antigen-binding fragments (Fab, Fab', Fv fragment, $F(ab')_2$, scFv, di-scFv and/or dAb), antibody-drug conjugates, multispecific antibodies (e.g., bispecific antibodies), antibody fragments, antibody derivatives, antibody analogs, fusion proteins or the like, as long as they exhibit the desired antigen-binding activity.

In the present application, the term "Fab" generally refers to a fragment comprising a heavy chain variable domain and a light chain variable domain, and also comprising the constant domain of the light chain and the first constant domain of the heavy chain (CH1); the term "Fab'" generally refers to a fragment different from Fab due to the addition of a few residues at the carboxyl terminus of the heavy chain CH1 domain (including one or more cysteines from the antibody hinge region); the term "$F(ab')_2$" generally refers to a dimer of Fab', an antibody fragment comprising two Fab fragments connected by a disulfide bridge at the hinge region. The term "Fv" generally refers to the smallest antibody fragment that contains an intact antigen recognition and binding site. In certain cases, the fragment may consist of a dimer of one heavy chain variable region and one light chain variable region in tight, non-covalent association; the term "dsFv" generally refers to disulfide-stabilized Fv fragments in which the bond between a single light chain variable region and a single heavy chain variable region is a disulfide bond. The term "dAb fragment" generally refers to an antibody fragment that consists of a VH domain. In the present application, the term "scFv" generally refers to a monovalent molecule formed by covalently connecting and pairing one heavy chain variable domain and one light chain variable domain of an antibody via a flexible peptide linker; such scFv molecules may have the general structure: $NH_2$-VL-linker-VH—COOH or $NH_2$-VH-linker-VL-COOH.

In the present application, the term "variable" generally refers to the fact that certain portions of the sequences of the variable domains of antibodies vary considerably, resulting in the binding and specificity of various particular antibodies to their particular antigens. However, variability is not evenly distributed throughout the variable region of the antibody. It is concentrated in three segments in each of the light chain and heavy chain variable regions called complementary determining regions (CDRs) or hypervariable regions (HVRs). The more highly conserved portions of the variable domains are called frameworks (FRs). The variable domains of native heavy and light chains each comprise four FRs (H-FR1, H-FR2, H-FR3, H-FR4, L-FR1, L-FR2, L-FR3, L-FR4) largely in a β-sheet configuration. The FRs are connected by three CDRs to form a loop connection, and in some cases to form part of a β-sheet structure. The CDRs in each chain are held in close proximity by the FRs and form, together with the CDRs from the other chain, antigen-binding sites of the antibody. The constant regions are not directly involved in the binding of the antibody to antigens, but they exhibit different effector functions, for example, being involved in antibody-dependent cytotoxicity of the antibody. In the art, the CDRs of an antibody can be defined using a variety of methods, such as the Kabat scheme based on sequence variability (see Kabat et al., *Sequences of Proteins of Immunological Interest*, Fifth Edition, National Institutes of Health (U.S.), Bethesda, Maryland (1991)), and the Chothia scheme based on the location of the structural loop regions (see A1-Lazikani et al., *J Mol Biol* 273: 927-948, 1997). In the present application, the Kabat scheme and the Chothia scheme are also be used to determine the amino acid residues in variable domain sequences and full-length antibody sequences. The numbering schemes for antibody CDRs are shown in Table 1.

TABLE 1

Numbering schemes for antibody CDRs

| | Kabat | Chothia | Combined |
|---|---|---|---|
| LCDR1 | L24--L34 | L24--L34 | L24-L34 |
| LCDR2 | L50--L56 | L50--L56 | L50-L56 |
| LCDR3 | L89--L97 | L89--L97 | L89-L97 |
| HCDR1 | H31--H35 | H26--H32 | H26-H35 |
| HCDR2 | H50--H65 | H52--H56 | H50-H65 |
| HCDR3 | H95--H102 | H95--H102 | H95-H102 |

Laa-Lbb can refer to an amino acid sequence from position aa (the Chothia scheme) to position bb (the Chothia scheme) beginning at the N-terminus of the light chain of the antibody; and Haa-Hbb can refer to an amino acid sequence from position aa (the Chothia scheme) to position bb (the Chothia scheme) beginning at the N-terminus of the heavy chain of the antibody. For example, L24-L34 can refer to the amino acid sequence from position 24 to position 34 according to the Chothia scheme beginning at the N-terminus of the light chain of the antibody; H26-H32 can refer to the amino acid sequence from position 26 to position 32 according to the Chothia scheme beginning at the N-terminus of the heavy chain of the antibody. For example, the Chothia numbering scheme can be used as an example for CDR definition in the present application.

In the present application, the term "isolated" antigen-binding protein generally refers to an antigen-binding protein that has been identified, isolated and/or recovered from a component of the environment where it is produced (e.g., native or recombinant). Contaminating components of the environment where it is produced are often substances that interfere with its research, diagnostic or therapeutic uses and may include enzymes, hormones and other proteinaceous or non-proteinaceous solutes. An isolated antigen-binding protein or antibody will generally be prepared by at least one purification step.

In the present application, the term "monoclonal antibody" generally refers to an antibody obtained from a population of substantially homogeneous antibodies, that is, the individual antibodies in the population are identical except for a small amount of natural mutations that may exist. Monoclonal antibodies are generally highly specific for a single antigenic site. Moreover, unlike conventional polyclonal antibody formulations (which generally have different antibodies directed against different determinants), each monoclonal antibody is directed against a single determinant on the antigen. In addition to their specificity, monoclonal antibodies have the advantage that they can be synthesized by hybridoma culture without contamination by other immunoglobulins. The modifier "monoclonal" indicates the characteristic of the antibody obtained from a population of substantially homogeneous antibodies, and is not to be construed as requiring production of the antibody by any particular method. For example, monoclonal antibodies used according to the present invention can be prepared in hybridoma cells or can be prepared by the recombinant DNA method.

In the present application, the term "chimeric antibody" generally refers to an antibody in which the variable region is derived from one species while the constant region is derived from another species. Generally, the variable region is derived from an antibody of an experimental animal such as a rodent ("parent antibody") and the constant region is derived from a human antibody, such that the resulting chimeric antibody is less likely to cause an adverse immune response in a human individual as compared to the parent (e.g., mouse-derived) antibody.

In the present application, the term "humanized antibody" generally refers to an antibody in which some of or all of the amino acids outside the CDR regions of a non-human antibody (e.g., a mouse antibody) are substituted with corresponding amino acids derived from a human immunoglobulin. In the CDR regions, small additions, deletions, insertions, replacements or modifications of amino acids may also be permissible, so long as they retain the binding ability of the antibody to a particular antigen. The humanized antibody may optionally comprise at least a portion of a human immunoglobulin constant region. "Humanized antibody" retains antigen specificity similar to the original antibody. "Humanized" forms of non-human (e.g., murine) antibodies may be chimeric antibodies that comprise minimal sequences derived from non-human immunoglobulins. In certain cases, residues in the CDR region of a human immunoglobulin (recipient antibody) can be replaced with residues in the CDR region of a non-human species (donor antibody) such as mouse, rat, rabbit, or non-human primate having the desired properties, affinity and/or ability. In certain cases, residues in the FR region of a human immunoglobulin can be replaced with corresponding non-human residues. In addition, humanized antibodies may comprise amino acid modifications that are not present in the recipient antibody or in the donor antibody. Those modifications may be made to further improve the properties of the antibody, such as binding affinity.

In the present application, the term "fully human antibody" generally refers to an antibody that is expressed by a genetically engineered antibody gene-deleted animal into which the gene that encodes an antibody in human is transferred. All parts of the antibody (including the variable and constant regions of the antibody) are encoded by genes of human origin. The fully human antibody can greatly reduce the immune side effects caused in the human body by the heterologous antibody. Methods for obtaining fully human antibodies in the art can include a phage display technique, a transgenic mice technique, a ribosome display technique, an RNA-peptide technique and the like.

In the present application, the term "specifically bind to" generally refers to that an antibody binds to an epitope via its antigen-binding domain, and that the binding requires some complementarity between the antigen-binding domain and the epitope. According to this definition, an antibody is said to "specifically bind to" an antigen when the antibody more easily binds to an epitope via its antigen-binding domain than binds to a random, unrelated epitope. "Epitope" refers to a specific atomic group (e.g., saccharide side chain, phosphoryl, sulfonyl) or an amino acid on an antigen that binds to an antigen-binding protein (e.g., an antibody).

In the present application, the terms "KD" and "$K_D$" are used interchangeably and generally refer to the equilibrium dissociation constant, and "KD" is the ratio of the dissociation rate constant (kdis, also referred to as "off-rate" (koff) or "kd") to the association rate constant (kon, also referred to as "association rate" or "ka"). The binding affinity of an antigen-binding protein (e.g., an antibody) for an antigen can be expressed using an association rate constant (kon), a dissociation rate constant (kdis) and an equilibrium dissociation constant (KD). Methods for determining the association and dissociation rate constants are well known in the art and include, but are not limited to, biolayer interferometry (BLI), radioimmunoassay (RIA), equilibrium dialysis, surface plasmon resonance (SPR), fluorescence resonance energy transfer (FRET), co-immunoprecipitation (Co-IP), and protein chip technology. The affinity of a particular protein-protein interaction measured may be different if measured under different conditions (e.g., salt concentration or pH).

In the present application, the term "primate" generally refers to monkey and ape species, and includes monkey species, such as monkeys from the genera *Macaca* (such as, and in particular, *Macaca fascicularis* and/or *Macaca mulatta*) and *Papio* (*Papio ursinus*), as well as marmosets (species from the genus *Callithrix*), squirrel monkeys (species from the genus *Saimiri*) and tamarind monkeys (species from the genus *Saguinus*), and ape species, such as *Pan troglodytes*, and also includes *Homo sapiens.*

In the present application, the term "epitope" generally refers to a certain region of an antigen to which an antigen-binding protein (e.g., an antibody) specifically binds. The epitopes generally consist of chemically active surface groups such as amino acids or carbohydrates or sugar side chain molecules, and generally have specific three-dimensional structural characteristics and specific charge characteristics. An epitope may be a "linear epitope" or a "conformational epitope". In a linear epitope, all points of interaction between a protein and an interacting molecule (such as an antibody) occur linearly along the primary amino acid sequence of the protein. In a conformational epitope, the points of interaction occur cross amino acids on proteins that are separated from each other. Methods for determining what an epitope a given antigen-binding protein (e.g., antibody) binds to (e.g., Epitope Mapping) are well known in the art, including, for example, immunoblotting and immunoprecipitation assays, e.g., to test the reactivity of overlapping or contiguous peptides (e.g., from CCR8) with a given antigen-binding protein (e.g., anti-CCR8 antibody). Methods for determining spatial conformation of an epitope include techniques in the art and techniques described herein, for example, X-ray crystallography, two-dimensional nuclear magnetic resonance, and HDX-MS.

In the present application, the term "cross-reactivity" refers to the ability of the antigen-binding protein described herein to bind to CCR8 from different species. For example, in certain cases, the antigen-binding protein that binds to human CCR8 can also bind to CCR8 from another species (e.g., cynomolgus monkey CCR8). As used herein, cross-reactivity can be determined by detecting specific reactivity with purified antigens in a binding assay (e.g., SPR, ELISA, or FACS), or detecting binding or functional interaction with cells that physiologically express CCR8. Methods for determining cross-reactivity include standard binding assays as described herein, for example by using the flow cytometry technique.

In the present application, the term “subject” generally refers to a mammal. The mammals include, but are not limited to, domesticated animals (e.g., cows, sheep, cats, dogs, and horses), primates (e.g., human and non-human primates such as monkeys), rabbits, and rodents (e.g., mice and rats).

In the present application, the term “nucleic acid molecule” generally refers to an isolated form of nucleotides, deoxyribonucleotides or ribonucleotides or analogs thereof of any length, isolated from their natural environment, or artificially synthesized.

In the present application, the term “vector” generally refers to a nucleic acid molecule capable of self-replication in a suitable host, which transfers a inserted nucleic acid molecule into a host cell and/or between host cells. The vector may include a vector for primarily inserting DNA or RNA into a cell, a vector for primarily replicating DNA or RNA, and a vector for primarily expressing transcription and/or translation of DNA or RNA. The vector also includes vectors having a variety of the above-described functions. The vector may be a polynucleotide capable of being transcribed and translated into a polypeptide when introduced into a suitable host cell. Generally, the vector can produce the desired expression product by culturing an appropriate host cell containing the vector. In the present application, the term “cell” generally refers to an individual cell, cell line or cell culture that may contain or has contained a plasmid or vector comprising the nucleic acid molecule described herein, or that is capable of expressing the antibody or the antigen-binding fragment thereof described herein. The cell may comprise progenies of a single host cell. Due to natural, accidental or deliberate mutations, progeny cells may not necessarily be identical in morphology or in genome to the original parent cell, but are capable of expressing the antibody or the antigen-binding fragment thereof described herein. The cell may be obtained by transfecting cells with the vector described herein in vitro. The cell may be a prokaryotic cell (e.g., *E. coli*) or a eukaryotic cell (e.g., a yeast cell, a COS cell, a Chinese hamster ovary (CHO) cell, a HeLa cell, an HEK293 cell, a COS-1 cell, an NS0 cell, or a myeloma cell). In certain cases, the cell may be a mammalian cell. For example, the mammalian cell may be a CHO-K1 cell. In the present application, the term “recombinant cell” generally refers to a cell into which a recombinant expression vector has been introduced. The recombinant host cell includes not only particular cells but also progeny of such cells.

In the present application, the term “pharmaceutical composition” generally refers to a formulation that is present in a form allowing the biological activity of the active ingredient to be effective and that does not contain additional ingredients having unacceptable toxicity to a subject to which the composition is to be administered. The composition is sterile. “Sterile” composition is sterilized or free of all living microorganisms and their spores.

In the present application, the term “pharmaceutically acceptable carrier” generally includes pharmaceutically acceptable carriers, excipients or stabilizers which are nontoxic to cells or mammals being exposed thereto at the dosages and concentrations employed. Generally, the physiologically acceptable carrier is an aqueous pH buffer solution. Examples of physiologically acceptable carriers can include buffers, antioxidants, low-molecular-weight (less than about 10 residues) polypeptides, proteins, hydrophilic polymers, amino acids, monosaccharides, disaccharides, other carbohydrates, chelating agents, sugar alcohols, salt-forming counterions such as sodium, and/or nonionic surfactants.

In the present application, the term “treatment” or “treating” generally refers to a clinical intervention that desires to alter the natural course of the individual being treated and can be performed either for prophylaxis or during the course of clinical pathology. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating disease conditions, and alleviating or improving prognosis. In some cases, antibodies (e.g., anti-CCR8 antibodies) can be used to delay disease progression or slow disease progression.

In the present application, the term “tumor” generally refers to all neoplastic cell growth and proliferation, whether being malignant or benign, and all pre-cancerous and cancerous cells and tissues. In the present application, the tumor can include a solid tumor and/or a non-solid tumor (e.g., hematological tumor or lymphoma).

In the present application, the term “antibody-drug conjugate” generally refers to a substance formed by linking an antigen-binding protein to other active agents, which may be small molecule active agents, such as chemotherapeutic agents, toxins, immunotherapeutic agents, imaging probes or spectroscopic probes.

In the present application, the term “kit” generally refers to a packaged product containing components for administering the antigen-binding proteins of the present application to treat PD-1-mediated related disorders. The components of the kit may be contained in separate vials (i.e., a kit with separate parts), or provided within a single vial. The kit may comprise reagents such as a buffer, a protein stabilizing reagent, a signal generating system (e.g., a fluorescent signal generating system), an antibody, a control protein, and a test container. The kit may further comprise instructions for carrying out the method.

In the present application, the term “administration device” comprises: (i) an infusion module for administering to a subject a pharmaceutical composition comprising a compound having an active ingredient; (ii) a pharmaceutical composition for infusion comprising an active ingredient selected from the following group: an antigen-binding protein, a multispecific antibody, an immune cell, an antibody-drug conjugate or a combination thereof; and (iii) optionally a pharmacodynamic monitoring module.

In the present application, the term “in combination” generally means that two or more therapeutic agents can be co-administered to a subject in a mixture, simultaneously as single agents or sequentially in any order as single agents.

In the present application, the term “between . . . ” generally means that the C-terminus of an amino acid fragment is linked directly or indirectly to the N-terminus of a first amino acid fragment and that its N-terminus is linked directly or indirectly to the C-terminus of a second amino acid fragment. In the light chain, for example, the N-terminus of the L-FR2 is linked directly or indirectly to the C-terminus of the LCDR1, and the C-terminus of the L-FR2 is linked directly or indirectly to the N-terminus of the LCDR2. For another example, the N-terminus of the L-FR3 is linked directly or indirectly to the C-terminus of the LCDR2, and the C-terminus of the L-FR3 is linked directly or indirectly to the N-terminus of the LCDR3. In the heavy chain, for example, the N-terminus of the H-FR2 is linked directly or indirectly to the C-terminus of the HCDR1, and the C-terminus of the H-FR2 is linked directly or indirectly to the N-terminus of the HCDR2. For another example, the N-terminus of the H-FR3 is linked directly or indirectly to the C-terminus of the HCDR2, and the C-terminus of the H-FR3 is linked directly or indirectly to the N-terminus of the HCDR3. In the present application, the "first amino acid fragment" and the "second amino acid fragment" may be any identical or different amino acid fragments.

In the present application, the term "CCR8", which may also be referred to as CY6, CKR-L1, CDw198, CMKBR8, GPRCY6, CMKBRL2, CC-CKR-8 or TER1, generally refers to a G-protein coupled 7-transmembrane CC chemokine receptor protein expressed in the thymus, spleen, etc., which is a member of the 0 chemokine receptor family. Chemokines and their receptors are important for the migration of various cell types to sites of inflammation. CCL1 (or 1-309), thymus activation-regulated cytokine (TARC) and macrophage inflammatory protein 1 beta (MIP-1 beta) have been identified as ligands for CCR8. Studies on CCR8 and its ligands have shown that they have a role in regulating monocyte chemotaxis and thymocyte apoptosis. The term "CCR8" encompasses any natural CCR8 of any vertebrate origin, including mammals such as primates (e.g., humans and monkeys) and rodents (e.g., mice and rats). The CCR8 also encompasses "full-length", unprocessed CCR8, as well as any form of CCR8 that results from processing in a cell. CCR8 may be present as a transmembrane protein or as a soluble protein. The term also encompasses variants of naturally occurring CCR8, such as splice variants or allelic variants. The sequence of CCR8 is known in the art. Information on the human CCR8 gene (including genomic DNA sequence) can be found, for example, under NCBI Gene ID No. 1237. Additional information on the cynomolgus monkey CCR8 gene (including genomic DNA sequence) can be found, for example, under NCBI Gene ID No. 102132857. The amino acid sequence of an exemplary full-length human CCR8 protein can be found under NCBI accession No. NP 005192.1. The sequence of an exemplary full-length cynomolgus monkey CCR8 protein can be found under NCBI accession No. NP 001274549.

In the present application, the term "CCL1", which may also be referred to as P500, SISe, TCA3, I-309 or SCYA1, is a member of the chemokine CC subfamily, which is involved in immune regulation and inflammatory processes, and may bind to CCR8. CCL1 is normally secreted by activated T cells and shows chemotactic activity on monocytes. The term "CCL1" encompasses any natural CCL1 of any vertebrate origin, including mammals such as primates (e.g., humans and monkeys) and rodents (e.g., mice and rats). The CCL1 also encompasses "full-length", unprocessed CCL1, as well as any form of CCL1 that results from processing in a cell. CCL1 may be present as a transmembrane protein or as a soluble protein. The term also encompasses variants of naturally occurring CCL1, such as splice variants or allelic variants. The sequence of CCL1 is known in the art. Information on the human CCL1 gene (including genomic DNA sequence) can be found, for example, under NCBI Gene ID No. 6346. The amino acid sequence of an exemplary full-length human CCL1 protein can be found under NCBI accession No. NP_002972.1.

In the present application, the term "comprise" or "comprising" generally means including, summarizing, containing or encompassing. In some cases, the term also means "being" or "consisting of . . . ".

In the present application, the term "about" generally means varying by 0.5%-10% above or below the stated value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below the stated value.

DETAILED DESCRIPTION OF THE INVENTION

Antigen-Binding Protein

In one aspect, the present application provides an isolated antigen-binding protein having one or more of the following properties:

1) being capable of binding to CCR8 derived from a primate, e.g., with an $EC_{50}$ value of $2\times10^{-8}$ M or lower in an ELISA assay;
2) being capable of blocking the binding of CCR8 to a ligand CCL1;
3) being capable of inhibiting calcium influx caused by CCR8; and
4) being capable of inhibiting cell migration induced by CCR8.

In the present application, the Fc region of the antigen-binding protein may comprise modifications to enhance the ADCC effect.

In certain cases, the antigen-binding protein is capable of binding to CCR8 derived from a human and/or a monkey.

In certain cases, the antigen-binding protein is capable of binding to CCR8 derived from a human and a monkey.

In certain cases, the antigen-binding protein specifically targets tumor issue-infiltrating Treg cells with immunosuppressive activity.

In certain cases, the antigen-binding protein does not target inflammatory Treg cells and non-Treg T cells.

In the present application, the isolated antigen-binding protein may comprise at least one CDR in the antibody heavy chain variable region VH. For example, the VH may comprise an amino acid sequence set forth in any one of SEQ ID NOs: 169, 172, 177 and 181-197.

In the present application, the antigen-binding protein may comprise an HCDR1, wherein the HCDR1 may comprise an amino acid sequence set forth in SEQ ID NO: 359: $GFTFX_5TX_7$ (SEQ ID NO: 359); wherein $X_5$=N, Q or S; and $X_7$=N or Y. For example, this sequence may be a sequence determined according to the Chothia scheme.

For example, the HCDR1 may comprise an amino acid sequence set forth in any one of SEQ ID NOs: 15, 16, 21 and 22.

In the present application, the antigen-binding protein may comprise an HCDR2, wherein the HCDR2 may comprise an amino acid sequence set forth in SEQ ID NO: 38. For example, this sequence may be a sequence determined according to the Chothia scheme.

In the present application, the antigen-binding protein may comprise an HCDR3, wherein the HCDR3 may comprise an amino acid sequence set forth in SEQ ID NO: 360: $GKEX_4X_5NYYAMDX_{12}$ (SEQ ID NO: 360); wherein $X_4$=N or Q; $X_5$=A or G; and $X_{12}$=F or Y.

For example, this sequence may be a sequence determined according to the Chothia scheme.

For example, the HCDR3 may comprise an amino acid sequence set forth in any one of SEQ ID NOs: 65, 68, 72 and 73.

In the present application, the antigen-binding protein may comprise an HCDR1, an HCDR2 and an HCDR3, wherein the HCDR1, HCDR2 and HCDR3 may comprise amino acid sequences set forth in SEQ ID NO: 359, SEQ ID NO: 38 and SEQ ID NO 360, respectively. In certain cases, in the antigen-binding protein, the HCDR1 may comprise an amino acid sequence set forth in any one of SEQ ID NOs:

15, 16, 21 and 22, the HCDR2 may comprise an amino acid sequence set forth in SEQ ID NO: 38, and the HCDR3 may comprise an amino acid sequence set forth in any one of SEQ ID NOs: 65, 68, 72 and 73.

For example, the antigen-binding protein may comprise an HCDR1, an HCDR2 and an HCDR3, wherein the combination of the HCDR1, HCDR2 and HCDR3 may be selected from any one of the groups in the following table.

TABLE 2

| Sequence combinations | | | |
|---|---|---|---|
| Combination | HCDR1 | HCDR2 | HCDR3 |
| 1 | 15 | 38 | 65 |
| 2 | 16 | 38 | 65 |
| 3 | 16 | 38 | 68 |
| 4 | 16 | 38 | 72 |
| 5 | 16 | 38 | 73 |
| 6 | 21 | 38 | 65 |
| 7 | 22 | 38 | 65 |
| 8 | 22 | 38 | 72 |
| 9 | 22 | 38 | 73 |

In the present application, the antigen-binding protein may comprise a framework region H-FR1. The C-terminus of the H-FR1 is linked directly or indirectly to the N-terminus of the HCDR1. For example, the H-FR1 may comprise an amino acid sequence set forth in any one of SEQ ID NOs: 1, 2, 5, 7 and 8. For example, this sequence may be a sequence determined according to the Chothia scheme.

In the present application, the antigen-binding protein may comprise an H-FR2, wherein the H-FR2 is positioned between the HCDR1 and the HCDR2. For example, the H-FR2 may comprise an amino acid sequence set forth in any one of SEQ ID NOs: 26, 27, 30 and 31. For example, this sequence may be a sequence determined according to the Chothia scheme.

In the present application, the antigen-binding protein may comprise an H-FR3, wherein the H-FR3 is positioned between the HCDR2 and the HCDR3. For example, the H-FR3 may comprise an amino acid sequence set forth in any one of SEQ ID NOs: 50, 56 and 57. For example, this sequence may be a sequence determined according to the Chothia scheme.

In the present application, the antigen-binding protein may comprise an H-FR4, wherein the N-terminus of the H-FR4 is linked to the C-terminus of the HCDR3. For example, the H-FR4 may comprise an amino acid sequence set forth in any one of SEQ ID NOs: 84, 85 and 89. For example, this sequence may be a sequence determined according to the Chothia scheme.

In the present application, the antigen-binding protein may comprise a heavy chain variable region VH, wherein the VH may comprise an amino acid sequence set forth in any one of SEQ ID NOs: 169, 172, 177 and 181-197. For example, this sequence may be a sequence determined according to the Chothia scheme.

In the present application, the antigen-binding protein may comprise an Fc region. For example, the Fc region may comprise modifications to enhance the ADCC effect.

In the present application, the antigen-binding protein may comprise an Fc region. For example, the Fc region may comprise a glycosylated side chain that does not comprise a fucosyl group, or the Fc region may not comprise a glycosylated side chain with a fucosyl group.

The antigen-binding protein described herein may comprise a heavy chain constant region CH, wherein the antibody heavy chain constant region may comprise a human IgG constant region. In certain cases, the human IgG constant region may comprise a human IgG1 constant region. The human IgG1 constant region may include natural and synthetic IgG1 constant regions or mutants thereof. The mutation may comprise mutations at one or more of the following positions: S239D and I332E. For example, the human IgG1 constant region of the fusion protein may comprise an amino acid sequence set forth in SEQ ID NO: 356 or 357.

In the present application, the antigen-binding protein may comprise an antibody heavy chain. For example, the antibody heavy chain may comprise an amino acid sequence set forth in any one of SEQ ID NOs: 251, 254, 259-262 and 266-284.

In the present application, the antigen-binding protein may comprise at least one CDR in an antibody light chain variable region VL, wherein the VL may comprise an amino acid sequence set forth in any one of SEQ ID NOs: 214, 217, 220, 223, 227-230, 232-234, 236, 237, 242, 243 and 244.

In the present application, the antigen-binding protein may comprise an LCDR1, wherein the LCDR1 may comprise an amino acid sequence set forth in SEQ ID NO: 361: $RSX_3KSLLHSX_{10}X_{11}X_{12}X_{13}YLY$ (SEQ ID NO: 361); wherein $X_3$=N or S; $X_{10}$=N or Q; $X_{11}$=A or G; $X_{12}$=N or K; and $X_{13}$=I or T. For example, this sequence may be a sequence determined according to the Chothia scheme.

For example, the LCDR1 may comprise an amino acid sequence set forth in any one of SEQ ID NOs: 105, 106, 107, 111 and 112.

In the present application, the antigen-binding protein may comprise an LCDR2, wherein the LCDR2 may comprise an amino acid sequence set forth in SEQ ID NO: 127. For example, this sequence may be a sequence determined according to the Chothia scheme.

In the present application, the antigen-binding protein may comprise an LCDR3, wherein the LCDR3 may comprise an amino acid sequence set forth in SEQ ID NO: 362: $MQHLEYPX_8T$ (SEQ ID NO: 362); wherein $X_8$=I, L, M or V. For example, this sequence may be a sequence determined according to the Chothia scheme.

For example, the LCDR3 may comprise an amino acid sequence set forth in any one of SEQ ID NOs: 142, 150, 151 and 152.

In the present application, the antigen-binding protein may comprise an LCDR1, an LCDR2 and an LCDR3, wherein the LCDR1 may comprise an amino acid sequence set forth in any one of SEQ ID NOs: 105, 106, 107, 111 and 112, the LCDR2 may comprise an amino acid sequence set forth in SEQ ID NO: 127, and the LCDR3 may comprise an amino acid sequence set forth in SEQ ID NO: 362.

In the present application, the antigen-binding protein may comprise an LCDR1, an LCDR2 and an LCDR3, wherein the LCDR1 may comprise an amino acid sequence set forth in SEQ ID NO: 361, the LCDR2 may comprise an amino acid sequence set forth in SEQ ID NO: 127, and the LCDR3 may comprise an amino acid sequence set forth in any one of SEQ ID NOs: 142, 150, 151 and 152. For example, the antigen-binding protein may comprise an LCDR1, an LCDR2 and an LCDR3, wherein the combination of the LCDR1, LCDR2 and LCDR3 may be selected from any one of the groups in Table 3 below.

TABLE 3

| Sequence combinations | | | |
|---|---|---|---|
| Combination | LCDR1 | LCDR2 | LCDR3 |
| 1 | 105 | 127 | 142 |
| 2 | 106 | 127 | 142 |
| 3 | 106 | 127 | 150 |
| 4 | 106 | 127 | 151 |
| 5 | 106 | 127 | 152 |
| 6 | 107 | 127 | 142 |
| 7 | 111 | 127 | 142 |
| 8 | 112 | 127 | 142 |

In the present application, the antigen-binding protein may comprise a framework region L-FR1. The C-terminus of the L-FR1 is linked directly or indirectly to the N-terminus of the LCDR1. For example, the L-FR1 may comprise an amino acid sequence set forth in any one of SEQ ID NOs: 92, 98 and 99. For example, this sequence may be a sequence determined according to the Chothia scheme.

In the present application, the antigen-binding protein may comprise an L-FR2, wherein the L-FR2 is positioned between the LCDR1 and the LCDR2. For example, the L-FR2 may comprise an amino acid sequence set forth in any one of SEQ ID NOs: 118, 122 and 123. For example, this sequence may be a sequence determined according to the Chothia scheme.

In the present application, the antigen-binding protein may comprise an L-FR3, wherein the L-FR3 is positioned between the LCDR2 and the LCDR3. For example, the L-FR3 may comprise an amino acid sequence set forth in any one of SEQ ID NOs: 135-136. For example, this sequence may be a sequence determined according to the Chothia scheme.

In the present application, the antigen-binding protein may comprise an L-FR4, wherein the N-terminus of the L-FR4 is linked to the C-terminus of the LCDR3. For example, the L-FR4 may comprise an amino acid sequence set forth in any one of SEQ ID NOs: 156, 158, 159 and 164. For example, this sequence may be a sequence determined according to the Chothia scheme.

In the present application, the antigen-binding protein may comprise a light chain variable region VL, wherein the VL may comprise an amino acid sequence set forth in any one of SEQ ID NOs: 214, 217, 220, 223, 227-230, 232-234, 236, 237, 242, 243 and 244. For example, this sequence may be a sequence determined according to the Chothia scheme.

The antigen-binding protein described herein may comprise a light chain constant region CL, wherein the antibody light chain constant region may comprise a human Igκ constant region. For example, the CL region may comprise an amino acid sequence set forth below: SEQ ID NO: 358.

In the present application, the antigen-binding protein may comprise an antibody light chain. For example, the antibody light chain may comprise an amino acid sequence set forth in any one of SEQ ID NOs: 321, 324, 327, 330, 334-337, 339-341, 343, 344, 349, 350 and 351.

In the present application, the antigen-binding protein may comprise an HCDR1, an HCDR2, an HCDR3, an LCDR1, an LCDR2 and an LCDR3, wherein the HCDR1, HCDR2, HCDR3, LCDR1, LCDR2 and LCDR3 may comprise amino acid sequences set forth in SEQ ID NO: 359, SEQ ID NO: 38, SEQ ID NO: 360, SEQ ID NO: 361, SEQ ID NO: 127, and SEQ ID NO: 362, respectively.

In certain cases, in the antigen-binding protein, the HCDR1 may comprise an amino acid sequence set forth in any one of SEQ ID NOs: 15, 16, 21 and 22, the HCDR2 may comprise an amino acid sequence set forth in SEQ ID NO: 38, and the HCDR3 may comprise an amino acid sequence set forth in any one of SEQ ID NOs: 65, 68, 72 and 73; and the LCDR1 may comprise an amino acid sequence set forth in any one of SEQ ID NOs: 105, 106, 107, 111 and 112, the LCDR2 may comprise an amino acid sequence set forth in SEQ ID NO: 127, and the LCDR3 may comprise an amino acid sequence set forth in any one of SEQ ID NOs: 142, 150, 151 and 152.

For example, the antigen-binding protein may comprise an HCDR1, an HCDR2, an HCDR3, an LCDR1, an LCDR2 and an LCDR3, wherein the combination of the HCDR1, HCDR2, HCDR3, LCDR1, LCDR2 and LCDR3 may be selected from any one of the groups in Table 4 below.

TABLE 4

| Sequence combinations | | | | | | |
|---|---|---|---|---|---|---|
| Combination | LCDR1 | LCDR2 | LCDR3 | HCDR1 | HCDR2 | HCDR3 |
| 1 | 105 | 127 | 142 | 15 | 38 | 65 |
| 2 | 105 | 127 | 142 | 16 | 38 | 65 |
| 3 | 106 | 127 | 142 | 15 | 38 | 65 |
| 4 | 106 | 127 | 142 | 16 | 38 | 65 |
| 5 | 106 | 127 | 142 | 16 | 38 | 68 |
| 6 | 106 | 127 | 142 | 16 | 38 | 72 |
| 7 | 106 | 127 | 142 | 16 | 38 | 73 |
| 8 | 106 | 127 | 142 | 21 | 38 | 65 |
| 9 | 106 | 127 | 142 | 22 | 38 | 65 |
| 10 | 106 | 127 | 142 | 22 | 38 | 72 |
| 11 | 106 | 127 | 142 | 22 | 38 | 73 |
| 12 | 106 | 127 | 150 | 16 | 38 | 65 |
| 13 | 106 | 127 | 151 | 16 | 38 | 65 |
| 14 | 106 | 127 | 152 | 16 | 38 | 65 |
| 15 | 107 | 127 | 142 | 16 | 38 | 65 |
| 16 | 107 | 127 | 142 | 16 | 38 | 68 |
| 17 | 111 | 127 | 142 | 16 | 38 | 65 |
| 18 | 111 | 127 | 142 | 22 | 38 | 72 |
| 19 | 111 | 127 | 142 | 22 | 38 | 73 |
| 20 | 112 | 127 | 142 | 16 | 38 | 65 |

In the present application, the antigen-binding protein may comprise an antibody heavy chain variable region VH and a light chain variable region VL. For example, the VH may comprise an amino acid sequence set forth in any one of SEQ ID NOs: 169, 172, 177 and 181-197, and the VL may comprise an amino acid sequence set forth in any one of SEQ ID NOs: 214, 217, 220, 223, 227-230, 232-234, 236, 237, 242, 243 and 244.

For example, the combination of VL and VH of the antigen-binding protein may comprise any one of the groups selected from Table 5 below.

TABLE 5

| Sequence combinations | | | | | | | | | | | | | | | | |
|---|---|---|---|---|---|---|---|---|---|---|---|---|---|---|---|---|
| Combination | 1 | 2 | 3 | 4 | 5 | 6 | 7 | 8 | 9 | 10 | 11 | 12 | 13 | 14 | 15 | 16 |
| VH | 169 | 172 | 172 | 177 | 172 | 172 | 181 | 182 | 183 | 184 | 185 | 186 | 187 | 188 | 189 | 190 |
| VL | 214 | 217 | 220 | 223 | 227 | 228 | 220 | 220 | 220 | 220 | 220 | 220 | 220 | 220 | 220 | 220 |

TABLE 5-continued

| Sequence combinations | | | | | | | | | | | | | | | | |
|---|---|---|---|---|---|---|---|---|---|---|---|---|---|---|---|---|
| Combination | 17 | 18 | 19 | 20 | 21 | 22 | 23 | 24 | 25 | 26 | 27 | 28 | 29 | 30 | 31 | 32 |
| VH | 191 | 192 | 193 | 172 | 172 | 172 | 172 | 172 | 185 | 188 | 191 | 185 | 188 | 191 | 185 | 188 |
| VL | 220 | 220 | 220 | 229 | 230 | 232 | 233 | 234 | 229 | 229 | 229 | 230 | 230 | 230 | 232 | 232 |
| Combination | 33 | 34 | 35 | 36 | 37 | 38 | 39 | 40 | 41 | 42 | 43 | 44 | 45 | 46 | | |
| VH | 191 | 194 | 195 | 194 | 195 | 196 | 197 | 196 | 197 | 188 | 185 | 172 | 172 | 172 | | |
| VL | 232 | 229 | 229 | 236 | 236 | 232 | 232 | 237 | 237 | 229 | 232 | 242 | 243 | 244 | | |

In the present application, the antigen-binding protein may comprise an antibody light chain and an antibody heavy chain, wherein the light chain may comprise an amino acid sequence set forth in any one of SEQ ID NOs: 321, 324, 327, 330, 334-337, 339-341, 343, 344, 349, 350 and 351, and the heavy chain may comprise an amino acid sequence set forth in any one of SEQ ID NOs: 251, 254, 259-262, and 266-284.

For example, the combination of the light chain and the heavy chain of the antigen-binding protein may comprise any one of the groups selected from Table 6 below.

TABLE 6

| Sequence combinations | | | | | | | | | | |
|---|---|---|---|---|---|---|---|---|---|---|
| Combination | 1 | 2 | 3 | 4 | 5 | 6 | 7 | 8 | 9 | 10 |
| Light chain | 321 | 324 | 327 | 330 | 321 | 324 | 327 | 330 | 334 | 335 |
| Heavy chain | 251 | 254 | 254 | 259 | 260 | 261 | 261 | 262 | 261 | 261 |
| Combination | 11 | 12 | 13 | 14 | 15 | 16 | 17 | 18 | 19 | 20 |
| Light chain | 327 | 327 | 327 | 327 | 327 | 327 | 327 | 327 | 327 | 327 |
| Heavy chain | 266 | 267 | 268 | 269 | 270 | 271 | 272 | 273 | 274 | 275 |
| Combination | 21 | 22 | 23 | 24 | 25 | 26 | 27 | 28 | 29 | 30 |
| Light chain | 327 | 327 | 327 | 336 | 337 | 339 | 340 | 341 | 336 | 336 |
| Heavy chain | 276 | 277 | 278 | 261 | 261 | 261 | 261 | 261 | 270 | 273 |
| Combination | 31 | 32 | 33 | 34 | 35 | 36 | 37 | 38 | 39 | 40 |
| Light chain | 336 | 337 | 337 | 337 | 339 | 339 | 339 | 336 | 336 | 343 |
| Heavy chain | 276 | 270 | 273 | 276 | 270 | 273 | 276 | 279 | 280 | 279 |
| Combination | 41 | 42 | 43 | 44 | 45 | 46 | 47 | 48 | 49 | 50 |
| Light chain | 343 | 339 | 339 | 344 | 344 | 336 | 339 | 349 | 350 | 351 |
| Heavy chain | 280 | 281 | 282 | 281 | 282 | 283 | 284 | 254 | 254 | 254 |

In the present application, the antigen-binding protein may comprise at least one CDR in the antibody heavy chain variable region VH. For example, the VH may comprise an amino acid sequence set forth in any one of SEQ ID NOs: 196 and 206-211.

In the present application, the antigen-binding protein may comprise an HCDR1, wherein the HCDR1 may comprise an amino acid sequence set forth in SEQ ID NO: 22. For example, this sequence may be a sequence determined according to the Chothia scheme.

In the present application, the antigen-binding protein may comprise an HCDR2, wherein the HCDR2 may comprise an amino acid sequence set forth in SEQ ID NO: 367: RSKSN$X_6$YA (SEQ ID NO: 367); wherein $X_6$=N or Y. For example, this sequence may be a sequence determined according to the Chothia scheme.

For example, the HCDR2 may comprise an amino acid sequence set forth in any one of SEQ ID NOs: 38 and 48.

In the present application, the antigen-binding protein may comprise an HCDR3, wherein the HCDR3 may comprise an amino acid sequence set forth in SEQ ID NO: 368: GKE$X_4X_5X_6$YYAMDF (SEQ ID NO: 368); wherein $X_4$=H, I or N; $X_5$=A or G; and $X_6$=K or N. For example, this sequence may be a sequence determined according to the Chothia scheme.

For example, the HCDR3 may comprise an amino acid sequence set forth in any one of SEQ ID NOs: 72 and 80-83.

In the present application, the antigen-binding protein may comprise an HCDR1, an HCDR2 and an HCDR3, wherein the HCDR1, HCDR2 and HCDR3 may comprise amino acid sequences set forth in SEQ ID NO: 22, SEQ ID NO: 367 and SEQ ID NO 368, respectively. In certain cases, in the antigen-binding protein, the HCDR1 may comprise an amino acid sequence set forth in SEQ ID NO: 22, the HCDR2 may comprise an amino acid sequence set forth in SEQ ID NO: 38 or 48, and the HCDR3 may comprise an amino acid sequence set forth in any one of SEQ ID NOs: 72 and 80-83.

For example, the antigen-binding protein may comprise an HCDR1, an HCDR2 and an HCDR3, wherein the combination of the HCDR1, HCDR2 and HCDR3 may comprise any one of the groups selected from Table 7 below.

TABLE 7

| Sequence combinations | | | |
|---|---|---|---|
| Combination | HCDR1 | HCDR2 | HCDR3 |
| 1 | 22 | 38 | 72 |
| 2 | 22 | 38 | 80 |
| 3 | 22 | 48 | 80 |
| 4 | 22 | 38 | 81 |
| 5 | 22 | 48 | 81 |
| 6 | 22 | 48 | 82 |
| 7 | 22 | 48 | 83 |

In the present application, the antigen-binding protein may comprise a framework region H-FR1. The C-terminus of the H-FR1 is linked directly or indirectly to the N-terminus of the HCDR1. For example, the H-FR1 may comprise an amino acid sequence set forth in SEQ ID NO: 7. For example, this sequence may be a sequence determined according to the Chothia scheme.

In the present application, the antigen-binding protein may comprise an H-FR2, wherein the H-FR2 is positioned between the HCDR1 and the HCDR2. For example, the H-FR2 may comprise an amino acid sequence set forth in SEQ ID NO: 27. For example, this sequence may be a sequence determined according to the Chothia scheme.

In the present application, the antigen-binding protein may comprise an H-FR3, wherein the H-FR3 is positioned between the HCDR2 and the HCDR3. For example, the H-FR3 may comprise an amino acid sequence set forth in SEQ ID NO: 56. For example, this sequence may be a sequence determined according to the Chothia scheme.

In the present application, the antigen-binding protein may comprise an H-FR4, wherein the N-terminus of the H-FR4 is linked to the C-terminus of the HCDR3. For example, the H-FR4 may comprise an amino acid sequence set forth in SEQ ID NO: 89. For example, this sequence may be a sequence determined according to the Chothia scheme.

In the present application, the antigen-binding protein may comprise a heavy chain variable region VH, wherein the VH may comprise an amino acid sequence set forth in any one of SEQ ID NOs: 196 and 206-211. For example, this sequence may be a sequence determined according to the Chothia scheme.

In the present application, the antigen-binding protein may comprise an Fc region. For example, the Fc region may comprise modifications to enhance the ADCC effect.

In the present application, the antigen-binding protein may comprise an Fc region. For example, the Fc region may comprise a glycosylated side chain that does not comprise a fucosyl group, or the Fc region may not comprise a glycosylated side chain with a fucosyl group.

The antigen-binding protein described herein may comprise a heavy chain constant region CH, wherein the antibody heavy chain constant region may comprise a human IgG constant region. In certain cases, the human IgG constant region may comprise a human IgG1 constant region. The human IgG1 constant region may include natural and synthetic IgG1 constant regions or mutants thereof. The mutation may comprise mutations at one or more of the following positions: S239D and I332E. For example, the human IgG1 constant region of the fusion protein may comprise an amino acid sequence set forth in SEQ ID NO: 356 or 357.

In the present application, the antigen-binding protein may comprise an antibody heavy chain. For example, the antibody heavy chain may comprise an amino acid sequence set forth in any one of SEQ ID NOs: 299-318.

In the present application, the antigen-binding protein described herein may comprise at least one CDR in an antibody light chain variable region VL, wherein the VL may comprise an amino acid sequence set forth in SEQ ID NO: 237.

In the present application, the antigen-binding protein may comprise an LCDR1, wherein the LCDR1 may comprise an amino acid sequence set forth in SEQ ID NO: 111. For example, this sequence may be a sequence determined according to the Chothia scheme.

In the present application, the antigen-binding protein may comprise an LCDR2, wherein the LCDR2 may comprise an amino acid sequence set forth in SEQ ID NO: 127. For example, this sequence may be a sequence determined according to the Chothia scheme.

In the present application, the antigen-binding protein may comprise an LCDR3, wherein the LCDR3 may comprise an amino acid sequence set forth in SEQ ID NO: 142. For example, this sequence may be a sequence determined according to the Chothia scheme.

In the present application, the antigen-binding protein may comprise an LCDR1, an LCDR2 and an LCDR3, wherein the LCDR1 may comprise an amino acid sequence set forth in SEQ ID NO: 111, the LCDR2 may comprise an amino acid sequence set forth in SEQ ID NO: 127, and the LCDR3 may comprise an amino acid sequence set forth in SEQ ID NO: 142.

In the present application, the antigen-binding protein may comprise a framework region L-FR1. The C-terminus of the L-FR1 is linked directly or indirectly to the N-terminus of the LCDR1. For example, the L-FR1 may comprise an amino acid sequence set forth in SEQ ID NO: 99. For example, this sequence may be a sequence determined according to the Chothia scheme.

In the present application, the antigen-binding protein may comprise an L-FR2, wherein the L-FR2 is positioned between the LCDR1 and the LCDR2. For example, the L-FR2 may comprise an amino acid sequence set forth in SEQ ID NO: 123. For example, this sequence may be a sequence determined according to the Chothia scheme.

In the present application, the antigen-binding protein may comprise an L-FR3, wherein the L-FR3 is positioned between the LCDR2 and the LCDR3. For example, the L-FR3 may comprise an amino acid sequence set forth in SEQ ID NO: 136. For example, this sequence may be a sequence determined according to the Chothia scheme.

In the present application, the antigen-binding protein may comprise an L-FR4, wherein the N-terminus of the L-FR4 is linked to the C-terminus of the LCDR3. For example, the L-FR4 may comprise an amino acid sequence set forth in SEQ ID NO: 164. For example, this sequence may be a sequence determined according to the Chothia scheme.

In the present application, the antigen-binding protein may comprise a light chain variable region VL, wherein the VL may comprise an amino acid sequence set forth in SEQ ID NO: 237. For example, this sequence may be a sequence determined according to the Chothia scheme.

The antigen-binding protein described herein may comprise a light chain constant region CL, wherein the antibody light chain constant region may comprise a human Igκ constant region. For example, the CL region may comprise an amino acid sequence set forth below: SEQ ID NO: 358.

In the present application, the antigen-binding protein may comprise an antibody light chain. For example, the antibody light chain may comprise an amino acid sequence set forth in SEQ ID NO: 344.

In the present application, the antigen-binding protein may comprise an HCDR1, an HCDR2, an HCDR3, an LCDR1, an LCDR2 and an LCDR3, wherein the HCDR1, HCDR2, HCDR3, LCDR1, LCDR2 and LCDR3 may comprise amino acid sequences set forth in SEQ ID NO: 22, SEQ ID NO: 367, SEQ ID NO: 368, SEQ ID NO: 111, SEQ ID NO: 127, and SEQ ID NO: 142, respectively.

In certain cases, in the antigen-binding protein, the HCDR1 may comprise an amino acid sequence set forth in SEQ ID NO: 22, the HCDR2 may comprise an amino acid sequence set forth in SEQ ID NO: 38 or 48, and the HCDR3 may comprise an amino acid sequence set forth in any one of SEQ ID NOs: 72, 80, 81, 82 and 83; the LCDR1 may comprise an amino acid sequence set forth in SEQ ID NO: 111, the LCDR2 may comprise an amino acid sequence set forth in SEQ ID NO: 127, and the LCDR3 may comprise an amino acid sequence set forth in SEQ ID NO:142.

For example, the antigen-binding protein may comprise an HCDR1, an HCDR2, an HCDR3, an LCDR1, an LCDR2 and an LCDR3, wherein the combination of the HCDR1, HCDR2, HCDR3, LCDR1, LCDR2 and LCDR3 may comprise any one of the groups selected from Table 8 below.

TABLE 8

| Sequence combinations | | | | | | |
|---|---|---|---|---|---|---|
| Combination | HCDR1 | HCDR2 | HCDR3 | LCDR1 | LCDR2 | LCDR3 |
| 1 | 22 | 38 | 72 | 111 | 127 | 142 |
| 2 | 22 | 38 | 80 | 111 | 127 | 142 |
| 3 | 22 | 48 | 80 | 111 | 127 | 142 |
| 4 | 22 | 38 | 81 | 111 | 127 | 142 |
| 5 | 22 | 48 | 81 | 111 | 127 | 142 |
| 6 | 22 | 48 | 82 | 111 | 127 | 142 |
| 7 | 22 | 48 | 83 | 111 | 127 | 142 |

In the present application, the antigen-binding protein may comprise an antibody heavy chain variable region VH and a light chain variable region VL. For example, the VH may comprise an amino acid sequence set forth in any one of SEQ ID NOs: 196 and 206-211, and the VL may comprise an amino acid sequence set forth in SEQ ID NO: 237.

For example, the antigen-binding protein may comprise a VH and a VL, wherein the combination of VH and VL may comprise any one of the groups selected from Table 9 belowl.

TABLE 9

| Sequence combinations | | | | | | | |
|---|---|---|---|---|---|---|---|
| Combination | 1 | 2 | 3 | 4 | 5 | 6 | 7 |
| VH | 196 | 206 | 207 | 208 | 209 | 210 | 211 |
| VL | 237 | 237 | 237 | 237 | 237 | 237 | 237 |

In the present application, the antigen-binding protein may comprise an antibody light chain and an antibody heavy chain, wherein the light chain may comprise an amino acid sequence set forth in SEQ ID NO: 344, and the heavy chain may comprise an amino acid sequence set forth in any one of SEQ ID NOs: 299-318.

For example, the combination of the light chain and the heavy chain of the antigen-binding protein may comprise any one of the groups selected from Table 10 below.

TABLE 10

| Sequence combinations | | | | | | | | | | |
|---|---|---|---|---|---|---|---|---|---|---|
| Combination | 1 | 2 | 3 | 4 | 5 | 6 | 7 | 8 | 9 | 10 |
| Heavy chain | 300 | 301 | 302 | 303 | 304 | 305 | 306 | 307 | 308 | 309 |
| Light chain | 344 | 344 | 344 | 344 | 344 | 344 | 344 | 344 | 344 | 344 |
| Combination | 11 | 12 | 13 | 14 | 15 | 16 | 17 | 18 | 19 | 20 |
| Heavy chain | 310 | 311 | 312 | 299 | 313 | 317 | 314 | 318 | 315 | 316 |
| Light chain | 344 | 344 | 344 | 344 | 344 | 344 | 344 | 344 | 344 | 344 |

In the present application, the isolated antigen-binding protein is capable of binding to CCR8 derived from a human.

In the present application, the isolated antigen-binding protein may comprise at least one CDR in the antibody heavy chain variable region VH. The VH may comprise an amino acid sequence set forth in SEQ ID NO: 331. For example, the VH may comprise an amino acid sequence set forth in any one of SEQ ID NOs: 167, 168 and 170-176.

In the present application, the antigen-binding protein may comprise an HCDR1, wherein the HCDR1 may comprise an amino acid sequence set forth in SEQ ID NO: 363: $X_1FTFX_5TX_7$ (SEQ ID NO: 363); wherein $X_1$=E or G; $X_5$=N or S; and $X_7$=N or Y. For example, this sequence may be a sequence determined according to the Chothia scheme.

For example, the HCDR1 may comprise an amino acid sequence set forth in any one of SEQ ID NOs: 15-18.

In the present application, the antigen-binding protein may comprise an HCDR2, wherein the HCDR2 may comprise an amino acid sequence set forth in SEQ ID NO: 364: $RX_2KX_4NNX_7A$ (SEQ ID NO: 364); wherein $X_2$=S or T; $X_4$=M or S; and X 7=F or Y. For example, this sequence may be a sequence determined according to the Chothia scheme.

For example, the HCDR2 may comprise an amino acid sequence set forth in any one of SEQ ID NOs: 37-39.

In the present application, the antigen-binding protein may comprise an HCDR3, wherein the HCDR3 may comprise an amino acid sequence set forth in SEQ ID NO: 365: $GKX_3X_4GNYYAMDX_{12}$ (SEQ ID NO: 365); wherein $X_3$=D or E; $X_4$=N or Y; and $X_{12}$=F or Y. For example, this sequence may be a sequence determined according to the Chothia scheme.

For example, the HCDR3 may comprise an amino acid sequence set forth in any one of SEQ ID NOs: 65-67.

In the present application, the antigen-binding protein may comprise an HCDR1, an HCDR2 and an HCDR3, wherein the HCDR1 may comprise an amino acid sequence set forth in SEQ ID NO: 363, the HCDR2 may comprise an amino acid sequence set forth in SEQ ID NO: 364, and the HCDR3 may comprise an amino acid sequence set forth in SEQ ID NO: 365.

In the present application, the antigen-binding protein may comprise an HCDR1, an HCDR2 and an HCDR3, wherein the HCDR1 may comprise an amino acid sequence set forth in any one of SEQ ID NOs: 15-18, the HCDR2 may comprise an amino acid sequence set forth in any one of SEQ ID NOs: 37-39, and the HCDR3 may comprise an amino acid sequence set forth in any one of SEQ ID NOs: 65-67.

For example, the antigen-binding protein may comprise an HCDR1, an HCDR2 and an HCDR3, wherein the combination of the HCDR1, HCDR2 and HCDR3 may be selected from any one of the groups in the following table.

TABLE 11

| Sequence combinations | | | |
|---|---|---|---|
| Combination | HCDR1 | HCDR2 | HCDR3 |
| 1 | 15 | 37 | 65 |
| 2 | 17 | 39 | 65 |
| 3 | 16 | 38 | 66 |
| 4 | 18 | 38 | 65 |
| 5 | 15 | 38 | 65 |
| 6 | 16 | 38 | 67 |
| 7 | 16 | 38 | 65 |

In the present application, the antigen-binding protein may comprise a framework region H-FR1. The C-terminus of the H-FR1 is linked directly or indirectly to the N-terminus of the HCDR1. For example, the H-FR1 may comprise an amino acid sequence set forth in any one of SEQ ID NOs: 1-4. For example, this sequence may be a sequence determined according to the Chothia scheme.

In the present application, the antigen-binding protein may comprise an H-FR2, wherein the H-FR2 is positioned between the HCDR1 and the HCDR2. For example, the H-FR2 may comprise an amino acid sequence set forth in any one of SEQ ID NOs: 26 and 27. For example, this sequence may be a sequence determined according to the Chothia scheme.

In the present application, the antigen-binding protein may comprise an H-FR3, wherein the H-FR3 is positioned between the HCDR2 and the HCDR3. For example, the H-FR3 may comprise an amino acid sequence set forth in any one of SEQ ID NOs: 49-52. For example, this sequence may be a sequence determined according to the Chothia scheme.

In the present application, the antigen-binding protein may comprise an H-FR4, wherein the N-terminus of the H-FR4 is linked to the C-terminus of the HCDR3. For example, the H-FR4 may comprise an amino acid sequence set forth in any one of SEQ ID NOs: 84-86. For example, this sequence may be a sequence determined according to the Chothia scheme.

In the present application, the antigen-binding protein may comprise a heavy chain variable region VH, wherein the VH may comprise an amino acid sequence set forth in any one of SEQ ID NOs: 167, 168 and 170-176.

In the present application, the antigen-binding protein may comprise an Fc region. For example, the Fc region may comprise modifications to enhance the ADCC effect.

In the present application, the antigen-binding protein may comprise an Fc region. For example, the Fc region may comprise a glycosylated side chain that does not comprise a fucosyl group, or the Fc region may not comprise a glycosylated side chain with a fucosyl group.

The antigen-binding protein described herein may comprise a heavy chain constant region CH, wherein the antibody heavy chain constant region may comprise a human IgG constant region. In certain cases, the human IgG constant region may comprise a human IgG1 constant region. The human IgG1 constant region may include natural and synthetic IgG1 constant regions or mutants thereof. The mutation may comprise mutations at one or more of the following positions: S239D and I332E. For example, the human IgG1 constant region of the fusion protein may comprise an amino acid sequence set forth in any one of SEQ ID NOs: 356-357.

In the present application, the antigen-binding protein may comprise an antibody heavy chain. For example, the antibody heavy chain may comprise an amino acid sequence set forth in any one of SEQ ID NOs: 249, 250, 252, 253, 255, 256, 257, 258 and 261.

In the present application, the antigen-binding protein may comprise at least one CDR in an antibody light chain variable region VL, wherein the VL may comprise an amino acid sequence set forth in any one of SEQ ID NOs: 212, 213, 215, 216, 218, 219, 221, 222, 231 and 235.

In the present application, the antigen-binding protein may comprise an LCDR1, wherein the LCDR1 may comprise an amino acid sequence set forth in SEQ ID NO: 366: RSSKSLL$X_8$SNGNTYLY (SEQ ID NO: 366); wherein $X_8$=H or Y. For example, this sequence may be a sequence determined according to the Chothia scheme.

For example, the LCDR1 may comprise an amino acid sequence set forth in any one of SEQ ID NOs: 104-105.

In the present application, the antigen-binding protein may comprise an LCDR2, wherein the LCDR2 may comprise an amino acid sequence set forth in SEQ ID NO: 127. For example, this sequence may be a sequence determined according to the Chothia scheme.

In the present application, the antigen-binding protein may comprise an LCDR3, wherein the LCDR3 may comprise an amino acid sequence set forth in SEQ ID NO: 141. For example, this sequence may be a sequence determined according to the Chothia scheme.

In the present application, the antigen-binding protein may comprise an LCDR1, an LCDR2 and an LCDR3, wherein the LCDR1, LCDR2 and LCDR3 may comprise amino acid sequences set forth in SEQ ID NO: 366, SEQ ID NO: 127 and SEQ ID NO: 141, respectively. In certain cases, the LCDR1 of the antigen-binding protein may comprise an amino acid sequence set forth in any one of SEQ ID NO: 104 and SEQ ID NO: 105.

For example, in the antigen-binding protein, the LCDR1 may comprise an amino acid sequence set forth in SEQ ID NO: 104, the LCDR2 may comprise an amino acid sequence set forth in SEQ ID NO: 127, and the LCDR3 may comprise an amino acid sequence set forth in SEQ ID NO: 141.

For example, in the antigen-binding protein, the LCDR1 may comprise an amino acid sequence set forth in SEQ ID NO: 105, the LCDR2 may comprise an amino acid sequence set forth in SEQ ID NO: 127, and the LCDR3 may comprise an amino acid sequence set forth in SEQ ID NO: 141.

In the present application, the antigen-binding protein may comprise a framework region L-FR1. The C-terminus of the L-FR1 is linked directly or indirectly to the N-terminus of the LCDR1. For example, the L-FR1 may comprise an amino acid sequence set forth in any one of SEQ ID NOs: 90-94 and 98-99. For example, this sequence may be a sequence determined according to the Chothia scheme.

In the present application, the antigen-binding protein may comprise an L-FR2, wherein the L-FR2 is positioned between the LCDR1 and the LCDR2. For example, the L-FR2 may comprise an amino acid sequence set forth in any one of SEQ ID NOs: 118, 122 and 123. For example, this sequence may be a sequence determined according to the Chothia scheme.

In the present application, the antigen-binding protein may comprise an L-FR3, wherein the L-FR3 is positioned between the LCDR2 and the LCDR3. For example, the L-FR3 may comprise an amino acid sequence set forth in any one of SEQ ID NOs: 135-136. For example, this sequence may be a sequence determined according to the Chothia scheme.

In the present application, the antigen-binding protein may comprise an L-FR4, wherein the N-terminus of the L-FR4 is linked to the C-terminus of the LCDR3. For example, the L-FR4 may comprise an amino acid sequence set forth in any one of SEQ ID NOs: 154-157, 160, 161 and 164. For example, this sequence may be a sequence determined according to the Chothia scheme.

In the present application, the antigen-binding protein may comprise a light chain variable region VL, wherein the VL may comprise an amino acid sequence set forth in any one of SEQ ID NOs: 212, 213, 215, 216, 218, 219, 221, 222, 231 and 235. For example, this sequence may be a sequence determined according to the Chothia scheme.

The antigen-binding protein described herein may comprise a light chain constant region CL, wherein the antibody light chain constant region may comprise a human Igκ constant region. For example, the CL region may comprise an amino acid sequence set forth below: SEQ ID NO: 358.

In the present application, the antigen-binding protein may comprise an antibody light chain. For example, the antibody light chain may comprise an amino acid sequence set forth in any one of SEQ ID NOs: 319, 320, 322, 323, 325, 326, 328, 329, 338 and 342.

In the present application, the antigen-binding protein may comprise an HCDR1, an HCDR2, an HCDR3, an LCDR1, an LCDR2 and an LCDR3, wherein the HCDR1, HCDR2, HCDR3, LCDR1, LCDR2 and LCDR3 may comprise amino acid sequences set forth in SEQ ID NO: 363, SEQ ID NO: 364, SEQ ID NO: 365, SEQ ID NO: 366, SEQ ID NO: 127, and SEQ ID NO: 141, respectively. In certain cases, in the antigen-binding protein, the HCDR1 may comprise an amino acid sequence set forth in any one of SEQ ID NOs: 15-18, the HCDR2 may comprise an amino acid sequence set forth in any one of SEQ ID NOs: 37-39, and the HCDR3 may comprise an amino acid sequence set forth in any one of SEQ ID NOs: 65-67; the LCDR1 may comprise an amino acid sequence set forth in any one of SEQ ID NOs: 104-105, the LCDR2 may comprise an amino acid sequence set forth in SEQ ID NO: 127, and the LCDR3 may comprise an amino acid sequence set forth in SEQ ID NO: 141.

For example, the antigen-binding protein may comprise an HCDR1, an HCDR2, an HCDR3, an LCDR1, an LCDR2 and an LCDR3, wherein the combination of the HCDR1, HCDR2, HCDR3, LCDR1, LCDR2 and LCDR3 may comprise any one of the groups selected from Table 12 below.

TABLE 12

| Sequence combinations | | | | | | |
|---|---|---|---|---|---|---|
| Combination | HCDR1 | HCDR2 | HCDR3 | LCDR1 | LCDR2 | LCDR3 |
| 1 | 15 | 37 | 65 | 104 | 127 | 141 |
| 2 | 17 | 39 | 65 | 105 | 127 | 141 |
| 3 | 16 | 38 | 66 | 105 | 127 | 141 |
| 4 | 18 | 38 | 65 | 105 | 127 | 141 |
| 5 | 15 | 38 | 65 | 104 | 127 | 141 |
| 6 | 16 | 38 | 67 | 105 | 127 | 141 |
| 7 | 16 | 38 | 65 | 105 | 127 | 141 |

In the present application, the antigen-binding protein may comprise an antibody heavy chain variable region VH and a light chain variable region VL. For example, the VH may comprise an amino acid sequence set forth in any one of SEQ ID NOs: 167, 168 and 170-176, wherein the VL may comprise an amino acid sequence set forth in any one of SEQ ID NOs: 212, 213, 215, 216, 218, 219, 221, 222, 231 and 235.

For example, the antigen-binding protein may comprise a VH and a VL, wherein the combination of VH and VL may comprise any one of the groups selected from Table 13 belowl.

TABLE 13

| Sequence combinations | | | | | | | | | | |
|---|---|---|---|---|---|---|---|---|---|---|
| Combination | 1 | 2 | 3 | 4 | 5 | 6 | 7 | 8 | 9 | 10 |
| VL | 212 | 213 | 215 | 216 | 218 | 219 | 221 | 222 | 231 | 235 |
| VH | 167 | 168 | 170 | 171 | 173 | 174 | 175 | 176 | 172 | 172 |

In the present application, the antigen-binding protein may comprise an antibody heavy chain and an antibody light chain. For example, the heavy chain may comprise an amino acid sequence set forth in any one of SEQ ID NOs: 249, 250, 252, 253, 255, 256, 257, 258 and 261, and the light chain may comprise an amino acid sequence set forth in any one of SEQ ID NOs: 319, 320, 322, 323, 325, 326, 328, 329, 338 and 342.

For example, the combination of the light chain and the heavy chain of the antigen-binding protein may comprise any one of the groups selected from Table 14 below.

TABLE 14

| Sequence combinations | | | | | | | | | | |
|---|---|---|---|---|---|---|---|---|---|---|
| Combination | 1 | 2 | 3 | 4 | 5 | 6 | 7 | 8 | 9 | 10 |
| Light chain | 319 | 320 | 322 | 323 | 325 | 326 | 328 | 329 | 338 | 342 |
| Heavy chain | 249 | 250 | 252 | 253 | 255 | 256 | 257 | 258 | 261 | 261 |

In the present application, the antigen-binding protein may comprise at least one CDR in an antibody heavy chain variable region VH, wherein the VH may comprise an amino acid sequence set forth in any one of SEQ ID NOs: 178, 179, 180 and 198-205.

In the present application, the antigen-binding protein may comprise an HCDR1. For example, the HCDR1 may comprise an amino acid sequence set forth in any one of SEQ ID NOs: 16, 19, 20, 23, 24 and 25. For example, this sequence may be a sequence determined according to the Chothia scheme.

In the present application, the antigen-binding protein may comprise an HCDR2. For example, the HCDR2 may comprise an amino acid sequence set forth in any one of SEQ ID NOs: 38 and 40-47.

For example, this sequence may be a sequence determined according to the Chothia scheme.

In the present application, the antigen-binding protein may comprise an HCDR3. For example, the HCDR3 may comprise an amino acid sequence set forth in any one of SEQ ID NOs: 66, 69, 70, 71, and 74-79. For example, this sequence may be a sequence determined according to the Chothia scheme.

In the present application, the antigen-binding protein may comprise an HCDR1, an HCDR2 and an HCDR3, wherein the HCDR1 may comprise an amino acid sequence set forth in any one of SEQ ID NOs: 16, 19, 20, 23, 24 and 25, the HCDR2 may comprise an amino acid sequence set forth in any one of SEQ ID NOs: 38 and 40-47, and the HCDR3 may comprise an amino acid sequence set forth in any one of SEQ ID NOs: 66, 69, 70, 71, and 74-79.

For example, the antigen-binding protein may comprise an HCDR1, an HCDR2 and an HCDR3, wherein the combination of the HCDR1, HCDR2 and HCDR3 may be selected from any one of the groups in Table 15 below.

TABLE 15

| Sequence combinations | | | | | | | | | | | |
|---|---|---|---|---|---|---|---|---|---|---|---|
| Combination | 1 | 2 | 3 | 4 | 5 | 6 | 7 | 8 | 9 | 10 | 11 |
| HCDR1 | 19 | 20 | 19 | 19 | 19 | 19 | 23 | 16 | 16 | 25 | 24 |
| HCDR2 | 40 | 41 | 40 | 42 | 44 | 45 | 43 | 46 | 38 | 47 | 42 |
| HCDR3 | 69 | 70 | 71 | 74 | 76 | 77 | 75 | 78 | 66 | 79 | 79 |

In the present application, the antigen-binding protein may comprise a framework region H-FR1. The C-terminus of the H-FR1 is linked directly or indirectly to the N-terminus of the HCDR1. For example, the H-FR1 may comprise an amino acid sequence set forth in any one of SEQ ID NOs: 5, 6 and 9-14. For example, this sequence may be a sequence determined according to the Chothia scheme.

In the present application, the antigen-binding protein may comprise an H-FR2, wherein the H-FR2 is positioned between the HCDR1 and the HCDR2. For example, the H-FR2 may comprise an amino acid sequence set forth in any one of SEQ ID NOs: 26, 28, 29, and 32-36. For example, this sequence may be a sequence determined according to the Chothia scheme.

In the present application, the antigen-binding protein may comprise an H-FR3, wherein the H-FR3 is positioned between the HCDR2 and the HCDR3. For example, the H-FR3 may comprise an amino acid sequence set forth in any one of SEQ ID NOs: 50, 53-55 and 58-64. For example, this sequence may be a sequence determined according to the Chothia scheme.

In the present application, the antigen-binding protein may comprise an H-FR4, wherein the N-terminus of the H-FR4 is linked to the C-terminus of the HCDR3. For example, the H-FR4 may comprise an amino acid sequence set forth in any one of SEQ ID NOs: 84-85 and 87-89. For example, this sequence may be a sequence determined according to the Chothia scheme.

In the present application, the antigen-binding protein may comprise a heavy chain variable region VH, wherein the VH may comprise an amino acid sequence set forth in any one of SEQ ID NOs: 178, 179, 180 and 198-205.

In the present application, the antigen-binding protein may comprise an Fc region. For example, the Fc region may comprise modifications to enhance the ADCC effect.

In the present application, the antigen-binding protein may comprise an Fc region. For example, the Fc region may comprise a glycosylated side chain that does not comprise a fucosyl group, or the Fc region may not comprise a glycosylated side chain with a fucosyl group.

The antigen-binding protein described herein may comprise a heavy chain constant region CH, wherein the antibody heavy chain constant region may comprise a human IgG constant region. In certain cases, the human IgG constant region may comprise a human IgG1 constant region. The human IgG1 constant region may include natural and synthetic IgG1 constant regions or mutants thereof. The mutation may comprise mutations at one or more of the following positions: S239D and I332E. For example, the human IgG1 constant region of the fusion protein may comprise an amino acid sequence set forth in any one of SEQ ID NOs: 356-357.

In the present application, the antigen-binding protein may comprise an antibody heavy chain. For example, the antibody heavy chain may comprise an amino acid sequence set forth in any one of SEQ ID NOs: 263, 264, 265 and 285-298.

In the present application, the antigen-binding protein may comprise at least one CDR in an antibody light chain variable region VL, wherein the VL may comprise an amino acid sequence set forth in any one of SEQ ID NOs: 224-226, 238-241 and 245-248.

In the present application, the antigen-binding protein may comprise an LCDR1. For example, the LCDR1 may comprise an amino acid sequence set forth in any one of SEQ ID NOs: 104, 105, 108-110 and 113-117. For example, this sequence may be a sequence determined according to the Chothia scheme.

In the present application, the antigen-binding protein may comprise an LCDR2. For example, the LCDR2 may comprise an amino acid sequence set forth in any one of SEQ ID NOs: 127-134. For example, this sequence may be a sequence determined according to the Chothia scheme.

In the present application, the antigen-binding protein may comprise an LCDR3. For example, the LCDR3 may comprise an amino acid sequence set forth in any one of SEQ ID NOs: 141, 143-149 and 153. For example, this sequence may be a sequence determined according to the Chothia scheme.

In the present application, the antigen-binding protein may comprise an LCDR1, an LCDR2 and an LCDR3, wherein the LCDR1 comprises an amino acid sequence set forth in any one of SEQ ID NOs: 104, 105, 108-110 and 113-117, the LCDR2 comprises an amino acid sequence set forth in any one of SEQ ID NOs: 127-134, and the LCDR3 comprises an amino acid sequence set forth in any one of SEQ ID NOs: 141, 143-149 and 153.

For example, the antigen-binding protein may comprise an LCDR1, an LCDR2 and an LCDR3, wherein the combination of the LCDR1, LCDR2 and LCDR3 may be selected from any one of the groups in Table 16 below.

TABLE 16

| Sequence combinations | | | | | | | | | | |
|---|---|---|---|---|---|---|---|---|---|---|
| Combination | 1 | 2 | 3 | 4 | 5 | 6 | 7 | 8 | 9 | 10 |
| LCDR1 | 108 | 109 | 110 | 113 | 115 | 116 | 114 | 105 | 104 | 117 |
| LCDR2 | 128 | 129 | 130 | 131 | 133 | 134 | 132 | 127 | 127 | 128 |
| LCDR3 | 143 | 144 | 145 | 146 | 148 | 149 | 147 | 141 | 141 | 153 |

In the present application, the antigen-binding protein may comprise a framework region L-FR1. The C-terminus of the L-FR1 is linked directly or indirectly to the N-terminus of the LCDR1. For example, the L-FR1 may comprise an amino acid sequence set forth in any one of SEQ ID NOs: 90, 92, 95-97 and 99-103. For example, this sequence may be a sequence determined according to the Chothia scheme.

In the present application, the antigen-binding protein may comprise an L-FR2, wherein the L-FR2 is positioned between the LCDR1 and the LCDR2. For example, the L-FR2 may comprise an amino acid sequence set forth in any one of SEQ ID NOs: 118-121 and 124-126. For example, this sequence may be a sequence determined according to the Chothia scheme.

In the present application, the antigen-binding protein may comprise an L-FR3, wherein the L-FR3 is positioned between the LCDR2 and the LCDR3. For example, the L-FR3 may comprise an amino acid sequence set forth in any one of SEQ ID NOs: 135-140. For example, this sequence may be a sequence determined according to the Chothia scheme.

In the present application, the antigen-binding protein may comprise an L-FR4, wherein the N-terminus of the L-FR4 is linked to the C-terminus of the LCDR3. For example, the L-FR4 may comprise an amino acid sequence set forth in any one of SEQ ID NOs: 156, 157, 159 and 162-166.

For example, this sequence may be a sequence determined according to the Chothia scheme.

In the present application, the antigen-binding protein may comprise a light chain variable region VL.

For example, the VL region may comprise an amino acid sequence set forth in any one of SEQ ID NOs: 224-226, 238-241 and 245-248. For example, this sequence may be a sequence determined according to the Chothia scheme.

The antigen-binding protein described herein may comprise a light chain constant region CL, wherein the antibody light chain constant region may comprise a human Igκ constant region. For example, the CL region may comprise an amino acid sequence set forth below: SEQ ID NO: 358.

In the present application, the antigen-binding protein may comprise an antibody light chain. For example, the antibody light chain may comprise an amino acid sequence set forth in any one of SEQ ID NOs: 331-333, 345-348 and 352-355.

In the present application, the antigen-binding protein may comprise an HCDR1, an HCDR2, an HCDR3, an LCDR1, an LCDR2 and an LCDR3. In certain cases, in the antigen-binding protein, the HCDR1 may comprise an amino acid sequence set forth in any one of SEQ ID NOs: 16, 19, 20, 23, 24 and 25, the HCDR2 may comprise an amino acid sequence set forth in any one of SEQ ID NOs: 38 and 40-47, the HCDR3 may comprise an amino acid sequence set forth in any one of SEQ ID NOs: 66, 69, 70, 71 and 74-79, the LCDR1 may comprise an amino acid sequence set forth in any one of SEQ ID NOs: 104, 105, 108-110 and 113-117, the LCDR2 may comprise an amino acid sequence set forth in any one of SEQ ID NOs: 127-134, and the LCDR3 may comprise an amino acid sequence set forth in any one of SEQ ID NOs: 141, 143-149 and 153.

For example, the antigen-binding protein may comprise an HCDR1, an HCDR2, an HCDR3, an LCDR1, an LCDR2 and an LCDR3, wherein the combination of the HCDR1, HCDR2, HCDR3, LCDR1, LCDR2 and LCDR3 may be selected from any one of the groups in Table 17 below.

TABLE 17

| Sequence combinations | | | | | | |
|---|---|---|---|---|---|---|
| Combination | LCDR1 | LCDR2 | LCDR3 | HCDR1 | HCDR2 | HCDR3 |
| 1 | 108 | 128 | 143 | 19 | 40 | 69 |
| 2 | 109 | 129 | 144 | 20 | 41 | 70 |
| 3 | 110 | 130 | 145 | 19 | 40 | 71 |
| 4 | 113 | 131 | 146 | 19 | 42 | 74 |
| 5 | 115 | 133 | 148 | 19 | 44 | 76 |
| 6 | 116 | 134 | 149 | 19 | 45 | 77 |
| 7 | 114 | 132 | 147 | 23 | 43 | 75 |
| 8 | 105 | 127 | 141 | 16 | 46 | 78 |
| 9 | 104 | 127 | 141 | 16 | 38 | 66 |
| 10 | 117 | 128 | 153 | 25 | 47 | 79 |
| 11 | 117 | 128 | 153 | 24 | 42 | 79 |

In the present application, the antigen-binding protein may comprise an antibody light chain variable region VL and an antibody heavy chain variable region VH, wherein the VH comprises an amino acid sequence set forth in any one of SEQ ID NOs: 178, 179, 180 and 198-205, and the VL comprises an amino acid sequence set forth in any one of SEQ ID NOs: 224-226, 238-241 and 245-248.

In the present application, the antigen-binding protein may comprise an antibody light chain variable region VL and an antibody heavy chain variable region VH, wherein the VH comprises an amino acid sequence set forth in any one of SEQ ID NOs: 178, 179, 180 and 198-205, and the VL comprises an amino acid sequence set forth in any one of SEQ ID NOs: 224-226, 238-241 and 245-248.

For example, the combination of VL and VH of the antigen-binding protein may comprise any one of the groups selected from Table 18 below.

TABLE 18

| Sequence combinations | | | | | | | | | | | |
|---|---|---|---|---|---|---|---|---|---|---|---|
| Combination | 1 | 2 | 3 | 4 | 5 | 6 | 7 | 8 | 9 | 10 | 11 |
| VL | 224 | 225 | 226 | 238 | 240 | 241 | 239 | 245 | 246 | 248 | 247 |
| VH | 178 | 179 | 180 | 198 | 200 | 201 | 199 | 202 | 203 | 205 | 204 |

In the present application, the antigen-binding protein may comprise an antibody light chain and an antibody heavy chain, wherein the antibody light chain may comprise an amino acid sequence set forth in any one of SEQ ID NOs: 331-333, 345-348 and 352-355, and the antibody heavy chain may comprise an amino acid sequence set forth in any one of SEQ ID NOs: 263, 264, 265 and 285-298.

For example, the combination of the light chain and the heavy chain of the antigen-binding protein may comprise any one of the groups selected from Table 19 below.

TABLE 19

| Sequence combinations | | | | | | | | | | | | | | | | | |
|---|---|---|---|---|---|---|---|---|---|---|---|---|---|---|---|---|---|
| Combination | 1 | 2 | 3 | 4 | 5 | 6 | 7 | 8 | 9 | 10 | 11 | 12 | 13 | 14 | 15 | 16 | 17 |
| Light chain | 331 | 332 | 333 | 345 | 346 | 347 | 348 | 347 | 348 | 346 | 352 | 353 | 354 | 352 | 353 | 355 | 354 |
| Heavy chain | 263 | 264 | 265 | 285 | 286 | 287 | 288 | 289 | 290 | 291 | 292 | 293 | 294 | 295 | 296 | 297 | 298 |

The protein, polypeptide and/or amino acid sequence involved in the present application is also to be understood as including at least the following ranges: variants or homologs having the same or similar function as the protein or polypeptide.

In the present application, the variant may be a protein or polypeptide obtained by substitution, deletion or addition of one or more amino acids in the amino acid sequence of the protein and/or the polypeptide (e.g., the antigen-binding protein described herein). For example, the functional variant may comprise a protein or polypeptide with amino acid change by substitutions, deletions and/or insertions of at least 1 (for example, 1-30, 1-20 or 1-10, for another example, 1, 2, 3, 4 or 5) amino acids. The functional variant may substantially retain the biological properties of the protein or the polypeptide prior to the alteration (e.g., substitution, deletion or addition). For example, the functional variant may retain at least 60%, 70%, 80%, 90% or 100% of the biological activity (e.g., antigen-binding capacity) of the protein or the polypeptide prior to the alteration.

In the present application, a portion of each heavy chain or light chain amino acid sequence of the antigen-binding protein may be homologous to a corresponding amino acid sequence in an antibody from a particular species or belong to a particular class. For example, the variable and constant regions of both the light and heavy chains are derived from the variable and constant regions of an antibody from one animal species (e.g., human). In the present application, the homolog may be a protein or polypeptide comprising an amino acid sequence having at least about 85% (e.g., having at least about 85%, about 90%, about 91%, about 92%, about 93%, about 94%, about 95%, about 96%, about 97%, about 98%, about 99% or higher) sequence homology to the amino acid sequence of the protein and/or the polypeptide (e.g., an antibody or a fragment thereof that specifically binds to a CCR8 protein).

In the present application, the homology generally refers to similarity, likeness or association between two or more sequences. The "percent sequence homology" can be calculated by the following steps: comparing two sequences to be aligned in a comparison window; determining the number of positions at which nucleic acid bases (e.g., A, T, C and G) or amino acid residues (e.g., Ala, Pro, Ser, Thr, Gly, Val, Leu, Ile, Phe, Tyr, Trp, Lys, Arg, His, Asp, Glu, Asn, Gln, Cys and Met) are identical in the two sequences to give the number of matched positions; dividing the number of matched positions by the total number of positions in the comparison window (i.e., the window size); and multiplying the result by 100 to give a percent sequence homology. Alignment for determining the percent sequence homology can be achieved in a variety of ways known in the art, for example, using publicly available computer software such as BLAST, BLAST-2, ALIGN or Megalign (DNASTAR) software. Those skilled in the art can determine suitable parameters for alignment of the sequences, including any algorithms necessary to achieve optimal alignment in a full-length sequence range or target sequence region being compared. The homology can also be determined by the following methods: FASTA and BLAST. For description of the FASTA algorithm, see W. R. Pearson and D. J. Lipman, "Improved Tools for Biological Sequence Comparison", *Proc. Natl. Acad. Sci.,* 85: 2444-2448, 1988; and D. J. Lipman and W. R. Pearson "Rapid and Sensitive Protein Similarity Searches", *Science,* 227: 1435-1441, 1989. For description of the BLAST algorithm, see S. Altschul, W. Gish, W. Miller, E. W. Myers and D. Lipman, "A Basic Local Alignment Search Tool", *Journal of Molecular Biology,* 215: 403-410, 1990.

Assay Method

The physical/chemical properties and/or biological activity of the CCR8 antigen-binding protein described herein can be identified, screened, or characterized through a variety of assays known in the art.

In one aspect, the antigen-binding activity of the CCR8 antigen-binding protein of the present application can be tested, for example, by known methods such as enzyme-linked immunosorbent assay (ELISA), immunoblotting (e.g., western blotting), flow cytometry (e.g., FACS), immunohistochemistry and immunofluorescence.

In the present application, the isolated antigen-binding protein is capable of binding to CCR8 derived from a primate with an $EC_{50}$ value of $2\times10^{-8}$ M or less. The binding affinity of the primate CCR8 antigen-binding protein for CCR8 can be determined by any method known in the art. In certain cases, the binding affinity can be determined by multiplex assay of in-chip. In certain cases, the binding affinity and the $EC_{50}$ value of the CCR8 antigen-binding proteins for CCR8 can be determined by flow cytometry (FACS).

In the present application, the isolated antigen-binding protein is assayed, for example, using a FACS analyzer.

In another case, the binding activity of the CCR8 antigen-binding protein described herein on CCR8 can be assayed by flow cytometry or enzyme-linked immunosorbent assay. For example, in an FACS assay, host cells (e.g., CHO-K1 cells) stably expressing human CCR8 are used, and the CCR8 antigen-binding protein is capable of binding to CCR8 derived from a primate with an $EC_{50}$ value of $2\times10^{-8}$ M or less. For example, the CCR8 antigen-binding protein can bind to CCR8 derived from a human with an $EC_{50}$ value of about $1\times10^{-8}$ M or less, about $9\times10^{-9}$ M or less, about $8\times10^{-9}$ M or less, about $7\times10^{-9}$ M or less, about $6\times10^{-9}$ M or less, about $5\times10^{-9}$ M or less, about $4\times10^{-9}$ M or less, about $3\times10^{-9}$ M or less, about $2\times10^{-9}$ M or less, or about $1\times10^{-9}$ M or less.

In another case, the competitive binding of the CCR8 antigen-binding proteins to an antigenic epitope is determined by flow cytometry (FACS).

In another case, the differential expression of CCR8 in human tumor-infiltrating lymphocyte-derived Tregs (TIL-Tregs) vs. in normal human PBMC-derived Tregs is determined by flow cytometry (FACS).

Nucleic Acid Molecule, Vector and Cell

In another aspect, the present application provides one or more nucleic acid molecules that can encode the isolated antigen-binding protein described herein and/or the multi-specific antibody described herein. The nucleic acid molecule described herein may be isolated. For example, it may be produced or synthesized by the following methods: (i) in vitro amplification, such as amplification by polymerase chain reaction (PCR); (ii) cloning and recombination; (iii) purification, such as separation by enzymatic digestion and gel electrophoresis fractionation; or (iv) synthesis, such as chemical synthesis. In certain embodiments, the isolated nucleic acid is a nucleic acid molecule prepared by recombinant DNA techniques.

In another aspect, the present application provides a vector, which may comprise the nucleic acid molecule described herein. In addition, the vector may further comprise other genes, such as marker genes that allow selection of the vector in an appropriate host cell and under appropriate conditions. In addition, the vector may further comprise expression control elements that allow proper expression of the coding region in an appropriate host. Such control elements are well known to those skilled in the art and may include, for example, promoters, ribosome binding sites, enhancers and other control elements for regulating gene transcription or mRNA translation. The vector may include, for example, a plasmid, a cosmid, a virus, a phage or other vectors commonly used in, for example, genetic engineering. For example, the vector is an expression vector.

In another aspect, the present application provides a cell, which may comprise the nucleic acid molecule described herein or the vector described herein. In certain embodiments, each type of or each host cell may comprise one type of or one nucleic acid molecule or vector described herein. In certain embodiments, each type of or each host cell may comprise multiple (e.g., two or more) or multiple types (e.g., two or more) of nucleic acid molecules or vectors described herein. For example, the vector described herein can be introduced into the host cell described herein, e.g., a eukaryotic cell, such as a plant-derived cell or a fungal or yeast cell. The vector described herein can be introduced into the host cell described herein based on methods known in the art, such as electroporation, lipofectine transfection and lipofectamin transfection.

Chimeric Antigen Receptor

In another aspect, the present application provides a chimeric antigen receptor (CAR), which may comprise the nucleic acid molecule described herein or the antigen-binding fragment described herein. In certain embodiments, it may comprise an extracellular domain (extracellular binding domain), a hinge domain and a transmembrane domain (transmembrane region) that are capable of binding to an antigen, and a polypeptide that passes a cytoplasmic signal to a domain (i.e., an intracellular signal domain). The hinge domain may be considered as a part for providing flexibility to an extracellular antigen-binding region. The intracellular signal domain refers to a protein that transmits information into a cell via a determined signaling pathway by generating a second messenger to regulate the activity of the cell, or a protein that functions as an effector by corresponding to such a messenger. It generates a signal that can promote the immune effector function of a cell of the CAR (e.g., a CAR-T cell). The intracellular signal domain may include a signaling domain, and may also include a co-stimulatory intracellular domain derived from a co-stimulatory molecule. For example, the co-stimulatory molecule may be selected from 4-1BB (i.e., CD137), CD27, ICOS and/or CD28. In another aspect, the present application provides a genetically modified cell, which may comprise the chimeric antigen receptor. In certain embodiments, the genetically modified cell may include a eukaryotic cell. In certain embodiments, the genetically modified cell may include an isolated human cell. In certain embodiments, the genetically modified cell may include an immune cell, such as a T cell or an NK cell.

Antibody-Drug Conjugate

In another aspect, the present application provides an antibody-drug conjugate, which may comprise a cytotoxic agent and the antigen-binding fragment described herein. The antibody-drug conjugate generally refers to a substance formed by linking an antibody and a small molecule cytotoxic agent using a specific linker, the main components of which include the antibody, the linker and the small molecule cytotoxic agent. For the antibody-drug conjugate, its targeting property can be from an antibody moiety, and most of its toxicity can be from a drug payload moiety, although the antibody moiety can also have its inherent toxicity (ADCC and CDC).

Pharmaceutical Composition

In another aspect, the present application provides a pharmaceutical composition, which may comprise the isolated antigen-binding protein, the nucleic acid molecule, the vector, the cell, the chimeric antigen receptor, the genetically modified cell, and/or the antibody-drug conjugate described herein, and optionally a pharmaceutically acceptable carrier. The pharmaceutically acceptable carrier is non-toxic to a recipient at the dosages and concentrations employed, and may include buffers, antioxidants, preservatives, low-molecular-weight (less than about 10 residues) polypeptides, proteins, hydrophilic polymers, amino acids, carbohydrates, salt-forming counterions, metal complexes, and/or non-ionic surfactants. The pharmaceutical composition of the present application may further comprise more than one active compound, generally those having complementary activities that do not adversely affect one another. The type and effective amount of such pharmaceuticals depend on, for example, the amount and type of antagonist present in the formulation, as well as the clinical parameters of the subject.

The pharmaceutical composition described herein may comprise a prophylactically and/or therapeutically effective amount of the antigen-binding protein or multispecific antibody. The prophylactically and/or therapeutically effective amount is the dose required to prevent and/or treat (at least partially treat) a disease or disorder and/or any complication thereof in a subject suffering from or at risk of developing the disease or disorder.

The route of administration for the pharmaceutical composition described herein is preferably parenteral administration, injection administration or oral administration. The injection administration preferably includes intravenous injection, intramuscular injection, intraperitoneal injection, intradermal injection, subcutaneous injection or the like. The pharmaceutical composition is in any conventional dosage form in the art, preferably in the form of a solid, semisolid or liquid, i.e., it may be an aqueous solution, a non-aqueous solution or a suspension, more preferably a tablet, capsule, granule, injection, infusion, or the like. More preferably, it is administered intravascularly, subcutaneously, intraperitoneally or intramuscularly. Preferably, the pharmaceutical composition may also be administered as an aerosol or a coarse spray, i.e., administered nasally; or administered intrathecally, intramedullarily or intraventricularly. More preferably, the pharmaceutical composition may also be administered transdermally, percutaneously, topically, enterally, intravaginally, sublingually or rectally. The pharmaceutical composition of the present invention may be formulated into various dosage forms as required, and can be administered by a physician in the light of the patient's type, age, weight, and general disease state, route of administration, etc. The administration may be performed, for example, by injection or other therapeutic modalities.

The dose level at which the pharmaceutical composition of the present invention is administered can be adjusted depending on the amount of the composition to achieve the desired diagnostic or therapeutic outcome. The administration regimen may also be a single injection or multiple injections, or an adjusted one. The selected dose level and regimen is appropriately adjusted depending on a variety of factors including the activity and stability (i.e., half-life) of the pharmaceutical composition, the formulation, the route of administration, combination with other drugs or treatments, the disease or disorder to be detected and/or treated, and the health condition and previous medical history of the subject to be treated.

Kit

In another aspect, the present application provides a kit, which may comprise the antigen-binding protein, the chimeric antigen receptor, the genetically modified cell, the antibody-drug conjugate, and/or the pharmaceutical composition described herein. The antigen-binding protein, the chimeric antigen receptor, the genetically modified cell, and/or the antibody-drug conjugate described herein may be comprised in a single common container, and may also be optionally used in combination with one or more therapeutic agents, and optionally formulated together in a pharmaceutical composition.

In certain cases, the kit may further comprise a device for administering the antigen-binding protein, the chimeric antigen receptor, the genetically modified cell, the antibody-drug conjugate or the pharmaceutical composition described herein; for example, the device depends on the mode of administration of the contents. In certain cases, the kit may comprise a package insert that includes information on the antigen-binding protein, the pharmaceutical composition, and the dosage form in the kit. Generally, such information helps patients and physicians to use the encapsulated antigen-binding protein, pharmaceutical composition, and dosage form effectively and safely. The containers used for such kits may generally comprise at least one vial, test tube, flask, bottle, syringe, or other suitable containers into which one or more of the detection and/or therapeutic compositions may be placed, and preferably are appropriately aliquoted. In the case where a second therapeutic agent is further provided, the kit may also contain a second different container in which the second detection and/or therapeutic composition may be placed. Alternatively, multiple compounds may be prepared as a single pharmaceutical composition and may be packaged in a single container such as a vial, flask, syringe, bottle, or other suitable single container.

Administration Device

In another aspect, the present application provides an administration device (e.g., plastic bottle or vial, such as a hollow pin or syringe barrel) that can be used to administer the antigen-binding protein or the pharmaceutical composition thereof described herein. The device may introduce a substance into a patient by a parenteral route (e.g., intramuscularly, subcutaneously or intravenously). For example, the injection device may be a syringe (e.g., a pre-filled syringe having the antigen-binding protein or the pharmaceutical composition thereof described herein, e.g., an automatic syringe) that may include a barrel and a needle (which may be used to pierce the skin and/or blood vessels) for containing a fluid to be injected (e.g., the antigen-binding protein or the pharmaceutical composition thereof described herein). The mode of administration may be changed. The route of administration may include oral, intramuscular, subcutaneous, rectal administration and the like.

Preparation Method

In another aspect, the present application provides a method for preparing the antigen-binding protein described herein. The method may comprise culturing the host cell described herein under conditions such that the antigen-binding protein is expressed, for example, by adopting an appropriate culture medium, an appropriate temperature, an appropriate incubation time and the like. These methods are known to those of ordinary skill in the art.

Any method suitable for producing monoclonal antibodies can be used to produce the antigen-binding protein of the present application. For example, an animal can be immunized with a linked or naturally occurring CCR8 protein or a fragment thereof. Suitable immunization methods, including adjuvants, immunostimulants and repeated booster immunizations, may be used, and one or more routes may be used.

Any suitable form of CCR8 may be used as an immunogen (antigen) to generate a non-human antibody specific for CCR8 and screen for the biological activity of the antibody. The stimulating immunogen may be a full-length mature human CCR8, including a natural homodimer, or a peptide containing a single epitope/multiple epitopes. The immunogen may be used alone or in combination with one or more immunogenicity enhancers known in the art.

The humanized antibody may be selected from any class of immunoglobulins, including IgM, IgD, IgG, IgA and IgE. In the present application, the antibody is an IgG antibody and is of IgG1 or IgG4 subtype. The optimization of the sequence of the essential constant domain can be achieved by screening antibodies by the biological assays described in the examples below to produce the desired biological activity. Likewise, any type of light chains can be used in the compounds and methods herein. Specifically, κ and λ chains or variants thereof are available in the compounds and methods of the present application.

The sequence of the DNA molecule of the antigen-binding protein or the fragment thereof of the present application can be obtained by conventional techniques such as PCR amplification or genomic library screening. In addition, the coding sequences of the light and heavy chains may be fused together to form a single chain antibody.

The relevant sequence, once obtained, can be replicated in large amount by recombination. This is usually implemented by cloning the sequence into a vector, transferring the vector into a cell, and then isolating the antibody from proliferated host cells based on conventional methods. In addition, the relevant sequence may be synthesized by artificial synthesis, especially when the fragment is short. Generally, a fragment with a long sequence is obtained by first synthesizing multiple small fragments and then ligating them together. The nucleic acid molecule can then be introduced into various existing DNA molecules (or such as vectors) and cells known in the art.

The present application also relates to a vector comprising the above appropriate nucleic acid molecule and an appropriate promoter or control sequence. These vectors can be used to transform appropriate host cells, allowing them to express proteins. The host cells may be prokaryotic cells, such as bacterial cells; or lower eukaryotic cells, such as yeast cells; or higher eukaryotic cells, such as mammalian cells. For example, animal cells may include (but are not limited to): CHO-S, CHO-K1 and HEK-293 cells.

The step of transforming host cells with recombinant DNA described herein may be performed using techniques well known in the art. The obtained transformants can be cultured by conventional methods to express the polypeptide encoded by the nucleic acid molecules of the present application. Depending on the host cells used, the culturing is performed with a conventional medium under suitable conditions. Generally, the transformed host cells are cultured under conditions suitable for expression of the antigen-binding protein of the present application. The antigen-binding protein of the present application is then obtained by purification by conventional immunoglobulin purification procedures, such as protein A-Sepharose, hydroxylapatite chromatography, gel electrophoresis, dialysis, ion exchange chromatography, hydrophobic chromatography, molecular sieve chromatography, affinity chromatography or other conventional separation and purification means well known to those skilled in the art.

The obtained monoclonal antibody can be identified by conventional means. For example, the binding specificity of the monoclonal antibody can be determined by immunoprecipitation or in vitro binding assays, such as fluorescence-activated cell sorting (FACS) or enzyme-linked immunosorbent assay (ELISA).

Method and Use

In another aspect, the present application provides use of the antigen-binding protein, the nucleic acid molecule, the vector, the cell, the chimeric antigen receptor, the genetically modified cell, the antibody-drug conjugate and/or the pharmaceutical composition in the preparation of a medicament. The medicament can be used for treating a cancer, inhibiting tumor growth and/or inhibiting tumor cell proliferation.

In another aspect, the present application provides a method for preventing, alleviating or treating a CCR8-mediated disease or disorder, which comprises administering to a subject in need thereof the antigen-binding protein, the nucleic acid molecule, the vector, the cell, the chimeric antigen receptor, the genetically modified cell, the antibody-drug conjugate, and/or the pharmaceutical composition.

In another aspect, the present application provides the antigen-binding protein, the nucleic acid molecule, the vector, the cell, the chimeric antigen receptor, the genetically modified cell, the antibody-drug conjugate and/or the pharmaceutical composition, for use in preventing, alleviating or treating a CCR8-mediated disease or disorder.

In certain embodiments, the tumor or cancer may be a tumor or cancer with abnormal CCR8 expression. For example, the tumor may include breast cancer, kidney cancer, pancreatic cancer, bladder cancer, gastric cancer, cervical cancer and/or colon cancer. The antigen-binding protein and/or pharmaceutical composition described herein can be used to inhibit tumor growth. The abnormal CCR8 expression may be abnormal CCR8 expression on regulatory T cells (Tregs). The abnormal CCR8 expression may be abnormal CCR8 expression on tumor-infiltrating regulatory T cells (Tregs). For example, the pharmaceutical composition of the present application may inhibit or delay the development or progression of a disease, may reduce the size of a tumor (even substantially eliminate the tumor), and/or may alleviate and/or stabilize the disease state.

In the present application, the method may be used in combination with one or more additional anti-tumor therapies. For example, the additional anti-tumor therapy includes immunotherapy. For example, the additional anti-tumor therapy includes an immune checkpoint inhibitor. For example, the additional anti-tumor therapy includes an PD-1 antibody and/or an PD-L1 antibody. For example, the PD-1 antibody includes Keytruda® and/or RMP1-14. For example, the PD-L1 antibody includes Tecentriq®.

In another aspect, the present application provides a method for inhibiting calcium influx caused by CCL1, which comprises administering the isolated antigen-binding protein and/or the pharmaceutical composition. For example, the method may be an ex vivo or in vitro method. For example, the method may be a method for non-diagnostic and/or non-therapeutic purposes.

In another aspect, the present application provides a method for inhibiting cell migration induced by CCL1, which comprises administering the isolated antigen-binding protein and/or the pharmaceutical composition. For example, the method may be an ex vivo or in vitro method. For example, the method may be a method for non-diagnostic and/or non-therapeutic purposes.

In another aspect, the present application provides the following embodiments:

1. An isolated antigen-binding protein, comprising an antibody heavy chain or a fragment thereof, wherein the antibody heavy chain or the fragment thereof comprises an HCDR1, an HCDR2 and an HCDR3, wherein the HCDR1 comprises an amino acid sequence set forth in SEQ ID NO: 363, the HCDR2 comprises an amino acid sequence set forth in SEQ ID NO: 364, and the HCDR3 comprises an amino acid sequence set forth in SEQ ID NO: 365.

2. The isolated antigen-binding protein according to embodiment 1, wherein the HCDR1 comprises an amino acid sequence set forth in any one of SEQ ID NOs: 15-18, the HCDR2 comprises an amino acid sequence set forth in any one of SEQ ID NOs: 37-39, and the HCDR3 comprises an amino acid sequence set forth in any one of SEQ ID NOs: 65-67; preferably, the HCDR1, HCDR2 and HCDR3 comprise amino acid sequences selected from any one of the following groups: (1) HCDR1: SEQ ID NO: 15, HCDR2: SEQ ID NO: 37, and HCDR3: SEQ ID NO: 65;

(2) HCDR1: SEQ ID NO: 15, HCDR2: SEQ ID NO: 38, and HCDR3: SEQ ID NO: 65;

(3) HCDR1: SEQ ID NO: 16, HCDR2: SEQ ID NO: 38, and HCDR3: SEQ ID NO: 65;

(4) HCDR1: SEQ ID NO: 16, HCDR2: SEQ ID NO: 38, and HCDR3: SEQ ID NO: 66;

(5) HCDR1: SEQ ID NO: 16, HCDR2: SEQ ID NO: 38, and HCDR3: SEQ ID NO: 67;

(6) HCDR1: SEQ ID NO: 17, HCDR2: SEQ ID NO: 39, and HCDR3: SEQ ID NO: 65; and (7) HCDR1: SEQ ID NO: 18, HCDR2: SEQ ID NO: 38, and HCDR3: SEQ ID NO: 65.

3. The isolated antigen-binding protein according to any one of embodiments 1-2, comprising an antibody heavy chain variable region VH, wherein the VH comprises an amino acid sequence set forth in any one of SEQ ID NOs: 167, 168 and 170-176.

4. The isolated antigen-binding protein according to any one of embodiments 1-3, comprising an antibody light chain or a fragment thereof, wherein the antibody light chain and the fragment thereof comprises an LCDR1, an LCDR2 and an LCDR3, wherein the LCDR1 comprises an amino acid sequence set forth in SEQ ID NO: 366, the LCDR2 comprises an amino acid sequence set forth in SEQ ID NO: 127, and the LCDR3 comprises an amino acid sequence set forth in SEQ ID NO: 141; preferably, the LCDR1, LCDR2 and LCDR3 comprise amino acid sequences selected from any one of the following groups:

(1) LCDR1: SEQ ID NO: 104, LCDR2: SEQ ID NO: 127, and LCDR3: SEQ ID NO: 141; and (2) LCDR1: SEQ ID NO: 105, LCDR2: SEQ ID NO: 127, and LCDR3: SEQ ID NO: 141.

5. The isolated antigen-binding protein according to any one of embodiments 1-4, comprising an antibody light chain variable region VL, wherein the VL comprises an amino acid sequence set forth in any one of SEQ ID NOs: 212, 213, 215, 216, 218, 219, 221, 222, 231 and 235.

6. The isolated antigen-binding protein according to any one of embodiments 1-5, comprising an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 104, LCDR2: SEQ ID NO: 127, LCDR3: SEQ ID NO: 141; HCDR1: SEQ ID NO: 15, HCDR2: SEQ ID NO: 37, and HCDR3: SEQ ID NO: 65;

(2) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 65;

(3) LCDR1: SEQ ID NO: 105, LCDR2: SEQ ID NO: 127, LCDR3: SEQ ID NO: 141; HCDR1: SEQ ID NO: 17, HCDR2: SEQ ID NO: 39, and HCDR3: SEQ ID NO: 65;

(4) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 66;

(5) LCDR1: SEQ ID NO: 105, LCDR2: SEQ ID NO: 127, LCDR3: SEQ ID NO: 141; HCDR1: SEQ ID NO: 18, HCDR2: SEQ ID NO: 38, and HCDR3: SEQ ID NO: 65;

(6) LCDR1: SEQ ID NO: 104, LCDR2: SEQ ID NO: 127, LCDR3: SEQ ID NO: 141; HCDR1: SEQ ID NO: 15, HCDR2: SEQ ID NO: 38, and HCDR3: SEQ ID NO: 65; and (7) LCDR1: SEQ ID NO: 105, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 67.

7. The isolated antigen-binding protein according to any one of embodiments 1-6, comprising an antibody heavy chain variable region VH and an antibody light chain variable region VL, wherein the VH and VL comprise amino acid sequences selected from any one of the following groups:

(1) VL: SEQ ID NO: 212, and VH: SEQ ID NO: 167;

(2) VL: SEQ ID NO: 213, and VH: SEQ ID NO: 168;

(3) VL: SEQ ID NO: 215, and VH: SEQ ID NO: 170;

(4) VL: SEQ ID NO: 216, and VH: SEQ ID NO: 171;

(5) VL: SEQ ID NO: 218, and VH: SEQ ID NO: 173;

(6) VL: SEQ ID NO: 219, and VH: SEQ ID NO: 174;

(7) VL: SEQ ID NO: 221, and VH: SEQ ID NO: 175;

(8) VL: SEQ ID NO: 222, and VH: SEQ ID NO: 176;

(9) VL: SEQ ID NO: 231, and VH: SEQ ID NO: 172; and

(10) VL: SEQ ID NO: 235, and VH: SEQ ID NO: 172.

8. An isolated antigen-binding protein comprising an antibody heavy chain or a fragment thereof, wherein the antibody heavy chain or the fragment thereof comprises an HCDR1, an HCDR2 and an HCDR3, wherein the HCDR1 comprises an amino acid sequence set forth in any one of SEQ ID NOs: 16, 19, 20, 23, 24 and 25, the HCDR2 comprises an amino acid sequence set forth in any one of SEQ ID NOs: 38 and 40-47, and the HCDR3 comprises an amino acid sequence set forth in any one of SEQ ID NOs: 66, 69, 70, 71 and 74-79; preferably, the HCDR1, HCDR2 and HCDR3 comprise amino acid sequences selected from any one of the following groups:

(1) HCDR1: SEQ ID NO: 19, HCDR2: SEQ ID NO: 40, and HCDR3: SEQ ID NO: 69;

(2) HCDR1: SEQ ID NO: 20, HCDR2: SEQ ID NO: 41, and HCDR3: SEQ ID NO: 70;

(3) HCDR1: SEQ ID NO: 19, HCDR2: SEQ ID NO: 40, and HCDR3: SEQ ID NO: 71;

(4) HCDR1: SEQ ID NO: 19, HCDR2: SEQ ID NO: 42, and HCDR3: SEQ ID NO: 74;

(5) HCDR1: SEQ ID NO: 19, HCDR2: SEQ ID NO: 44, and HCDR3: SEQ ID NO: 76;

(6) HCDR1: SEQ ID NO: 19, HCDR2: SEQ ID NO: 45, and HCDR3: SEQ ID NO: 77;

(7) HCDR1: SEQ ID NO: 23, HCDR2: SEQ ID NO: 43, and HCDR3: SEQ ID NO: 75;

(8) HCDR1: SEQ ID NO: 16, HCDR2: SEQ ID NO: 46, and HCDR3: SEQ ID NO: 78;

(9) HCDR1: SEQ ID NO: 16, HCDR2: SEQ ID NO: 38, and HCDR3: SEQ ID NO: 66;

(10) HCDR1: SEQ ID NO: 25, HCDR2: SEQ ID NO: 47, and HCDR3: SEQ ID NO: 79; and

(11) HCDR1: SEQ ID NO: 24, HCDR2: SEQ ID NO: 42, and HCDR3: SEQ ID NO: 79.

9. The isolated antigen-binding protein according to embodiment 8, comprising an antibody heavy chain variable region VH, wherein the VH comprises an amino acid sequence set forth in any one of SEQ ID NOs: 178, 179, 180 and 198-205.

10. The isolated antigen-binding protein according to any one of embodiments 8-9, comprising an antibody light chain or a fragment thereof, wherein the antibody light chain comprises an LCDR1, an LCDR2 and an LCDR3, wherein the LCDR1 comprises an amino acid sequence set forth in any one of SEQ ID NOs: 104, 105, 108-110 and 113-117, the LCDR2 comprises an amino acid sequence set forth in any one of SEQ ID NOs: 127-134 and the LCDR3 comprises an amino acid sequence set forth in any one of SEQ ID NOs: 141, 143-149 and 153; preferably, the LCDR1, LCDR2 and LCDR3 comprise amino acid sequences selected from any one of the following groups:

(1) LCDR1: SEQ ID NO: 108, LCDR2: SEQ ID NO: 128, and LCDR3: SEQ ID NO: 143;
(2) LCDR1: SEQ ID NO: 109, LCDR2: SEQ ID NO: 129, and LCDR3: SEQ ID NO: 144;
(3) LCDR1: SEQ ID NO: 110, LCDR2: SEQ ID NO: 130, and LCDR3: SEQ ID NO: 145;
(4) LCDR1: SEQ ID NO: 113, LCDR2: SEQ ID NO: 131, and LCDR3: SEQ ID NO: 146;
(5) LCDR1: SEQ ID NO: 115, LCDR2: SEQ ID NO: 133, and LCDR3: SEQ ID NO: 148;
(6) LCDR1: SEQ ID NO: 116, LCDR2: SEQ ID NO: 134, and LCDR3: SEQ ID NO: 149;
(7) LCDR1: SEQ ID NO: 114, LCDR2: SEQ ID NO: 132, and LCDR3: SEQ ID NO: 147;
(8) LCDR1: SEQ ID NO: 105, LCDR2: SEQ ID NO: 127, and LCDR3: SEQ ID NO: 141;
(9) LCDR1: SEQ ID NO: 104, LCDR2: SEQ ID NO: 127, and LCDR3: SEQ ID NO: 141; and
(10) LCDR1: SEQ ID NO: 117, LCDR2: SEQ ID NO: 128, and LCDR3: SEQ ID NO: 153.

11. The isolated antigen-binding protein according to any one of embodiments 8-10, comprising an antibody light chain variable region VL, wherein the VL comprises an amino acid sequence set forth in any one of SEQ ID NOs: 224-226, 238-241 and 245-248.

12. The isolated antigen-binding protein according to any one of embodiments 8-11, comprising an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 108, LCDR2: SEQ ID NO: 128, LCDR3: SEQ ID NO: 143; HCDR1: SEQ ID NO: 19, HCDR2: SEQ ID NO: 40, and HCDR3: SEQ ID NO: 69;
(2) LCDR1: SEQ ID NO: 109, LCDR2: SEQ ID NO: 129, LCDR3: SEQ ID NO: 144; HCDR1: SEQ ID NO: 20, HCDR2: SEQ ID NO: 41, and HCDR3: SEQ ID NO: 70;
(3) LCDR1: SEQ ID NO: 110, LCDR2: SEQ ID NO: 130, LCDR3: SEQ ID NO: 145; HCDR1: SEQ ID NO: 19, HCDR2: SEQ ID NO: 40, and HCDR3: SEQ ID NO: 71;
(4) LCDR1: SEQ ID NO: 113, LCDR2: SEQ ID NO: 131, LCDR3: SEQ ID NO: 146; HCDR1: SEQ ID NO: 19, HCDR2: SEQ ID NO: 42, and HCDR3: SEQ ID NO: 74;
(5) LCDR1: SEQ ID NO: 115, LCDR2: SEQ ID NO: 133, LCDR3: SEQ ID NO: 148; HCDR1: SEQ ID NO: 19, HCDR2: SEQ ID NO: 44, and HCDR3: SEQ ID NO: 76;
(6) LCDR1: SEQ ID NO: 116, LCDR2: SEQ ID NO: 134, LCDR3: SEQ ID NO: 149; HCDR1: SEQ ID NO: 19, HCDR2: SEQ ID NO: 45, and HCDR3: SEQ ID NO: 77;
(7) LCDR1: SEQ ID NO: 114, LCDR2: SEQ ID NO: 132, LCDR3: SEQ ID NO: 147; HCDR1: SEQ ID NO: 23, HCDR2: SEQ ID NO: 43, and HCDR3: SEQ ID NO: 75;
(8) LCDR1: SEQ ID NO: 105, LCDR2: SEQ ID NO: 127, LCDR3: SEQ ID NO: 141; HCDR1: SEQ ID NO: 16, HCDR2: SEQ ID NO: 46, and HCDR3: SEQ ID NO: 78;
(9) LCDR1: SEQ ID NO: 104, LCDR2: SEQ ID NO: 127, LCDR3: SEQ ID NO: 141; HCDR1: SEQ ID NO: 16, HCDR2: SEQ ID NO: 38, and HCDR3: SEQ ID NO: 66;
(10) LCDR1: SEQ ID NO: 117, LCDR2: SEQ ID NO: 128, LCDR3: SEQ ID NO: 153; HCDR1: SEQ ID NO: 25, HCDR2: SEQ ID NO: 47, and HCDR3: SEQ ID NO: 79; and
(11) LCDR1: SEQ ID NO: 117, LCDR2: SEQ ID NO: 128, LCDR3: SEQ ID NO: 153; HCDR1: SEQ ID NO: 24, HCDR2: SEQ ID NO: 42, and HCDR3: SEQ ID NO: 79.

13. The isolated antigen-binding protein according to any one of embodiments 8-12, comprising an antibody heavy chain variable region VH and an antibody light chain variable region VL, wherein the VH and VL comprise amino acid sequences selected from any one of the following groups:

(1) VL: SEQ ID NO: 224, and VH: SEQ ID NO: 178;
(2) VL: SEQ ID NO: 225, and VH: SEQ ID NO: 179;
(3) VL: SEQ ID NO: 226, and VH: SEQ ID NO: 180;
(4) VL: SEQ ID NO: 238, and VH: SEQ ID NO: 198;
(5) VL: SEQ ID NO: 240, and VH: SEQ ID NO: 200;
(6) VL: SEQ ID NO: 241, and VH: SEQ ID NO: 201;
(7) VL: SEQ ID NO: 239, and VH: SEQ ID NO: 199;
(8) VL: SEQ ID NO: 245, and VH: SEQ ID NO: 202;
(9) VL: SEQ ID NO: 246, and VH: SEQ ID NO: 203;
(10) VL: SEQ ID NO: 248, and VH: SEQ ID NO: 205; and
(11) VL: SEQ ID NO: 247, and VH: SEQ ID NO: 204.

14. The isolated antigen-binding protein according to any one of embodiments 1-13, comprising a full-length antibody; a Fab; a Fab'; an $F(ab')_2$; an Fv, preferably scFv; a di-scFv, a bispecific antibody, a multispecific antibody, a heavy-chain antibody, and/or a single-domain antibody, or a monoclonal and/or polyclonal antibody made from the above antibodies.

15. The isolated antigen-binding protein according to embodiment 14, wherein the antibody is selected from the following group: a monoclonal antibody, a chimeric antibody, a humanized antibody, and a fully human antibody.

16. One or more isolated nucleic acid molecules encoding the isolated antigen-binding protein according to any one of embodiments 1-15.

17. A vector comprising the nucleic acid molecule according to embodiment 16.

18. A cell comprising a nucleic acid molecule according to embodiment 16 or a vector according to embodiment 17.

19. A method for preparing the isolated antigen-binding protein according to any one of embodiments 1-15, comprising culturing the cell according to embodiment 18 under conditions that enables the expression of the isolated antigen-binding protein according to any one of embodiments 1-15.

20. A chimeric antigen receptor comprising the antigen-binding protein according to any one of embodiments 1-15.

21. A genetically modified cell comprising the chimeric antigen receptor according to embodiment 20; preferably, the genetically modified cell is a eukaryotic cell, preferably an isolated human cell, and more preferably an immune cell such as a T cell or an NK cell.

22. An antibody-drug conjugate comprising a cytotoxic agent and the antigen-binding protein according to any one of embodiments 1-15.

23. A pharmaceutical composition comprising the isolated antigen-binding protein according to any one of embodiments 1-15, the nucleic acid molecule according to embodiment 16, the vector according to embodiment 17, the cell according to embodiment 18, the chimeric antigen receptor according to embodiment 20, the genetically modified cell according to embodiment 21, and/or the antibody-drug conjugate according to embodiment 22, and optionally a pharmaceutically acceptable carrier.

24. A kit or an administration device comprising the isolated antigen-binding protein according to any one of embodiments 1-15, the nucleic acid molecule according to embodiment 16, the vector according to embodiment 17, the cell according to embodiment 18, the chimeric antigen receptor according to embodiment 20, the genetically modified cell according to embodiment 21, the antibody-drug conjugate according to embodiment 22, and/or the pharmaceutical composition according to embodiment 23; preferably, the kit further comprises (i) a device for administering the antigen-binding protein, the nucleic acid molecule, the vector, the cell, the chimeric antigen receptor, the genetically modified cell, the antibody-drug conjugate, and/or the pharmaceutical composition; and/or (ii) instructions.

25. Use of the isolated antigen-binding protein according to any one of embodiments 1-15, the nucleic acid molecule according to embodiment 16, the vector according to embodiment 17, the cell according to embodiment 18, the chimeric antigen receptor according to embodiment 20, the genetically modified cell according to embodiment 21, the antibody-drug conjugate according to embodiment 22, and/or the pharmaceutical composition according to embodiment 23 in the preparation of a medicament for preventing, alleviating and/or treating a CCR8-mediated disease or disorder.

26. The use according to embodiment 25, wherein the CCR8-mediated disease or disorder comprises a tumor, wherein the tumor is preferably breast cancer, kidney cancer, pancreatic cancer, bladder cancer, gastric cancer, cervical cancer and/or colon cancer.

27. A method for inhibiting calcium influx caused by CCL1, comprising administering the isolated antigen-binding protein according to any one of embodiments 1-15 and/or the pharmaceutical composition according to embodiment 23; preferably, the method is an in vitro method or a method for non-diagnostic purposes.

28. A method for inhibiting cell migration induced by CCL1, comprising administering the isolated antigen-binding protein according to any one of embodiments 1-15 and/or the pharmaceutical composition according to embodiment 23; preferably, the method is an in vitro method or a method for non-diagnostic purposes.

29. A method for preventing, alleviating and/or treating a CCR8-mediated disease or disorder, comprising administering to a subject in need thereof the isolated antigen-binding protein according to any one of embodiments 1-15, the nucleic acid molecule according to embodiment 16, the vector according to embodiment 17, the cell according to embodiment 18, the chimeric antigen receptor according to embodiment 20, the genetically modified cell according to embodiment 21, the antibody-drug conjugate according to embodiment 22 and/or the pharmaceutical composition according to embodiment 23.

30. The method according to embodiment 29, wherein the CCR8-mediated disease or disorder comprises a tumor, wherein the tumor is preferably breast cancer, kidney cancer, pancreatic cancer, bladder cancer, gastric cancer, cervical cancer or colon cancer.

Without being limited by any theory, the following examples are intended only to illustrate the fusion protein, preparation method, use, etc., of the present application, and are not intended to limit the scope of the present application.

EXAMPLES

Example 1. Immunization of Mice

Balb/c mice and fully human H2L2 mice (Harbour BioMed) were adopted and immunized multiple times with CCR8-HEK293 cells (prepared by conventional methods). A booster immunization was performed every two weeks for 5-6 times. Serum titers of anti-human CCR8 antibodies were detected every two to three weeks by the FACS method during immunization. After multiple rounds of immunization, mice with the optimal titer were selected, from which spleen cells were collected.

Example 2. Antibody Screening 2.1 Phage Library Screening 2.1.1 Construction of Phage Libraries for H2L2 and Balb/c Mice Immunized with CCR8

Spleen cells were collected from the immunized mice, from which splenic B cells were isolated. After RNA was extracted by TRIZO1 with reference to the product instructions (Thermofisher, Cat. No. 15596018), RT-PCR was performed with reference to the product instructions (Thermofisher, Cat. No. 11756500). The VH (heavy chain variable region) and VL (light chain variable region) were obtained by amplification by first PCR using cDNA as a template, and scFv fragments were obtained by overlap PCR.

First PCR:

| | Volume |
|---|---|
| Total RNA-cDNA | 1 μl |
| 5x Q5 reaction buffer | 10 μl |

PCR Procedure:

| | |
|---|---|
| 2.5 mM dNTPs | 4 μl |
| Forward primer (10 uL) | 2 μl |
| Reverse primer (10 uL) | 2 μl |

-continued

| | |
|---|---|
| Q5 DNA polymerase | 0.5 μl |
| Total volume | 30.5 μl |

| Temperature (° C.) | Time (s) | |
|---|---|---|
| 98 | 30 | 30 cycles |
| 98 | 10 | |
| 64 | 30 | |
| 72 | 30 | |
| 72 | 10 min | |

Overlap PCR Program Settings:

| Temperature (° C.) | Time (s) | |
|---|---|---|
| 98 | 30 | 30 cycles |
| 98 | 10 | |
| 66 | 30 | |
| 72 | 30 | |
| 72 | 5 min | |

The reaction system of the overlap PCR was as follows: VH mixed solution, Vic mixed solution, 5× Q5 reaction buffer, forward primer (10 μM), reverse primer (10 μM), 2.5 mM dNTPs, Q5 DNA polymerase and $ddH_2O$, in a total volume of 25 μL.

The resulting ligation products were transformed into SS320 (Lucigen, Cat. No. 60512-1), and a phage library was prepared. Three rounds of bio-panning (with steps described below) were performed, and screening was performed by FACS using cells overexpressing CCR8, CHO-K1-hCCR8. All the selected candidates (hits) were sequenced (with steps described below), and specific molecules were produced.

2.1.2 Bio-Panning

The phage library (1E13 phage particles) was depleted with CHO-K1 cells and incubated with CHO-K1-hCCR8 cells for 2 h at 4° C.; and the mixture was washed 3 times with 1×PBS. After washing, a citrate buffer at pH 3.0 was added to the cell/phage mixture, and the mixture was incubated at room temperature for 10 min. Then, a Tris-HCl neutralization buffer at pH 9.0 was added, and the mixture was used to infect 10 mL of SS320 cells at 37° C. for 45 min. Then, 50 μL of M13K07 helper phages (NEB, Cat. No. N0315S) at 2E12/mL was added to the infected cells, and finally 100 mL of 2× YT (containing 100 μg/mL Amp, 50 μg/mL Kan, and 1 mM IPTG) was added, and the mixture was incubated at 30° C. overnight. 100 mL of the overnight culture was centrifuged, and the supernatant was collected. 20% PEG8000/2.5 M NaCl was added to the supernatant (1:5, volume ratio), and the mixture was centrifuged at 8000 rpm for 20 min at 4° C. The phage pellet obtained after centrifugation was resuspended in 1 mL of 1×PBS. The resulting supernatant (phage particles) was transferred to a new tube for the second round of panning. The procedures of the second, third and fourth rounds of panning were the same as the previous steps.

2.1.3 Preliminary Screening

Colonies were picked into a 96-well plate containing 2YT/Amp medium (Sangon Biotech, Cat. No. A507016-0250) and grown at 37° C. for 3 h. IPTG was added to give a final concentration of 1 mM, and the mixture was induced at 30° C. overnight. The supernatant was then pelleted by centrifugation, and the supernatant was collected and separately incubated with CHO-K1 and Baf3 cell lines overexpressing CCR8 for an FACS assay. Clones with good binding activity were obtained by screening, variable region sequences were obtained by sequencing, and IgG recombinant antibodies were constructed, including PR004122, PR004125, PR004128, PR004131, PR004120, PR004121, PR004123, PR004124, PR004126, PR004127, PR004129, PR004130, PR004264, PR004265, PR004275, PR005124, PR005125, PR005127, PR005128, PR005329, PR005330, PR005331, PR005332, PR005333, PR005335 and PR005336. The heavy chain constant regions of these antibodies were derived from a human IgG1 constant region. Meanwhile, DE double mutants (S239D and I332E) were introduced into IgG1 heavy chain constant regions of PR004122, PR004125, PR004128 and PR004131 to enhance the ADCC function, and the obtained antibodies are numbered as PR004249, PR004250, PR004251 and PR004252, respectively.

The sequence numbers (SEQ ID NOs) and CDR sequences of initial antibodies obtained from phage library screening are shown in Tables 20 and 21 below. The sequence numbers (SEQ ID NOs) and CDR sequences of the antibodies with enhanced ADCC function obtained by "DE" mutation of the heavy chain constant region are shown in Tables 22 and 23 below.

TABLE 20

Sequence numbers of initial antibodies having binding activity on human CCR8

| Antibody No. | Light chain | Heavy chain | VL | VH | LCDR1 | LCDR2 | LCDR3 | HCDR1 | HCDR2 | HCDR3 |
|---|---|---|---|---|---|---|---|---|---|---|
| PR004120 | 319 | 249 | 212 | 167 | 104 | 127 | 141 | 15 | 37 | 65 |
| PR004121 | 320 | 250 | 213 | 168 | 105 | 127 | 141 | 16 | 38 | 65 |
| PR004122 | 321 | 251 | 214 | 169 | 105 | 127 | 142 | 15 | 38 | 65 |
| PR004123 | 322 | 252 | 215 | 170 | 105 | 127 | 141 | 17 | 39 | 65 |
| PR004124 | 323 | 253 | 216 | 171 | 105 | 127 | 141 | 16 | 38 | 66 |
| PR004125 | 324 | 254 | 217 | 172 | 105 | 127 | 142 | 16 | 38 | 65 |
| PR004126 | 325 | 255 | 218 | 173 | 105 | 127 | 141 | 18 | 38 | 65 |
| PR004127 | 326 | 256 | 219 | 174 | 104 | 127 | 141 | 15 | 38 | 65 |
| PR004128 | 327 | 254 | 220 | 172 | 106 | 127 | 142 | 16 | 38 | 65 |
| PR004129 | 328 | 257 | 221 | 175 | 105 | 127 | 141 | 16 | 38 | 67 |
| PR004130 | 329 | 258 | 222 | 176 | 105 | 127 | 141 | 16 | 38 | 65 |
| PR004131 | 330 | 259 | 223 | 177 | 107 | 127 | 142 | 16 | 38 | 68 |
| PR004264 | 331 | 263 | 224 | 178 | 108 | 128 | 143 | 19 | 40 | 69 |
| PR004265 | 332 | 264 | 225 | 179 | 109 | 129 | 144 | 20 | 41 | 70 |
| PR004275 | 333 | 265 | 226 | 180 | 110 | 130 | 145 | 19 | 40 | 71 |
| PR005124 | 347 | 287 | 240 | 200 | 115 | 133 | 148 | 19 | 44 | 76 |
| PR005125 | 348 | 288 | 241 | 201 | 116 | 134 | 149 | 19 | 45 | 77 |

TABLE 20-continued

Sequence numbers of initial antibodies having binding activity on human CCR8

| Antibody No. | Light chain | Heavy chain | VL | VH | LCDR1 | LCDR2 | LCDR3 | HCDR1 | HCDR2 | HCDR3 |
|---|---|---|---|---|---|---|---|---|---|---|
| PR005127 | 347 | 289 | 240 | 200 | 115 | 133 | 148 | 19 | 44 | 76 |
| PR005128 | 348 | 290 | 241 | 201 | 116 | 134 | 149 | 19 | 45 | 77 |
| PR005329 | 352 | 292 | 245 | 202 | 105 | 127 | 141 | 16 | 46 | 78 |
| PR005330 | 353 | 293 | 246 | 203 | 104 | 127 | 141 | 16 | 38 | 66 |
| PR005331 | 354 | 294 | 247 | 204 | 117 | 128 | 153 | 24 | 42 | 79 |
| PR005332 | 352 | 295 | 245 | 202 | 105 | 127 | 141 | 16 | 46 | 78 |
| PR005333 | 353 | 296 | 246 | 203 | 104 | 127 | 141 | 16 | 38 | 66 |
| PR005335 | 355 | 297 | 248 | 205 | 117 | 128 | 153 | 25 | 47 | 79 |
| PR005336 | 354 | 298 | 247 | 204 | 117 | 128 | 153 | 24 | 42 | 79 |

TABLE 21

CDR sequences of initial antibodies having binding activity on human CCR8

| Antibody No. | HCDR1 | HCDR2 | HCDR3 | LCDR1 | LCDR2 | LCDR3 |
|---|---|---|---|---|---|---|
| PR004120 | GFTFNTN | RSKMNNYA | GKENGNYYAMDF | RSSKSLLYSNGNTYLY | RMSNLAS | MQHLEYPFT |
| PR004121 | GFTFNTY | RSKSNNYA | GKENGNYYAMDF | RSSKSLLHSNGNTYLY | RMSNLAS | MQHLEYPFT |
| PR004122 | GFTFNTN | RSKSNNYA | GKENGNYYAMDF | RSSKSLLHSNGNTYLY | RMSNLAS | MQHLEYPLT |
| PR004123 | EFTFNTY | RTKSNNFA | GKENGNYYAMDF | RSSKSLLHSNGNTYLY | RMSNLAS | MQHLEYPFT |
| PR004124 | GFTFNTY | RSKSNNYA | GKDYGNYYAMDF | RSSKSLLHSNGNTYLY | RMSNLAS | MQHLEYPFT |
| PR004125 | GFTFNTY | RSKSNNYA | GKENGNYYAMDF | RSSKSLLHSNGNTYLY | RMSNLAS | MQHLEYPLT |
| PR004126 | GFTFSTN | RSKSNNYA | GKENGNYYAMDF | RSSKSLLHSNGNTYLY | RMSNLAS | MQHLEYPFT |
| PR004127 | GFTFNTN | RSKSNNYA | GKENGNYYAMDF | RSSKSLLYSNGNTYLY | RMSNLAS | MQHLEYPFT |
| PR004128 | GFTFNTY | RSKSNNYA | GKENGNYYAMDF | RSSKSLLHSNGKIYLY | RMSNLAS | MQHLEYPLT |
| PR004129 | GFTFNTY | RSKSNNYA | GKDYGNYYAMDY | RSSKSLLHSNGNTYLY | RMSNLAS | MQHLEYPFT |
| PR004130 | GFTFNTY | RSKSNNYA | GKENGNYYAMDF | RSSKSLLHSNGNTYLY | RMSNLAS | MQHLEYPFT |
| PR004131 | GFTFNTY | RSKSNNYA | GKENGNYYAMDY | RSNKSLLHSNGNTYLY | RMSNLAS | MQHLEYPLT |
| PR004264 | GFTFSSY | SGSGGS | QGFDY | RSSQSLVYSDGNTYLN | KVSNRDS | MQGTHWPPIT |
| PR004265 | GFTFSSF | SSGSRT | GGLRPYWYFDV | SASSSVSYMY | RTSNLAS | QQRSSYPPT |
| PR004275 | GFTFSSY | SGSGGS | RWGKGGLFDY | RASQSISSWLA | KASSLES | QKYNSAPPT |
| PR005124 | GFTFSSY | WHDGSN | HRRSDYWYYGMDV | RSSQSLLHSNGYNYLD | LGSNRAS | MQALQTPYT |
| PR005125 | GFTFSSY | WYDGSK | GGFYYGSGNYSLFDY | RSSQSLVFSNGNTYLN | KVSKRDS | MQGTHWIT |
| PR005127 | GFTFSSY | WHDGSN | HRRSDYWYYGMDV | RSSQSLLHSNGYNYLD | LGSNRAS | MQALQTPYT |

TABLE 21-continued

CDR sequences of initial antibodies having binding activity on human CCR8

| Antibody No. | HCDR1 | HCDR2 | HCDR3 | LCDR1 | LCDR2 | LCDR3 |
|---|---|---|---|---|---|---|
| PR005128 | GFTFSSY | WYDGSK | GGFYYGSGNYSLFDY | RSSQSLVFSNGNTYLN | KVSKRDS | MQGTHWIT |
| PR005329 | GFTFNTY | RTKSNNYA | GKDNGNYYAMDF | RSSKSLLHSNGNTYLY | RMSNLAS | MQHLEYPFT |
| PR005330 | GFTFNTY | RSKSNNYA | GKDYGNYYAMDF | RSSKSLLYSNGNTYLY | RMSNLAS | MQHLEYPFT |
| PR005331 | GFTFSNY | KQDGSA | NWGFDY | RSSQSLVYSNGNTYLN | KVSNRDS | MQGTHWPIT |
| PR005332 | GFTFNTY | RTKSNNYA | GKDNGNYYAMDF | RSSKSLLHSNGNTYLY | RMSNLAS | MQHLEYPFT |
| PR005333 | GFTFNTY | RSKSNNYA | GKDYGNYYAMDF | RSSKSLLYSNGNTYLY | RMSNLAS | MQHLEYPFT |
| PR005335 | GFTFSYY | KQDGST | NWGFDY | RSSQSLVYSNGNTYLN | KVSNRDS | MQGTHWPIT |
| PR005336 | GFTFSNY | KQDGSA | NWGFDY | RSSQSLVYSNGNTYLN | KVSNRDS | MQGTHWPIT |

TABLE 22

Sequence numbers of antibodies after "DE" mutation

| Antibody No. | Light chain | Heavy chain | VL | VH | LCDR1 | LCDR2 | LCDR3 | HCDR1 | HCDR2 | HCDR3 |
|---|---|---|---|---|---|---|---|---|---|---|
| PR004249 | 321 | 260 | 214 | 169 | 105 | 127 | 142 | 15 | 38 | 65 |
| PR004250 | 324 | 261 | 217 | 172 | 105 | 127 | 142 | 16 | 38 | 65 |
| PR004251 | 327 | 261 | 220 | 172 | 106 | 127 | 142 | 16 | 38 | 65 |
| PR004252 | 330 | 262 | 223 | 177 | 107 | 127 | 142 | 16 | 38 | 68 |

TABLE 23

CDR sequences of antibodies after "DE" mutation

| Antibody No. | HCDR1 | HCDR2 | HCDR3 | LCDR1 | LCDR2 | LCDR3 |
|---|---|---|---|---|---|---|
| PR004249 | GFTFNTN | RSKSNNYA | GKENGNYYAMDF | RSSKSLLHSNGNTYLY | RMSNLAS | MQHLEYPLT |
| PR004250 | GFTFNTY | RSKSNNYA | GKENGNYYAMDF | RSSKSLLHSNGNTYLY | RMSNLAS | MQHLEYPLT |
| PR004251 | GFTFNTY | RSKSNNYA | GKENGNYYAMDF | RSSKSLLHSNGKIYLY | RMSNLAS | MQHLEYPLT |
| PR004252 | GFTFNTY | RSKSNNYA | GKENGNYYAMDY | RSNKSLLHSNGNTYLY | RMSNLAS | MQHLEYPLT |

2.2 Single Cell Clone Screening

The spleen cells and bone marrow cells of mice isolated from H2L2 mice with high titer, after being enriched using a plasma cell sorting kit (Miltenyi Biotec, cat 130-092-530, lot 5190121409), were delivered to the chip site by a microfluidic system of Beacon platform (Berkeley Lights), and the single cells were isolated and added into individual chambers of the chip by the opto-electro positioning (OEP) technique. After incubation of single B cells for a certain period of time (20 min), multiplex assays of in-chip can be performed: not only can the assay on the specific binding of an antigen to an antibody based on magnetic beads be completed, but also the binding of an antibody to an antigen on the cell surface can be detected using cell lines overexpressing the antigen. If the cells were capable of secreting antigen-specific antibodies, a fluorescent signal will be generated and recognized by the instrument. In this step, the detection assay can be flexibly adjusted as required. Single positive cells were exported and delivered to a 96-well plate containing cell lysate (Qiagen, cat. 1031586, lot. 163013365) and mineral oil (Sigma, cat. M5904-500ML, lot. MKBZ6778V) by the OEP technique for further sequencing, analysis and expression. The obtained antibodies were PR004970, PR004974, and PR005293.

The sequence numbers (SEQ ID NOs) of initial antibodies obtained by single cell clone screening are shown in Table 24, and the CDR sequences of the antibodies are shown in Table 25.

TABLE 24

| Sequence numbers of initial antibodies having binding activity on CCR8 | | | | | | | | | | |
|---|---|---|---|---|---|---|---|---|---|---|
| Antibody No. | Light chain | Heavy chain | VL | VH | LCDR1 | LCDR2 | LCDR3 | HCDR1 | HCDR2 | HCDR3 |
| PR004970 | 345 | 285 | 238 | 198 | 113 | 131 | 146 | 19 | 42 | 74 |
| PR004974 | 346 | 286 | 239 | 199 | 114 | 132 | 147 | 23 | 43 | 75 |
| PR005293 | 346 | 291 | 239 | 199 | 114 | 132 | 147 | 23 | 43 | 75 |

TABLE 25

| CDR sequences of initial antibodies having binding activity on CCR8 | | | | | | |
|---|---|---|---|---|---|---|
| Antibody No. | HCDR1 | HCDR2 | HCDR3 | LCDR1 | LCDR2 | LCDR3 |
| PR004970 | GFTFSSY | KQDGSA | SWGFAY | RASQGISNYLA | AASTLQS | QKYNSAPWT |
| PR004974 | GFSLSTSGV | YWNDD | RRLRYSGRYYYYYGTDV | RASQSVSSNLV | GASIRAT | QQYNNWPYT |
| PR005293 | GFSLSTSGV | YWNDD | RRLRYSGRYYYYYGTDV | RASQSVSSNLV | GASIRAT | QQYNNWPYT |

Example 3. Sequence Optimization of Monoclonal Antibodies

3.1 Analysis of Germline Genes and Optimization of Post-Translational Modification (PTM) Sites The sequence of the heavy chain variable region of the antibody is derived from events such as gene rearrangements of germline gene V, D and J segments of heavy chain gene clusters and somatic hypermutations on chromosomes; and the sequence of the light chain variable domain is derived from events such as gene rearrangements of germline gene V, D and J segments of light chain gene clusters and somatic hypermutations. Gene rearrangement and somatic hypermutation are major factors in increasing antibody diversity. Antibodies derived from the same germline V gene segment may also produce different sequences, but with relatively high similarity overall. The germline gene segments that are likely to undergo gene rearrangement can be deduced from the antibody variable region sequences using algorithms such as IMGT/DomainGapAlign (http://imgt.org/3Dstructure-DB/cgi/DomainGapAlign.cgi) or NCB I/IgB LAST (https://www.ncbi.nlm.nih.gov/igblast/).

Chemical modifications sometimes introduced after translation and synthesis of protein or polypeptide amino acid chains in cells are known as post-translational modifications (PTMs). For antibodies, some PTM sites are very conservative. For example, the conservative amino acid asparagine (Asn) at position 297 (EU numbering) of the constant region of the human IgG1 antibody is generally glycosylated to form a saccharide chain whose structure is critical for antibody structure and associated effector functions. However, PTMs may have a greater effect on antigen binding or result in changes in the physicochemical properties of the antibody, if they are present in the variable regions, particularly in the antigen-binding regions (e.g., CDRs) of an antibody. For example, glycosylation, deamidation, isomerization, oxidation, and the like may increase the instability or heterogeneity of antibody molecules, thereby increasing the difficulty and risk of antibody development. Thus, it is very important for the development of therapeutic antibodies to avoid some potential PTMs. As experience has accumulated, it has been found that some PTMs are highly correlated with the composition of amino acid sequences, especially the "pattern" of the composition of adjacent amino acids, which makes it possible to predict potential PTMs from the primary amino acid sequences of a protein. For example, it is predicted that there is an N-linked glycosylation site from the N-x-S/T sequence pattern (asparagine at the first position, any amino acid other than non-proline at the second position, and serine or threonine at the third position). The amino acid sequence patterns leading to PTMs may be derived from germline gene sequences, e.g., the human germline gene fragment IGHV3-33 naturally having a glycosylation pattern NST in the FR3 region; or they may also be derived from somatic hypermutations.

Based on germline gene V gene segments of the heavy chain variable domain (VH) and light chain variable domain (VL) of the PR004128 sequence (from monoclonal, clone M3E3), it is predicted that NG or NT may be potential PTM mutation sites.

The amino acid sequence patterns of PTMs may be disrupted by amino acid mutations, thereby reducing or eliminating the formation of specific PTMs. There are different methods for designing mutations depending on the antibody sequences and PTM sequence patterns. One method is to replace a "hot spot" amino acid (e.g., N or S in the NS pattern) with an amino acid with similar physicochemical properties (e.g., to mutate N into Q). If the PTM sequence pattern is derived from somatic hypermutations and is not present in the germline gene sequence, the other method can be to replace the sequence pattern with the corresponding germline gene sequence. In practice, a variety of methods for designing mutations may be used for the same PTM sequence pattern.

Amino acid mutation is performed on potential PTM sites of a monoclonal antibody RP004128 to obtain new variants derived from the heavy chain variable region or the light chain variable region (referred to as PTM variants), which are used for constructing IgG1 recombinant sequences, and "DE" (S239D and I332E) double mutant are introduced into heavy chain constant regions to enhance the ADCC function. The obtained antibodies of PTM variants are numbered as PR004324, PR004325, PR004326, PR004327, PR004328 and PR004329, respectively. The sequence numbers of the PTM mutant antibodies of RP004128 are shown in Table 8 below, and the CDR sequences of the antibodies are shown in Table 9 below.

TABLE 26

| Sequence numbers of PTM mutant antibodies of RP004128 | | | | | | | | | | |
|---|---|---|---|---|---|---|---|---|---|---|
| Antibody No. | Light chain | Heavy chain | VL | VH | LCDR1 | LCDR2 | LCDR3 | HCDR1 | HCDR2 | HCDR3 |
| PR004324 | 334 | 261 | 227 | 172 | 111 | 127 | 142 | 16 | 38 | 65 |
| PR004325 | 335 | 261 | 228 | 172 | 112 | 127 | 142 | 16 | 38 | 65 |
| PR004326 | 327 | 266 | 220 | 181 | 106 | 127 | 142 | 16 | 38 | 72 |
| PR004327 | 327 | 267 | 220 | 182 | 106 | 127 | 142 | 21 | 38 | 65 |
| PR004328 | 327 | 268 | 220 | 183 | 106 | 127 | 142 | 22 | 38 | 65 |
| PR004329 | 327 | 269 | 220 | 184 | 106 | 127 | 142 | 16 | 38 | 73 |

TABLE 27

| CDR sequences of PTM mutant antibodies of RP004128 | | | | | | |
|---|---|---|---|---|---|---|
| Antibody No. | HCDR1 | HCDR2 | HCDR3 | LCDR1 | LCDR2 | LCDR3 |
| PR004324 | GFTFNTY | RSKSNGKENGNNYA | YYAMDF | RSSKSLLHSNAKIYLY | RMSNLAS | MQHLEYPLT |
| PR004325 | GFTFNTY | RSKSNGKENGNNYA | YYAMDF | RSSKSLLHSQGKIYLY | RMSNLAS | MQHLEYPLT |
| PR004326 | GFTFNTY | RSKSNGKENANNYA | YYAMDF | RSSKSLLHSNGKIYLY | RMSNLAS | MQHLEYPLT |
| PR004327 | GFTFQTY | RSKSNGKENGNNYA | YYAMDF | RSSKSLLHSNGKIYLY | RMSNLAS | MQHLEYPLT |
| PR004328 | GFTFSTY | RSKSNGKENGNNYA | YYAMDF | RSSKSLLHSNGKIYLY | RMSNLAS | MQHLEYPLT |
| PR004329 | GFTFNTY | RSKSNGKEQGNNYA | YYAMDF | RSSKSLLHSNGKIYLY | RMSNLAS | MQHLEYPLT |

3.2 Humanization of Variable Region Sequences of RP004128

In this example, the method of "CDR grafting" was used for humanization of the sequences, that is, the CDRs of VH of a mouse antibody are grafted to the framework regions of VH of a human antibody, and the CDRs of VL of the mouse antibody are grafted to the framework regions of VL of the human antibody. The sequences of the framework regions of the VH or VL of the human antibody may be derived from human germline gene sequences or from antibody sequences following V(D)J rearrangement or from consensus sequences of specific VH or VL gene family of a human antibody.

In this example, the sequences of the framework regions provided by the human germline gene sequences were used as humanization template sequences. Specifically, the sequences of the framework regions FR1, FR2 and FR3 were provided by the human germline V gene segment and the sequences of the framework region FR4 was provided by the human germline J gene segment. Finally, humanized variable region (VH or VL) sequences were constructed in the arrangement of (human) FR1-(mouse) CDR1-(human) FR2-(mouse) CDR2-(human) FR3-(mouse) CDR3-(human) FR4.

In this example, the sequence of the human germline V gene segment IGHV3-73*01 or the human germline V gene segment IGHV3-23*04 or the human germline V gene segment IGHV3-15*07 in combination with the human germline J gene segment IGHJ6*01 was used as a humanization template to provide the sequences of the framework regions. Moreover, amino acid mutations were introduced in one or more of positions 32, 73, 76, 78, 93, 94 and 102 (according to the Chothia numbering scheme) to obtain a plurality of different VH-humanized variant sequences.

In this example, the sequence of the human germline V gene segment IGKV2-28*01 or the human germline V gene segment IGKV2-30*02 in combination with the human germline J gene segment IGKJ2*01 was used as a humanization template to provide the sequences of the framework regions. Moreover, amino acid mutations were introduced in zero or one or more of positions 2, 26, 30e, 31, 36, 46 and 96 (according to the Chothia numbering scheme) to obtain a plurality of different VL-humanized variant sequences. Specifically, in some VL variants, Leu at position 96 (according to Chothia numbering scheme) was mutated to Phe to investigate the effect of this site on binding to the target.

3.3 Study on Saturation Mutagenesis of Amino Acid at Position 96 of the Light Chain of RP004128

3.3.1 Saturation Mutagenesis

Saturation mutagenesis was performed on amino acid at position 96 (according to Chothia numbering scheme) of the light chain of RP004128 molecule, and the PCR product was electroporated into BL21 cells. 192 single clones were picked for sequencing, and the sequences were analyzed to find mutants other than the wild type.

3.3.2 Preliminary Screening

Colonies of the wild type and mutants were picked and added into a 96-well plate containing 2YT/Amp medium (Sangon Biotech, Cat. No. A507016-0250) and grown at 37° C. for 3 h. IPTG was added to give a final concentration of 1 mM, and the mixture was induced at 30° C. overnight. The supernatant was then pelleted by centrifugation, and the supernatant was subjected to an FACS assay. The antibody supernatant was separately incubated with a CHO-K1 cell line overexpressing monkey CCR8 and a CHO-K1 cell line overexpressing human CCR8, and screening was performed to obtain antibodies that can bind to CCR8 on the CHO-K1 cell line.

3.4 Preparation and Identification of Recombinant Antibody Molecules Derived from RP004128

The VH variant sequences and VL variant sequences derived from RP004128 were combined in pairs to construct IgG recombinant antibodies, and "DE" double mutants (S239D and I332E) were introduced in the IgG1 heavy chain constant regions to enhance the ADCC function. Purified recombinant antibodies were obtained by the method as described in Example 4 and subjected to further verification in subsequent functional experiments.

The sequence numbers of recombinant antibody molecules derived from the variable regions of RP004128 are listed in Table 28, and the CDR sequences of recombinant antibody molecules derived from the variable regions of RP004128 are listed in Table 29.

TABLE 28

Sequence numbers of humanized antibodies of RP004128

| Antibody No. | Light chain | Heavy chain | VL | VH | LCDR1 | LCDR2 | LCDR3 | HCDR1 | HCDR2 | HCDR3 |
|---|---|---|---|---|---|---|---|---|---|---|
| PR004330 | 327 | 270 | 220 | 185 | 106 | 127 | 142 | 16 | 38 | 65 |
| PR004331 | 327 | 271 | 220 | 186 | 106 | 127 | 142 | 15 | 38 | 65 |
| PR004332 | 327 | 272 | 220 | 187 | 106 | 127 | 142 | 16 | 38 | 68 |
| PR004333 | 327 | 273 | 220 | 188 | 106 | 127 | 142 | 16 | 38 | 65 |
| PR004334 | 327 | 274 | 220 | 189 | 106 | 127 | 142 | 15 | 38 | 65 |
| PR004335 | 327 | 275 | 220 | 190 | 106 | 127 | 142 | 16 | 38 | 68 |
| PR004336 | 327 | 276 | 220 | 191 | 106 | 127 | 142 | 16 | 38 | 65 |
| PR004337 | 327 | 277 | 220 | 192 | 106 | 127 | 142 | 15 | 38 | 65 |
| PR004338 | 327 | 278 | 220 | 193 | 106 | 127 | 142 | 16 | 38 | 68 |
| PR004339 | 336 | 261 | 229 | 172 | 106 | 127 | 142 | 16 | 38 | 65 |
| PR004340 | 337 | 261 | 230 | 172 | 105 | 127 | 142 | 16 | 38 | 65 |
| PR004342 | 338 | 261 | 231 | 172 | 105 | 127 | 141 | 16 | 38 | 65 |
| PR004343 | 339 | 261 | 232 | 172 | 106 | 127 | 142 | 16 | 38 | 65 |
| PR004344 | 340 | 261 | 233 | 172 | 105 | 127 | 142 | 16 | 38 | 65 |
| PR004345 | 341 | 261 | 234 | 172 | 107 | 127 | 142 | 16 | 38 | 65 |
| PR004346 | 342 | 261 | 235 | 172 | 105 | 127 | 141 | 16 | 38 | 65 |
| PR004519 | 336 | 270 | 229 | 185 | 106 | 127 | 142 | 16 | 38 | 65 |
| PR004520 | 336 | 273 | 229 | 188 | 106 | 127 | 142 | 16 | 38 | 65 |
| PR004521 | 336 | 276 | 229 | 191 | 106 | 127 | 142 | 16 | 38 | 65 |
| PR004522 | 337 | 270 | 230 | 185 | 105 | 127 | 142 | 16 | 38 | 65 |
| PR004523 | 337 | 273 | 230 | 188 | 105 | 127 | 142 | 16 | 38 | 65 |
| PR004524 | 337 | 276 | 230 | 191 | 105 | 127 | 142 | 16 | 38 | 65 |
| PR004525 | 339 | 270 | 232 | 185 | 106 | 127 | 142 | 16 | 38 | 65 |
| PR004526 | 339 | 273 | 232 | 188 | 106 | 127 | 142 | 16 | 38 | 65 |
| PR004527 | 339 | 276 | 232 | 191 | 106 | 127 | 142 | 16 | 38 | 65 |
| PR004660 | 336 | 279 | 229 | 194 | 106 | 127 | 142 | 22 | 38 | 72 |
| PR004661 | 336 | 280 | 229 | 195 | 106 | 127 | 142 | 22 | 38 | 73 |
| PR004662 | 343 | 279 | 236 | 194 | 111 | 127 | 142 | 22 | 38 | 72 |
| PR004663 | 343 | 280 | 236 | 195 | 111 | 127 | 142 | 22 | 38 | 73 |
| PR004664 | 339 | 281 | 232 | 196 | 106 | 127 | 142 | 22 | 38 | 72 |
| PR004665 | 339 | 282 | 232 | 197 | 106 | 127 | 142 | 22 | 38 | 73 |
| PR004666 | 344 | 281 | 237 | 196 | 111 | 127 | 142 | 22 | 38 | 72 |
| PR004667 | 344 | 282 | 237 | 197 | 111 | 127 | 142 | 22 | 38 | 73 |
| PR004668 | 336 | 283 | 229 | 188 | 106 | 127 | 142 | 16 | 38 | 65 |
| PR004669 | 339 | 284 | 232 | 185 | 106 | 127 | 142 | 16 | 38 | 65 |
| PR005170 | 349 | 254 | 242 | 172 | 106 | 127 | 150 | 16 | 38 | 65 |
| PR005171 | 350 | 254 | 243 | 172 | 106 | 127 | 151 | 16 | 38 | 65 |
| PR005172 | 351 | 254 | 244 | 172 | 106 | 127 | 152 | 16 | 38 | 65 |

TABLE 29

CDR sequences of humanized antibodies of RP004128

| Antibody No. | HCDR1 | HCDR2 | HCDR3 | LCDR1 | LCDR2 | LCDR3 |
|---|---|---|---|---|---|---|
| PR004330 | GFTFNTY | RSKSNNYA | GKENGNYYAMDF | RSSKSLLHSNGKIYLY | RMSNLAS | MQHLEYPLT |
| PR004331 | GFTENTN | RSKSNNYA | GKENGNYYAMDF | RSSKSLLHSNGKIYLY | RMSNLAS | MQHLEYPLT |
| PR004332 | GFTFNTY | RSKSNNYA | GKENGNYYAMDY | RSSKSLLHSNGKIYLY | RMSNLAS | MQHLEYPLT |
| PR004333 | GFTFNTY | RSKSNNYA | GKENGNYYAMDF | RSSKSLLHSNGKIYLY | RMSNLAS | MQHLEYPLT |
| PR004334 | GFTFNTN | RSKSNNYA | GKENGNYYAMDF | RSSKSLLHSNGKIYLY | RMSNLAS | MQHLEYPLT |
| PR004335 | GFTFNTY | RSKSNNYA | GKENGNYYAMDY | RSSKSLLHSNGKIYLY | RMSNLAS | MQHLEYPLT |
| PR004336 | GFTFNTY | RSKSNNYA | GKENGNYYAMDF | RSSKSLLHSNGKIYLY | RMSNLAS | MQHLEYPLT |
| PR004337 | GFTFNTN | RSKSNNYA | GKENGNYYAMDF | RSSKSLLHSNGKIYLY | RMSNLAS | MQHLEYPLT |
| PR004338 | GFTFNTY | RSKSNNYA | GKENGNYYAMDY | RSSKSLLHSNGKIYLY | RMSNLAS | MQHLEYPLT |

TABLE 29-continued

CDR sequences of humanized antibodies of RP004128

| Antibody No. | HCDR1 | HCDR2 | HCDR3 | LCDR1 | LCDR2 | LCDR3 |
|---|---|---|---|---|---|---|
| PR004339 | GFTFNTY | RSKSNNYA | GKENGNYYAMDF | RSSKSLLHSNGKIYLY | RMSNLAS | MQHLEYPLT |
| PR004340 | GFTFNTY | RSKSNNYA | GKENGNYYAMDF | RSSKSLLHSNGNTYLY | RMSNLAS | MQHLEYPLT |
| PR004342 | GFTFNTY | RSKSNNYA | GKENGNYYAMDF | RSSKSLLHSNGNTYLY | RMSNLAS | MQHLEYPFT |
| PR004343 | GFTFNTY | RSKSNNYA | GKENGNYYAMDF | RSSKSLLHSNGKIYLY | RMSNLAS | MQHLEYPLT |
| PR004344 | GFTFNTY | RSKSNNYA | GKENGNYYAMDF | RSSKSLLHSNGNTYLY | RMSNLAS | MQHLEYPLT |
| PR004345 | GFTFNTY | RSKSNNYA | GKENGNYYAMDF | RSNKSLLHSNGNTYLY | RMSNLAS | MQHLEYPLT |
| PR004346 | GFTFNTY | RSKSNNYA | GKENGNYYAMDF | RSSKSLLHSNGNTYLY | RMSNLAS | MQHLEYPFT |
| PR004519 | GFTFNTY | RSKSNNYA | GKENGNYYAMDF | RSSKSLLHSNGKIYLY | RMSNLAS | MQHLEYPLT |
| PR004520 | GFTFNTY | RSKSNNYA | GKENGNYYAMDF | RSSKSLLHSNGKIYLY | RMSNLAS | MQHLEYPLT |
| PR004521 | GFTFNTY | RSKSNNYA | GKENGNYYAMDF | RSSKSLLHSNGKIYLY | RMSNLAS | MQHLEYPLT |
| PR004522 | GFTFNTY | RSKSNNYA | GKENGNYYAMDF | RSSKSLLHSNGNTYLY | RMSNLAS | MQHLEYPLT |
| PR004523 | GFTFNTY | RSKSNNYA | GKENGNYYAMDF | RSSKSLLHSNGNTYLY | RMSNLAS | MQHLEYPLT |
| PR004524 | GFTFNTY | RSKSNNYA | GKENGNYYAMDF | RSSKSLLHSNGNTYLY | RMSNLAS | MQHLEYPLT |
| PR004525 | GFTFNTY | RSKSNNYA | GKENGNYYAMDF | RSSKSLLHSNGKIYLY | RMSNLAS | MQHLEYPLT |
| PR004526 | GFTENTY | RSKSNNYA | GKENGNYYAMDF | RSSKSLLHSNGKIYLY | RMSNLAS | MQHLEYPLT |
| PR004527 | GFTFNTY | RSKSNNYA | GKENGNYYAMDF | RSSKSLLHSNGKIYLY | RMSNLAS | MQHLEYPLT |
| PR004660 | GFTFSTY | RSKSNNYA | GKENANYYAMDF | RSSKSLLHSNGKIYLY | RMSNLAS | MQHLEYPLT |
| PR004661 | GFTFSTY | RSKSNNYA | GKEQGNYYAMDF | RSSKSLLHSNGKIYLY | RMSNLAS | MQHLEYPLT |
| PR004662 | GFTFSTY | RSKSNNYA | GKENANYYAMDF | RSSKSLLHSNAKIYLY | RMSNLAS | MQHLEYPLT |
| PR004663 | GFTFSTY | RSKSNNYA | GKEQGNYYAMDF | RSSKSLLHSNAKIYLY | RMSNLAS | MQHLEYPLT |
| PR004664 | GFTFSTY | RSKSNNYA | GKENANYYAMDF | RSSKSLLHSNGKIYLY | RMSNLAS | MQHLEYPLT |
| PR004665 | GFTFSTY | RSKSNNYA | GKEQGNYYAMDF | RSSKSLLHSNGKIYLY | RMSNLAS | MQHLEYPLT |
| PR004666 | GFTFSTY | RSKSNNYA | GKENANYYAMDF | RSSKSLLHSNAKIYLY | RMSNLAS | MQHLEYPLT |
| PR004667 | GFTFSTY | RSKSNNYA | GKEQGNYYAMDF | RSSKSLLHSNAKIYLY | RMSNLAS | MQHLEYPLT |
| PR004668 | GFTFNTY | RSKSNNYA | GKENGNYYAMDF | RSSKSLLHSNGKIYLY | RMSNLAS | MQHLEYPLT |

TABLE 29-continued

| CDR sequences of humanized antibodies of RP004128 | | | | | | |
|---|---|---|---|---|---|---|
| Antibody No. | HCDR1 | HCDR2 | HCDR3 | LCDR1 | LCDR2 | LCDR3 |
| PR004669 | GFTFNTY | RSKSNNYA | GKENGNYYAMDF | RSSKSLLHSNGKIYLY | RMSNLAS | MQHLEYPLT |
| PR005170 | GFTFNTY | RSKSNNYA | GKENGNYYAMDF | RSSKSLLHSNGKIYLY | RMSNLAS | MQHLEYPIT |
| PR005171 | GFTFNTY | RSKSNNYA | GKENGNYYAMDF | RSSKSLLHSNGKIYLY | RMSNLAS | MQHLEYPMT |
| PR005172 | GFTFNTY | RSKSNNYA | GKENGNYYAMDF | RSSKSLLHSNGKIYLY | RMSNLAS | MQHLEYPVT |

Example 4. Affinity Maturation of PR004666

4.1 Establishment of Mutant Phage Libraries

Random mutagenesis was performed on 4 CDRs (HCDR2, HCDR3, LCDR1, and LCDR3) of the PR004666 molecule to establish 4 phage libraries with a library capacity of about $10^{10}$.

4.2 Bio-Panning

The phage libraries (1E13 phage particles) were depleted with CHO-K1 cells and incubated with CHO-K1-hCCR8 cells for 1 h at 4° C.; and the mixture was washed 5 times with 1×PBS. After washing, a citrate buffer at pH 3.0 was added to the cell/phage mixture, and the mixture was incubated at room temperature for 10 min. Then, a Tris-HCl neutralization buffer at pH 9.0 was added, and the mixture was used to infect SS320 cells at 37° C. for 45 min. Then, 50 μL of M13K07 helper phages (NEB, Cat. No. N0315S) at 2E12/mL was added to the infected cells, and finally fresh 2× YT (containing 100 μg/mL Amp, 50 μg/mL Kan, and 1 mM IPTG) was added, and the mixture was incubated at 30° C. overnight. The overnight culture was centrifuged, and the supernatant was collected. 20% PEG6000/2.5 M NaCl was added to the supernatant (1:5, volume ratio), and the mixture was centrifuged at 8000 rpm for 20 min at 4° C. The phage pellet obtained after centrifugation was resuspended in 1 mL of 1×PBS. The resulting supernatant (phage particles) was transferred to a new tube for the second round of panning. The procedures of the second and third rounds of panning were the same as the previous steps.

4.3 Preliminary Screening

Colonies were picked into a 96-well plate containing 2YT/Amp medium (Sangon Biotech, Cat. No. A507016-0250) and grown at 37° C. for 3 h. IPTG was added to give a final concentration of 1 mM, and the mixture was induced at 30° C. overnight. The supernatant was then pelleted by centrifugation, and the supernatant was subjected to ELISA and FACS assays.

4.4 Confirmation of Positive Clones

Positive clones were induced to express by IPTG by sequencing analysis. The expressed proteins were first quantified by quantitative ELISA for preliminary quantification. Then, FACS identification was performed, and mutation hotspots were analyzed by combining FACS identification results and sequence information.

4.5 Identification of Combination Mutant Molecules

Combination mutation was designed according to the hotspots, and 6 mutants were constructed into mammalian expression vectors for the expression and purification of proteins. The purified mutants were then identified by FACS.

In the obtained PR004666 mutants, PR005750, PR005751, PR005752, PR005753, PR005754, PR005763 and PR005787 are Fab antibodies, PR006154, PR006155, PR006156, PR006157, PR006161 and PR006166 are IgG antibodies with a "DE" mutation in the IgG1 constant region, PR005565, PR006272, PR006276, PR006273, PR006277, PR006274 and PR006275 are IgG antibodies with the IgG1 constant region. The sequence numbers of the antibodies are shown in Table 30 below, and the CDR sequences are shown in Table 31 below.

TABLE 30

| Sequence number of PR004666 mutants | | | | | | | | | | |
|---|---|---|---|---|---|---|---|---|---|---|
| Antibody No. | Light chain | Heavy chain | VL | VH | LCDR1 | LCDR2 | LCDR3 | HCDR1 | HCDR2 | HCDR3 |
| PR005750 | 344 | 300 | 237 | 196 | 111 | 127 | 142 | 22 | 38 | 72 |
| PR005751 | 344 | 301 | 237 | 206 | 111 | 127 | 142 | 22 | 38 | 80 |
| PR005752 | 344 | 302 | 237 | 207 | 111 | 127 | 142 | 22 | 48 | 80 |
| PR005753 | 344 | 303 | 237 | 208 | 111 | 127 | 142 | 22 | 38 | 81 |
| PR005754 | 344 | 304 | 237 | 209 | 111 | 127 | 142 | 22 | 48 | 81 |
| PR005763 | 344 | 305 | 237 | 210 | 111 | 127 | 142 | 22 | 48 | 82 |
| PR005787 | 344 | 306 | 237 | 211 | 111 | 127 | 142 | 22 | 48 | 83 |
| PR006154 | 344 | 307 | 237 | 206 | 111 | 127 | 142 | 22 | 38 | 80 |
| PR006155 | 344 | 308 | 237 | 207 | 111 | 127 | 142 | 22 | 48 | 80 |
| PR006156 | 344 | 309 | 237 | 208 | 111 | 127 | 142 | 22 | 38 | 81 |
| PR006157 | 344 | 310 | 237 | 209 | 111 | 127 | 142 | 22 | 48 | 81 |
| PR006161 | 344 | 311 | 237 | 210 | 111 | 127 | 142 | 22 | 48 | 82 |
| PR006166 | 344 | 312 | 237 | 211 | 111 | 127 | 142 | 22 | 48 | 83 |
| PR005565 | 344 | 299 | 237 | 196 | 111 | 127 | 142 | 22 | 38 | 72 |
| PR006272 | 344 | 313 | 237 | 206 | 111 | 127 | 142 | 22 | 38 | 80 |

TABLE 30-continued

| Sequence number of PR004666 mutants | | | | | | | | | | |
|---|---|---|---|---|---|---|---|---|---|---|
| Antibody No. | Light chain | Heavy chain | VL | VH | LCDR1 | LCDR2 | LCDR3 | HCDR1 | HCDR2 | HCDR3 |
| PR006276 | 344 | 317 | 237 | 207 | 111 | 127 | 142 | 22 | 48 | 80 |
| PR006273 | 344 | 314 | 237 | 208 | 111 | 127 | 142 | 22 | 38 | 81 |
| PR006277 | 344 | 318 | 237 | 209 | 111 | 127 | 142 | 22 | 48 | 81 |
| PR006274 | 344 | 315 | 237 | 210 | 111 | 127 | 142 | 22 | 48 | 82 |
| PR006275 | 344 | 316 | 237 | 211 | 111 | 127 | 142 | 22 | 48 | 83 |

TABLE 31

| CDR sequences of PR004666 mutants | | | | | | |
|---|---|---|---|---|---|---|
| Antibody No. | HCDR1 | HCDR2 | HCDR3 | LCDR1 | LCDR2 | LCDR3 |
| PR005750 | GFTFSTY | RSKSNNYA | GKENANYYAMDF | RSSKSLLHSNAKIYLY | RMSNLAS | MQHLEYPLT |
| PR005751 | GFTFSTY | RSKSNNYA | GKEHGNYYAMDF | RSSKSLLHSNAKIYLY | RMSNLAS | MQHLEYPLT |
| PR005752 | GFTFSTY | RSKSNYYA | GKEHGNYYAMDF | RSSKSLLHSNAKIYLY | RMSNLAS | MQHLEYPLT |
| PR005753 | GFTFSTY | RSKSNNYA | GKEIGNYYAMDF | RSSKSLLHSNAKIYLY | RMSNLAS | MQHLEYPLT |
| PR005754 | GFTFSTY | RSKSNYYA | GKEIGNYYAMDF | RSSKSLLHSNAKIYLY | RMSNLAS | MQHLEYPLT |
| PR005763 | GFTFSTY | RSKSNYYA | GKEHGKYYAMDF | RSSKSLLHSNAKIYLY | RMSNLAS | MQHLEYPLT |
| PR005787 | GFTFSTY | RSKSNYYA | GKEIGKYYAMDF | RSSKSLLHSNAKIYLY | RMSNLAS | MQHLEYPLT |
| PR006154 | GFTFSTY | RSKSNNYA | GKEHGNYYAMDF | RSSKSLLHSNAKIYLY | RMSNLAS | MQHLEYPLT |
| PR006155 | GFTFSTY | RSKSNYYA | GKEHGNYYAMDF | RSSKSLLHSNAKIYLY | RMSNLAS | MQHLEYPLT |
| PR006156 | GFTFSTY | RSKSNNYA | GKEIGNYYAMDF | RSSKSLLHSNAKIYLY | RMSNLAS | MQHLEYPLT |
| PR006157 | GFTFSTY | RSKSNYYA | GKEIGNYYAMDF | RSSKSLLHSNAKIYLY | RMSNLAS | MQHLEYPLT |
| PR006161 | GFTFSTY | RSKSNYYA | GKEHGKYYAMDF | RSSKSLLHSNAKIYLY | RMSNLAS | MQHLEYPLT |
| PR006166 | GFTFSTY | RSKSNYYA | GKEIGKYYAMDF | RSSKSLLHSNAKIYLY | RMSNLAS | MQHLEYPLT |
| PR005565 | GFTFSTY | RSKSNNYA | GKENANYYAMDF | RSSKSLLHSNAKIYLY | RMSNLAS | MQHLEYPLT |
| PR006272 | GFTFSTY | RSKSNNYA | GKEHGNYYAMDF | RSSKSLLHSNAKIYLY | RMSNLAS | MQHLEYPLT |
| PR006276 | GFTFSTY | RSKSNYYA | GKEHGNYYAMDF | RSSKSLLHSNAKIYLY | RMSNLAS | MQHLEYPLT |
| PR006273 | GFTFSTY | RSKSNNYA | GKEIGNYYAMDF | RSSKSLLHSNAKIYLY | RMSNLAS | MQHLEYPLT |
| PR006277 | GFTFSTY | RSKSNYYA | GKEIGNYYAMDF | RSSKSLLHSNAKIYLY | RMSNLAS | MQHLEYPLT |

TABLE 31-continued

CDR sequences of PR004666 mutants

| Antibody No. | HCDR1 | HCDR2 | HCDR3 | LCDR1 | LCDR2 | LCDR3 |
|---|---|---|---|---|---|---|
| PR006274 | GFTFST Y | RSKSNY YA | GKEHGKYYAM DF | RSSKSLLHSNAKI YLY | RMSNL AS | MQHLEYP LT |
| PR006275 | GFTFST Y | RSKSNY YA | GKEIGKYYAM DF | RSSKSLLHSNAKI YLY | RMSNL AS | MQHLEYP LT |

Example 5. Expression and Purification of Antibodies

In this example, a general method for preparing antibodies in mammalian host cells (e.g., human embryonic kidney cell HEK293 or Chinese hamster ovary CHO cells and cells derived therefrom) by such techniques as transient transfection and expression, and affinity capture and separation was described. This method is applicable to an target antibody containing an Fc region. The target antibody may consist of one or more protein polypeptide chains, and may be derived from one or more expression plasmids.

The amino acid sequences of the polypeptide chains of the antibody were converted into nucleotide sequences by codon optimization. The encoding nucleotide sequences were synthesized and cloned into expression vectors compatible with the host cell. The mammalian host cells were transfected simultaneously with plasmids encoding the polypeptide chains of the antibody in a specific ratio, and the recombinant antibody with correct folding and assembly of polypeptide chains could be obtained by the conventional recombinant protein expression and purification techniques. Specifically, ExpiCHO-S™ cells were expanded in ExpiCHO™ Expression Medium (Gibco, #A2910001). Before the transient transfection, the cells were adjusted to a concentration of $3\times10^6$-$4\times10^6$ cells/mL, cultured in a shaker at 37° C. with 8% $CO_2$ shaker for 24 h to make a cell concentration of $7\times10^6$-$10\times10^6$ cells/mL. The cells were then diluted to $6\times10^6$ cells/mL, and 10 mL of the cultured cells were taken. Plasmids encoding the polypeptide chains of the antibody were mixed in certain a ratio, and a total of 8 μg of plasmids (the ratio of the plasmids to cells was 0.8 μg:1 mL) were dissolved in 0.4 mL of OptiPRO™ SFM medium. The resulting mixture was filtered through a 0.22 μm filter membrane for sterilization. Then, 32 μL of Expi-Fectamine™ CHO reagent (Gibco, #A29129) was added to 0.37 mL of OptiPRO™ SFM medium. Immediately, the ExpiFectamine™ CHO reagent solution was slowly added to the plasmid solution. The mixture was inverted to be mixed well. The mixed solution of plasmids and transfection reagent was slowly added dropwise while shaking the culture flask. In the production of afucosylated (AF) protein, a solution of 2FF (2-fluoro peracetylated fucose, synthesized by WuXi AppTec Co. Ltd.) in DMSO was slowly added dropwise into the flask immediately while shaking the flask to give a final concentration of 50 μM. The mixture was cultured in a shaker at 37° C. with 8% $CO_2$ for 8-9 days. Cell viability was measured after 8 days. The culture was collected and centrifuged at 3300 g for 10 min, and then the supernatant was collected and centrifuged at high speed to remove impurities. The gravity column containing MabSelect™ was equilibrated with a PBS buffer at pH 7.4 and rinsed with 2-5 column volumes of the PBS buffer. The column was loaded with the supernatant sample, and rinsed with 5-10 column volumes of the PBS buffer, followed by 0.1 M glycine at pH 3.5 to elute the target protein. The eluate was adjusted to neutrality with Tris-HCl at pH 8.0, and concentrated and buffer exchanged into a PBS buffer with an ultrafiltration tube to obtain a purified recombinant antibody solution. Finally, the purified antibody solution was determined for concentration using NanoDrop (Thermo Scientific™ NanoDrop™ One), subpackaged and stored for later use.

Example 6. The Antigen-Binding Proteins Described Herein being Capable of Binding to Human CCR8 (FACS)

Cells overexpressing human CCR8 were digested with pancreatin, counted and resuspended to a cell density of 1E6 cells/mL. The cell suspension was added to a 96-well V-bottom plate at 100 μL/well and centrifuged at 300 g for 5 min, and the supernatant was discarded. The anti-CCR8 antibodies provided herein was used as a primary antibody and diluted in a 5-fold gradient with an FACS buffer (DPBS containing 2% FBS) from 200 nM. The diluted primary antibody was added at 100 μL/well to resuspend the cells, and the mixture was incubated at 4° C. for 1 h. The plate was washed twice with DPBS and centrifuged at 300×g for 5 min, and the supernatant was discarded. The secondary antibody diluted in a 1:1000 ratio with an FACS buffer was added at 100 μL/well to suspend the cells, and the mixture was incubated at 4° C. for 40 min. The plate was washed twice with DPBS and centrifuged at 300×g for 5 min, and the supernatant was discarded. DPBS was added at 200 μL/well to suspend the cells, and the mixture was loaded on an FACS machine for analysis.

The assay results of the binding of the chimeric CCR8 antibodies to cell lines overexpressing human CCR8 are shown in FIGS. 1A-1D. The chimeric antibody molecules PR004120, PR004121, PR004122, PR004123, PR004124, PR004125, PR004126, PR004127, PR004128, PR004129, PR004130 and PR004131 all showed strong binding activity on the CHO-K1 cell line (Table 32 and FIG. 1A), HEK293 cell line (Table 32 and FIG. 1B) and Baf3 cell line (Table 32 and FIG. 1C) overexpressing human CCR8, with $EC_{50}$ values on the cell lines in ranges of 0.25-0.56 nM, 0.34-1.1 nM and 0.06-0.26 nM, respectively; the CCR8 chimeric antibodies PR005329, PR005330, PR005332 and PR005333 had strong binding activity on the cells lines overexpressing human CCR8, with EC50 values in the range of 0.47-0.63 nM (Table 32 and FIG. 1D).

TABLE 32

Assay results of the binding of the CCR8 chimeric antibodies to the cells overexpressing human CCR8

| CHO-K1 overexpressing human CCR8 | | HEK293 overexpressing human CCR8 | | Baf3 overexpressing human CCR8 | |
|---|---|---|---|---|---|
| Antibody | EC50(nM) | Antibody | EC50(nM) | Antibody | EC50(nM) |
| PR004120 | 0.54 | PR004120 | 1.10 | PR004120 | 0.24 |
| PR004121 | 0.41 | PR004121 | 0.63 | PR004121 | 0.22 |
| PR004122 | 0.50 | PR004122 | 0.66 | PR004122 | 0.17 |
| PR004123 | 0.46 | PR004123 | 0.62 | PR004123 | 0.20 |
| PR004124 | 0.45 | PR004124 | 0.58 | PR004124 | 0.17 |
| PR004125 | 0.50 | PR004125 | 0.72 | PR004125 | 0.21 |
| PR004126 | 0.43 | PR004126 | 0.58 | PR004126 | 0.18 |
| PR004127 | 0.56 | PR004127 | 0.86 | PR004127 | 0.26 |
| PR004128 | 0.42 | PR004128 | 0.87 | PR004128 | 0.14 |
| PR004129 | 0.25 | PR004129 | 0.34 | PR004129 | 0.06 |
| PR004130 | 0.46 | PR004130 | 0.80 | PR004130 | 0.20 |
| PR004131 | 0.52 | PR004131 | 0.79 | PR004131 | 0.20 |
| hIgG1 | NA | hIgG1 | NA | hIgG1 | NA |

TABLE 33

Assay results of the binding of CCR8 chimeric antibodies to CHO-K1 overexpressing human CCR8

| Antibody | EC50(nM) |
|---|---|
| PR005329 | 0.49 |
| PR005330 | 0.47 |
| PR005332 | 0.63 |
| PR005333 | 0.52 |
| hIgG1 | NA |

Figure 2:
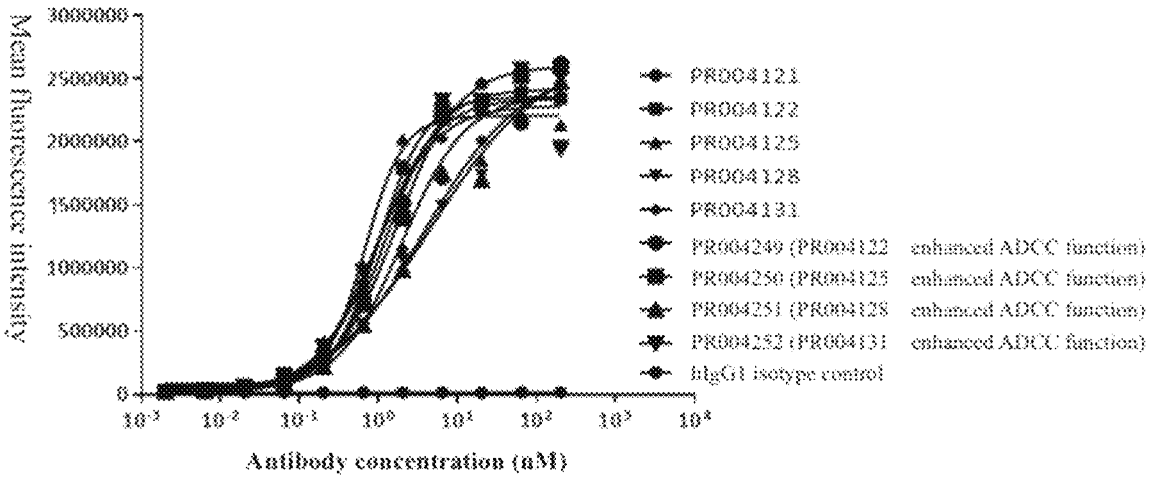
FIG. 2 shows the results of the binding of chimeric antibodies with enhanced ADCC function and their parent antibodies to human CCR8 on the surface of HEK293 cells.

The CCR8 antibody molecules PR004249, PR004250, PR004251 and PR004252 with enhanced ADCC had strong binding activity on the HEK293 cell line overexpressing human CCR8 (FIG. 2), with $EC_{50}$ values in the range of 0.98-3.69 nM (Table 34).

TABLE 34

Assay results of the binding of the CCR8 antibody molecules with enhanced ADCC to HEK293 overexpressing human CCR8

| Antibody | EC50(nM) |
|---|---|
| PR004121 | 0.90 |
| PR004122 | 0.99 |
| PR004125 | 0.66 |
| PR004128 | 4.53 |
| PR004131 | 1.94 |
| PR004249 | 1.22 |
| PR004250 | 1.66 |
| PR004251 | 3.69 |
| PR004252 | 0.98 |
| hIgG1 | NA |

Figure 3:
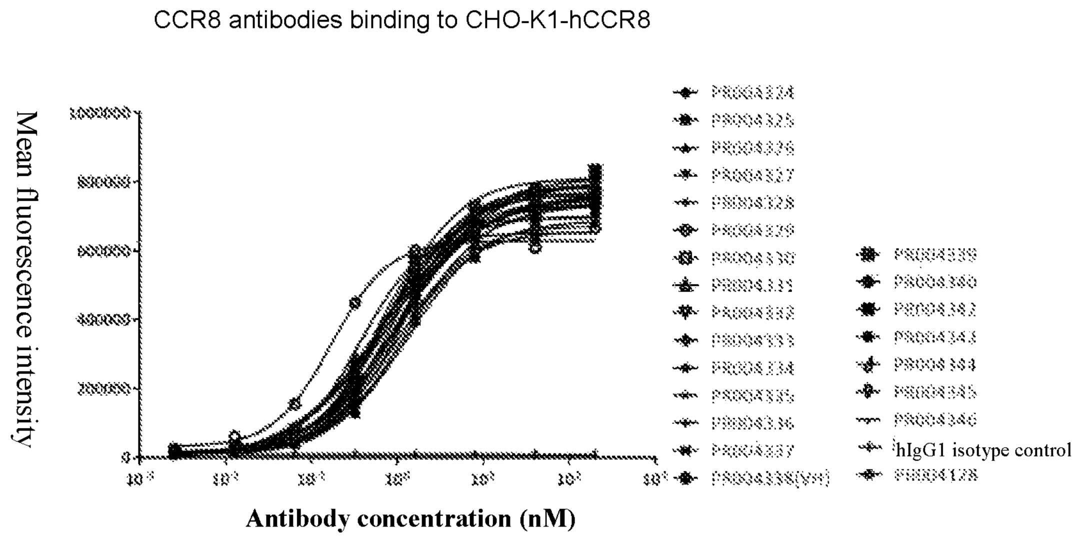
FIG. 3 shows the results of the binding of mutant molecules of PR004128 to human CCR8 on the surface of CHO-K1 cells.

As shown in FIG. 3 and Table 35, the single-site PTM mutant molecules PR004324, PR004325, PR004326, PR004327, PR004328 and PR004329 of the CCR8 chimeric antibody PR004128, the heavy-chain semi-humanized molecules PR004330, PR004331, PR004332, PR004333, PR004334, PR004335, PR004336, PR004337 and PR004338 of the CCR8 chimeric antibody PR004128, and the light-chain semi-humanized molecules PR004339, PR004340, PR004342, PR004343, PR004344, PR004345 and PR004346 of the CCR8 chimeric antibody PR004128 all retained strong binding activity on the CHO-K1 cell line overexpressing human CCR8, with $EC_{50}$ values in the range of 0.17-1.33 nM.

TABLE 35

Assay results of the binding of the single-site PTM mutant molecules of PR004128 to CHO-K1 overexpressing human CCR8

| Antibody | EC50(nM) |
|---|---|
| PR004324 | 0.67 |
| PR004325 | 1.31 |
| PR004326 | 0.37 |
| PR004327 | 1.08 |
| PR004328 | 1 |
| PR004329 | 0.17 |
| PR004330 | 0.85 |
| PR004331 | 1.03 |
| PR004332 | 0.73 |
| PR004333 | 0.91 |
| PR004334 | 1.33 |
| PR004335 | 0.97 |
| PR004336 | 0.79 |
| PR004337 | 0.76 |
| PR004338 | 0.72 |
| PR004339 | 0.95 |
| PR004340 | 1.06 |
| PR004342 | 0.8 |
| PR004343 | 1.08 |
| PR004344 | 1 |
| PR004345 | 1.12 |
| PR004346 | 0.91 |
| PR004128 | 0.55 |
| hIgG1 | NA |

Figure 4:
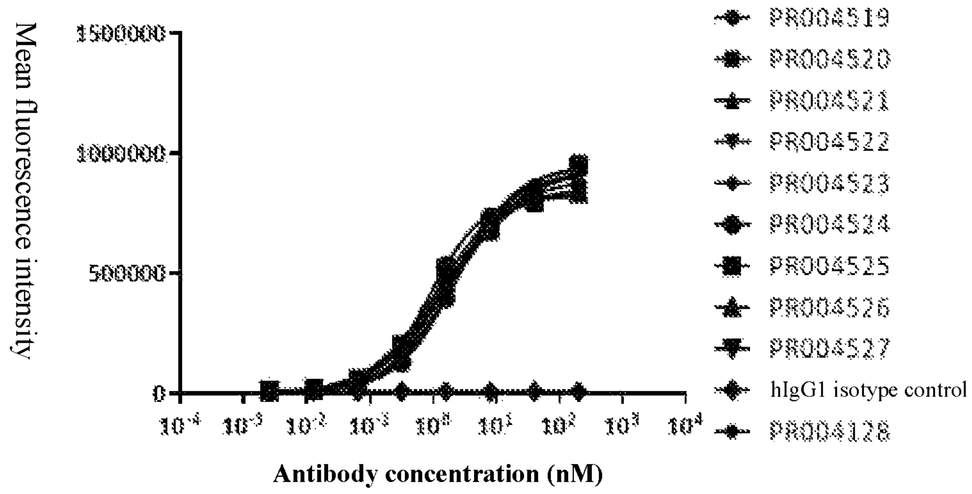
FIG. 4 shows the results of the binding of humanized variants PR004519-PR004527 of PR004128 to human CCR8 on the cell surface of CHO-K1.
Figure 5:
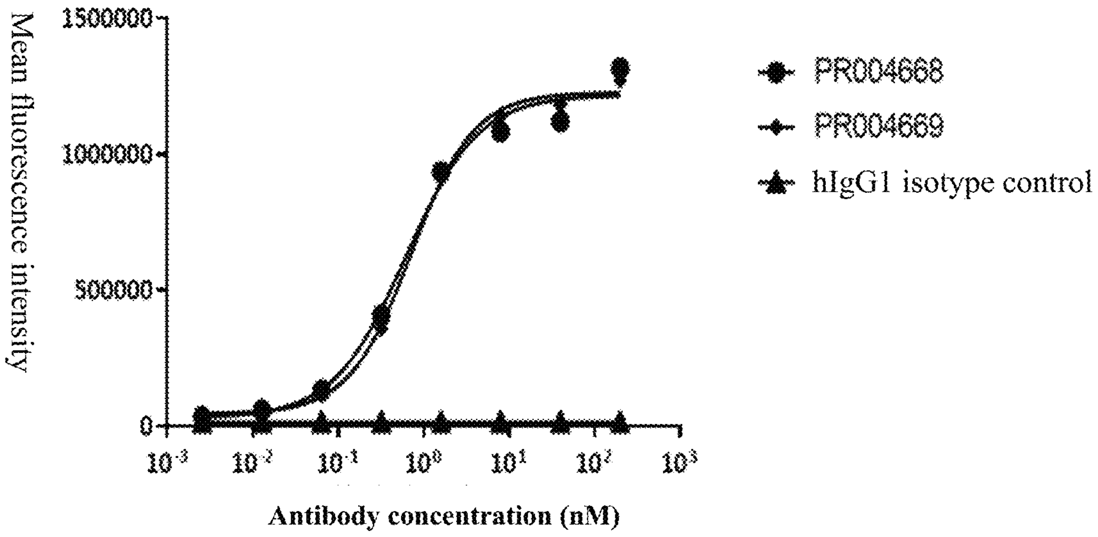
FIG. 5 shows the results of the binding of humanized variants PR004668 and PR004669 of PR004128 to human CCR8 on the surface of CHO-K1 cells.

The CCR8 humanized antibody molecules PR004519, PR004520, PR004521, PR004522, PR004523, PR004524, PR004525, PR004526 and PR004527 (FIG. 4 and Table 36), and PR004668 and PR004669 (FIG. 5 and Table 37), all showed strong binding activity on the CHO-K1 cell line overexpressing human CCR8, wherein the $EC_{50}$ values of the molecules PR004668 and PR004669 were 0.62 nM and 0.72 nM, respectively.

TABLE 36

Assay results of the binding of humanized antibodies to CHO-K1 overexpressing human CCR8

| Antibody | EC50(nM) |
|---|---|
| PR004519 | 0.67 |
| PR004520 | 1.31 |
| PR004521 | 0.37 |
| PR004522 | 1.08 |
| PR004523 | 1 |
| PR004524 | 0.17 |
| PR004525 | 0.85 |
| PR004526 | 1.03 |
| PR004527 | 0.73 |
| PR004128 | 0.91 |
| hIgG1 | NA |

TABLE 37

Assay results of the binding of humanized antibodies to CHO-K1 overexpressing human CCR8

| Antibody | EC50(nM) |
|---|---|
| PR004668 | 0.62 |
| PR004669 | 0.72 |
| hIgG1 | NA |

Figure 6:
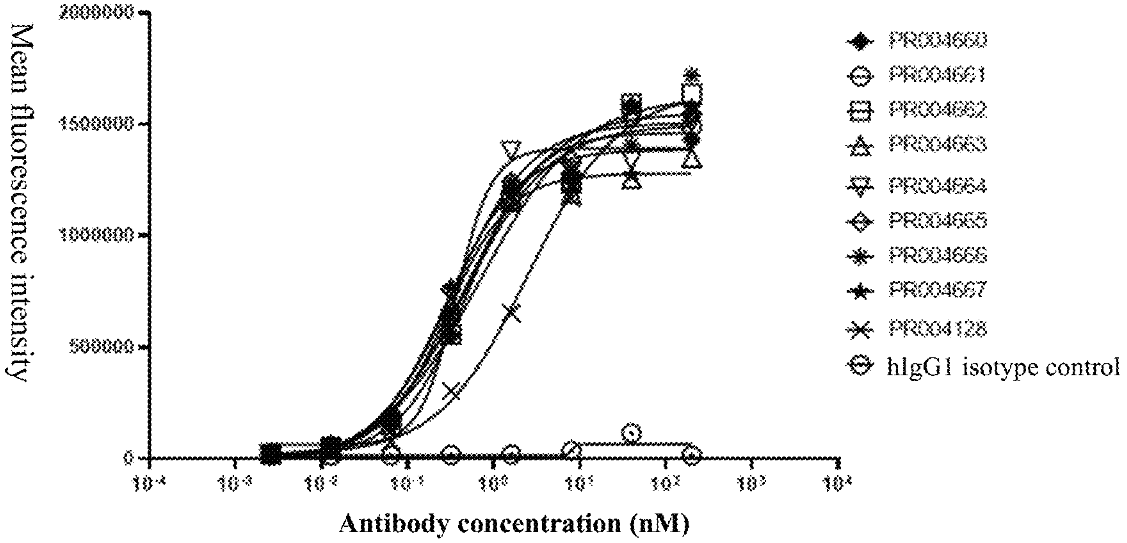
FIG. 6 shows the results of the binding of PTM site-removed and humanized variant antibodies of PR004128 to human CCR8 on the surface of CHO-K1 cells.

The PTM site-removed CCR8 humanized antibody molecules PR004660, PR004661, PR004662, PR004663, PR004664, PR004665, PR004666 and PR004667 (FIG. 6 and Table 38) retained strong binding activity on the CHO- K1 cell line overexpressing human CCR8, with $EC_{50}$ values in the range of 0.28-0.68 nM.

TABLE 38

Assay results of the binding of the PTM site-removed humanized antibodies to CHO-K1 overexpressing human CCR8

| Antibody | EC50(nM) |
|---|---|
| PR004660 | 0.490 |
| PR004661 | 0.456 |
| PR004662 | 0.681 |
| PR004663 | 0.286 |
| PR004664 | 0.365 |
| PR004665 | 0.341 |
| PR004666 | 0.466 |
| PR004667 | 0.279 |
| PR004128 | 2.539 |
| hIgG1 | NA |

Figure 7A:
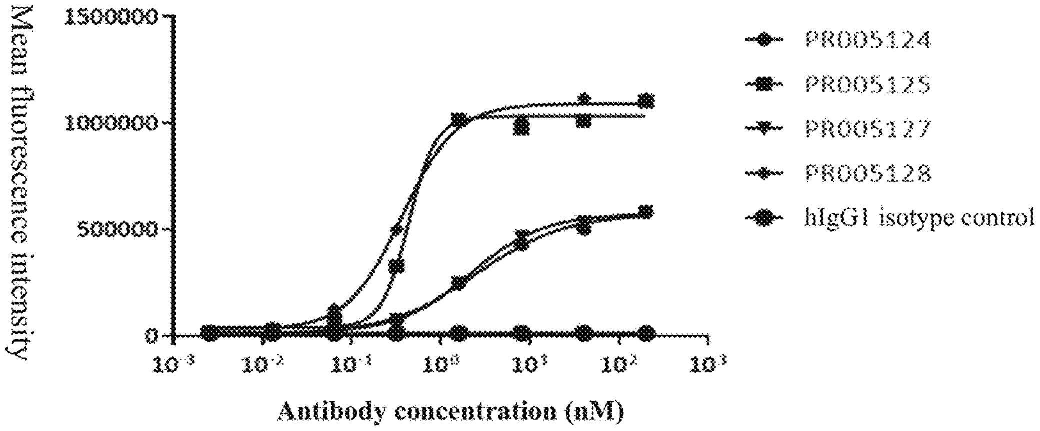
FIGS. 7A, 7B and 7C show the results of the binding of CCR8 fully human antibodies to human CCR8 on the surface of CHO-K1 cells.
Figure 7B:
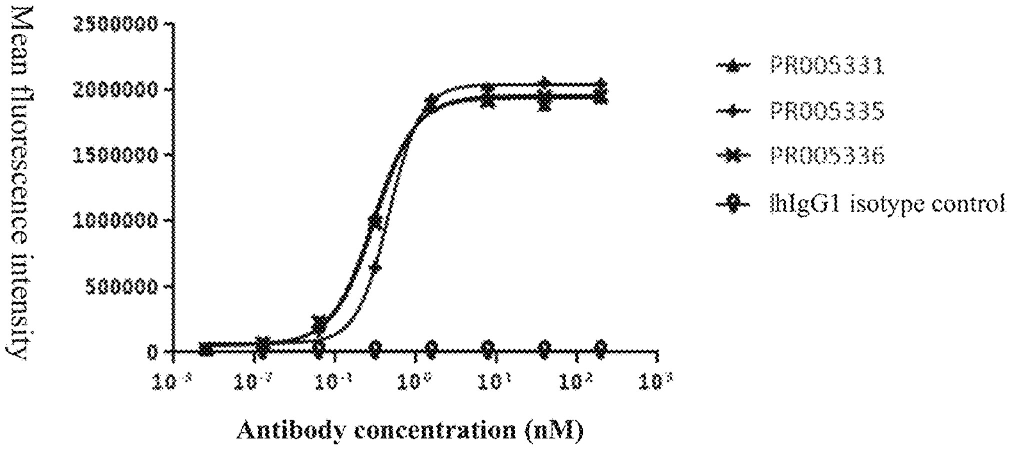
Figure 7C:
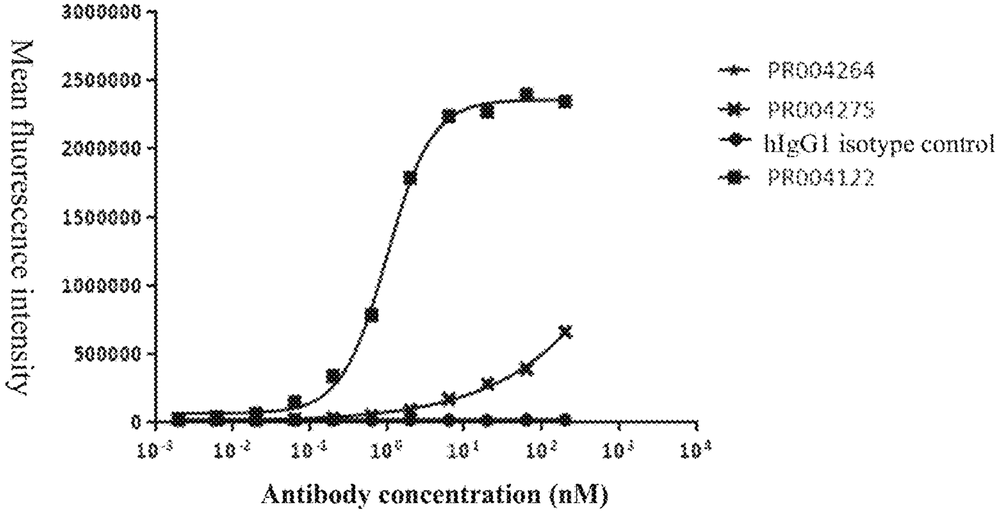

The CCR8 fully human antibody molecules PR005125, PR005128, PR005331, PR005335 and PR005336 showed binding activity on the CHO-K1 cell line overexpressing human CCR8, with $EC_{50}$ values in the range of 0.32-0.47 nM (Table 39), and PR005124 and PR005127 showed binding activity (FIGS. 7A and 7B). The CCR8 fully human antibody molecule PR004122 showed binding activity on the HEK293 cell line overexpressing human CCR8 (FIG. 7C).

TABLE 39

Assay results of the binding of fully humanized antibodies to CHO-K1 overexpressing human CCR8

| Antibody | EC50(nM) |
|---|---|
| PR005124 | 2.52 |
| PR005125 | 0.44 |
| PR005127 | 2.19 |
| PR005128 | 0.37 |
| PR005331 | 0.30 |
| PR005335 | 0.47 |
| PR005336 | 0.32 |
| hIgG1 | NA |

Figure 8A:
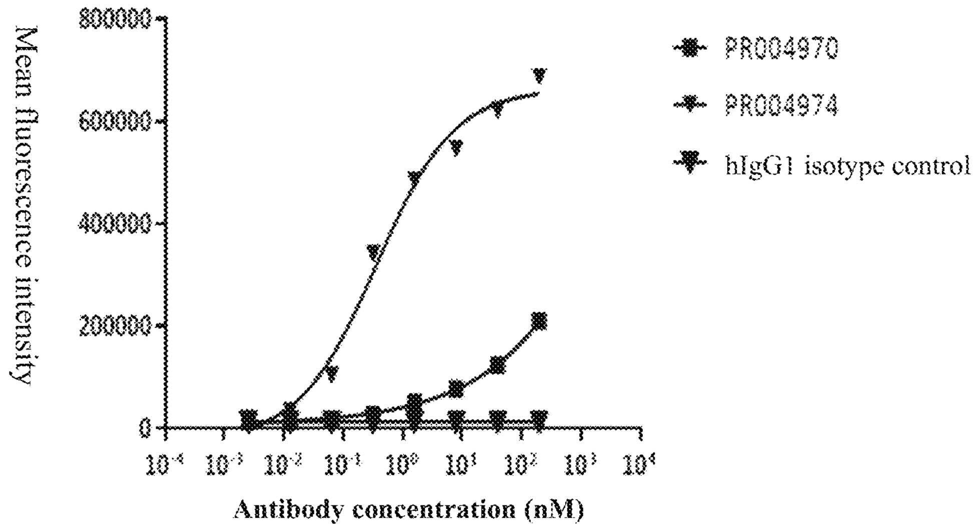
FIGS. 8A and 8B show the results of the binding of fully human antibodies derived from single cell clones to human CCR8 on the surface of CHO-K1 cells.
Figure 8B:
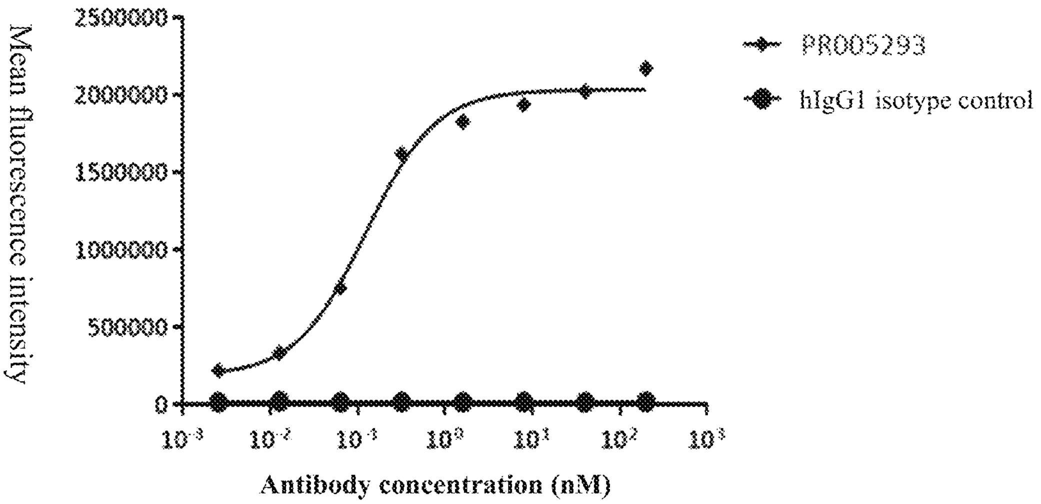

The CCR8 fully human antibodies PR004974, PR004970 and PR005293 derived from single cell clones showed binding activity on the overexpressing CHO-K1 cell line (FIGS. 8A and 8B).

Figure 9:
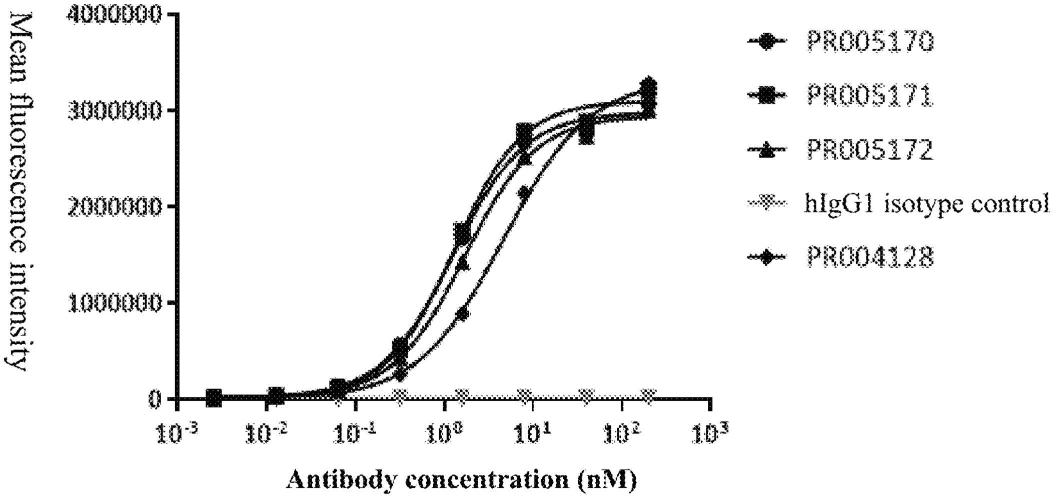
FIG. 9 shows the results of the binding of antibodies with saturation mutagenesis at position 96 of the light chain of RP004128 to human CCR8 on the surface of CHO-K1 cells.

The antibodies PR005170, PR005171 and PR005172 with saturation mutagenesis at position 96 of the light chain of PR004128 still retained binding activity on the CHO-K1 cell line overexpressing human CCR8 as compared to PR004128 (FIG. 9).

Figure 10A:
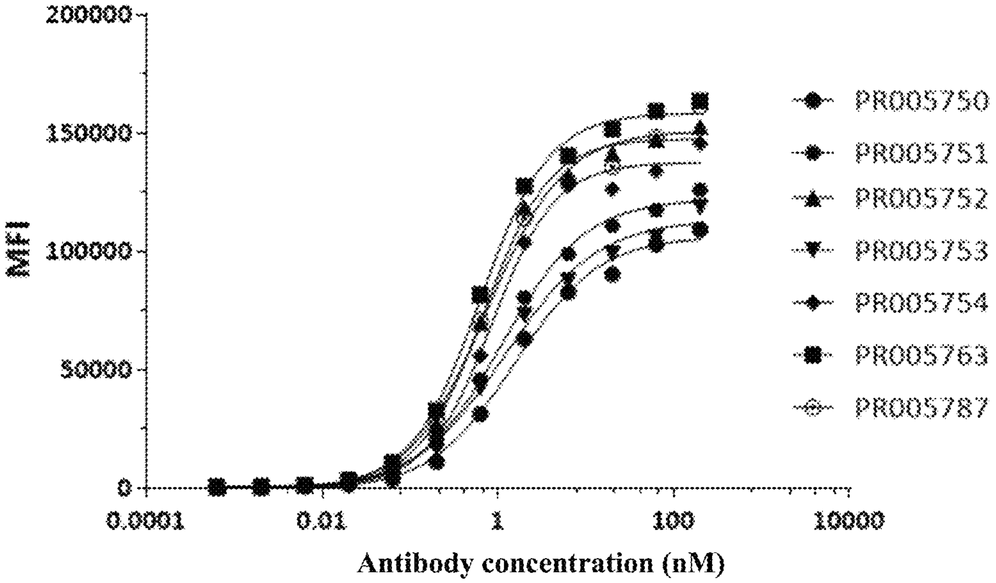
FIGS. 10A and 10B show the results of the binding of the PR004666 mutants to human CCR8 on the surface of CHO-K1 cells.
Figure 10B:
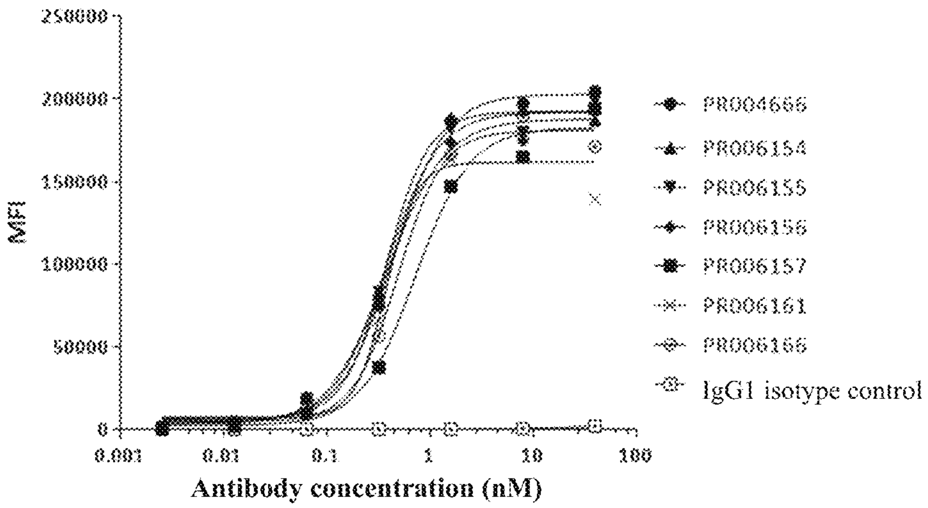

The affinity-matured Fab-binding domain mutants PR005751, PR005752, PR005753, PR005754, PR005763 and PR005787 (PR005750 is a Fab form of the same variable region of PR004666) (FIG. 10A) and intact IgG mutants PR006154, PR006155, PR006156, PR006157, PR006161 and PR006166 (FIG. 10B) of PR004666 showed higher binding on the overexpressing CHO-K1 cell line. The $EC_{50}$ values of the affinity-matured Fab-binding domain mutants were in the range of 0.62-1.56 nM (FIG. 10A and Table 40), and the $EC_{50}$ values of the intact IgG mutants were in the range of 0.38-0.73 nM (FIG. 10B and Table 41).

TABLE 40

Assay results of the binding of the affinity-matured Fab-binding domain mutants of PR004666 to CHO-K1 overexpressing human CCR8

| Antibody | EC50(nM) |
|---|---|
| PR005750 | 1.56 |
| PR005751 | 1.10 |
| PR005752 | 0.69 |
| PR005753 | 1.19 |
| PR005754 | 0.84 |
| PR005763 | 0.62 |
| PR005787 | 0.74 |

TABLE 41

Assay results of the binding of the affinity-matured mutants of PR004666 to CHO-K1 overexpressing human CCR8

| Antibody | EC50(nM) |
|---|---|
| PR004666 | 0.44 |
| PR006154 | 0.38 |
| PR006155 | 0.38 |
| PR006156 | 0.38 |
| PR006157 | 0.73 |
| PR006161 | 0.38 |
| PR006166 | 0.49 |

Figure 11:
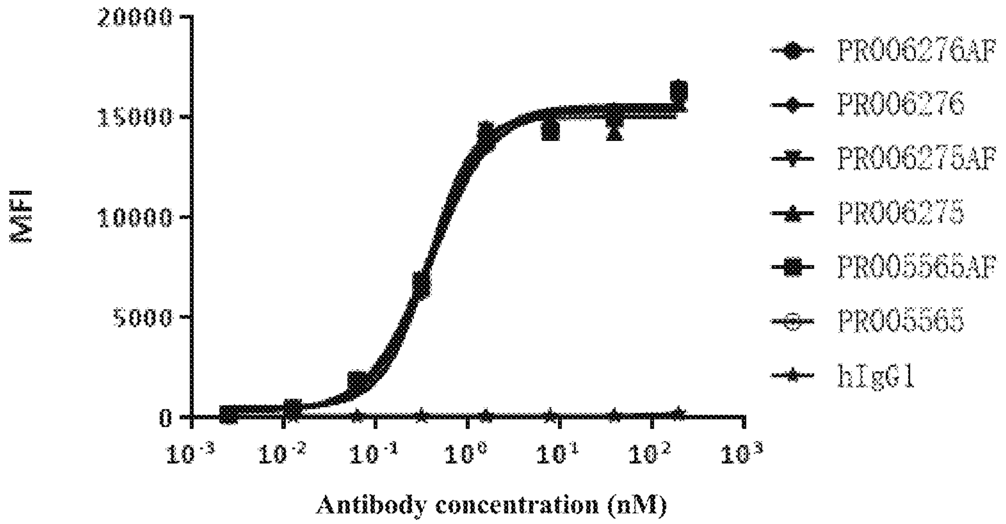
FIG. 11 shows the results of the binding of PR006276AF, PR006276, PR006275AF, PR006275, PR005565AF and PR005565 to human CCR8 on the surface of CHO-K1 cells.

The affinity-matured mutants PR006275 and PR006276 of PR005565, as well as the afucosylated antibody PR005565AF of PR005565, the afucosylated antibody PR006275AF of PR006275, and the afucosylated antibody PR006276AF of PR006276 showed binding activity on the overexpressing CHO-K1 cell line, with $EC_{50}$ values in the range of 0.38-0.40 nM (FIG. 11 and Table 42).

TABLE 42

Assay results of the binding of the affinity-matured mutants of PR005565 and PR005565AF to CHO-K1 overexpressing human CCR8

| Antibody | EC50(nM) |
|---|---|
| PR006276AF | 0.39 |
| PR006276 | 0.40 |
| PR006275AF | 0.40 |
| PR006275 | 0.38 |
| PR005565AF | 0.38 |
| PR005565 | 0.42 |

Example 7. The Antigen-Binding Proteins Described Herein being Capable of Binding to Monkey CCR8 (FACS)

Cells overexpressing cynomolgus monkey CCR8, CHO-K1-CynoCCR8, were digested with pancreatin, counted and resuspended to a cell density of 1E6 cells/mL. The cell suspension was added to a 96-well V-bottom plate at 100 μL/well and centrifuged at 300 g for 5 min, and the supernatant was discarded. The anti-CCR8 antibodies provided herein was used as a primary antibody and diluted in a 5-fold gradient with an FACS buffer (DPBS containing 2% FBS) from 200 nM. The diluted primary antibody was added at 100 μL/well to resuspend the cells, and the mixture was incubated at 4° C. for 1 h. The plate was washed twice with DPBS and centrifuged at 300×g for 5 min, and the supernatant was discarded. The secondary antibody diluted in a 1:1000 ratio with an FACS buffer was added at 100 μL/well to suspend the cells, and the mixture was incubated at 4° C.

for 40 min. The plate was washed twice with DPBS and centrifuged at 300×g for 5 min, and the supernatant was discarded. DPBS was added at 200 μL/well to suspend the cells, and the mixture was loaded on an FACS machine for analysis.

Figure 12:
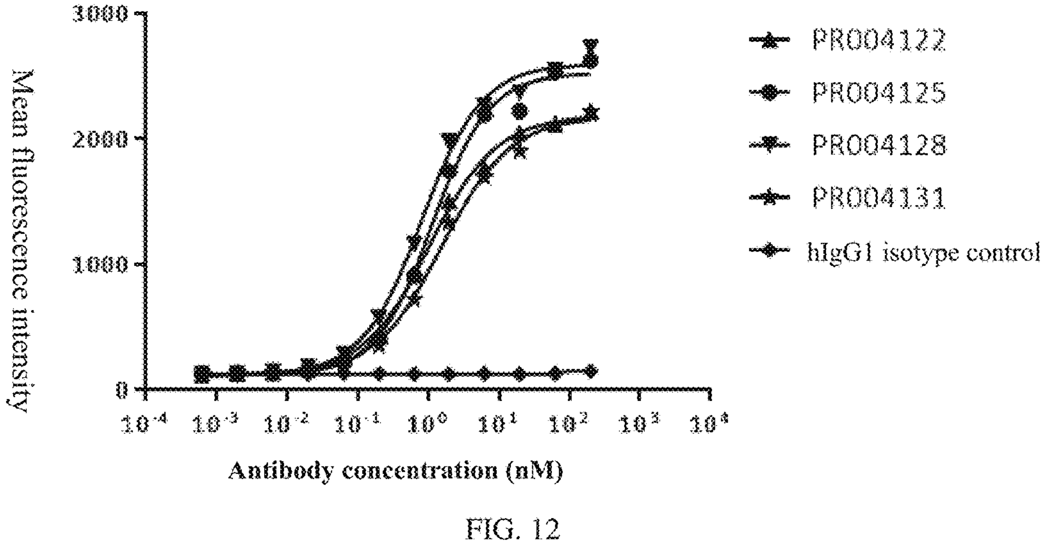
FIG. 12 shows the results of the binding of chimeric antibodies to monkey CCR8 on the cell surface.
Figure 13:
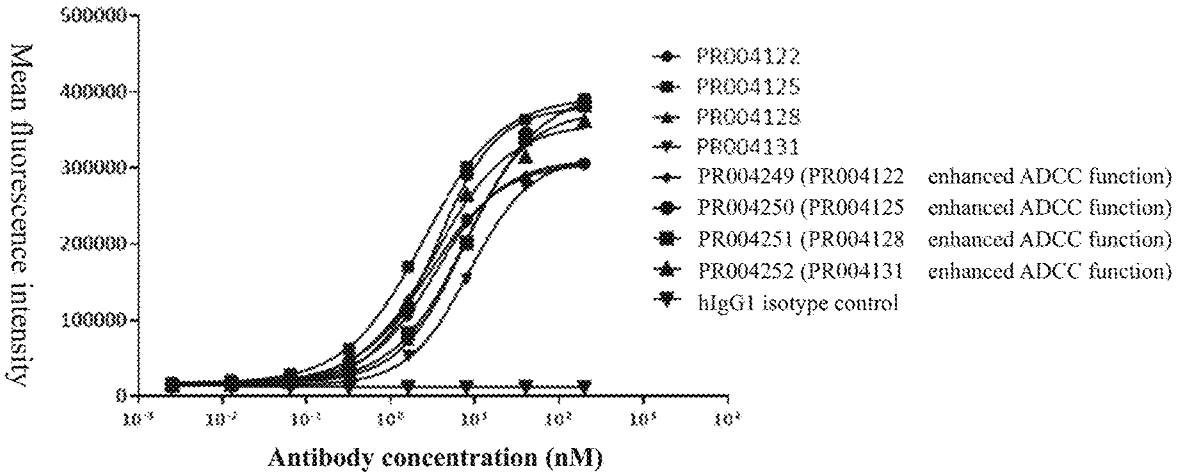
FIG. 13 shows the results of the binding of chimeric antibodies with enhanced ADCC function to monkey CCR8 on the cell surface.
Figure 14:
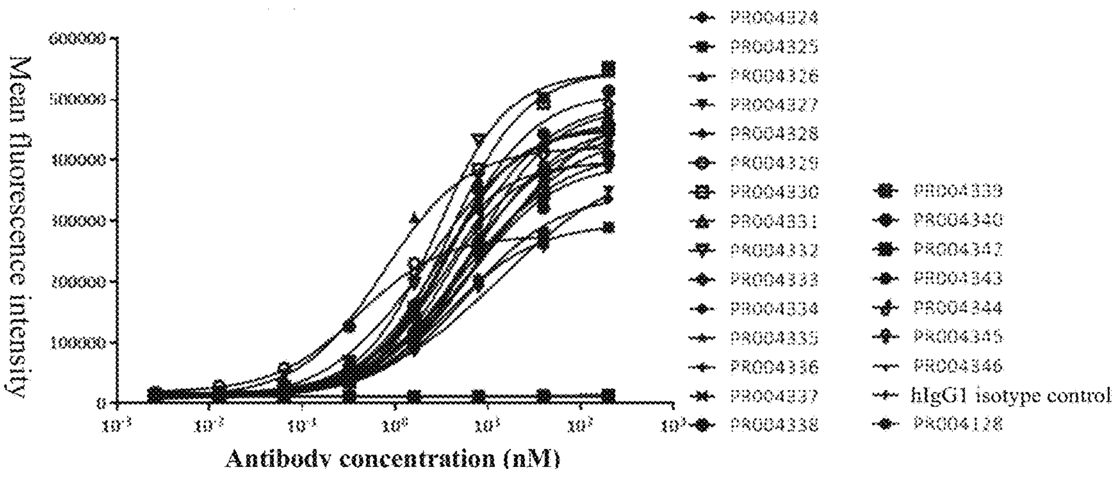
FIG. 14 shows the results of the binding of mutant molecules of PR004128 to monkey CCR8 on the cell surface.
Figure 15:
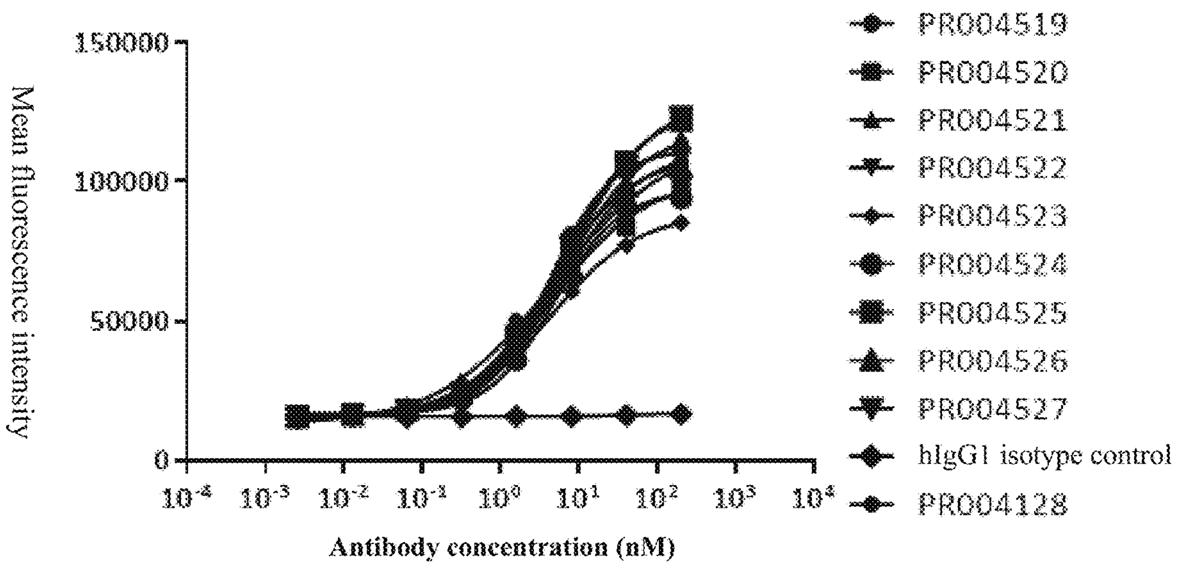
FIG. 15 shows the results of the binding of humanized antibodies PR004519-PR004527 to monkey CCR8 on the cell surface.
Figure 16:
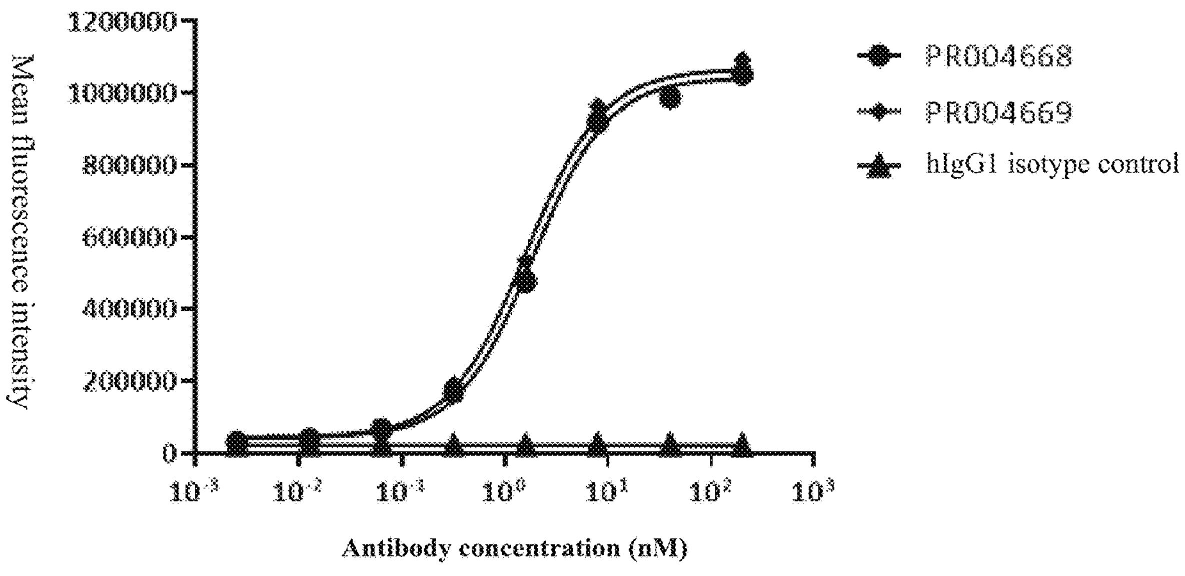
FIG. 16 shows the results of the binding of humanized antibodies PR004668 and PR004669 to monkey CCR8 on the cell surface.
Figure 17:
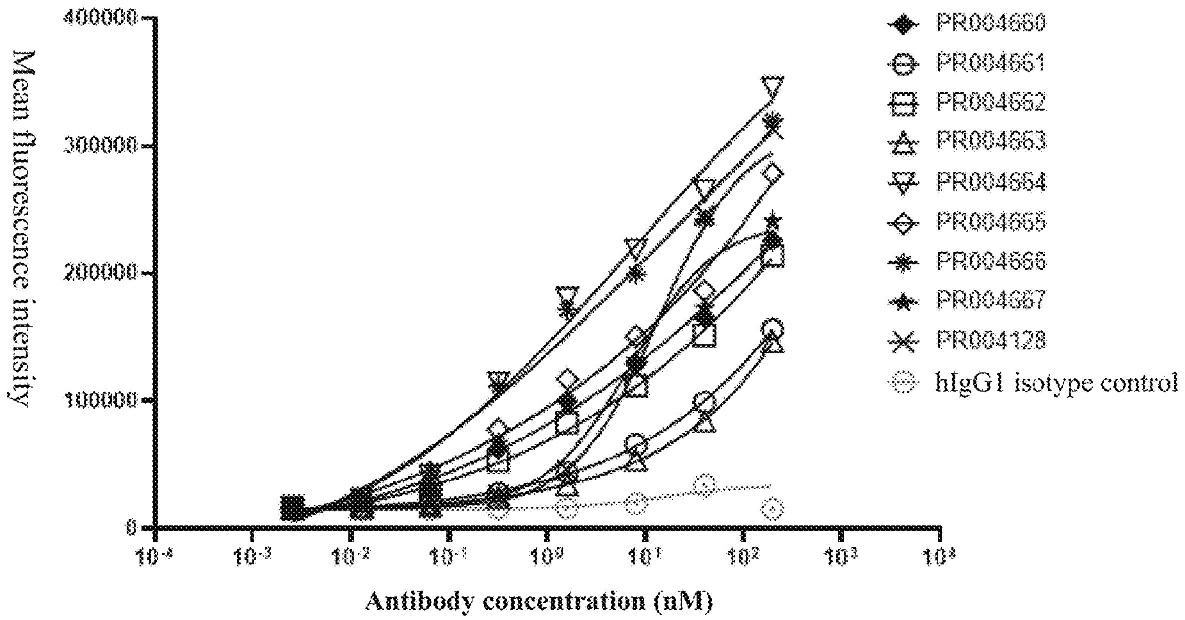
FIG. 17 shows the results of the binding of PTM site-removed humanized antibodies to monkey CCR8 on the cell surface.

The CCR8 chimeric antibody molecules PR004122, PR004125, PR004128 and PR004131 showed strong binding activity on the CHO-K1 cell line overexpressing monkey CCR8, as shown in FIG. 12 and Table 43, with $EC_{50}$ values in the range of 0.83-1.6 nM. The CCR8 antibody molecules PR004249, PR004250, PR004251 and PR004252 (FIG. 13 and Table 44) with enhanced ADCC, the PTM variant molecules PR004324, PR004325, PR004326, PR004327, PR004328 and PR004329 of the CCR8 chimeric antibody PR004128, and the semi-humanized antibody molecules PR004330, PR004331, PR004332, PR004333, PR004334, PR004335, PR004336, PR004337, PR004338, PR004339, PR004340, PR004343, PR004344 and PR004345 of the CCR8 chimeric antibody PR004128 (FIG. 14 and Table 45), as shown in FIG. 14 and Table 45, the mutant molecules PR004342 and PR004346 lost cross-binding activity on monkey CCR8. The humanized antibody molecules PR004519, PR004520, PR004521, PR004522, PR004523, PR004524, PR004525, PR004526 and PR004527 (FIG. 15 and Table 46), and the humanized antibody molecules PR004668 and PR004669 (FIG. 16 and Table 46) of CCR8 had strong binding on the CHO-K1 cell line overexpressing monkey CCR8, and showed cross-binding activity on monkey CCR8, with $EC_{50}$ values in the range of 4.01-7.33 nM. The PTM-removed humanized molecules PR004660, PR004661, PR004662, PR004663, PR004664, PR004665, PR004666 and PR004667 of PRO4128 all retained cross-binding activity on monkey CCR8 (FIG. 17).

TABLE 43

Assay results of the binding of the chimeric antibodies to the cell line overexpressing monkey CCR8

| Antibody | EC50(nM) |
|---|---|
| PR004122 | 1.06 |
| PR004125 | 1.16 |
| PR004128 | 0.83 |
| PR004131 | 1.6 |
| hIgG1 | NA |

TABLE 44

Assay results of the binding of the chimeric antibodies with enhanced ADCC function to the cell line overexpressing monkey CCR8

| Antibody | EC50(nM) |
|---|---|
| PR004122 | 2.83 |
| PR004125 | 2.44 |
| PR004128 | 7.39 |
| PR004131 | 8.65 |
| PR004249 | 3.42 |
| PR004250 | 3.50 |
| PR004251 | 8.26 |
| PR004252 | 3.32 |
| hIgG1 | NA |

TABLE 45

Assay results of the binding of PR004128 mutant molecules to the cell line overexpressing monkey CCR8

| Antibody | EC50(nM) |
|---|---|
| PR004324 | 2.3 |
| PR004325 | 3.89 |
| PR004326 | 0.75 |
| PR004327 | 13.43 |
| PR004328 | 6.05 |
| PR004329 | 0.41 |
| PR004330 | 3.96 |
| PR004331 | 6.99 |
| PR004332 | 2.75 |
| PR004333 | 4.97 |
| PR004334 | 7.5 |
| PR004335 | 3.52 |
| PR004336 | 3.33 |
| PR004337 | 5.47 |
| PR004338 | 4.21 |
| PR004339 | 9.58 |
| PR004340 | 5.35 |
| PR004342 | NA |
| PR004343 | 6.38 |
| PR004344 | 3.51 |
| PR004345 | 5.96 |
| PR004346 | NA |
| PR004128 | 2.26 |
| hIgG1 | NA |

TABLE 46

Assay results of the binding of the humanized antibodies to the cell line overexpressing monkey CCR8

| Antibody | EC50(nM) |
|---|---|
| PR004519 | 4.17 |
| PR004520 | 4.60 |
| PR004521 | 6.22 |
| PR004522 | 5.87 |
| PR004523 | 4.42 |
| PR004524 | 4.79 |
| PR004525 | 6.21 |
| PR004526 | 4.01 |
| PR004527 | 7.33 |
| PR004128 | 4.73 |
| PR004668 | 1.88 |
| PR004669 | 1.61 |
| hIgG1 | NA |

Figure 18:
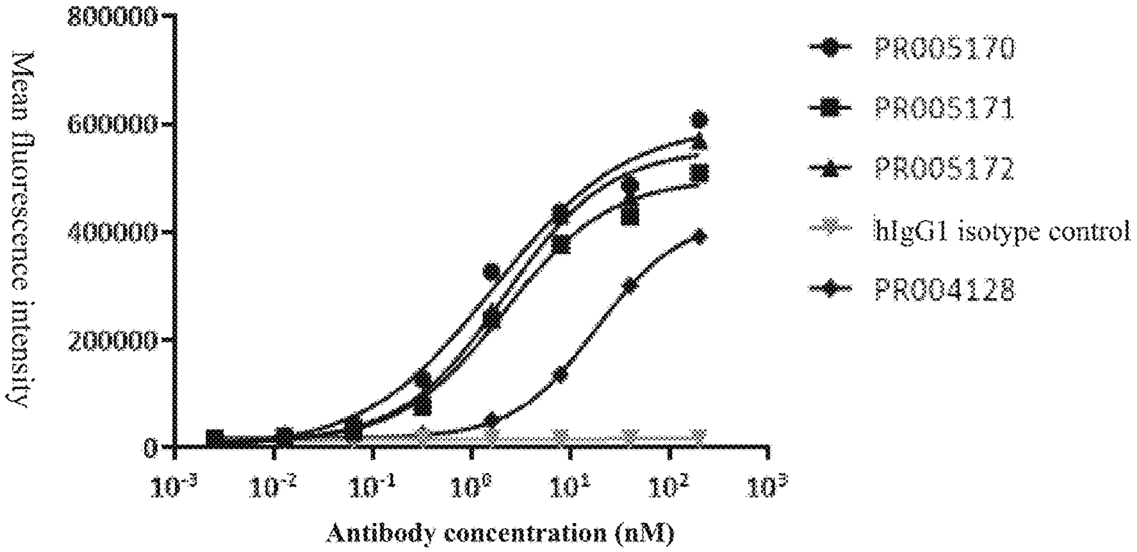
FIG. 18 shows the results of the binding of antibodies with saturation mutagenesis at position 96 of the light chain of RP004128 to monkey CCR8 on the cell surface.

The antibodies PR005170, PR005171 and PR005172 with saturation mutagenesis at position 96 of the light chain of PR004128 retained binding activity on the cell line overexpressing monkey CCR8 as compared to PR004128 (FIG. 18).

Figure 19:
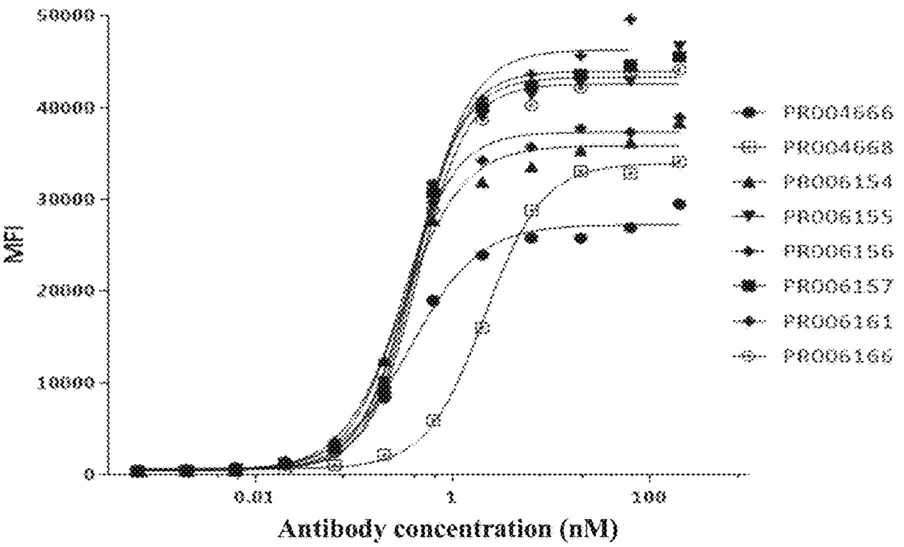
FIG. 19 shows the results of the binding of PR004666 mutants to monkey CCR8 on the cell surface.

The affinity-matured mutants PR006154, PR006155, PR006156, PR006157, PR006161 and PR006166 of PR004666 showed higher binding on the CHO-K1 cell line overexpressing monkey CCR8, with $EC_{50}$ values in the range of 0.31-0.44 nM (FIG. 19 and Table 47).

TABLE 47

Assay results of the binding of the affinity-matured mutants of PR004666 to CHO-K1 overexpressing monkey CCR8

| Antibody | EC50(nM) |
|---|---|
| PR004666 | 0.37 |
| PR006154 | 0.31 |
| PR006155 | 0.39 |
| PR006156 | 0.30 |
| PR006157 | 0.42 |

TABLE 47-continued

| Assay results of the binding of the affinity-matured mutants of PR004666 to CHO-K1 overexpressing monkey CCR8 | |
|---|---|
| Antibody | EC50(nM) |
| PR006161 | 0.43 |
| PR006166 | 0.44 |

Figure 20:
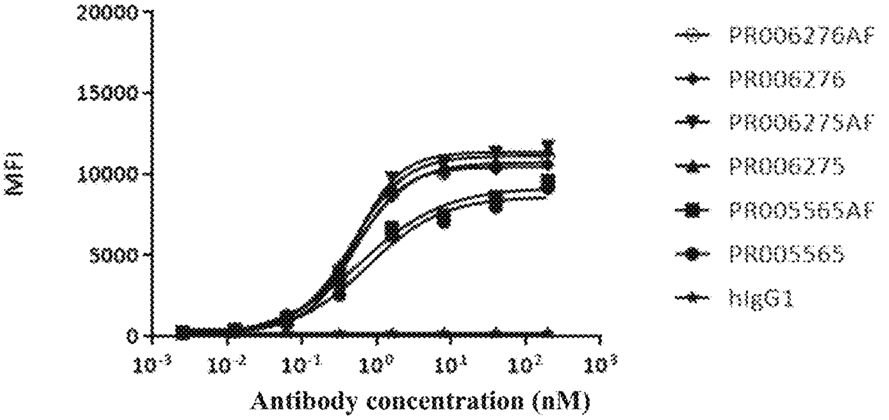
FIG. 20 shows the results of the binding of PR006276AF, PR006276, PR006275AF, PR006275, PR005565AF and PR005565 to monkey CCR8 on the cell surface.

The affinity-matured mutants PR006275 and PR006276 of PR005565 and the affinity-matured mutants PR006275AF and PR006276AF of PR005565AF showed binding activity on the CHO-K1 cell line overexpressing monkey CCR8, with $EC_{50}$ values in the range of 0.47-0.51 nM (FIG. 20 and Table 48).

TABLE 48

| Assay results of the binding of the affinity-matured mutants of PR005565 and PR005565AF to CHO-K1 overexpressing monkey CCR8 | |
|---|---|
| Antibody | EC50(nM) |
| PR006276AF | 0.50 |
| PR006276 | 0.51 |
| PR006275AF | 0.51 |
| PR006275 | 0.47 |
| PR005565AF | 0.62 |
| PR005565 | 0.76 |

Example 8. Assay on the Affinity of the Antigen-Binding Proteins Described Herein To 200 mg of PMMA hard beads was added 30 μg of Goat Anti-Human IgG Fc antibody, and the mixture was supplemented with a coating solution to 1.0 mL, with a buffer composition of 1×PBS, pH7.4, to ensure that the beads were completely suspended in the solution. After being spun at room temperature for 2 h, the beads were either allowed to settle naturally or centrifuged briefly at low speed, and the supernatant was removed. 1 mL of blocking buffer (1×PBS, pH7.4, containing 10 mg/mL BSA) was added to ensure that the beads were resuspended in the blocking solution, and the beads were spun at room temperature for 1 h. An appropriate concentration of PR005565, PR006155 or PR006166 was used as the 100% signal value, and PBS blank was used as the background value. The net signal values were detected using 0.5 μg/mL Alexa Fluor® 647 Goat Anti-Human IgG. The cell line overexpressing human or monkey CCR8 was collected by centrifugation at 1500 g for 5 min, washed 2 times with 2 PBS and centrifuged at 350 g. The cells were collected in a 1.5 mL centrifuge tube. 10 mL of 0.2 nM PR005565, PR006155 or PR006166 solution was prepared. The total cells were supplemented with 0.2 nM PR005565, PR006155 or PR006166 solution to 0.82 mL, and diluted in a 2-fold gradient with 0.2 nM PR005565, PR006155 or PR006166 as a buffer. The suspension of cells and 0.2 nM PR005565, PR006155 or PR006166 was incubated at room temperature for 3 h with shaking. After that, the mixture was centrifuged at 350 g for 5 min, and the supernatant was collected. 10 mL of Alexa Fluor® 647 Goat Anti-Human IgG solution was prepared, and the sample was placed in the corresponding position in a tube rack. The "start" button on the instrument KinExA 4000 (Sapidyne Instruments Inc.) was clicked. PR005565 had an affinity constant of 129.55 pM with the cell line overexpressing human CCR8, with a 95% confidence interval in the range of 36.18-374.42 pM. PR005565 had an affinity constant of 177.27 pM with the cell line overexpressing monkey CCR8, with a 95% confidence interval in the range of 65.22-536.39 pM. PR006155 had an affinity constant of 21.35 pM with the cell line overexpressing human CCR8, with a 95% confidence interval in the range of 7.96-35.46 pM. PR006166 had an affinity constant of 49.29 pM with the cell line overexpressing monkey CCR8, with a 95% confidence interval in the range of 25.63-87.38 pM.

Example 9. The Antigen-Binding Proteins Described Herein being Capable of Blocking Calcium Influx Signals Cells overexpressing human CCR8, CHO-K1-Gα16-hCCR8, were seeded in a 96-well black-bottom plate at a density of 250,000 cells/well and cultured overnight in an incubator at 37° C. The next day, the culture medium in the 96-well plate was discarded, and 50 μL of freshly prepared staining calcium buffer containing 2 μM Fluo-4 AM was added to each well, and the mixture was incubated at 37° C. for 50 min. The staining calcium buffer was removed, and the plate was washed once with a washing buffer at 50 μL/well. The test antibody was diluted with 1× HBSS buffer to obtain three concentrations of 200 nM, 20 nM and 2 nM. The diluted antibodies were added to a 96-well plate at 50 μL and incubated for 20 min. 25 μL human CCL1 was added to each well, and the intracellular calcium flux signals of 80 s was read at an excitation wavelength of 485 nm and absorbance wavelength of 525 nm in a FlexStation II 384 microplate reader. Data were analyzed using GraphPad Prism 6.0.

Figure 21A:
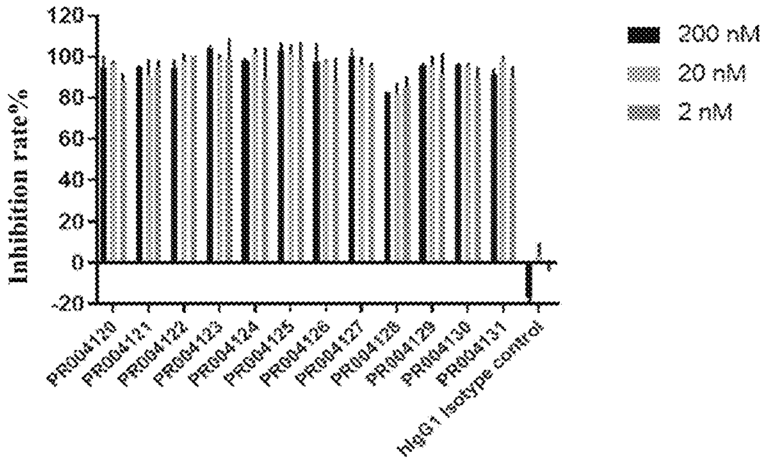
FIGS. 21A and 21B show the results of the blocking of intracellular calcium flux caused by CCL1 by CCR8 chimeric antibody molecules.
Figure 21B:
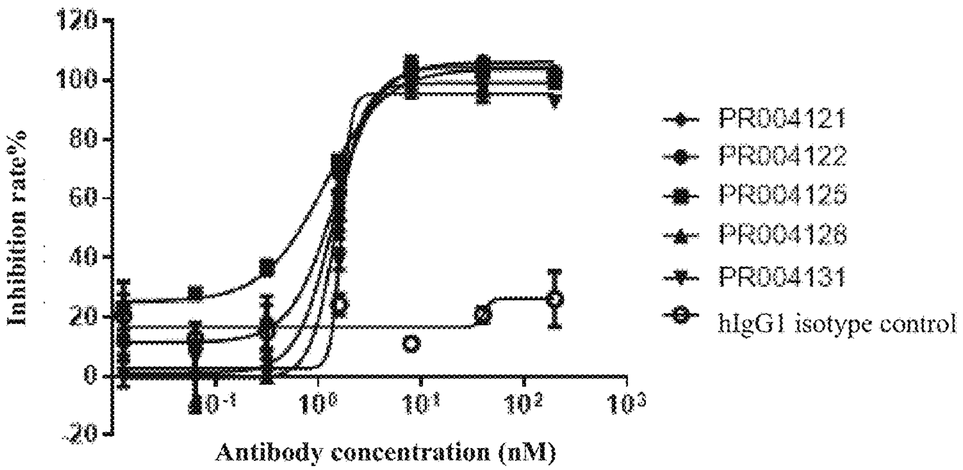
Figure 22:
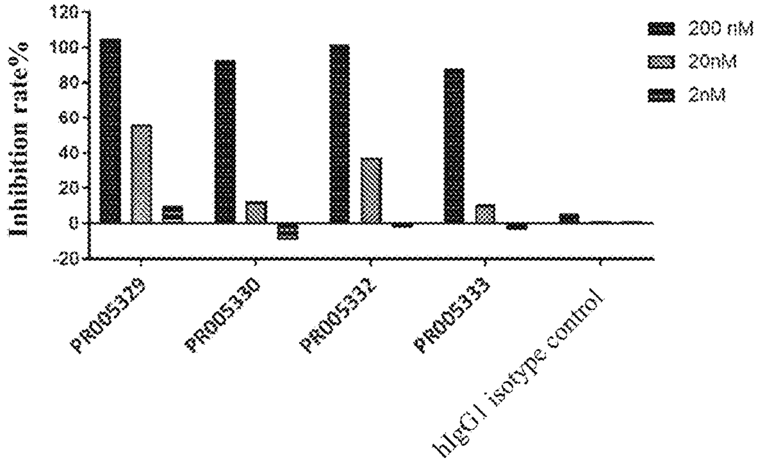
FIG. 22 shows the results of the blocking of intracellular calcium flux caused by CCL1 by PR005329, PR005330, PR005332 and PR005333.

The results of the blocking of intracellular calcium flux signals stimulated by CCL1 by the CCR8 chimeric antibodies are shown in FIG. 21. The molecules PR004120, PR004121, PR004122, PR004123, PR004124, PR004125, PR004126, PR004127, PR004128, PR004129, PR004130 and PR004131 all showed good blocking functional activity (FIG. 21A). Among them, the $IC_{50}$ values for blocking intracellular calcium flux caused by CCL1 by PR004121, PR004122, PR004125, PR004128 and PR004131 with cross-binding activity on monkey CCR8 were in the range of 1.16-1.67 nM (FIG. 21B and Table 49). $IC_{50}$ values of other CCR8 chimeric antibodies are shown in FIG. 22. PR005329, PR005330, PR005332 and PR005333 also showed good blocking functional activity.

TABLE 49

| Results of the blocking of intracellular calcium flux signals stimulated by CCL1 by the CCR8 chimeric antibodies | | |
|---|---|---|
| Antibody | IC50(nM) | Bottom % |
| PR004121 | 1.44 | 0 |
| PR004122 | 1.47 | 12 |
| PR004125 | 1.16 | 23 |
| PR004128 | 1.51 | 7 |
| PR004131 | 1.67 | 0 |
| hIgG1 | NA | NA |

Figure 23:
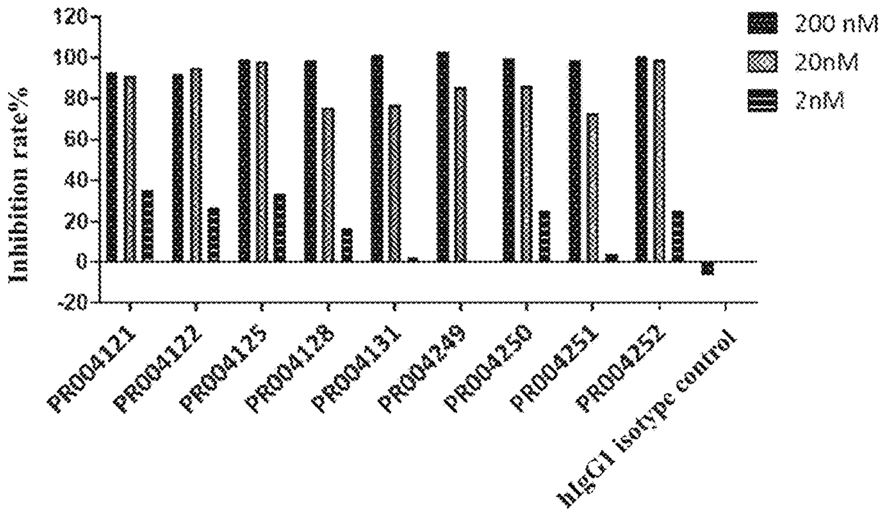
FIG. 23 shows the results of the blocking of intracellular calcium flux caused by CCL1 by PR004121, PR004122, PR004225, PR004128, PR004131, PR004249, PR004250, PR004251 and PR004252.

The results of the blocking of intracellular calcium flux signals stimulated by CCL1 by the CCR8 chimeric antibodies with enhanced ADCC function are shown in FIG. 23. The molecules PR004249, PR004250, PR004251 and PR004252 all retained good blocking functional activity.

Figure 24:
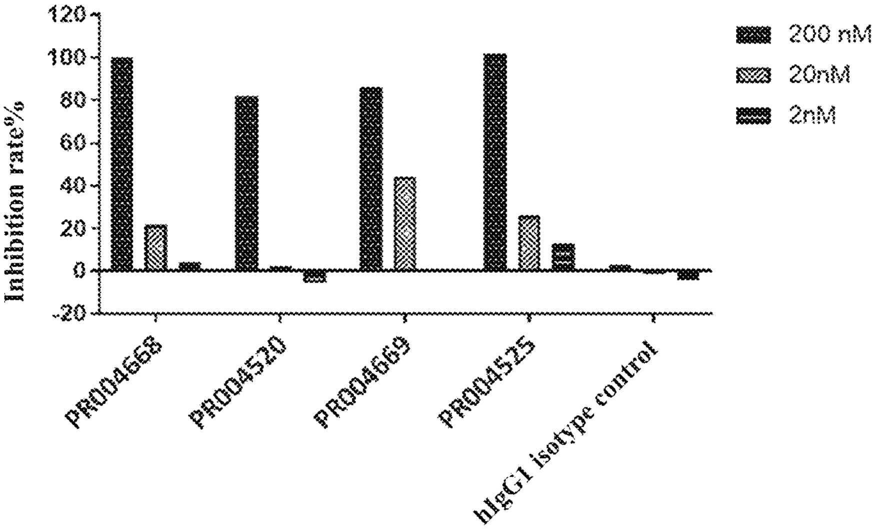
FIG. 24 shows the results of the blocking of intracellular calcium flux caused by CCL1 by PR004668, PR004520, PR004669 and PR004525.
Figure 25:
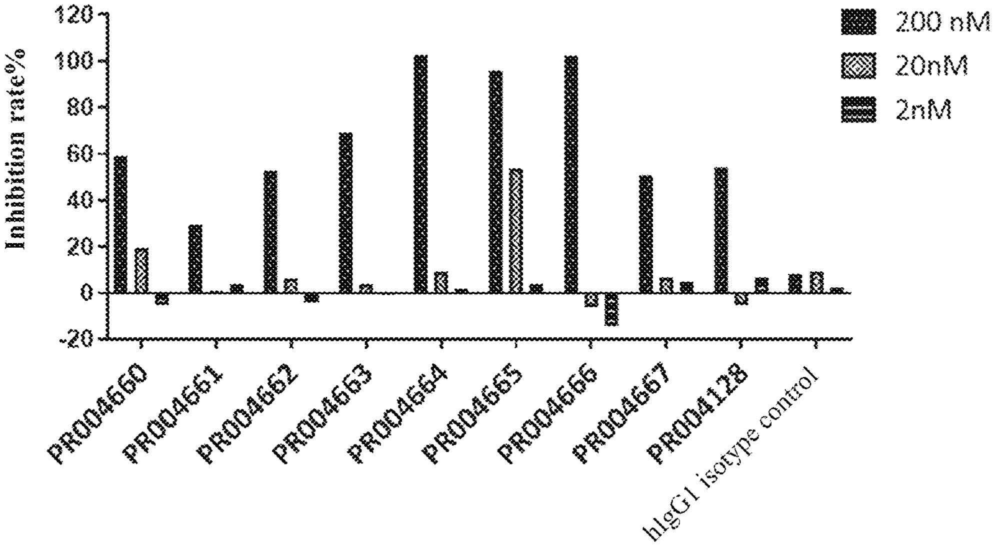
FIG. 25 shows the results of the blocking of intracellular calcium flux caused by CCL1 by PR004660, PR004661, PR004662, PR004663, PR004664, PR004665, PR004666, PR004667 and PR004128.

The CCR8 humanized antibodies PR004668, PR004669, PR004520 and PR004525 all retained good calcium flux blocking functional activity (FIG. 24). The PTM site-removed humanized antibodies PR004660, PR004661, PR004662, PR004663, PR004664, PR004665, PR004666 and PR004667 of PR004128 all retained the calcium flux blocking function (FIG. 25).

Figure 26:
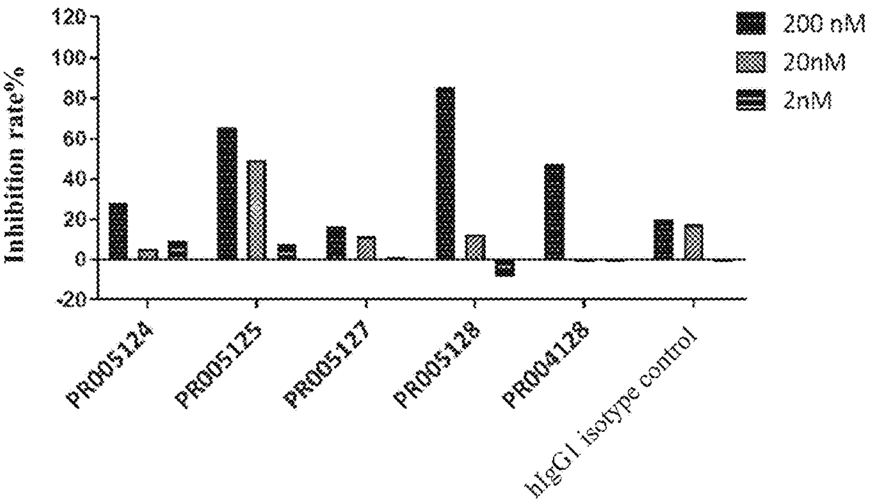
FIG. 26 shows the results of the blocking of intracellular calcium flux caused by CCL1 by PR005124, PR005125, PR005127, PR005128 and PR004128.
Figure 27:
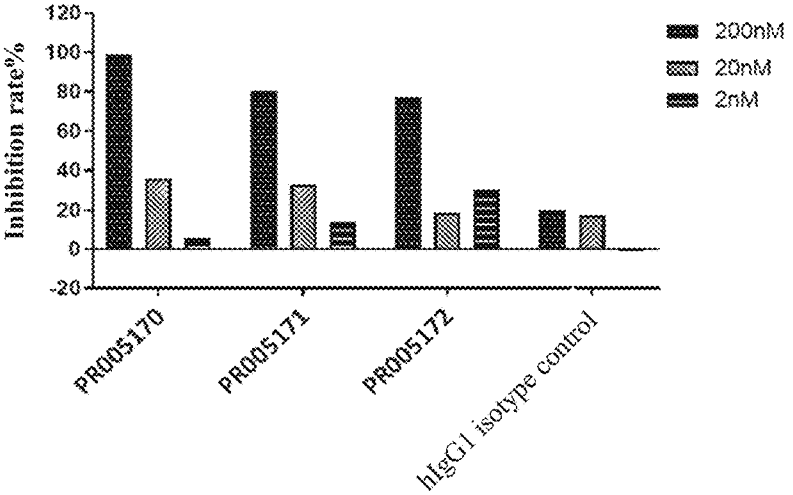
FIG. 27 shows the results of the blocking of intracellular calcium flux caused by CCL1 by PR005170, PR005171 and PR005172.

The fully human antibodies PR005125 and PR005128 also had the function of blocking intracellular calcium flux induced by CCL1 (FIG. 26). The antibodies PR005170, PR005171 and PR005172 with saturation mutagenesis at position 96 of the light chain of RP004128 had good calcium flux blocking functional activity (FIG. 27).

Example 10. The Antigen-Binding Proteins Described Herein being Capable of Blocking CCL1-Mediated Cell Migration Cells overexpressing human CCR8, Baf3-hCCR8, were resuspended in RPMI1640 medium containing 0.2% BSA as an assay buffer, and the suspension was adjusted to a concentration of 2E6 cells/mL. The test antibody was diluted (2×) in a gradient with the assay buffer to obtain three final concentrations of 200 nM, 20 nM and 2 nM. The cells and the antibody were mixed in a 1:1 ratio, and the mixture was incubated at 37° C. for 30 min. The ligand CCL1 was diluted in a gradient with the assay buffer, the dilution was added to the lower chamber of a Transwell plate (Corning, Cat No. 3387) at 150 μL/well, and a blank buffer well was set as a negative control. The incubated antibody/cell mixture was added to the upper chamber of the Transwell plate at 100 μL/well, and a cell-only well was set as a positive control. The Transwell plate was incubated in an incubator. 5 h later, the Transwell plate was taken, and the cells migrated into the lower chamber were gently resuspended. 100 μL of the suspension was transferred to a black transparent-bottom 96-well plate (PerkinElmer, Cat No. 6005225). Cell-Titer glo (PerkinElmer, Cat No. G7573) was added at 100 μL/well for reaction for 10 min, and the luminescence (RLU) was read in a plate reader. The calculation formula for the inhibition rate (%) is as follows.

Inhibition rate (%)=[RLU(positive control well)−RLU(sample well)]/[RLU(positive control well)−RLU(negative control well)]×100

Figure 28A:
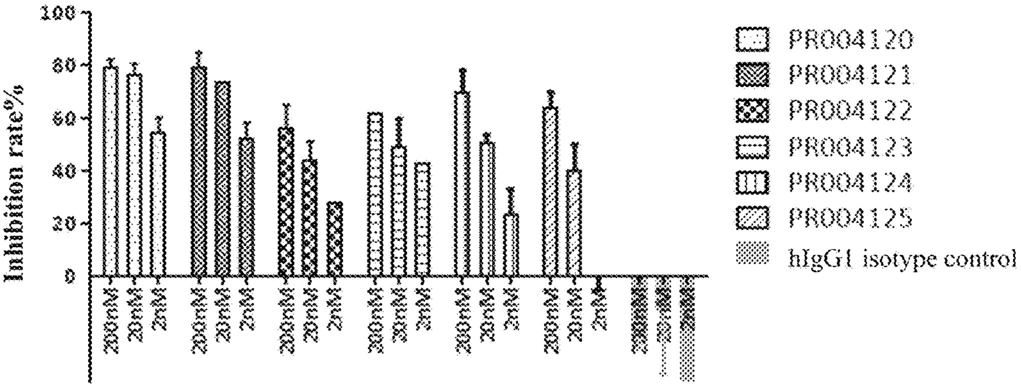
FIG. 28A shows the results of the blocking of cell migration caused by CCL1 by PR004120, PR004121, PR004122, PR004123, PR004124 and PR004125.
Figure 28B:
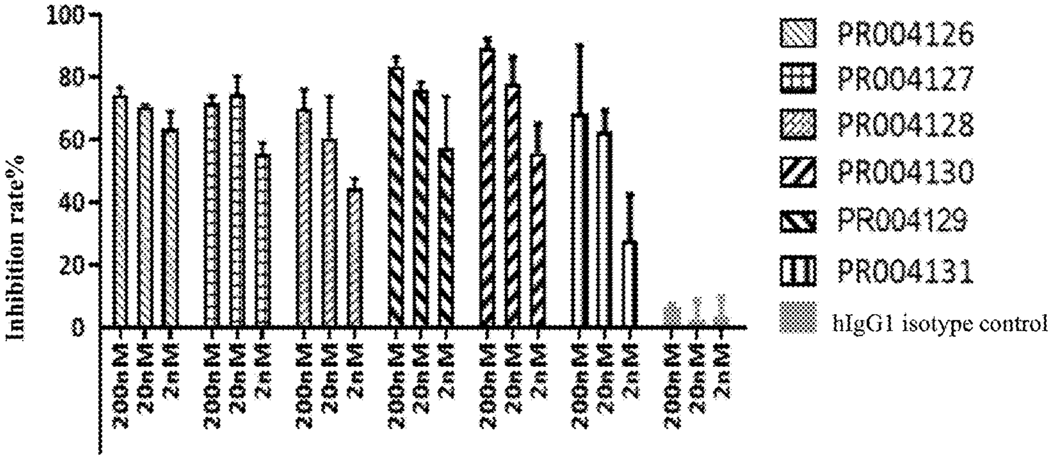
FIG. 28B shows the results of the blocking of cell migration caused by CCL1 by PR004126, PR004127, PR004128, PR004130, PR004129 and PR004131.
Figure 29:
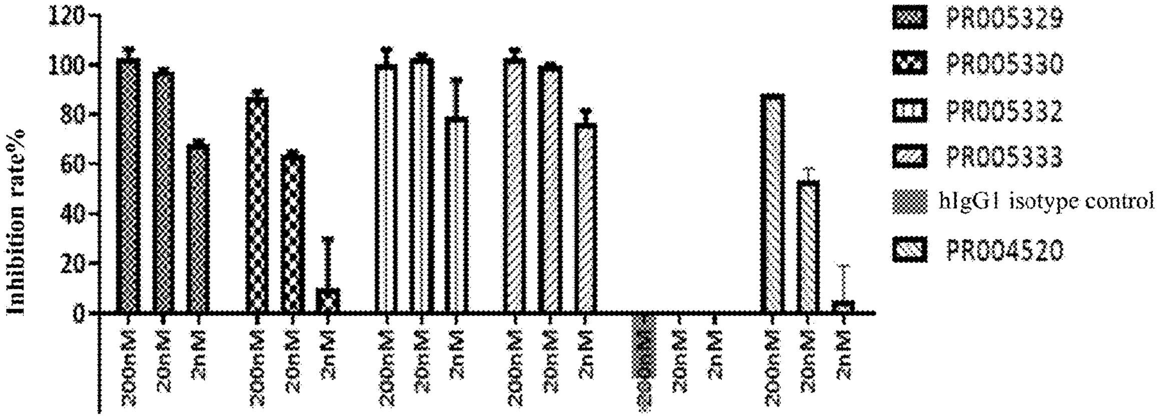
FIG. 29 shows the results of the blocking of cell migration caused by CCL1 by PR005329, PR005330, PR005332, PR005333 and PR004520.

The assay results of the cell migration blocking functional activity of the CCR8 chimeric antibodies are shown in FIGS. 28A-28B. The molecules PR004120, PR004121, PR004122, PR004123, PR004124, PR004125, PR004126, PR004127, PR004128, PR004129, PR004130 and PR004131 were all able to block the CCL1-mediated cell migration, and showed good blocking functional activity. The assay results of other CCR8 chimeric antibodies are shown in FIG. 29. PR005329, PR005330, PR005332 and PR005333 also showed good blocking functional activity.

Figure 30A:
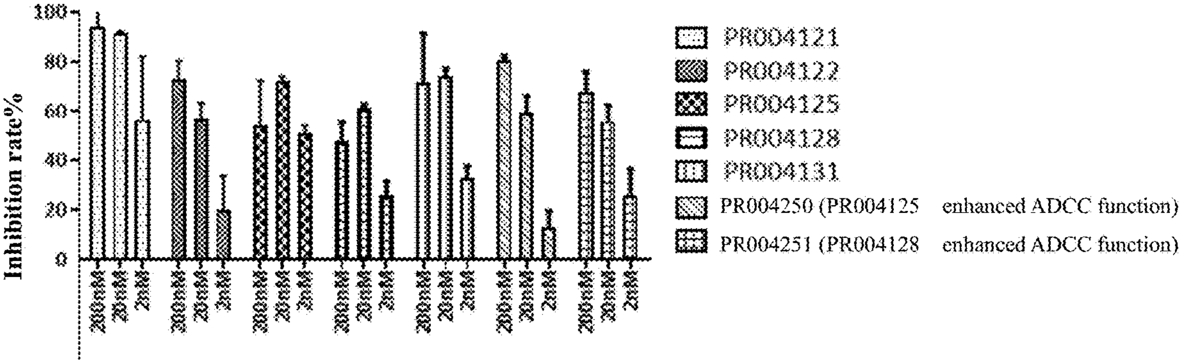
FIG. 30A shows the results of the blocking of cell migration caused by CCL1 by PR004121, PR004122, PR004125, PR004128, PR004131, PR004250 and PR004251.
Figure 30B:
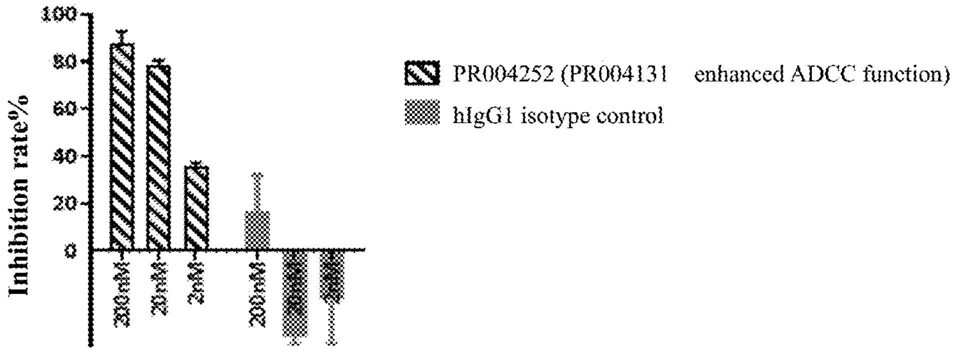
FIG. 30B shows the results of the blocking of cell migration caused by CCL1 by PR004525.
Figure 30C:
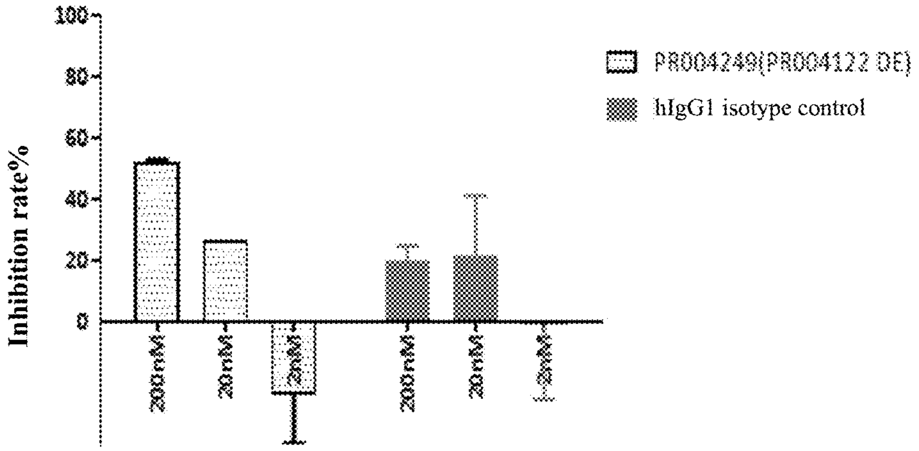
FIG. 30C shows the results of the blocking of cell migration caused by CCL1 by PR004249.

The assay results of the CCR8 antibodies with enhanced ADCC are as shown in FIGS. 30A-30C. PR004249, PR004250, PR004251 and PR004252 all retained functional activity of blocking the CCL1-mediated cell migration.

Figure 31A:
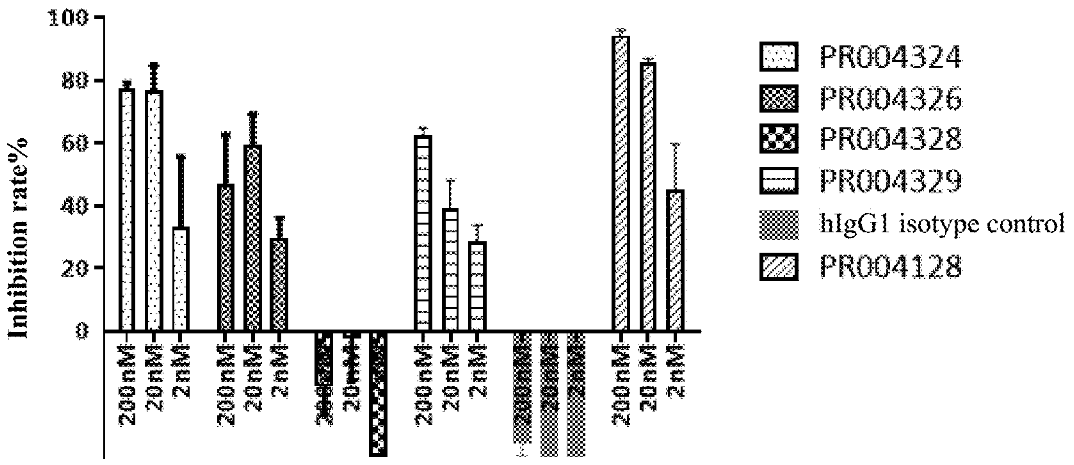
FIG. 31A shows the results of the blocking of cell migration caused by CCL1 by PR004324, PR004326, PR004328, PR004329 and PR004128.
Figure 31B:
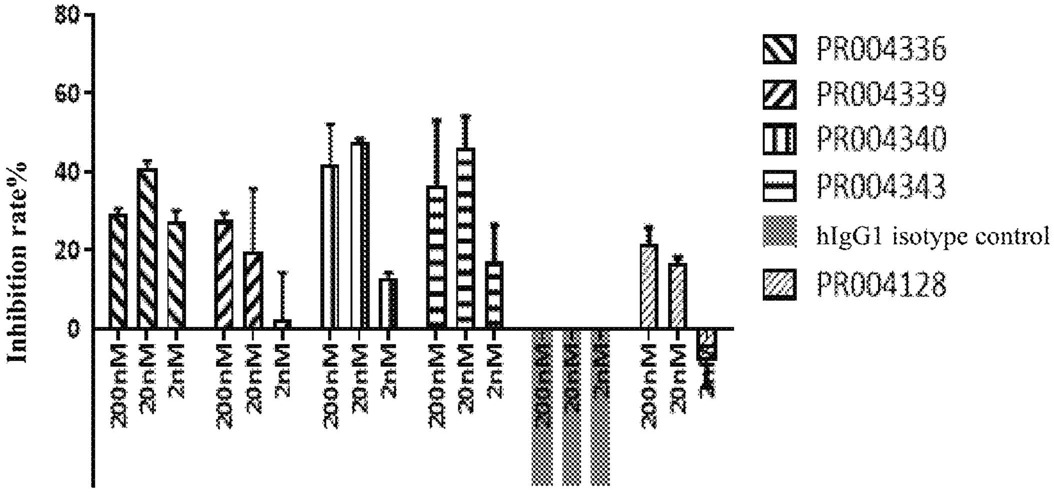
FIG. 31B shows the results of the blocking of cell migration caused by CCL1 by PR004336, PR004339, PR004340, PR004343 and PR004128.
Figure 31C:
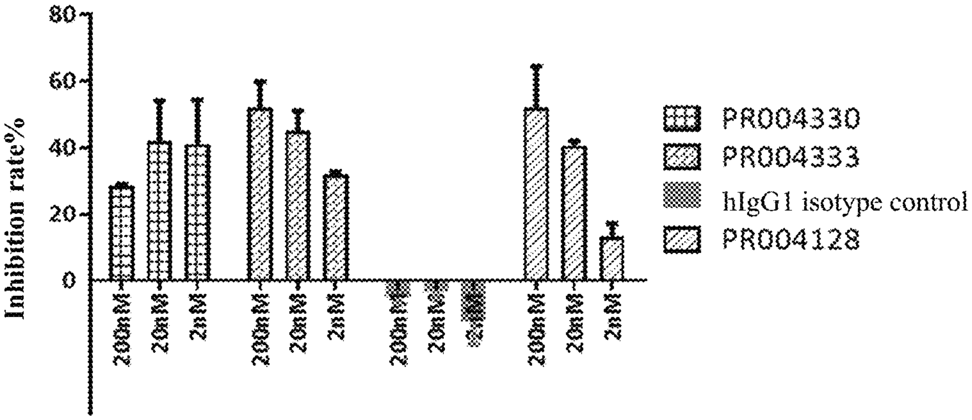
FIG. 31C shows the results of the blocking of cell migration caused by CCL1 by PR004330, PR004333 and PR004128.
Figure 32A:
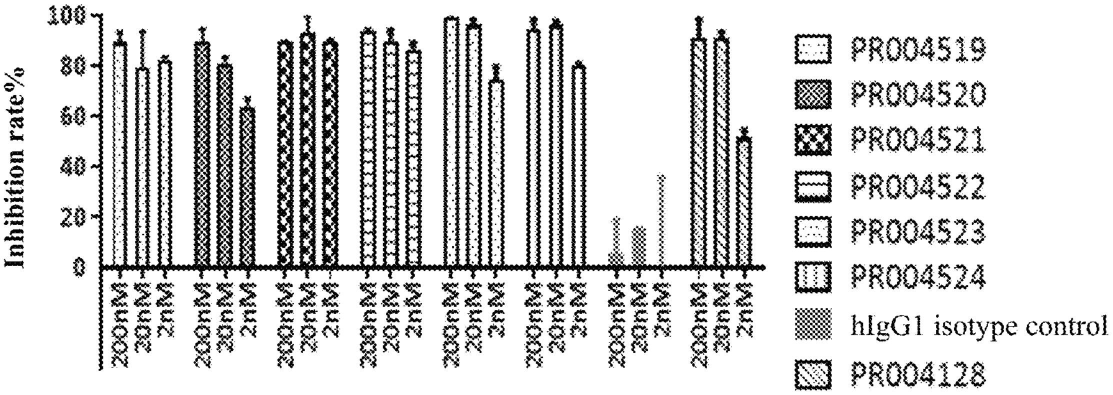
FIG. 32A shows the results of the blocking of cell migration caused by CCL1 by PR004519, PR004520, PR004521, PR004522, PR004523, PR004524 and PR004128.
Figure 32B:
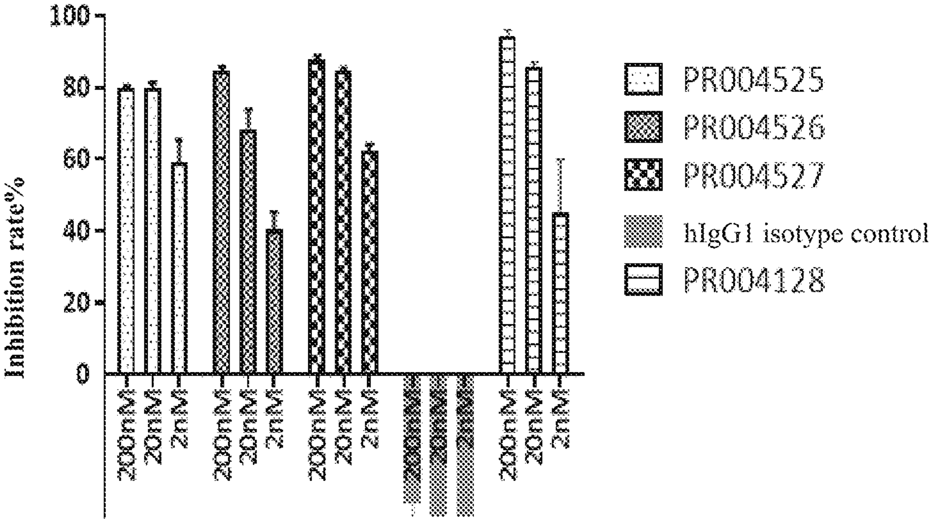
FIG. 32B shows the results of the blocking of cell migration caused by CCL1 by PR004525, PR004526, PR004527 and PR004128.
Figure 32C:
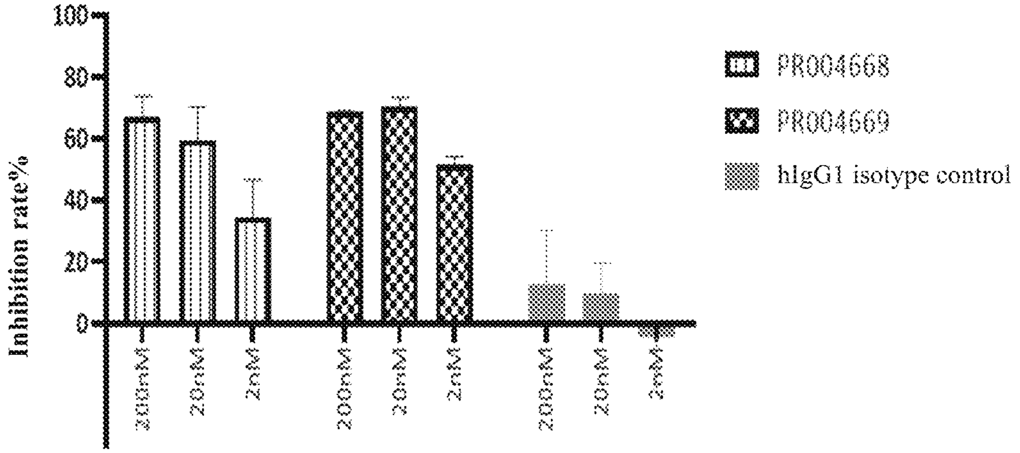
FIG. 32C shows the results of the blocking of cell migration caused by CCL1 by PR004668 and PR004669.

The mutant molecules PR004324, PR004326, PR004329, PR004330, PR004333, PR004336, PR004339, PR004340 and PR004343 of the CCR8 chimeric antibody molecule PR004128 (FIGS. 31A-31C) all retained functional activity of blocking the CCL1-mediated cell migration. The humanized antibody molecules PR004519, PR004520, PR004521, PR004522, PR004523, PR004524, PR004525, PR004526, PR004527, PR004668 and PR004669 (FIGS. 32A-32C) all had functional activity of blocking the CCL1-mediated cell migration.

Figure 33:
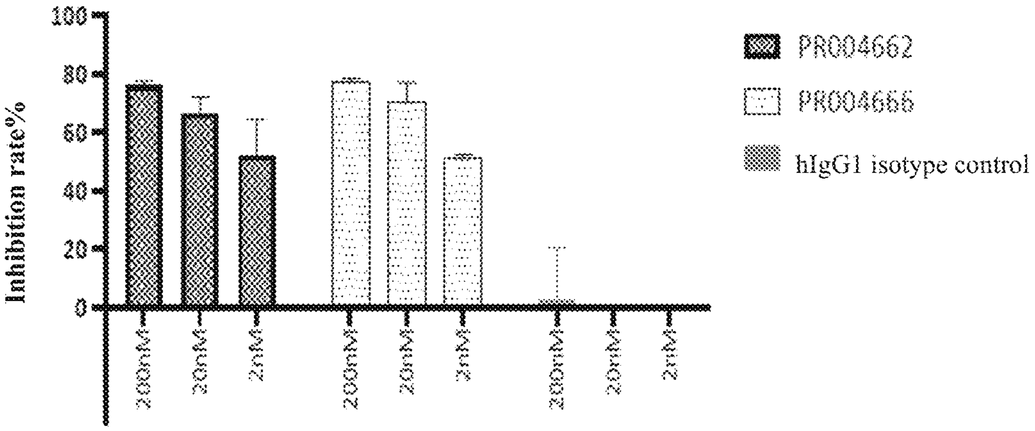
FIG. 33 shows the results of the blocking of cell migration caused by CCL1 by PR004662 and PR004666.

The PTM site-removed humanized antibodies PR004662 and PR004666 retained the functional activity of CCL1-mediated cell migration (FIG. 33).

Figure 34A:
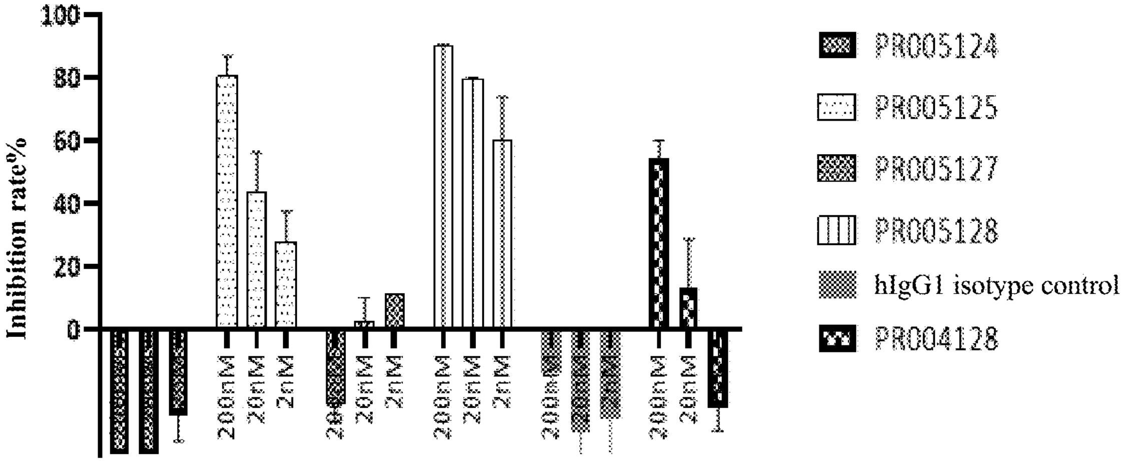
FIG. 34A shows the results of the blocking of cell migration caused by CCL1 by PR005124, PR005125, PR005127, PR005128 and PR004128.
Figure 34B:
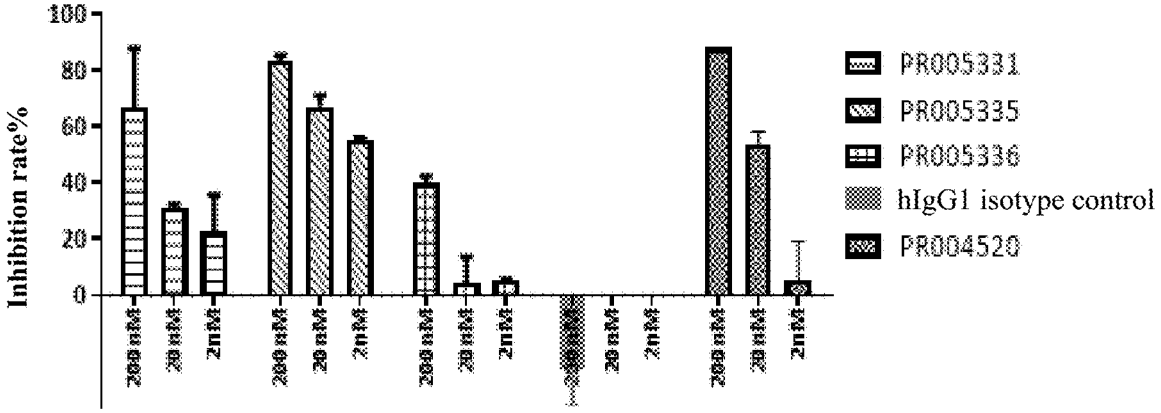
FIG. 34B shows the results of the blocking of cell migration caused by CCL1 by PR005331, PR005335, PR005336 and PR004520.
Figure 35A:
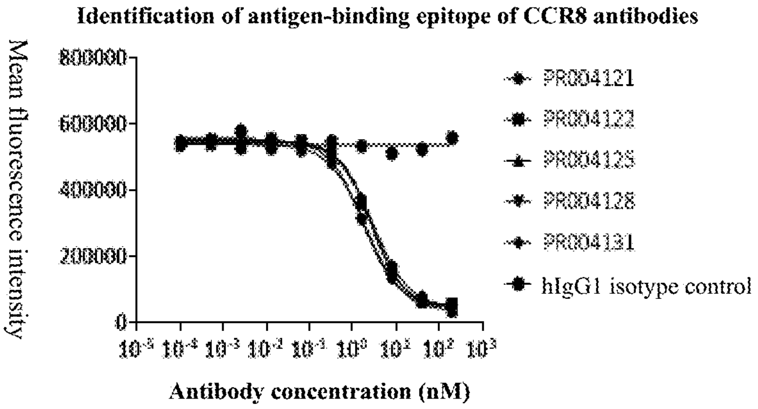
FIGS. 35A, 35B, 35C, 35D and 35E show the assay results of competitive binding of PR004121, PR004122, PR004125, PR004128 and PR004131 to an antigenic epitope.
Figure 35B:
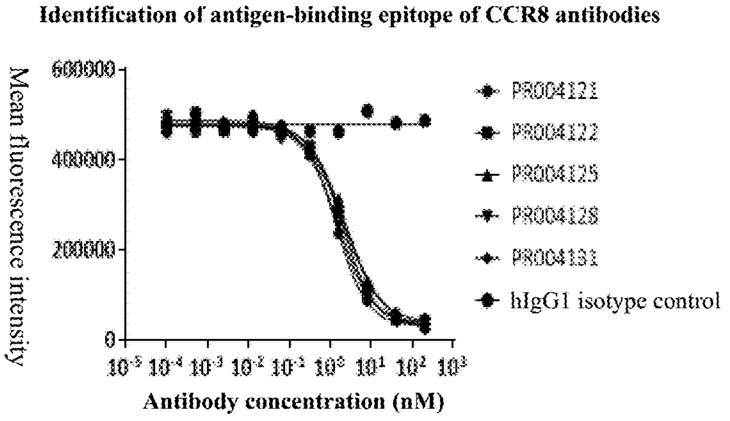
Figure 35C:
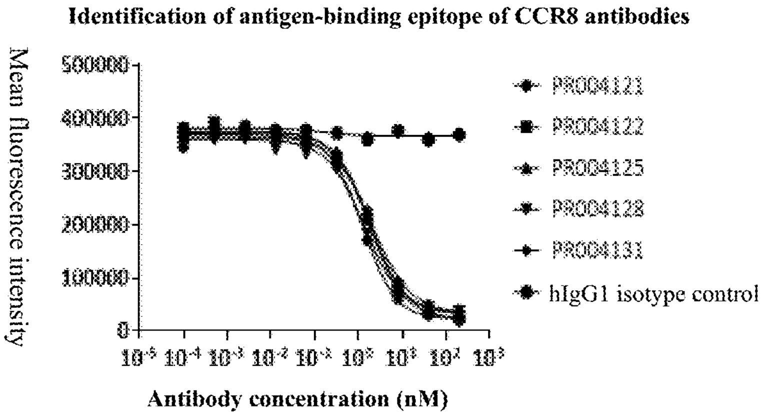
Figure 35D:
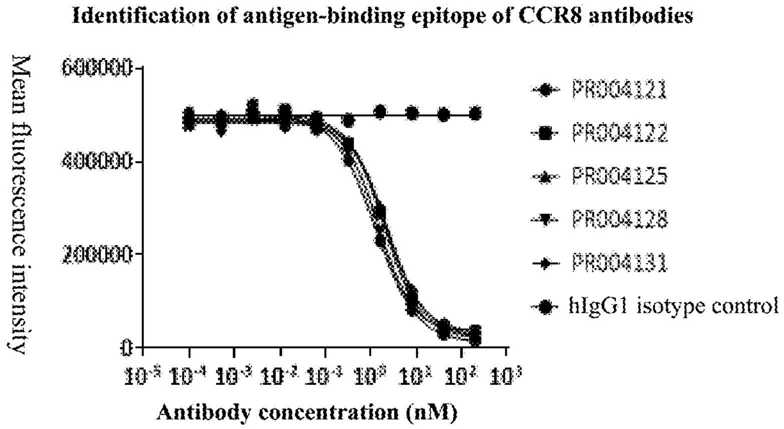
Figure 35E:
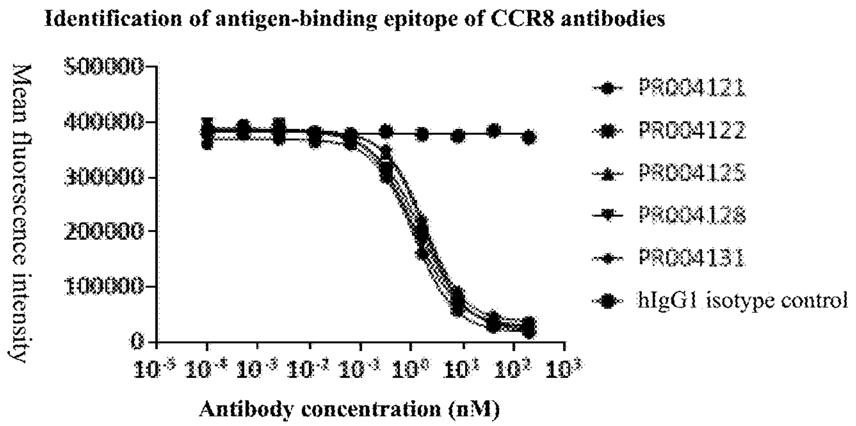

The fully human antibodies PR005125, PR005128, PR005331, PR005335, PR005336 and PR004520 also had functional activity of blocking CCL1-mediated cell migration (FIGS. 34A and 34B).

Example 11. Assay on Competitive Binding of Antibodies to an Antigenic Epitope The antibody was conjugated with Sulfo-NHS-LC-Biotin at a molar ratio of 5:1 (1 mol antibody was added to 5 mol Sulfo-NHS-LC-Biotin) with reference to the product instructions (ThermoFisher, Cat No. A39257) and incubated on ice for 2 h. The coupled antibody was purified with a Zeba desalting column (ThermoFisher, Cat No. 89882). Cells overexpressing human CCR8, HEK293-hCCR8, were added to a V-bottom 96-well plate at a density of 1E5 cells/well and centrifuged at 300 g for 5 min, and the supernatant was discarded. The competitive antibody was serially diluted in a ratio of 1:10 from 200 nM to obtain 8 concentration points. The Biotin-antibody and the competition antibody were mixed in a 1:1 ratio on an HEK293 cell line overexpressing human CCR8 by the binding $EC_{80}$ concentration. The cells in the 96-well plate were resuspended and incubated at 4° C. for 1 h. The plate was washed twice with DPBS at 200 μL/well. The secondary antibody diluted in a 1:1000 ratio was added at 100 μL/well, and the mixture was incubated at 4° C. for 40 min. The plate was washed twice with DPBS at 200 μL/well. Finally, DPBS was with at 200 μL/well to suspend the cells, and the mixture was loaded on an FACS machine for analysis. If the competitive antibody can compete with the Biotin-labeled antibody for binding to an antigen, it indicates that the two antibodies bind to the same or similar antigen-binding epitope.

The results of competitive binding of the chimeric CCR8 antibodies to an antigenic epitope are shown in FIGS. 35A-35E. The results showed that the molecules PR004121, PR004122, PR004125, PR004128 and PR004131 all bound to the same CCR8 antigenic epitope.

Example 12. The Antigen-Binding Proteins Described Herein Having ADCC Reporter Gene Biological Activity CHO-K1-hCCR8 overexpressing human CCR8 was digested and collected, counted, and resuspended in RPMI1640 containing 4% FBS, and the suspension was added to a white ViewPlate 96-well plate (PerkinElmer, Cat No. 6005181). Jurkat/FcγR III-NFAT cells (Vazyme, Cat No. DD1301-01) were collected, counted, and resuspended in RPMI1640 containing 4% FBS, and the suspension was added to a white ViewPlate 96-well plate (E/T ratio=5). The test antibody (final concentration of 3×) was serially diluted in a 10-fold gradient with RPMI1640 containing 4% FBS from an initial concentration of 200 nM to obtain 8 concentrations. The diluted antibodies were added to a white Viewplate 96-well plate at 50 μL/well. The 96-well plate was incubated in an incubator at 37° C. for 6 h, and transferred to room temperature and equilibrated for 30 min. One-Glo (Perkinerlmer, Cat No. E6120) was added to the plate at 75 μL/well for reaction for 10 min, and RLU was read in a microplate reader. Data were analyzed using GraphPad Prism 6.0.

Figure 36:
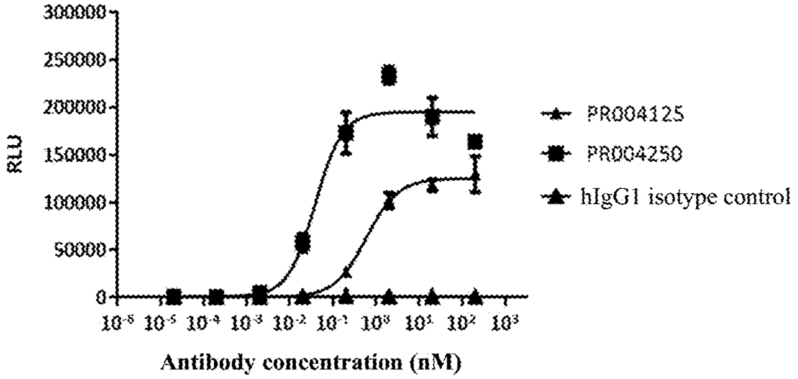
FIG. 36 shows the assay results of the ADCC reporter gene biological activities of PR004125 and PR004250.

The assay results of the ADCC reporter gene biological activities of the CCR8 chimeric antibody molecule PR004125 and the CCR8 chimeric antibody molecule PR004250 with enhanced ADCC are shown in FIG. 36. The results showed that both PR004125 and PR004250 have strong ADCC effect, wherein $EC_{50}$ of PR004250 was 0.04 nM and $EC_{50}$ of PR004125 was 0.59 nM.

Figure 37:
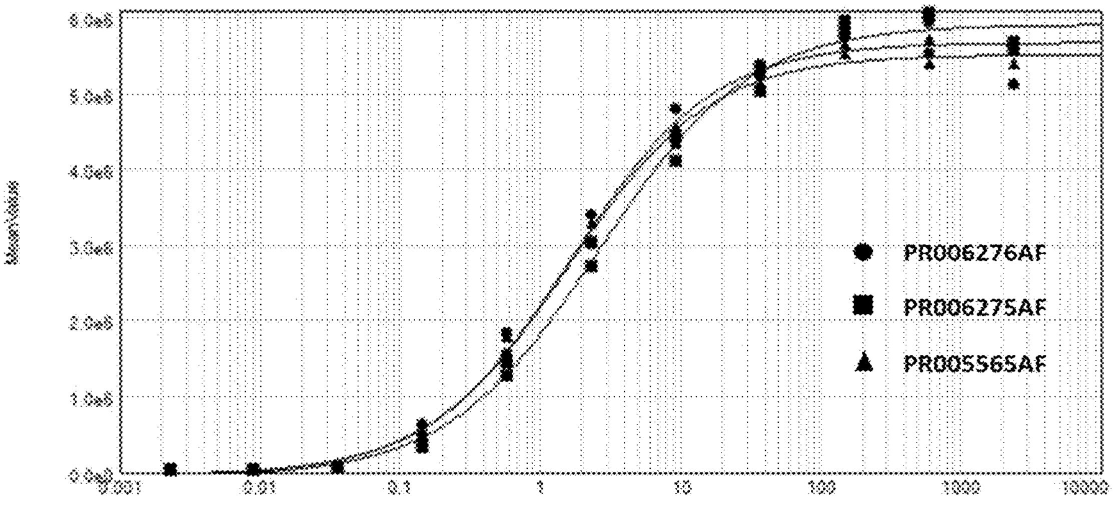
FIG. 37 shows the assay results of the ADCC reporter gene biological activities of PR005565AF, PR006275AF and PR006276AF.
Figure 38A:
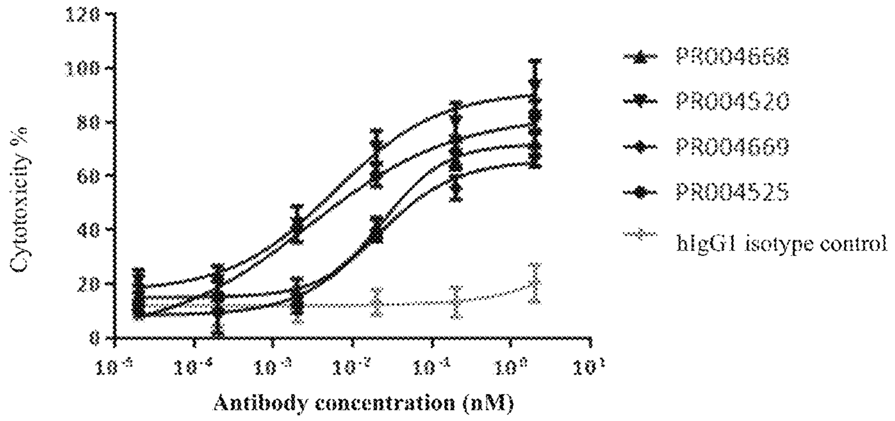
FIG. 38A shows the assay results of NK cell-mediated ADCC biological activity on which PR004668, PR004520, PR004669 and PR004525 depend.
Figure 38B:
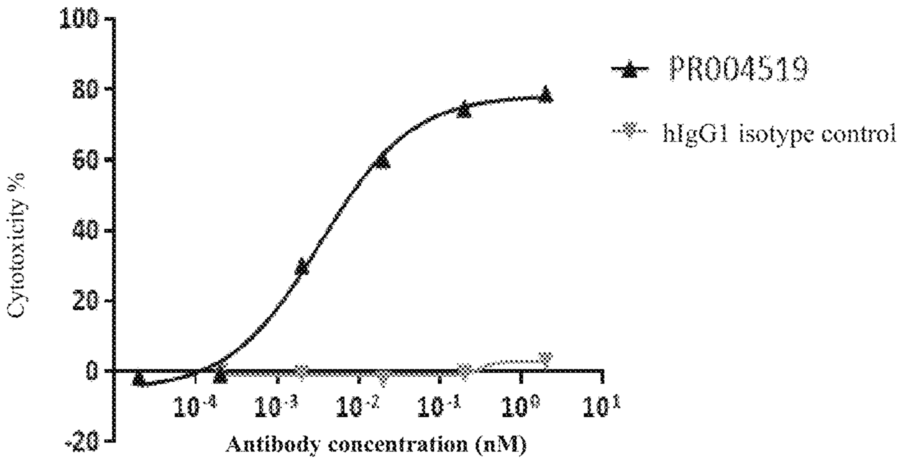
FIG. 38B shows the assay results of NK cell-mediated ADCC biological activity on which PR004519 depends.
Figure 38C:
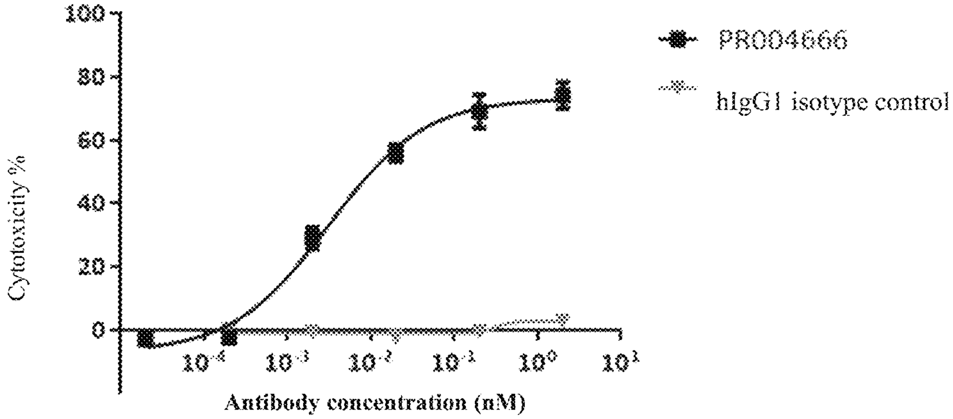
FIG. 38C shows the assay results of NK cell-mediated ADCC biological activity on which PR004666 depends.
Figure 38D:
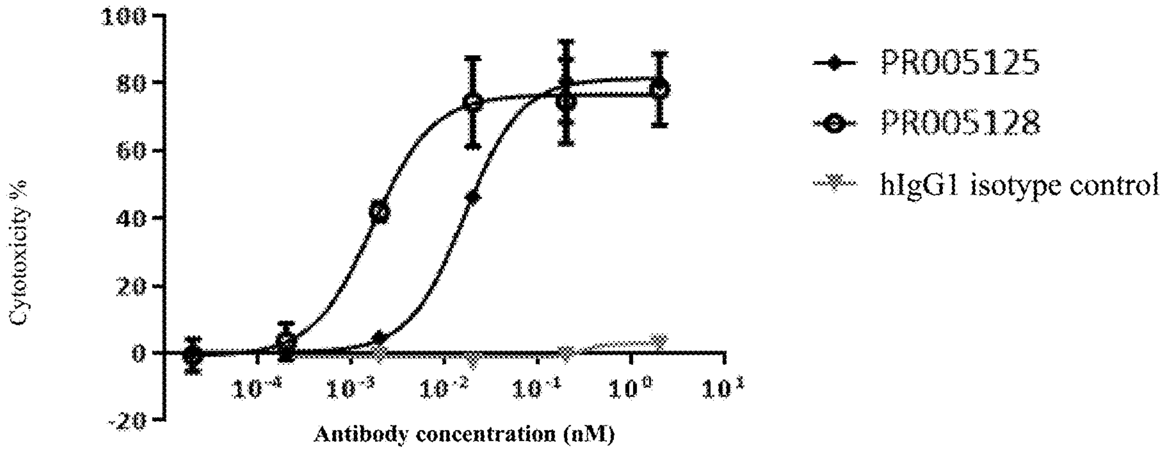
FIG. 38D shows the assay results of NK cell-mediated ADCC biological activity on which PR005125 and PR005128 depend.
Figure 38E:
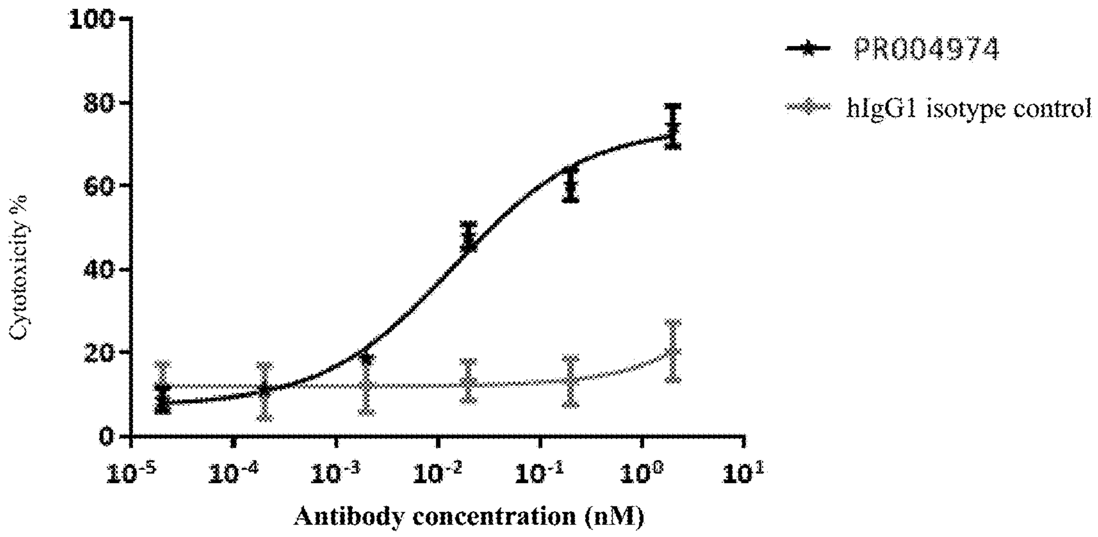
FIG. 38E shows the assay results of NK cell-mediated ADCC biological activity on which PR004974 depends.

The assay results of the ADCC reporter gene biological activities of the affinity-matured mutants PR006275AF and PR006276AF of PR005565AF are shown in FIG. 37. The results showed that both PR00PR006275AF and PR006276AF had strong ADCC effect, wherein $EC_{50}$ of R00PR006275AF was 2.60 nM, and $EC_{50}$ of PR006276AF was 1.66 nM.

Example 13. NK Cell-Mediated ADCC Biological Activity

CHO-K1-hCCR8 overexpressing human CCR8 was digested and collected, counted, and resuspended in RPMI1640 containing 2% FBS, and the suspension was added to a 96-well plate (Corning, Cat No. 3599) at 10,000 cells/25 μL/well. Fresh or frozen PBMC cells were collected, counted, and resuspended in RPMI1640 containing 2% FBS and added to a 96-well plate at 250,000 cells/25 μL/well (E/T ratio=25). The test antibody (final concentration of 2×) was serially diluted in a 10-fold gradient with RPMI1640 containing 2% FBS from an initial concentration of 2 nM to obtain 6 concentrations. The diluted antibodies were added to a 96-well plate at 50 μL/well, and the whole system was incubated in an incubator at 37° C. for 6 h. With reference to the instructions of kit (Promega, Cat No. G1781), 10 μL of lysis buffer (10×) was added to the corresponding control wells 45 min before the end of incubation. When 6 h of incubation was completed, 250 g of the culture was centrifuged for 4 min. 50 μL of the supernatant was taken, 50 μL of the prepared mixed substrate in the kit was added, and the mixture was incubated at 37° C. for 15-30 min. The reading was read at 490 nm in a microplate reader. The killing percentage was calculated with reference to the formula in the instructions. Data were analyzed using GraphPad Prism 6.0.

As shown in FIGS. 38A-38E, the humanized antibodies PR004668, PR004669, PR004519, PR004520 and PR004525, the PTM-removed humanized antibody PR004666, the fully humanized antibody molecules PR005125 and PR005128, and the fully human antibody molecule PR004974 derived from single cell clones all had strong ADCC biological activity.

Figure 39:
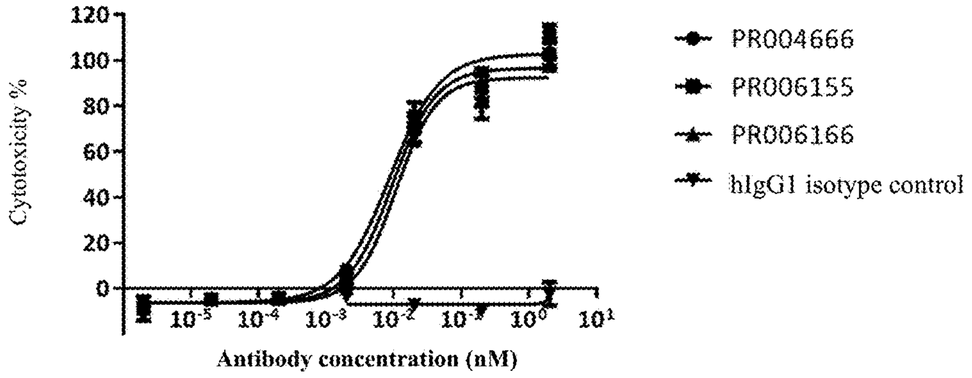
FIG. 39 shows the assay results of NK cell-mediated ADCC biological activity on which PR004666, PR006155 and PR006166 depend.

As shown in FIG. 39, the affinity-matured mutants PR006155 and PR006166 of PR004666 both had strong ADCC biological activity.

Example 14. Differential Expression of CCR8 in Human Tumor-Infiltrating Lymphocyte-Derived Tregs (TIL-Tregs) Vs. In Normal Human PBMC-Derived Tregs TIL cells derived from human clear cell renal cell carcinoma (ccRCC) and breast cancer (BC) were resuspended in medium restored to room temperature and counted using a cytometer. Cells were first treated with Live/Dead cell dye for 30 min, then treated with an Fc receptor blocking regent for 15 min. After that, the following group of antibodies was diluted to a certain concentration with a staining buffer for cell surface staining: a CD45 antibody, a CD3 antibody, a CD4 antibody, and a PR004666 antibody. Endonuclear Foxp3 staining was then performed using a FoxP3 staining kit. After staining was completed, the samples were analyzed using a flow cytometer.

Figure 40:
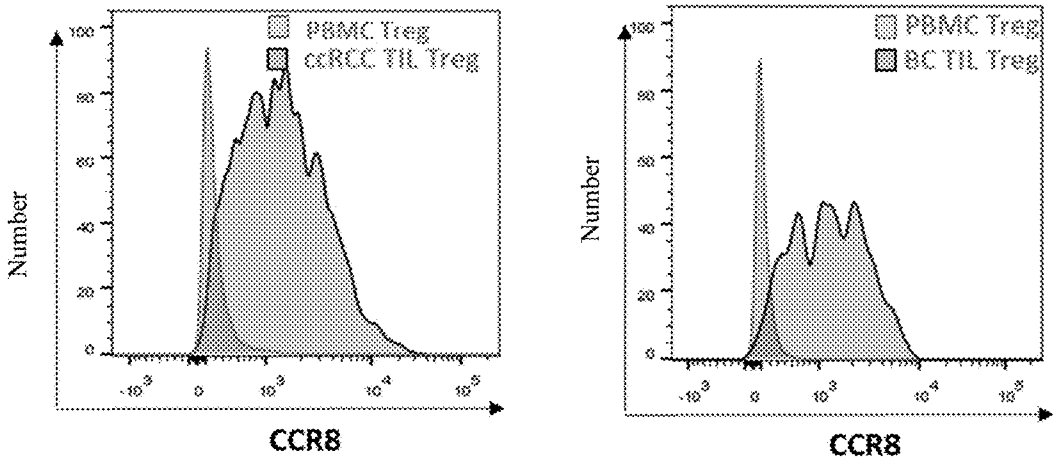
FIG. 40 shows the assay results of differential expression of CCR8 in human tumor-infiltrating lymphocyte-derived Tregs (ccRCC TIL Tregs and BC TIL Tregs) vs. in normal human PBMC-derived Tregs.

As shown in FIG. 40, CCR8 was barely expressed in Tregs derived from normal human PBMCs, but highly expressed in Tregs derived from human tumor-infiltrating lymphocytes.

Example 15. Assay on the Specific Binding of PR005565

To identify binding targets of PR005565, about 6000 different membrane proteins were expressed in each of individual wells of HEK-293T or QT6 cells arranged in 384-well plates. The matrix was then formed by pooling the individual columns and rows of each 384-well plate, such that a unique combination of two different wells of the matrix plate represented each protein. Protein targets are identified by detecting the binding of PR005565 to pools of overlapping columns and rows for specific deconvolution. Each membrane protein target was assigned a value corresponding to the binding value of its unique pool of rows and columns, then the target protein that showed a binding value greater than 3 standard deviations from the background value in both wells was selected for downstream verification experiments. The resulting paired binding data would then be normalized and transformed to yield a single data for the binding of PR005565 to each protein. The value less than 3 standard deviations from the mean background value was defined as non-specific fluorescence. The target proteins to which PR005565 binds were then identified.

Figure 41A:
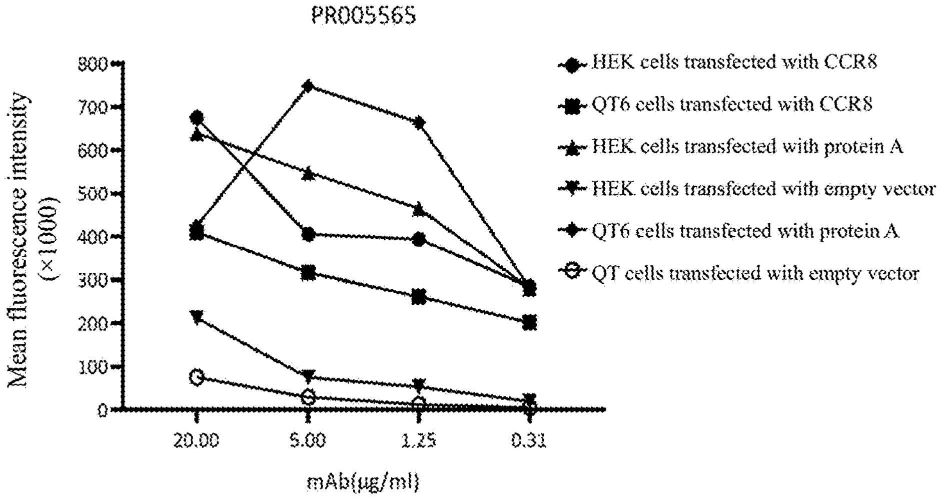
FIGS. 41A and 41B show the binding of PR005565 (FIG. 41A) and a commercial CCR8 antibody (Biolegend, Cat N360602) (FIG. 41B) to cells overexpressing CCR8.
Figure 41B:
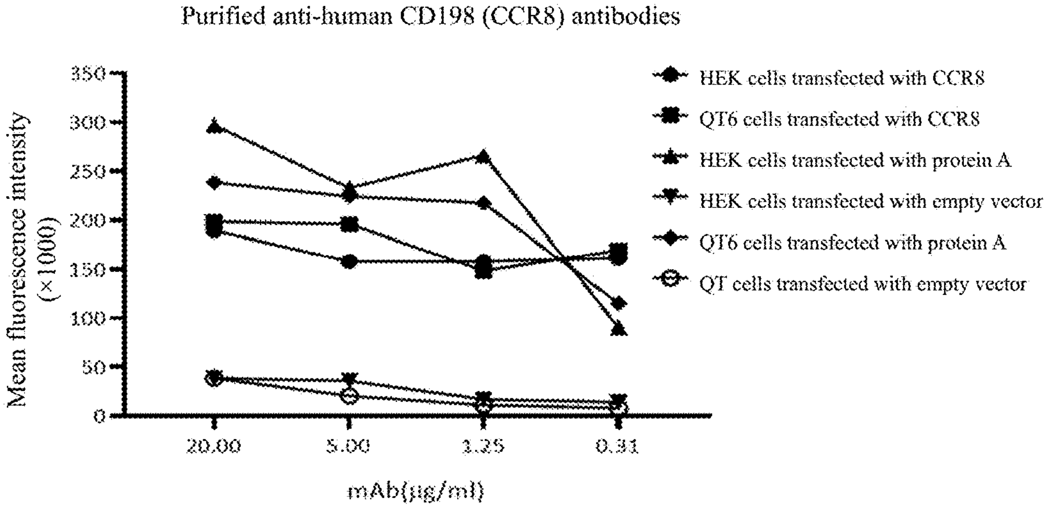

In the 384-well plates, cells were transfected with these plasmids with binding target proteins (MMP16, CD40LG, CD147, TSPAN4, and TSPAN12), protein A, or empty vector. PR005565 was diluted in 4-fold gradient from 20 μg/mL. The transfected cells were added, and the mixture was incubated. Their binding was then detected by high-throughput immunofluorescence flow cytometry. Meanwhile, in a separate experiment, after transfection of cells with the CCR8 vector, binding to PR005565 or a commercial anti-CCR8 antibody (Biolegend, Cat N360602) was possible, as shown in FIGS. 41A and 41B.

After that, HEK293 cells were transfected with commercial MMP16 (protein information can be found under Uniprot P51512), CD40LG (protein information can be found under Uniprot P29965), CD147 (protein information can be found under Uniprot P35612), TSPAN4 (protein information can be found under Uniprot O14817), and TSPAN12 (protein information can be found under Uniprot O95859) plasmids for further verification of the binding of PR005565, PR006275 and PR006276 to these proteins. The results showed that MMP16, CD40LG and CD147 had significant binding to their specific antibodies, while TSPAN4-FLAG and TSPAN12-FLAG could specifically bind to the anti-FLAG antibody, suggesting the successful protein transient overexpression. However, the binding values of PR005565, PR006275 and PR006276 to MMP16, CD40LG, CD147, TSPAN4 and TSPAN12 after transfection of HEK293 cells were all consistent with the signal values of HEK293 cells themselves. Thus, PR005565, PR006275 and PR006276 had no non-specific binding to MMP16, CD40LG, CD147, TSPAN4 and TSPAN12 proteins (see Table 50). This indicates that the antigen-binding proteins of the present application do not bind to antigens other than CCR8.

TABLE 50

Identification of non-specific binding of PR005565, PR006275 and PR006276 to proteins

| Cell | MFI | | | | | | |
|---|---|---|---|---|---|---|---|
| | PR005565 | PR006275 | PR006276 | Anti-CD40L | Anti-CD147 | Anti-MMP16 | Anti-FLAG |
| HEK293-CD40LG | 241 | 352 | 152 | 5071 | | | |
| HEK293-CD147 | 212 | 362 | 152 | | 261573 | | |
| HEK293-MMP16 | 146 | 204 | 160 | | | 2275 | |
| HEK293-TSPAN4 | 207 | 424 | 203 | | | | 3004 |
| HEK293-TSPAN12 | 219 | 398 | 185 | | | | 812 |
| HEK293 | 322 | 478 | 161 | 96.4 | 84.8 | 107 | 347 |

Example 16. Experiment on the Tumor Inhibition of PR004520 in Mice

On the day of cell inoculation, each NCG mouse was inoculated subcutaneously with $1\times10^7$ MDA-MB-231 tumor cells. The cells were resuspended in a PBS/Matrigel (1:1) mixture (0.1 mL/mouse) and inoculated subcutaneously. When the mean tumor volume of mice reached 102 $mm^3$, 36 mice were divided into 6 groups, each mouse was inoculated intravenously with $5\times10^6$ human PBMCs, and the cells were resuspended in 200 μL of PBS. The administration was started the next day with an administration cycle of twice a week for 6 administrations via intraperitoneal administration. After the start of administration, the body weight and the tumor volume were measured twice a week. The tumor volume was calculated as follows: tumor volume ($mm^3$) =0.5×long diameter of tumor×short diameter of tumor. The experiment was terminated on day 22 after the administration, then all of the mice were euthanized. Data were analyzed using Graphpad Prism 8.0, one-way ANOVA.

Figure 42:
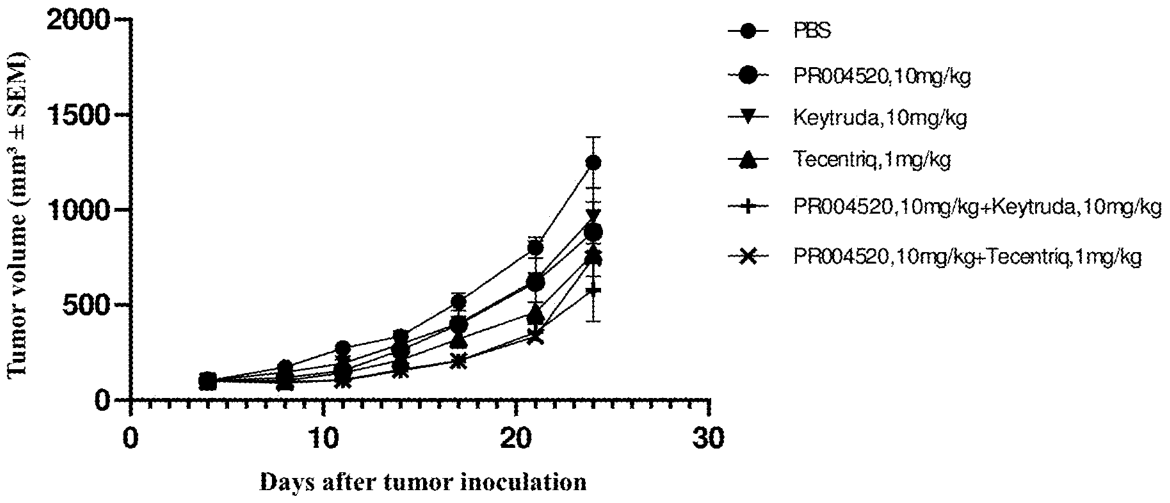
FIG. 42 shows the inhibition of tumor growth by PR004520, anti-PD-1 antibody Keytruda®, and anti-PD-L1 antibody Tecentrip alone or in combination.

As shown in FIG. 42, the mean tumor volume of the mice in the control group on day 22 after the administration was 1248 $mm^3$. The mean tumor volume of the test drug PR004520 (10 mg/kg) therapy group on day 22 after the administration was 883 $mm^3$, showing no significant difference (p value was 0.083) from that of the vehicle control group, with the tumor growth inhibition rate TGI (%) being 29.29%. The mean tumor volume of the test drug Keytruda (10 mg/kg) therapy group on day 22 after the administration was 963 mm 3, showing no significant difference (p value was 0.340) from that of the vehicle control group, with the tumor growth inhibition rate TGI (%) being 22.87%. The mean tumor volume of the test drug Tecentriq (1 mg/kg) therapy group on day 22 after the administration was 771 $mm^3$, showing no significant difference (p value was 0.007) from that of the vehicle control group, with the tumor growth inhibition rate TGI (%) being 38.26%. The mean tumor volume of the combination therapy group of PR004520 (10 mg/kg) and Keytruda (10 mg/kg) on day 22 after the administration was 581 mm 3, showing significant difference (p value was 0.0001) from that of the vehicle control group, with the tumor growth inhibition rate TGI (%) being 53.46%. The mean tumor volume of the combination therapy group of PR004520 (10 mg/kg) and Tecentriq (1 mg/kg) on day 22 after the administration was 745 mm 3, showing significant difference (p value was 0.004) from that of the vehicle control group, with the tumor growth inhibition rate TGI (%) being 40.32%. The mean tumor volume of the combination therapy group of PR004520 (10 mg/kg) and Keytruda (10 mg/kg) showed no significant difference from that of the monotherapy groups of PR004520 (10 mg/kg) and Keytruda (10 mg/kg). The mean value of the combination therapy group of PR004520 (10 mg/kg) and Tecentriq (1 mg/kg) showed no significant difference from that of the monotherapy groups of PR004520 (10 mg/kg) and Tecentriq (1 mg/kg).

Example 17. Experiment on the Tumor Inhibition of PR004520, PR004525 and PR004668 in Mice On the day of cell inoculation, each NCG mouse was inoculated subcutaneously with $1\times10^7$ MDA-MB-231 tumor cells. The cells were resuspended in a PBS/Matrigel (1:1) mixture (0.1 mL/mouse) and inoculated subcutaneously. When the mean tumor volume of each group of mice reached 100 $mm^3$, 60 mice were divided into 10 groups, each mouse was inoculated intravenously with $5\times10^6$ human PBMCs, and the cells were resuspended with 200 μL of PBS. The administration was started the next day with an administration cycle of twice a week for 6 administrations via intraperitoneal administration. After the start of administration, the body weight and the tumor volume were measured twice a week. The tumor volume was calculated as follows: tumor volume ($mm^3$)=0.5×long diameter of tumor× short diameter of tumor$^2$. The experiment was terminated on day 20 after the administration, then all of the mice were euthanized. Data were analyzed using Graphpad Prism 8.0, one-way ANOVA.

Figure 43:
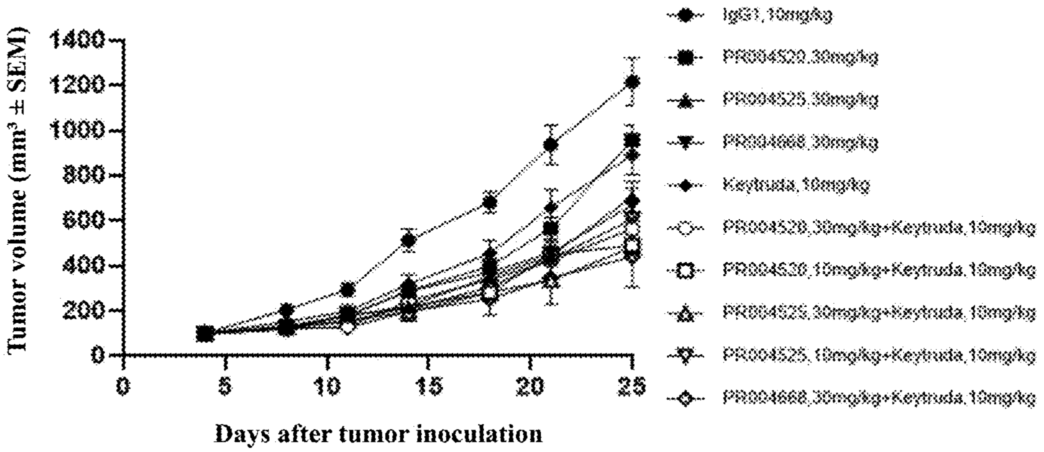
FIG. 43 shows the inhibition of tumor growth by PR004520, PR004525, PR004668 and anti-PD-1 antibody Keytruda® alone or in combination.

As shown in FIG. 43, the mean tumor volume of the mice in the control group on day 20 after the administration was 1217 mm 3. The mean tumor volume of the test drug PR004520 (30 mg/kg) therapy group on day 20 after the administration was 958 mm 3, showing no significant difference (p value was 0.354) from that of the vehicle control group, with the tumor growth inhibition rate TGI (%) being 21.29%. The mean tumor volume of the test drug PR004525 (30 mg/kg) therapy group on day 20 after the administration was 706 mm 3, showing a significant difference from that of the vehicle control group (p value was 0.0004), with the tumor growth inhibition rate TGI (%) being 42.02%. The mean tumor volume of the test drug PR004668 (30 mg/kg) therapy group on day 20 after the administration was 671 mm 3, showing a significant difference from that of the vehicle control group (p value was 0.005), with the tumor growth inhibition rate TGI (%) being 44.85%. The mean tumor volume of the test drug Keytruda (10 mg/kg) therapy group on day 20 after the administration was 892 mm 3, showing significant difference (p value was 0.020) from that of the vehicle control group, with the tumor growth inhibition rate TGI (%) being 26.72%. The mean tumor volume of the combination therapy group of PR004520 (30 mg/kg) and Keytruda (10 mg/kg) on day 20 after the administration was 564 mm 3, showing significant difference ($p$ value$<0.0001$) from that of the control group, with the tumor growth inhibition rate TGI (%) being 53.65%; and showing significant difference (P value was 0.018) from that of the PR004520 (30 mg/kg) monotherapy group, and showing no significant difference (P value was 0.324) from that of the Keytruda (10 mg/kg) monotherapy group. The mean tumor volume of the combination therapy group of PR004525 (30 mg/kg) and Keytruda (10 mg/kg) on day 20 after the administration was 482 $mm^3$, showing significant difference (p value<0.0001) from that of the control group, with the tumor growth inhibition rate TGI (%) being 60.39%; and showing no significant difference (P value was 0.812) from that of the PR004525 (30 mg/kg) monotherapy group, and showing no significant difference (P value was 0.104) from that of the Keytruda (10 mg/kg) monotherapy group. The mean tumor volume of the combination therapy group of PR004668 (30 mg/kg) and Keytruda (10 mg/kg) on day 20 after the administration was 441 mm 3, showing significant difference (p value was 0.0001) from that of the control group, with the tumor growth inhibition rate TGI (%) being 63.77%; and showing no significant difference (P value was 0.161) from that of the PR004668 (30 mg/kg) monotherapy group, and showing no significant difference (P value was 0.056) from that of the Keytruda (10 mg/kg) monotherapy group.

Example 18 Experiment on the Tumor Inhibition of PR005565AF Alone and in Combination with Anti-Murine PD-1 and Anti-Murine PD-L1 Monoclonal Antibodies in Mice On the day of cell inoculation, each C57BL/6-CCR8knockin mouse was inoculated subcutaneously with $1\times10^6$ MC38 tumor cells. The cells were resuspended in PBS (0.1 mL/mouse) and inoculated subcutaneously. When the mean tumor volume of each group of mice reached 88 $mm^3$, 48 mice were divided into 6 groups for administration, with an administration cycle being twice a week for 6 administrations via intraperitoneal administration. After the start of administration, the body weight and the tumor volume were measured twice a week. The tumor volume was calculated as follows: tumor volume ($mm^3$)=0.5×long diameter of tumor×short diameter of tumor 2. On day 17 after the administration, one mouse of the combination therapy group of PR005565F (10 mg/kg)+Tecentriq (1 mg/kg) was found dead, and the corpse was experiencing autoproteolysis when being found. The rest of the mice in the same group were in normal condition, and all mice in the other administration groups were in normal condition. The entire experiment was terminated on day 21 after the administration, then all of the mice were euthanized. Analysis was performed on day 14 after the administration using GraphpadPrism9.0, one-way ANOVA. P<0.05 was defined as having a significant difference.

Figure 44:
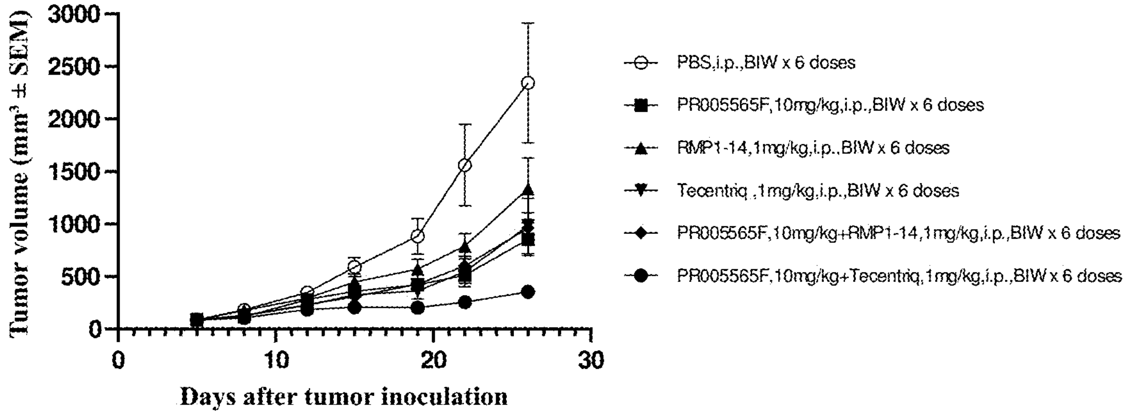
FIG. 44 shows the inhibition of tumor growth by afucosylated PR005565AF, anti-PD-1 antibody RMP1-14, and anti-PD-L1 antibody Tecentriq® alone or in combination, wherein i.p.: intraperitoneal injection, and BIW×6: the administration is performed twice a week for 6 times.

As shown in FIG. 44, the mean tumor volume of the mice in the control group (IgG1, 3 mg/kg) on day 14 after the administration was 884 $mm^3$. The mean tumor volume of the test drug PR005565F (10 mg/kg) therapy group on day 14 after the administration was 421 $mm^3$, showing significant difference from that of the control group (p value was 0.0105), with the tumor growth inhibition rate TGI (%) being 52.36%. The mean tumor volume of the test drug RPM1-14 (1 mg/kg) therapy group on day 14 after the administration was 572 mm 3, showing significant difference from that of the control group (p value was 0.1729), with the tumor growth inhibition rate TGI (%) being 35.34%. The mean tumor volume of the test drug Tecentriq (1 mg/kg) therapy group on day 14 after the administration was 363 $mm^3$, showing significant difference (p value was 0.0029) from that of the control group, with the tumor growth inhibition rate TGI (%) being 58.93%. The mean tumor volume of the combination therapy group of PR005565F (10 mg/kg)+RPM1-14 (1 mg/kg) on day 14 after the administration was 427 mm 3, showing significant difference from that of the control group (p value was 0.0119), with the tumor growth inhibition rate TGI (%) being 51.74%; and showing no significant difference from that of the PR005565F (10 mg/kg) therapy group (P>0.9999), and showing no significant difference from that of the RPM1-14 (1 mg/kg) therapy group (P=0.8693). The mean tumor volume of the combination therapy group PR005565F (10 mg/kg)+Tecentriq (1 mg/kg) on day 14 after the administration was 204 mm 3, showing significant difference from that of the control group (p<0.0001), with the tumor growth inhibition rate TGI (%) being 76.94%; and showing no significant difference from that of the PR005565F (10 mg/kg) therapy group (P=0.5503), and showing no significant difference from that of the Tecentriq (1 mg/kg) therapy group (P=0.8184).

Example 19. Experiment on the Tumor Inhibition of PR005565AF, PR006275AF and PR006276AF in Mice On the day of cell inoculation, each C57BL/6-CCR8knockin mouse was inoculated subcutaneously with $1\times10^6$ MC38 tumor cells. The cells were resuspended in PBS (0.1 mL/mouse) and inoculated subcutaneously. When the mean tumor volume of each group of mice reached 90 $mm^3$, 42 mice were divided into 7 groups for administration, with an administration cycle being twice a week for 5 administrations via intraperitoneal administration. After the start of administration, the body weight and the tumor volume were measured twice a week. The tumor volume was calculated as follows: tumor volume (mm 3)=0.5×long diameter of tumor×short diameter of tumor$^2$. On day 18 after the administration, one mouse of the test drug PR006275AF (10 mg/kg) therapy group was found dead, and the corpse was experiencing autoproteolysis when being found. The rest of the mice in the same group were in normal condition, and all mice in the other administration groups were in normal condition. The entire experiment was terminated on day 18 after the administration, then all of the mice were euthanized. The analysis was performed according to the data on day 14 after the administration. The independent sample T-test was used to determine whether there were significant differences between the different therapy groups and the control group, and the data were analyzed using SPSS. P<0.05 was defined as having a significant difference.

Figure 45:
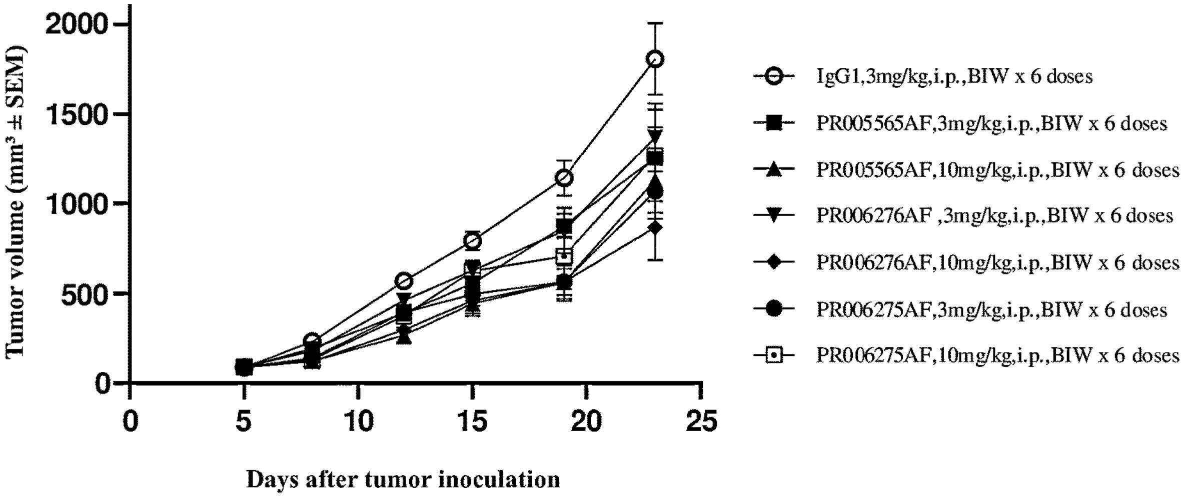
FIG. 45 shows the inhibition of tumor growth by afucosylated PR005565AF, PR006276AF and PR006275AF at 3 mg/kg, 10 mg/kg, wherein i.p.: intraperitoneal injection, and BIW×6: the administration is performed twice a week for 6 times.

As shown in FIG. 45, the mean tumor volume of the mice in the control group (IgG1, 3 mg/kg) on day 14 after the administration was 1142 $mm^3$. The mean tumor volume of the test drug PR005565AF (3 mg/kg) therapy group on day 14 after the administration was 874 $mm^3$, showing significant difference from that of the control group (p value was 0.0467), with the tumor growth inhibition rate TGI (%) being 23.46%. The mean tumor volume of the test drug PR005565AF (10 mg/kg) therapy group on day 14 after the administration was 561 $mm^3$, showing significant difference (p value was 0.0022) from that of the control group, with the tumor growth inhibition rate TGI (%) being 50.86%. The mean tumor volume of the test drug PR006276AF (3 mg/kg) therapy group on day 14 after the administration was 849 $mm^3$, showing no significant difference (p value was 0.0973) from that of the control group, with the tumor growth inhibition rate TGI (%) being 25.65%. The mean tumor volume of the test drug PR006276AF (10 mg/kg) therapy group on day 14 after the administration was 563 $mm^3$, showing significant difference from that of the control group (p value was 0.0016), with the tumor inhibition rate TGI (%) being 50.67%. The mean tumor volume of the test drug PR006275AF (3 mg/kg) therapy group on day 14 after the administration was 564 $mm^3$, showing no significant difference (p value was 0.0008) from that of the control group, with the tumor growth inhibition rate TGI (%) being 50.6%. The mean tumor volume of the test drug PR006275AF (10 mg/kg) therapy group on day 14 after the administration was 705 $mm^3$, showing no significant difference (p value was 0.0147) from that of the control group, with the tumor growth inhibition rate TGI (%) being 38.24%.

What is claimed is:

1. An isolated antigen-binding protein that binds CCR8, comprising an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences selected from any one of the following groups:

(1) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 80;

(2) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72;

(3) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 80;

(4) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 81;

(5) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 81;

(6) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 82;

(7) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 83;

(8) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(9) LCDR1: SEQ ID NO: 105, LCDR2: SEQ ID NO: 127, LCDR3: SEQ ID NO: 142; HCDR1: SEQ ID NO: 15, HCDR2: SEQ ID NO: 38, and HCDR3: SEQ ID NO: 65;

(10) LCDR1: SEQ ID NO: 105, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(11) LCDR1: SEQ ID NO: 106, LCDR2: SEQ ID NO: 127, LCDR3: SEQ ID NO: 142; HCDR1: SEQ ID NO: 15, HCDR2: SEQ ID NO: 38, and HCDR3: SEQ ID NO: 65;

(12) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 68;

(13) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 72;

(14) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 73;

(15) LCDR1: SEQ ID NO: 106, LCDR2: SEQ ID NO: 127, LCDR3: SEQ ID NO: 142; HCDR1: SEQ ID NO: 21, HCDR2: SEQ ID NO: 38, and HCDR3: SEQ ID NO: 65;

(16) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 65;

(17) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72;

(18) LCDR1: SEQ ID NO: 106, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 73;

(19) LCDR1: SEQ ID NO: 106, LCDR2: SEQ ID NO: 127, LCDR3: SEQ ID NO: 150; HCDR1: SEQ ID NO: 16, HCDR2: SEQ ID NO: 38, and HCDR3: SEQ ID NO: 65;

(20) LCDR1: SEQ ID NO: 106, LCDR2: SEQ ID NO: 127, LCDR3: SEQ ID NO: 151; HCDR1: SEQ ID NO: 16, HCDR2: SEQ ID NO: 38, and HCDR3: SEQ ID NO: 65;

(21) LCDR1: SEQ ID NO: 106, LCDR2: SEQ ID NO: 127, LCDR3: SEQ ID NO: 152; HCDR1: SEQ ID NO: 16, HCDR2: SEQ ID NO: 38, and HCDR3: SEQ ID NO: 65;

(22) LCDR1: SEQ ID NO: 107, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;

(23) LCDR1: SEQ ID NO: 107, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 68;
(24) LCDR1: SEQ ID NO: 111, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65;
(25) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 73; and
(26) LCDR1: SEQ ID NO: 112, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65.

2. The isolated antigen-binding protein according to claim 1, comprising an antibody heavy chain variable region VH and an antibody light chain variable region VL, wherein the VH and VL comprise amino acid sequences selected from any one of the following groups:
(1) VL: SEQ ID NO: 237, and VH: SEQ ID NO: 207;
(2) VL: SEQ ID NO: 237, and VH: SEQ ID NO: 196;
(3) VL: SEQ ID NO: 237, and VH: SEQ ID NO: 206;
(4) VL: SEQ ID NO: 237, and VH: SEQ ID NO: 208;
(5) VL: SEQ ID NO: 237, and VH: SEQ ID NO: 209;
(6) VL: SEQ ID NO: 237, and VH: SEQ ID NO: 210;
(7) VL: SEQ ID NO: 237, and VH: SEQ ID NO: 211;
(8) VL: SEQ ID NO: 220, and VH: SEQ ID NO: 172;
(9) VL: SEQ ID NO: 214, and VH: SEQ ID NO: 169;
(10) VL: SEQ ID NO: 217, and VH: SEQ ID NO: 172;
(11) VL: SEQ ID NO: 223, and VH: SEQ ID NO: 177;
(12) VL: SEQ ID NO: 227, and VH: SEQ ID NO: 172;
(13) VL: SEQ ID NO: 228, and VH: SEQ ID NO: 172;
(14) VL: SEQ ID NO: 220, and VH: SEQ ID NO: 181;
(15) VL: SEQ ID NO: 220, and VH: SEQ ID NO: 182;
(16) VL: SEQ ID NO: 220, and VH: SEQ ID NO: 183;
(17) VL: SEQ ID NO: 220, and VH: SEQ ID NO: 184;
(18) VL: SEQ ID NO: 220, and VH: SEQ ID NO: 185;
(19) VL: SEQ ID NO: 220, and VH: SEQ ID NO: 186;
(20) VL: SEQ ID NO: 220, and VH: SEQ ID NO: 187;
(21) VL: SEQ ID NO: 220, and VH: SEQ ID NO: 188;
(22) VL: SEQ ID NO: 220, and VH: SEQ ID NO: 189;
(23) VL: SEQ ID NO: 220, and VH: SEQ ID NO: 190;
(24) VL: SEQ ID NO: 220, and VH: SEQ ID NO: 191;
(25) VL: SEQ ID NO: 220, and VH: SEQ ID NO: 192;
(26) VL: SEQ ID NO: 220, and VH: SEQ ID NO: 193;
(27) VL: SEQ ID NO: 229, and VH: SEQ ID NO: 172;
(28) VL: SEQ ID NO: 230, and VH: SEQ ID NO: 172;
(29) VL: SEQ ID NO: 232, and VH: SEQ ID NO: 172;
(30) VL: SEQ ID NO: 233, and VH: SEQ ID NO: 172;
(31) VL: SEQ ID NO: 234, and VH: SEQ ID NO: 172;
(32) VL: SEQ ID NO: 229, and VH: SEQ ID NO: 185;
(33) VL: SEQ ID NO: 229, and VH: SEQ ID NO: 191;
(34) VL: SEQ ID NO: 230, and VH: SEQ ID NO: 185;
(35) VL: SEQ ID NO: 230, and VH: SEQ ID NO: 188;
(36) VL: SEQ ID NO: 230, and VH: SEQ ID NO: 191;
(37) VL: SEQ ID NO: 232, and VH: SEQ ID NO: 188;
(38) VL: SEQ ID NO: 232, and VH: SEQ ID NO: 191;
(39) VL: SEQ ID NO: 229, and VH: SEQ ID NO: 194;
(40) VL: SEQ ID NO: 229, and VH: SEQ ID NO: 195;
(41) VL: SEQ ID NO: 236, and VH: SEQ ID NO: 194;
(42) VL: SEQ ID NO: 236, and VH: SEQ ID NO: 195;
(43) VL: SEQ ID NO: 232, and VH: SEQ ID NO: 196;
(44) VL: SEQ ID NO: 232, and VH: SEQ ID NO: 197;
(45) VL: SEQ ID NO: 237, and VH: SEQ ID NO: 197;
(46) VL: SEQ ID NO: 229, and VH: SEQ ID NO: 188;
(47) VL: SEQ ID NO: 232, and VH: SEQ ID NO: 185;
(48) VL: SEQ ID NO: 242, and VH: SEQ ID NO: 172;
(49) VL: SEQ ID NO: 243, and VH: SEQ ID NO: 172; and
(50) VL: SEQ ID NO: 244, and VH: SEQ ID NO: 172.

3. The isolated antigen-binding protein according to claim 1, comprising a full-length antibody; a Fab; a Fab'; an $F(ab')_2$; an Fv, an scFv; a di-scFv; a bispecific antibody; or a multispecific antibody.

4. The isolated antigen-binding protein according to claim 3, wherein the antibody is selected from the following group: a monoclonal antibody, a chimeric antibody, a humanized antibody and a fully human antibody.

5. One or more isolated nucleic acid molecules encoding the isolated antigen-binding protein according to claim 1.

6. A vector comprising the nucleic acid molecule according to claim 5.

7. A cell comprising the nucleic acid molecule according to claim 5.

8. A chimeric antigen receptor comprising the antigen-binding protein according to claim 1.

9. A genetically modified cell comprising the chimeric antigen receptor according to claim 8; wherein the genetically modified cell is a T cell or an NK cell.

10. An antibody-drug conjugate comprising a cytotoxic agent and the antigen-binding protein according to claim 1.

11. A pharmaceutical composition comprising the isolated antigen-binding protein according to claim 1, and optionally a pharmaceutically acceptable carrier.

12. A method for alleviating and/or treating a tumor, comprising administering to a subject in need thereof the isolated antigen-binding protein according claim 1, wherein the tumor is a tumor with abnormal CCR8 expression or wherein the tumor microenvironment of the tumor contains CCR8+ regulatory T cells (Tregs).

13. The method according to claim 12, wherein the tumor is breast cancer, kidney cancer, pancreatic cancer, bladder cancer, gastric cancer, cervical cancer or colon cancer.

14. The isolated antigen-binding protein according to claim 1, wherein the antigen-binding protein further comprises an antibody heavy chain constant region.

15. The isolated antigen-binding protein according to claim 14, wherein the constant region is derived from a human IgG1 constant region.

16. The isolated antigen-binding protein according to claim 1, wherein the antigen-binding protein comprises an antibody heavy chain and an antibody light chain, wherein the antibody heavy chain comprises an amino acid sequence set forth in any one of SEQ ID NOs: 317, 281, 254, 299-316, 318, 251, 259-262, 266-280 and 282-284, and wherein the antibody light chain comprises an amino acid sequence set forth in any one of SEQ ID NOs: 344, 327, 321, 324, 330, 334-337, 339-341, 343, 349, 350 and 351.

17. An isolated antigen-binding protein that binds CCR8, comprising an antibody heavy chain or a fragment thereof and an antibody light chain or a fragment thereof, wherein the antibody heavy chain or the fragment thereof comprises an HCDR1, an HCDR2 and an HCDR3, and the antibody light chain or the fragment thereof comprises an LCDR1, an LCDR2 and an LCDR3, wherein the HCDR1, HCDR2, HCDR3, LCDR1, LCDR2 and LCDR3 comprise amino acid sequences of:
(1) LCDR1: SEQ ID NO: 111, LCDR2: SEQ ID NO: 127, LCDR3: SEQ ID NO: 142; HCDR1: SEQ ID NO: 22, HCDR2: SEQ ID NO: 48, and HCDR3: SEQ ID NO: 80;

(2) LCDR1: SEQ ID NO: 111, LCDR2: SEQ ID NO: 127, LCDR3: SEQ ID NO: 142; HCDR1: SEQ ID NO: 22, HCDR2: SEQ ID NO: 38, and HCDR3: SEQ ID NO: 72; or (3) LCDR1: SEQ ID NO: 106, LCDR2: SEQ ID NO: 127, LCDR3: SEQ ID NO: 142; HCDR1: SEQ ID NO: 16, HCDR2: SEQ ID NO: 38, and HCDR3: SEQ ID NO: 65.

18. The isolated antigen-binding protein according to claim 17, wherein the antibody heavy chain comprises an antibody heavy chain variable region VH, which comprises the HCDR1, the HCDR2 and the HCDR3, wherein the antibody light chain comprises an antibody light chain variable region VL, which comprises the LCDR1, the LCDR2 and the LCDR3; and wherein the VH and VL comprise amino acid sequences of:

(1) VL: SEQ ID NO: 237, and VH: SEQ ID NO: 207;

(2) VL: SEQ ID NO: 237, and VH: SEQ ID NO: 196; or (3) VL: SEQ ID NO: 220, and VH: SEQ ID NO: 172.

19. The isolated antigen-binding protein according to claim 17, comprising the antibody heavy chain and the antibody light chain, wherein the antibody heavy chain and antibody light chain comprise amino acid sequences of:

(1) SEQ ID NO: 317 and SEQ ID NO: 344;

(2) SEQ ID NO: 281 and SEQ ID NO: 344; or (3) SEQ ID NO: 254 and SEQ ID NO: 327.

20. A method for alleviating and/or treating a tumor, comprising administering to a subject in need thereof the isolated antigen-binding protein according claim 19, wherein the tumor is a tumor with abnormal CCR8 expression or wherein the tumor microenvironment of the tumor contains CCR8+ regulatory T cells (Tregs).

* * * * *